(12) United States Patent
Luo et al.

(10) Patent No.: US 12,105,084 B2
(45) Date of Patent: *Oct. 1, 2024

(54) NUCLEIC ACID LINKED IMMUNE-SANDWICH ASSAY (NULISA)

(71) Applicant: Alamar Biosciences, Inc., Hayward, CA (US)

(72) Inventors: Yuling Luo, San Ramon, CA (US); Wei Feng, Union City, CA (US); Adrian Grzybowski, San Leandro, CA (US); Yiyuan Yin, Fremont, CA (US); Shiping Chen, Fremont, CA (US)

(73) Assignee: Alamar Biosciences, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/330,331

(22) Filed: May 25, 2021

(65) Prior Publication Data

US 2021/0278398 A1 Sep. 9, 2021

Related U.S. Application Data

(63) Continuation of application No. PCT/US2020/062791, filed on Dec. 2, 2020.

(60) Provisional application No. 62/943,135, filed on Dec. 3, 2019.

(51) Int. Cl.
*G01N 33/543* (2006.01)
*C12Q 1/6813* (2018.01)
*G01N 33/68* (2006.01)

(52) U.S. Cl.
CPC ..... *G01N 33/54306* (2013.01); *C12Q 1/6813* (2013.01); *G01N 33/6872* (2013.01); *G01N 2333/71* (2013.01)

(58) Field of Classification Search
CPC ......... G01N 33/54306; G01N 33/6872; G01N 2333/71; C12Q 1/6813
See application file for complete search history.

(56) References Cited

U.S. PATENT DOCUMENTS

| | | |
|---|---|---|
| 4,988,617 A | 1/1991 | Landegren et al. |
| 5,236,830 A | 8/1993 | Ishikawa |
| 5,236,849 A | 8/1993 | Ishikawa |
| 5,328,985 A | 7/1994 | Sano et al. |
| 5,521,066 A | 5/1996 | Menzel et al. |
| 5,532,351 A | 7/1996 | Stefansson |
| 5,538,866 A | 7/1996 | Israeli et al. |
| 5,561,043 A | 10/1996 | Cantor et al. |
| 5,580,736 A | 12/1996 | Brent et al. |
| 5,599,660 A | 2/1997 | Ramanujam et al. |
| 5,610,282 A | 3/1997 | Sibley et al. |
| 5,618,701 A | 4/1997 | Landegren |
| 5,635,602 A | 6/1997 | Cantor et al. |
| 5,652,107 A | 7/1997 | Lizardi et al. |
| 5,660,990 A | 8/1997 | Rao et al. |
| 5,665,539 A | 9/1997 | Sano et al. |
| 5,744,303 A | 4/1998 | Iggo et al. |
| 5,744,314 A | 4/1998 | Menzel et al. |
| 5,750,369 A | 5/1998 | Lake et al. |
| 5,759,773 A | 6/1998 | Tyagi et al. |
| 5,759,784 A | 6/1998 | Asp et al. |
| 5,763,175 A | 6/1998 | Brenner |
| 5,786,169 A | 7/1998 | Brent et al. |
| 5,811,231 A | 9/1998 | Farr et al. |
| 5,849,878 A | 12/1998 | Cantor et al. |
| 5,849,906 A | 12/1998 | Cavalieri et al. |
| 5,856,155 A | 1/1999 | Li |
| 5,871,921 A | 2/1999 | Landegren et al. |
| 5,876,941 A | 3/1999 | Ishikawa et al. |
| 5,888,834 A | 3/1999 | Ishikawa et al. |
| 5,922,855 A | 7/1999 | Liskay et al. |
| 5,952,201 A | 9/1999 | Landegren et al. |
| 5,958,673 A | 9/1999 | LaClair |
| 5,965,133 A | 10/1999 | Cantor et al. |
| 5,976,794 A | 11/1999 | Katz et al. |
| 5,985,577 A | 11/1999 | Bulinski |
| 6,004,746 A | 12/1999 | Brent et al. |
| 6,024,920 A | 2/2000 | Cunanan |
| 6,027,887 A | 2/2000 | Zavada et al. |
| 6,030,657 A | 2/2000 | Butland et al. |
| 6,033,913 A | 3/2000 | Morozov et al. |
| 6,040,192 A | 3/2000 | Tuunanen |
| 6,051,381 A | 4/2000 | Kornacker |
| 6,063,564 A | 5/2000 | Ishikawa et al. |
| 6,106,832 A | 8/2000 | Spriggs et al. |
| 6,136,533 A | 10/2000 | Bekkaoui et al. |
| 6,136,580 A | 10/2000 | Fukuda et al. |
| 6,140,041 A | 10/2000 | LaClair |
| 6,140,135 A | 10/2000 | Landegren et al. |
| 6,146,877 A | 11/2000 | Fisher |
| 6,207,463 B1 | 3/2001 | Tuunanen |
| 6,235,472 B1 | 5/2001 | Landegren et al. |
| 6,242,183 B1 | 6/2001 | Brent et al. |
| 6,258,942 B1 | 7/2001 | O'Brien et al. |
| 6,287,773 B1 | 9/2001 | Newell |
| 6,291,669 B1 | 9/2001 | Kwiatkowski et al. |
| 6,313,284 B1 | 11/2001 | Kwiatkowski et al. |
| 6,344,324 B2 | 2/2002 | Howell et al. |
| 6,416,972 B1 | 7/2002 | Lake et al. |

(Continued)

FOREIGN PATENT DOCUMENTS

| | | |
|---|---|---|
| EP | 0832431 B1 | 8/2001 |
| EP | 1255861 B1 | 7/2008 |

(Continued)

OTHER PUBLICATIONS

Darmanis (PLOS One (2011) vol. 6, e25583).*

(Continued)

*Primary Examiner* — Steven Pohnert
(74) *Attorney, Agent, or Firm* — Morgan, Lewis & Bockius LLP

(57) ABSTRACT

Disclosed herein are highly sensitive immunoassays that utilize a capture/release mechanism to reduce non-specific binding and achieve detection with attomolar-level sensitivity. Kits that can be used for carrying out these highly sensitive immunoassays are also disclosed herein.

7 Claims, 44 Drawing Sheets

Specification includes a Sequence Listing.

(56) References Cited

U.S. PATENT DOCUMENTS

| | | |
|---|---|---|
| 6,429,309 B1 | 8/2002 | Kwiatkowski et al. |
| 6,447,729 B1 | 9/2002 | Tuunanen |
| 6,448,092 B1 | 9/2002 | Tuunanen |
| 6,485,921 B1 | 11/2002 | Shyjan et al. |
| 6,486,382 B1 | 11/2002 | Gordan-Kamm et al. |
| 6,489,099 B1 | 12/2002 | Walmsley |
| 6,489,120 B1 | 12/2002 | Stevens |
| 6,511,809 B2 | 1/2003 | Baez et al. |
| 6,531,278 B1 | 3/2003 | Weimer |
| 6,531,585 B1 | 3/2003 | Blaudin de The et al. |
| 6,541,244 B1 | 4/2003 | Auernhammer et al. |
| 6,558,928 B1 | 5/2003 | Landegren |
| 6,596,162 B2 | 7/2003 | Tuunanen |
| 6,596,475 B2 | 7/2003 | Bulinski |
| 6,642,008 B1 | 11/2003 | Harley et al. |
| 6,646,118 B2 | 11/2003 | Kwiatkowski et al. |
| 6,660,844 B1 | 12/2003 | Siegel et al. |
| 6,667,153 B1 | 12/2003 | Thomas |
| 6,774,119 B1 | 8/2004 | Wechsler et al. |
| 6,790,946 B2 | 9/2004 | Kwiatkowski et al. |
| 6,842,703 B2 | 1/2005 | Newell |
| 6,846,622 B1 | 1/2005 | Heffron et al. |
| 6,878,515 B1 | 4/2005 | Landegren |
| 6,900,291 B2 | 5/2005 | Holmes et al. |
| 7,049,071 B2 | 5/2006 | Walmsley et al. |
| 7,074,564 B2 | 7/2006 | Landegren |
| 7,078,173 B2 | 7/2006 | Harley et al. |
| 7,122,313 B2 | 10/2006 | Eberwine |
| 7,148,043 B2 | 12/2006 | Kordunsky et al. |
| 7,211,710 B2 | 5/2007 | Gonsalves et al. |
| 7,214,546 B2 | 5/2007 | Sparks |
| 7,294,460 B2 | 11/2007 | Pompon et al. |
| 7,306,904 B2 | 12/2007 | Landegren et al. |
| 7,320,860 B2 | 1/2008 | Landegren et al. |
| 7,348,010 B2 | 3/2008 | Zielinski |
| 7,351,528 B2 | 4/2008 | Landegren |
| 7,410,642 B2 | 8/2008 | Harley et al. |
| 7,427,483 B2 | 9/2008 | Nguyen |
| 7,521,188 B2 | 4/2009 | Yim et al. |
| 7,575,866 B2 | 8/2009 | Cornish |
| 7,659,058 B2 | 2/2010 | Deml |
| 7,709,243 B2 | 5/2010 | Park et al. |
| 7,749,736 B2 | 7/2010 | Kordunsky et al. |
| 7,790,388 B2 | 9/2010 | Landegren et al. |
| 7,807,347 B2 | 10/2010 | Lu et al. |
| 7,825,231 B2 | 11/2010 | Wolfe |
| 7,883,848 B2 | 2/2011 | Ericsson |
| 7,883,849 B1 | 2/2011 | Dahl |
| 7,883,903 B2 | 2/2011 | Sparks |
| 7,910,702 B2 | 3/2011 | Kav et al. |
| 7,914,987 B2 | 3/2011 | Fredriksson et al. |
| 7,935,790 B2 | 5/2011 | Moritz et al. |
| 7,939,284 B2 | 5/2011 | Johnsson |
| 7,972,838 B2 | 7/2011 | Korpimaki |
| 7,999,080 B2 | 8/2011 | Hornbeck |
| 8,003,622 B2 | 8/2011 | Wolfe et al. |
| 8,013,134 B2 | 9/2011 | Fredriksson |
| 8,053,188 B2 | 11/2011 | Gullberg et al. |
| 8,080,393 B2 | 12/2011 | Koch et al. |
| 8,187,586 B2 | 5/2012 | Brown et al. |
| 8,198,039 B2 | 6/2012 | Shi et al. |
| 8,227,213 B2 | 7/2012 | Narimatsu |
| 8,236,504 B2 | 8/2012 | Kordunsky et al. |
| 8,268,554 B2 | 9/2012 | Schallmeiner |
| 8,268,962 B2 | 9/2012 | Heemskerk |
| 8,268,970 B2 | 9/2012 | Terrett et al. |
| 8,293,501 B2 | 10/2012 | Fredriksson et al. |
| 8,293,972 B2 | 10/2012 | Kav et al. |
| 8,318,438 B2 | 11/2012 | Vivekananda et al. |
| 8,367,361 B2 | 2/2013 | Johnsson et al. |
| 8,383,779 B2 | 2/2013 | Terrett et al. |
| 8,399,623 B2 | 3/2013 | Terrett et al. |
| 8,425,904 B2 | 4/2013 | Terrett et al. |
| 8,431,365 B2 | 4/2013 | Narimatsu et al. |
| RE44,265 E | 6/2013 | Landegren et al. |
| 8,492,343 B2 | 7/2013 | Kim et al. |
| 8,512,678 B2 | 8/2013 | Zhuo et al. |
| 8,519,097 B2 | 8/2013 | Heemskerk et al. |
| 8,535,878 B2 | 9/2013 | Ruff et al. |
| 8,580,504 B2 | 11/2013 | Fredriksson et al. |
| 8,609,065 B2 | 12/2013 | Van Kuik-Romeijn et al. |
| 8,664,164 B2 | 3/2014 | Ericsson et al. |
| 8,689,982 B2 | 4/2014 | Karmeniemi et al. |
| 8,691,149 B2 | 4/2014 | Fritchie et al. |
| 8,709,722 B2 | 4/2014 | Tan et al. |
| 8,735,601 B2 | 5/2014 | Peng et al. |
| 8,784,734 B2 | 7/2014 | Campbell et al. |
| 8,796,184 B2 | 8/2014 | Chilkoti et al. |
| 8,835,118 B2 | 9/2014 | Kordunsky et al. |
| 8,846,889 B2 | 9/2014 | Wolfe |
| 8,906,700 B2 | 12/2014 | Lim et al. |
| 8,951,736 B2 | 2/2015 | Schmidt |
| 8,969,008 B2 | 3/2015 | Hastwell et al. |
| 9,029,086 B2 | 5/2015 | Moghaddam |
| 9,096,856 B2 | 8/2015 | Wang et al. |
| 9,151,767 B2 | 10/2015 | Yang |
| 9,163,276 B2 | 10/2015 | Ohtsuki et al. |
| 9,284,559 B2 | 3/2016 | Gmeiner |
| 9,335,292 B2 | 5/2016 | Hu et al. |
| 9,387,257 B2 | 7/2016 | Wu et al. |
| 9,518,296 B2 | 12/2016 | Ruff et al. |
| 9,551,032 B2 | 1/2017 | Landegren et al. |
| 9,568,403 B2 | 2/2017 | Tuunanen |
| 9,677,131 B2 | 6/2017 | Fredriksson et al. |
| 9,777,315 B2 | 10/2017 | Fredriksson et al. |
| 9,902,993 B2 | 2/2018 | Fredriksson et al. |
| 9,938,524 B2 | 4/2018 | Fernandez et al. |
| 9,974,302 B2 | 5/2018 | Anderson et al. |
| 9,983,203 B2 | 5/2018 | Ivansson et al. |
| 9,995,680 B2 | 6/2018 | Easley et al. |
| 10,041,116 B2 | 8/2018 | Hindson et al. |
| 10,174,366 B2 | 1/2019 | Landegren et al. |
| 10,288,607 B2 | 5/2019 | Chilkoti et al. |
| 10,338,066 B2 | 7/2019 | Fan et al. |
| 10,344,329 B2 | 7/2019 | Hindson et al. |
| 10,465,235 B2 | 11/2019 | Gullberg et al. |
| 10,472,671 B2 | 11/2019 | Chen et al. |
| 10,597,701 B2 | 3/2020 | Landegren et al. |
| 10,605,814 B2 | 3/2020 | Jeney |
| 10,669,576 B2 | 6/2020 | Kordunsky et al. |
| 10,724,084 B2 | 7/2020 | Kordunsky et al. |
| 2002/0051994 A1 | 5/2002 | Kwiatkowski et al. |
| 2002/0064779 A1 | 5/2002 | Landegren et al. |
| 2002/0035247 A1 | 8/2002 | Kwiatkowski et al. |
| 2002/0102592 A1 | 8/2002 | Landegren |
| 2002/0177698 A1 | 11/2002 | Kwiatkowski et al. |
| 2004/0004000 A1 | 1/2004 | Kenjo |
| 2004/0065560 A1 | 4/2004 | Kenjo |
| 2004/0106112 A1 | 6/2004 | Nilsson et al. |
| 2005/0026204 A1 | 2/2005 | Landegren |
| 2005/0027116 A1 | 2/2005 | Kwiatkowski et al. |
| 2005/0037356 A1 | 2/2005 | Gullberg et al. |
| 2005/0233351 A1 | 10/2005 | Landegren |
| 2005/0282158 A1 | 12/2005 | Landegren |
| 2005/0287526 A1 | 12/2005 | Landegren et al. |
| 2007/0225487 A1 | 9/2007 | Nilsson et al. |
| 2007/0243601 A1 | 10/2007 | Korpimaki et al. |
| 2008/0003604 A1 | 1/2008 | Ruff et al. |
| 2008/0090238 A1 | 4/2008 | Yang et al. |
| 2008/0131899 A1 | 6/2008 | Landegren et al. |
| 2010/0021890 A1 | 1/2010 | Schallmeiner |
| 2010/0227329 A1* | 9/2010 | Cuppens .......... C12Q 1/6874 435/6.12 |
| 2010/0291636 A1 | 11/2010 | Johansson et al. |
| 2011/0223585 A1 | 9/2011 | Gullberg et al. |
| 2012/0220479 A1 | 8/2012 | Ericsson et al. |
| 2012/0258870 A1 | 10/2012 | Schwartz et al. |
| 2013/0171652 A1 | 7/2013 | Fredriksson et al. |
| 2013/0288249 A1 | 10/2013 | Gullberg et al. |
| 2013/0323729 A1 | 12/2013 | Landegren et al. |
| 2014/0030721 A1 | 1/2014 | Fredriksson et al. |
| 2014/0102915 A1 | 4/2014 | Hu et al. |
| 2014/0134624 A1 | 5/2014 | Ruff et al. |
| 2014/0170654 A1 | 6/2014 | Landegren et al. |

(56) References Cited

U.S. PATENT DOCUMENTS

| | | | |
|---|---|---|---|
| 2014/0194311 | A1 | 7/2014 | Gullberg et al. |
| 2015/0044674 | A1 | 2/2015 | Fredriksson et al. |
| 2015/0111788 | A1 | 4/2015 | Fernandez et al. |
| 2015/0212087 | A1 | 7/2015 | Le Romancer-Cherifi et al. |
| 2015/0275295 | A1 | 10/2015 | Wang et al. |
| 2016/0047800 | A1 | 2/2016 | Collier et al. |
| 2016/0108458 | A1 | 4/2016 | Frei et al. |
| 2016/0213754 | A1 | 7/2016 | Landegren et al. |
| 2016/0289750 | A1 | 10/2016 | Landegren et al. |
| 2016/0369321 | A1 | 12/2016 | Landegren et al. |
| 2016/0376642 | A1 | 12/2016 | Landegren et al. |
| 2017/0096648 | A1 | 4/2017 | Mazur et al. |
| 2017/0184590 | A1 | 6/2017 | Wan et al. |
| 2017/0211133 | A1 | 7/2017 | Landegren et al. |
| 2017/0212101 | A1 | 7/2017 | Zhu et al. |
| 2017/0335369 | A1* | 11/2017 | Fields ............... C12Q 1/6806 |
| 2017/0362643 | A9 | 12/2017 | Landegren et al. |
| 2017/0362647 | A1 | 12/2017 | Palhan et al. |
| 2018/0088112 | A1 | 3/2018 | Fan et al. |
| 2018/0292394 | A1* | 10/2018 | Soldo ............... G01N 33/5306 |
| 2018/0312901 | A1 | 11/2018 | Fredriksson et al. |
| 2018/0320241 | A1 | 11/2018 | Nolan |
| 2018/0327818 | A1 | 11/2018 | Landegren et al. |
| 2019/0025304 | A1 | 1/2019 | Vigneault et al. |
| 2020/0024601 | A1 | 1/2020 | Haisma et al. |
| 2022/0390442 | A1* | 12/2022 | Luo ............... G01N 33/54326 |

FOREIGN PATENT DOCUMENTS

| | | | |
|---|---|---|---|
| EP | 1985714 B1 | 2/2012 | |
| EP | 2920320 B1 | 12/2016 | |
| EP | 2633081 B1 | 1/2017 | |
| EP | 2714925 B1 | 6/2017 | |
| EP | 2707502 B1 | 6/2018 | |
| EP | 3263703 B1 | 4/2020 | |
| EP | 3365460 B1 | 4/2020 | |
| WO | WO 97/00446 | 1/1997 | |
| WO | WO2001061037 A1 * | 8/2001 | |
| WO | WO 2012/104261 A1 | 8/2012 | |
| WO | WO 2017/068116 A1 | 4/2017 | |
| WO | WO 2017/205344 | 11/2017 | |
| WO | WO 2018/045200 A2 | 3/2018 | |
| WO | WO-2018160397 A1 * | 9/2018 | ........... C12Q 1/6804 |
| WO | WO 2019/104155 A2 | 5/2019 | |
| WO | WO 2019/149692 A1 | 8/2019 | |
| WO | WO 2019/191838 A1 | 10/2019 | |

OTHER PUBLICATIONS

Nong (Nature Protocols (2013) vol. 8, pp. 1234-1248).*
Wan (PLOS one (2018) vol. 13, e0191987).*
Jalili (Proceedings National Academy of Sciences USA (2018), E925-E933).*
Lundberg (Molecular & Cellular Proteomics 10.4 (2011).*
Bystrykh (.Hematopoietic Stem Cell Protocols, Methods in Molecular Biology,vol. 1185, pp. 345-360).*
Corey et al., "Generation of a hybrid sequence-specific single-stranded deoxyribonuclease." Science 238.4832 (1987): 1401-1403.
Darmanis et al., "ProteinSeq: high-performance proteomic analyses by proximity ligation and next generation sequencing." PloS one 6.9 (2011): e25583.
Day et al., "Immobilization of polynucleotides on magnetic particles. Factors influencing hybridization efficiency." Biochemical Journal 278.3 (1991): 735-740.
Ex-Parte Re-Examination Certificate No. U.S. Pat. No. 6,511,809 C1, issued Aug. 17, 2010 for U.S. Pat. No. 6,511,809 (134 pages).
Gong et al., "Simple method to prepare oligonucleotide-conjugated antibodies and its application in multiplex protein detection in single cells." Bioconjugate chemistry 27.1 (2016): 217-225.
Ham et al., "In situ regeneration of bioactive coatings enabled by an evolved Staphylococcus aureus sortase A." Nature communications 7.1 (2016): 1-8.
Hashida et al., "Novel and ultrasensitive sandwich enzyme immunoassay (sandwich transfer enzyme immunoassay) for antigens." Analytical letters 21.7 (1988): 1141-1154.
Hendrickson et al., "High sensitivity multianalyte immunoassay using covalent DNA-labeled antibodies and polymerase chain reaction." Nucleic acids research 23.3 (1995): 522-529.
Hu et al., "Quantitation of femtomolar protein levels via direct readout with the electrochemical proximity assay." Journal of the American Chemical Society 134.16 (2012): 7066-7072.
Lundberg et al., "Homogeneous antibody-based proximity extension assays provide sensitive and specific detection of low-abundant proteins in human blood." Nucleic acids research 39.15 (2011): e102-e102.
Nguyen et al., "Mild conditions for releasing mono and bis-biotinylated macromolecules from immobilized streptavidin." Biomolecular engineering 22.4 (2005): 147-150.
Niemeyer, Christof M. "Bioorganic applications of semisynthetic DNA-protein conjugates." Chemistry—A European Journal 7.15 (2001): 3188-3195.
Niemeyer, Christof M. "The developments of semisynthetic DNA-protein conjugates." Trends in biotechnology 20.9 (2002): 395-401.
Niemeyer et al., "Combination of DNA-directed immobilization and immuno-PCR: very sensitive antigen detection by means of self-assembled DNA-protein conjugates." Nucleic acids research 31.16 (2003): e90-e90.
Nong et al., "Solid-phase proximity ligation assays for individual or parallel protein analyses with readout via real-time PCR or sequencing." Nature protocols 8.6 (2013): 1234.
Numata et al., "Development of a novel ultrasensitive enzyme immunoassay for human glutamic acid decarboxylase 65 antibody." Annals of clinical biochemistry 53.4 (2016): 495-503.
Sano et al., "Immuno-PCR: very sensitive antigen detection by means of specific antibody-DNA conjugates." Science 258.5079 (1992): 120-122.
Saxena et al., "Immunotechnology in Disease Diagnosis." International Journal of Pharmaceutical Research 4.2 (2012): 1-6.
Scouten et al., "Reversible immobilization of antibodies on magnetic beads." Analytical biochemistry 205.2 (1992): 313-318.
Shahi et al., "Abseq: Ultrahigh-throughput single cell protein profiling with droplet microfluidic barcoding." Scientific reports 7.1 (2017): 1-12.
Shannon et al., "High-throughput Approach for Multi-omic Testing for Prostate Cancer Research." Journal of Molecular Diagnostics. vol. 20. No. 6. 360 Park Ave South, New York, NY 10010-1710 (2018).
Tekin et al., "Attomolar protein detection using a magnetic bead surface coverage assay." Lab on a Chip 13.6 (2013): 1053-1059.
Thompson et al., "Enzymatic amplification of RNA purified from crude cell lysate by reversible target capture." Clinical chemistry 35.9 (1989): 1878-1881.
Wan et al., "Photocleavage-based affinity purification of biomarkers from serum: Application to multiplex allergy testing." Plos one 13.2 (2018): e0191987.
Watanabe et al., "The immune complex transfer enzyme immunoassay: Mechanism of improved sensitivity compared with conventional sandwich enzyme immunoassay." Journal of immunological methods 459 (2018): 76-80.
Yamamoto et al., "A study of high-, middle- and low-molecular weight adiponectin in urine as a surrogate marker for early diabetic nephropathy using ultrasensitive immune complex transfer enzyme immunoassay." Annals of clinical biochemistry 55.5 (2018): 525-534.
International Search Report and Written Opinion issued for International Application No. PCT/US2020/062791, dated Mar. 26, 2021 (6 pages).
Hammond, M., et al., "Profiling Cellular Protein Complexes by Proximity Ligation with Dual Tag Microarray Readout," PLOS ONE, Jul. 10, 2012, pp. 1-11.
SOMAlogic, "SOMAscan Proteomic Assay Technical White Paper," 2016, pp. 1-14.

* cited by examiner

PLA, PEA and solid phase PLA

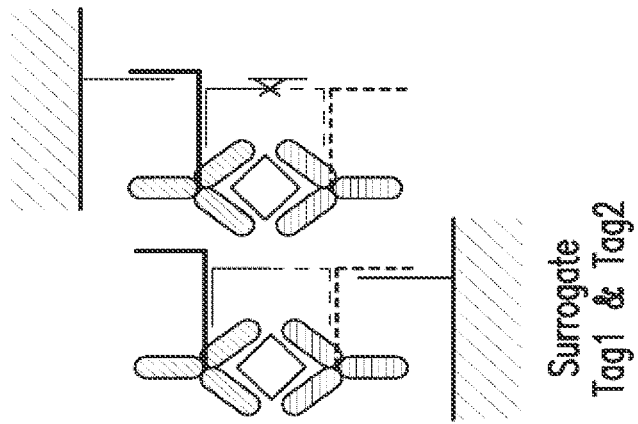
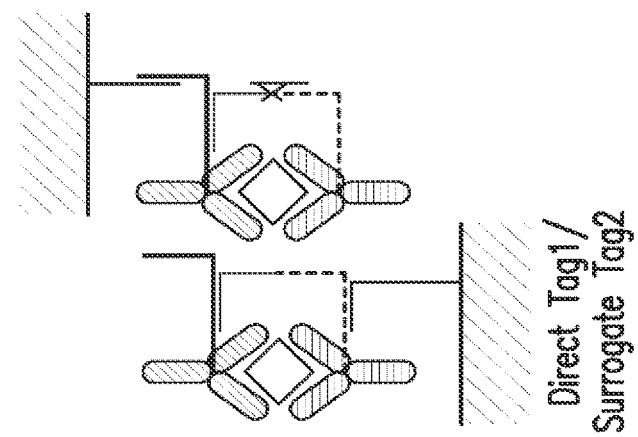
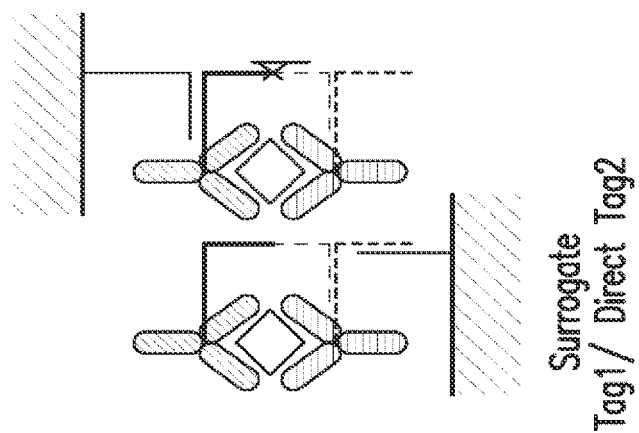

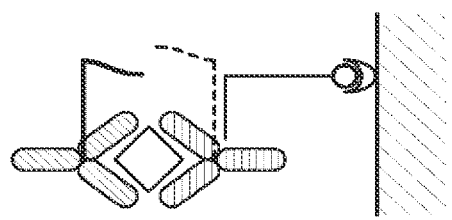
FIG. 6A Direct capture
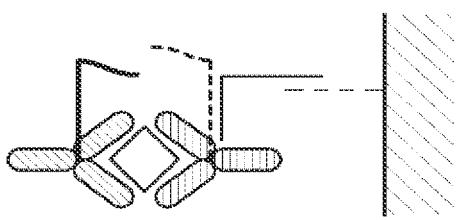
FIG. 6B Indirect capture with universal probe
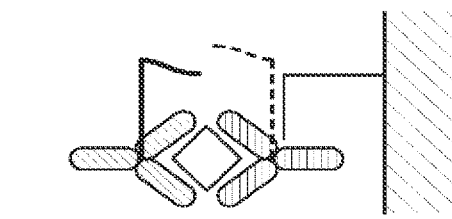
FIG. 6C Indirect capture with biochemistry
FIG. 6D Direct collaborative capture
Example methods of capture to surface using nucleic acid Different configurations of collaborative capture

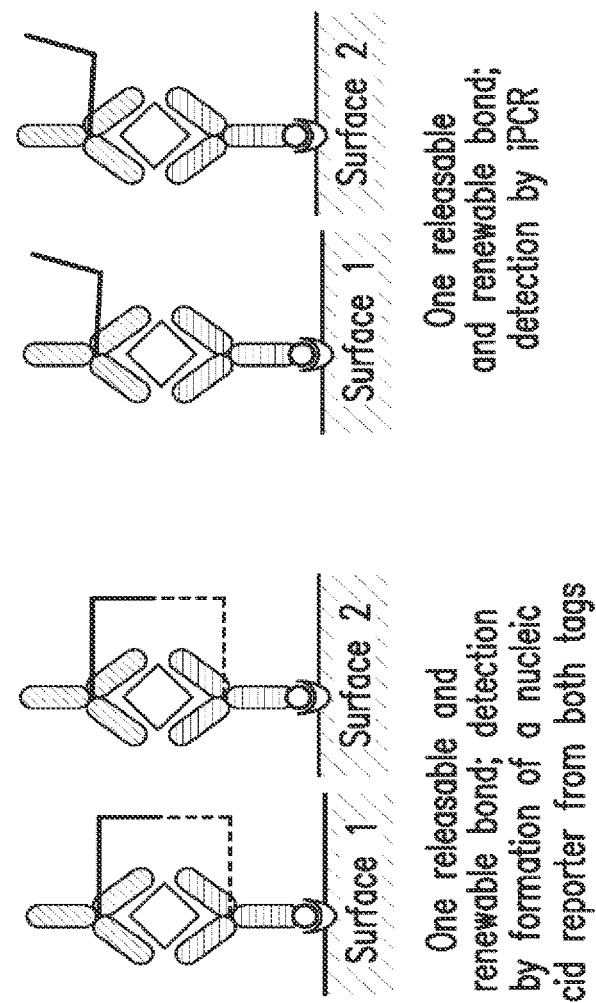

Embodiments of NULISA

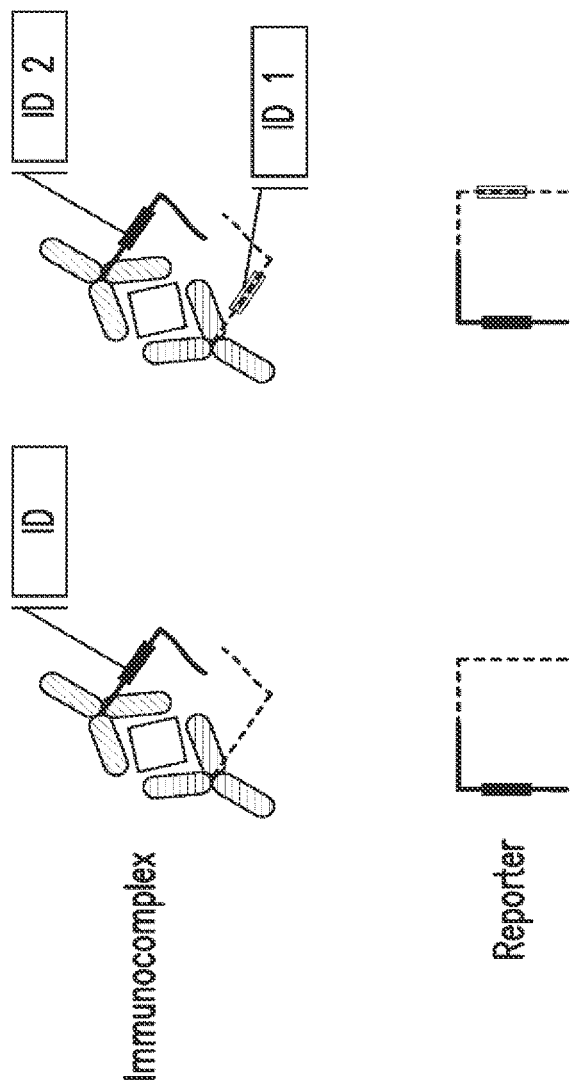

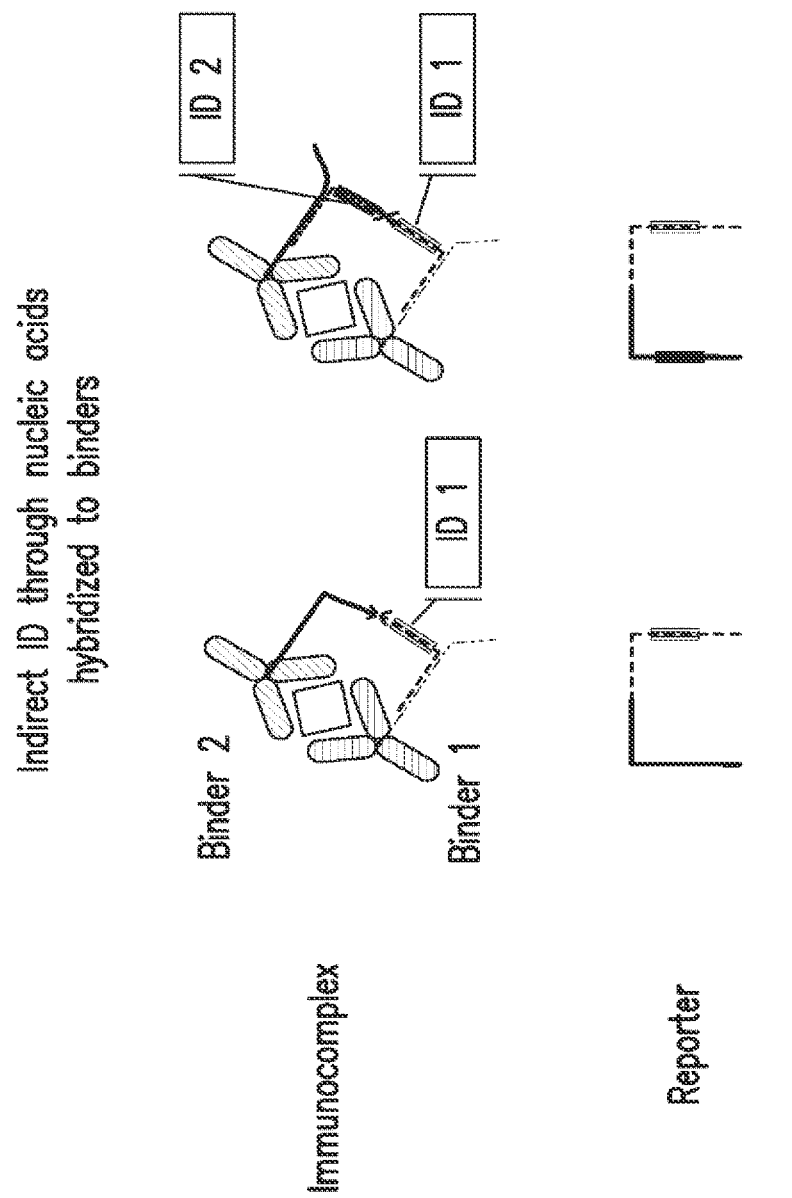

Configuration of a NULISA assay

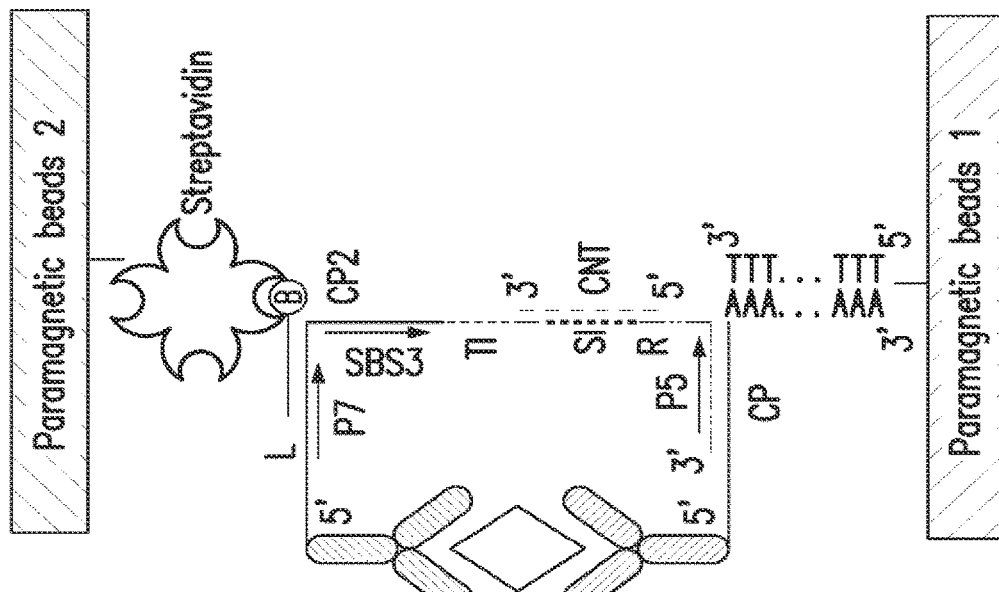

- Antibody-antigen binding complex detected by qPCR, ddPCR or NGS through an oligo-linked single molecule detection system
- Immuno-complex formation in solution
- Oligo-based capture of immuno-complex
- Two sequential capture steps resulting in extremely low assay background
- 0 – 400 µL sample input ensuring robust detection of extremely low abundance targets
- Target Index (TI) and Sample Index (SI) incorporated to allow high plex and high sample throughput in NGS-based analysis
- Fully automatable

FIG. 16

Nucleic Acid Linked Immunocomplex

Nucleic Acid Linked Immunocomplex (Continued)

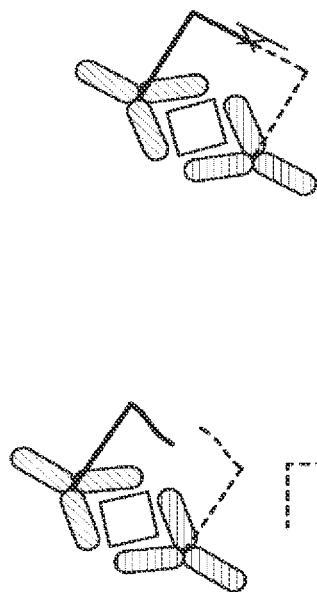
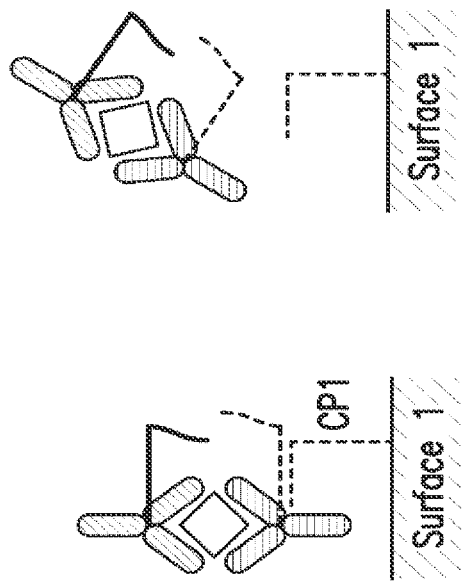
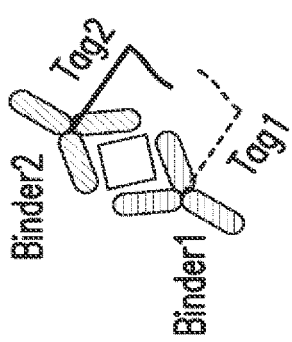
FIG.20A  FIG.20B  FIG.20C  FIG.20D

SEQUENCE LISTING

```
<160> NUMBER OF SEQ ID NOS: 60

<210> SEQ ID NO 1
<211> LENGTH: 41
<212> TYPE: DNA
<213> ORGANISM: Artificial Sequence
<220> FEATURE:
<223> OTHER INFORMATION: Conjugate Oligo_1 for P24 capture Ab

<400> SEQUENCE: 1
tcgagtctcc acaagaaatc tcgtatgccg tcttctgctt g           41

<210> SEQ ID NO 2
<211> LENGTH: 74
<212> TYPE: DNA
<213> ORGANISM: Artificial Sequence
<220> FEATURE:
<223> OTHER INFORMATION: Conjugate Oligo_2 for P24 capture Ab

<400> SEQUENCE: 2
ccttagcact gaacttatct agacacaagc agaagacggc atacgagata aaaaaaaaa    60 aaaaaaaaaa aaaa                                                    74

<210> SEQ ID NO 3
<211> LENGTH: 75
<212> TYPE: DNA
<213> ORGANISM: Artificial Sequence
<220> FEATURE:
<223> OTHER INFORMATION: Conjugate Oligo_1 for P24 detection Ab

<400> SEQUENCE: 3
aatgatacgg cgaccaccga gatctacact ctttccctac acgacgctct tccgatcttc    60
cacaagaatc tgcac                                                    75
```

<210> SEQ ID NO 4
<211> LENGTH: 33
<212> TYPE: DNA
<213> ORGANISM: Artificial Sequence
<220> FEATURE:
<223> OTHER INFORMATION: Conjugate Oligo_2 for P24 detection Ab

<400> SEQUENCE: 4
agatcggaag agcgtcgtgt agggaaagag tgt        33

<210> SEQ ID NO 5
<211> LENGTH: 41
<212> TYPE: DNA
<213> ORGANISM: Artificial Sequence
<220> FEATURE:
<223> OTHER INFORMATION: Conjugate Oligo_1 for IL-4 capture Ab

<400> SEQUENCE: 5
tcgagtctca cctcaggatc tcgtatgccg tcttctgctt g        41

<210> SEQ ID NO 6
<211> LENGTH: 74
<212> TYPE: DNA
<213> ORGANISM: Artificial Sequence
<220> FEATURE:
<223> OTHER INFORMATION: Conjugate Oligo_2 for IL-4 capture Ab

<400> SEQUENCE: 6
ccttagcact gaacttatct agacacaagc agaagacggc atacgagata aaaaaaaaa        60 aaaaaaaaaa aaaa        74

<210> SEQ ID NO 7
<211> LENGTH: 75
<212> TYPE: DNA
<213> ORGANISM: Artificial Sequence
<220> FEATURE:
<223> OTHER INFORMATION: Conjugate Oligo_1 for IL-4 detection Ab

<400> SEQUENCE: 7
aatgatacgg cgaccaccga gatctacact ctttccctac acgacgctct tccgatcttc        60
acctcaggtc tgcac        75

<210> SEQ ID NO 8
<211> LENGTH: 33
<212> TYPE: DNA
<213> ORGANISM: Artificial Sequence
<220> FEATURE:
<223> OTHER INFORMATION: Conjugate Oligo_2 for IL-4 detection Ab

<400> SEQUENCE: 8
agatcggaag agcgtcgtgt agggaaagag tgt        33

<210> SEQ ID NO 9
<211> LENGTH: 41
<212> TYPE: DNA
<213> ORGANISM: Artificial Sequence
<220> FEATURE:
<223> OTHER INFORMATION: Conjugate Oligo_1 for IL-6 capture Ab

<400> SEQUENCE: 9
tcgagtccag ttaatccatc tcgtatgccg tcttctgctt g        41

<210> SEQ ID NO 10
<211> LENGTH: 74
<212> TYPE: DNA

```
<213> ORGANISM: Artificial Sequence
<220> FEATURE:
<223> OTHER INFORMATION: Conjugate Oligo_2 for IL-6 capture Ab

<400> SEQUENCE: 10
ccttagcact gaacttatct agacacaagc agaagacggc atacgagata aaaaaaaaaa      60
aaaaaaaaaa aaaa                                                        74

<210> SEQ ID NO 11
<211> LENGTH: 75
<212> TYPE: DNA
<213> ORGANISM: Artificial Sequence
<220> FEATURE:
<223> OTHER INFORMATION: Conjugate Oligo_1 for IL-6 detection Ab

<400> SEQUENCE: 11
aatgatacgg cgaccaccga gatctacact ctttccctac acgacgctct tccgatctca      60
gttaatcctc tgcac                                                       75

<210> SEQ ID NO 12
<211> LENGTH: 33
<212> TYPE: DNA
<213> ORGANISM: Artificial Sequence
<220> FEATURE:
<223> OTHER INFORMATION: Conjugate Oligo_2 for IL-6 detection Ab

<400> SEQUENCE: 12
agatcggaag agcgtcgtgt agggaaagag tgt                                   33

<210> SEQ ID NO 13
<211> LENGTH: 41
<212> TYPE: DNA
<213> ORGANISM: Artificial Sequence
<220> FEATURE:
<223> OTHER INFORMATION: Conjugate Oligo_1 for IL-10 capture Ab

<400> SEQUENCE: 13
tcgagtcgaa cagctcaatc tcgtatgccg tcttctgctt g                          41

<210> SEQ ID NO 14
<211> LENGTH: 74
<212> TYPE: DNA
<213> ORGANISM: Artificial Sequence
<220> FEATURE:
<223> OTHER INFORMATION: Conjugate Oligo_2 for IL-10 capture Ab

<400> SEQUENCE: 14
ccttagcact gaacttatct agacacaagc agaagacggc atacgagata aaaaaaaaaa      60
aaaaaaaaaa aaaa                                                        74

<210> SEQ ID NO 15
<211> LENGTH: 75
<212> TYPE: DNA
<213> ORGANISM: Artificial Sequence
<220> FEATURE:
<223> OTHER INFORMATION: Conjugate Oligo_1 for IL-10 detection Ab

<400> SEQUENCE: 15
aatgatacgg cgaccaccga gatctacact ctttccctac acgacgctct tccgatctga      60
acagctcatc tgcac                                                       75

<210> SEQ ID NO 16
<211> LENGTH: 33
```

-continued

```
<212> TYPE: DNA
<213> ORGANISM: Artificial Sequence
<220> FEATURE:
<223> OTHER INFORMATION: Conjugate Oligo_2 for IL-10 detection Ab

<400> SEQUENCE: 16
agatcggaag agcgtcgtgt agggaaagag tgt                          33

<210> SEQ ID NO 17
<211> LENGTH: 41
<212> TYPE: DNA
<213> ORGANISM: Artificial Sequence
<220> FEATURE:
<223> OTHER INFORMATION: Conjugate Oligo_1 for TNF-alpha capture Ab

<400> SEQUENCE: 17
tcgagtccgc tataatgatc tcgtatgccg tcttctgctt g                 41

<210> SEQ ID NO 18
<211> LENGTH: 74
<212> TYPE: DNA
<213> ORGANISM: Artificial Sequence
<220> FEATURE:
<223> OTHER INFORMATION: Conjugate Oligo_2 for TNF-alpha capture Ab

<400> SEQUENCE: 18
ccttagcact gaacttatct agacacaagc agaagacggc atacgagata aaaaaaaaa   60 aaaaaaaaaa aaaa                                               74

<210> SEQ ID NO 19
<211> LENGTH: 75
<212> TYPE: DNA
<213> ORGANISM: Artificial Sequence
<220> FEATURE:
<223> OTHER INFORMATION: Conjugate Oligo_1 for TNF-alpha detection Ab

<400> SEQUENCE: 19
aatgatacgg cgaccaccga gatctacact ctttccctac acgacgctct tccgatctcg   60
ctataatgtc tgcac                                              75

<210> SEQ ID NO 20
<211> LENGTH: 33
<212> TYPE: DNA
<213> ORGANISM: Artificial Sequence
<220> FEATURE:
<223> OTHER INFORMATION: Conjugate Oligo_2 for TNF-alpha detection Ab

<400> SEQUENCE: 20
agatcggaag agcgtcgtgt agggaaagag tgt                          33

<210> SEQ ID NO 21
<211> LENGTH: 10
<212> TYPE: DNA
<213> ORGANISM: Artificial Sequence
<220> FEATURE:
<223> OTHER INFORMATION: Sample Barcode 1 for 1pM

<400> SEQUENCE: 21
cacctgtagt                                                    10

<210> SEQ ID NO 22
<211> LENGTH: 10
<212> TYPE: DNA
<213> ORGANISM: Artificial Sequence
<220> FEATURE:
```

```
<223> OTHER INFORMATION: Sample Barcode 2 for 1pM

<400> SEQUENCE: 22
cttcggcgaa                                                                  10

<210> SEQ ID NO 23
<211> LENGTH: 10
<212> TYPE: DNA
<213> ORGANISM: Artificial Sequence
<220> FEATURE:
<223> OTHER INFORMATION: Sample Barcode 3 for 1pM

<400> SEQUENCE: 23
acaacgacaa                                                                  10

<210> SEQ ID NO 24
<211> LENGTH: 10
<212> TYPE: DNA
<213> ORGANISM: Artificial Sequence
<220> FEATURE:
<223> OTHER INFORMATION: Sample Barcode 4 for 1pM

<400> SEQUENCE: 24
aagccaccaa                                                                  10

<210> SEQ ID NO 25
<211> LENGTH: 10
<212> TYPE: DNA
<213> ORGANISM: Artificial Sequence
<220> FEATURE:
<223> OTHER INFORMATION: Sample Barcode 1 for 100 fM

<400> SEQUENCE: 25
tgtcgcggaa                                                                  10

<210> SEQ ID NO 26
<211> LENGTH: 10
<212> TYPE: DNA
<213> ORGANISM: Artificial Sequence
<220> FEATURE:
<223> OTHER INFORMATION: Sample Barcode 2 for 100 fM

<400> SEQUENCE: 26
gtcaggtgaa                                                                  10

<210> SEQ ID NO 27
<211> LENGTH: 10
<212> TYPE: DNA
<213> ORGANISM: Artificial Sequence
<220> FEATURE:
<223> OTHER INFORMATION: Sample Barcode 3 for 100 fM

<400> SEQUENCE: 27
gataaggcaa                                                                  10

<210> SEQ ID NO 28
<211> LENGTH: 10
<212> TYPE: DNA
<213> ORGANISM: Artificial Sequence
<220> FEATURE:
<223> OTHER INFORMATION: Sample Barcode 4 for 100 fM

<400> SEQUENCE: 28
cacgactcaa                                                                  10
```

-continued

```
<210> SEQ ID NO 29
<211> LENGTH: 10
<212> TYPE: DNA
<213> ORGANISM: Artificial Sequence
<220> FEATURE:
<223> OTHER INFORMATION: Sample Barcode 1 for 10 fM

<400> SEQUENCE: 29
agatgtagga                                                          10

<210> SEQ ID NO 30
<211> LENGTH: 10
<212> TYPE: DNA
<213> ORGANISM: Artificial Sequence
<220> FEATURE:
<223> OTHER INFORMATION: Sample Barcode 2 for 10 fM

<400> SEQUENCE: 30
gtgagattga                                                          10

<210> SEQ ID NO 31
<211> LENGTH: 10
<212> TYPE: DNA
<213> ORGANISM: Artificial Sequence
<220> FEATURE:
<223> OTHER INFORMATION: Sample Barcode 3 for 10 fM

<400> SEQUENCE: 31
tatccatcca                                                          10

<210> SEQ ID NO 32
<211> LENGTH: 10
<212> TYPE: DNA
<213> ORGANISM: Artificial Sequence
<220> FEATURE:
<223> OTHER INFORMATION: Sample Barcode 4 for 10 fM

<400> SEQUENCE: 32
acgagtcgta                                                          10

<210> SEQ ID NO 33
<211> LENGTH: 10
<212> TYPE: DNA
<213> ORGANISM: Artificial Sequence
<220> FEATURE:
<223> OTHER INFORMATION: Sample Barcode 1 for 2.5 fM

<400> SEQUENCE: 33
ttccttacga                                                          10

<210> SEQ ID NO 34
<211> LENGTH: 10
<212> TYPE: DNA
<213> ORGANISM: Artificial Sequence
<220> FEATURE:
<223> OTHER INFORMATION: Sample Barcode 2 for 2.5 fM

<400> SEQUENCE: 34
agctgttaca                                                          10

<210> SEQ ID NO 35
<211> LENGTH: 10
<212> TYPE: DNA
<213> ORGANISM: Artificial Sequence
<220> FEATURE:
<223> OTHER INFORMATION: Sample Barcode 3 for 2.5 fM
```

```
<400> SEQUENCE: 35
ccaaccgtca                                                              10

<210> SEQ ID NO 36
<211> LENGTH: 10
<212> TYPE: DNA
<213> ORGANISM: Artificial Sequence
<220> FEATURE:
<223> OTHER INFORMATION: Sample Barcode 4 for 2.5 fM

<400> SEQUENCE: 36
cctcaatcta                                                              10

<210> SEQ ID NO 37
<211> LENGTH: 10
<212> TYPE: DNA
<213> ORGANISM: Artificial Sequence
<220> FEATURE:
<223> OTHER INFORMATION: Sample Barcode 1 for 625 aM

<400> SEQUENCE: 37
cctcagatga                                                              10

<210> SEQ ID NO 38
<211> LENGTH: 10
<212> TYPE: DNA
<213> ORGANISM: Artificial Sequence
<220> FEATURE:
<223> OTHER INFORMATION: Sample Barcode 2 for 625 aM

<400> SEQUENCE: 38
ggtagctgca                                                              10

<210> SEQ ID NO 39
<211> LENGTH: 10
<212> TYPE: DNA
<213> ORGANISM: Artificial Sequence
<220> FEATURE:
<223> OTHER INFORMATION: Sample Barcode 3 for 625 aM

<400> SEQUENCE: 39
cagtcctata                                                              10

<210> SEQ ID NO 40
<211> LENGTH: 10
<212> TYPE: DNA
<213> ORGANISM: Artificial Sequence
<220> FEATURE:
<223> OTHER INFORMATION: Sample Barcode 4 for 625 aM

<400> SEQUENCE: 40
ggcgatctta                                                              10

<210> SEQ ID NO 41
<211> LENGTH: 10
<212> TYPE: DNA
<213> ORGANISM: Artificial Sequence
<220> FEATURE:
<223> OTHER INFORMATION: Sample Barcode 1 for 156 aM

<400> SEQUENCE: 41
tccgtgatag                                                              10

<210> SEQ ID NO 42
<211> LENGTH: 10
```

```
<212> TYPE: DNA
<213> ORGANISM: Artificial Sequence
<220> FEATURE:
<223> OTHER INFORMATION: Sample Barcode 2 for 156 aM

<400> SEQUENCE: 42
tagaacatgg                                                          10

<210> SEQ ID NO 43
<211> LENGTH: 10
<212> TYPE: DNA
<213> ORGANISM: Artificial Sequence
<220> FEATURE:
<223> OTHER INFORMATION: Sample Barcode 3 for 156 aM

<400> SEQUENCE: 43
tggcagatcg                                                          10

<210> SEQ ID NO 44
<211> LENGTH: 10
<212> TYPE: DNA
<213> ORGANISM: Artificial Sequence
<220> FEATURE:
<223> OTHER INFORMATION: Sample Barcode 4 for 156 aM

<400> SEQUENCE: 44
tcggctgttg                                                          10

<210> SEQ ID NO 45
<211> LENGTH: 10
<212> TYPE: DNA
<213> ORGANISM: Artificial Sequence
<220> FEATURE:
<223> OTHER INFORMATION: Sample Barcode 1 for 39 aM

<400> SEQUENCE: 45
ggcataacgg                                                          10

<210> SEQ ID NO 46
<211> LENGTH: 10
<212> TYPE: DNA
<213> ORGANISM: Artificial Sequence
<220> FEATURE:
<223> OTHER INFORMATION: Sample Barcode 2 for 39 aM

<400> SEQUENCE: 46
gttgacctgg                                                          10

<210> SEQ ID NO 47
<211> LENGTH: 10
<212> TYPE: DNA
<213> ORGANISM: Artificial Sequence
<220> FEATURE:
<223> OTHER INFORMATION: Sample Barcode 3 for 39 aM

<400> SEQUENCE: 47
gtggtcgatg                                                          10

<210> SEQ ID NO 48
<211> LENGTH: 10
<212> TYPE: DNA
<213> ORGANISM: Artificial Sequence
<220> FEATURE:
<223> OTHER INFORMATION: Sample Barcode 4 for 39 aM

<400> SEQUENCE: 48
```
ccatataggc          10

<210> SEQ ID NO 49
<211> LENGTH: 10
<212> TYPE: DNA
<213> ORGANISM: Artificial Sequence
<220> FEATURE:
<223> OTHER INFORMATION: Sample Barcode 1 for 0 aM

<400> SEQUENCE: 49
atacatccgg          10

<210> SEQ ID NO 50
<211> LENGTH: 10
<212> TYPE: DNA
<213> ORGANISM: Artificial Sequence
<220> FEATURE:
<223> OTHER INFORMATION: Sample Barcode 2 for 0 aM

<400> SEQUENCE: 50
agagttggcg          10

<210> SEQ ID NO 51
<211> LENGTH: 10
<212> TYPE: DNA
<213> ORGANISM: Artificial Sequence
<220> FEATURE:
<223> OTHER INFORMATION: Sample Barcode 3 for 0 aM

<400> SEQUENCE: 51
acagaggctg          10

<210> SEQ ID NO 52
<211> LENGTH: 10
<212> TYPE: DNA
<213> ORGANISM: Artificial Sequence
<220> FEATURE:
<223> OTHER INFORMATION: Sample Barcode 4 for 0 aM

<400> SEQUENCE: 52
ttagttcacc          10

<210> SEQ ID NO 53
<211> LENGTH: 44
<212> TYPE: DNA
<213> ORGANISM: Artificial Sequence
<220> FEATURE:
<223> OTHER INFORMATION: oligonucleotides CP of EGFR binder 1

<400> SEQUENCE: 53
aatgatacgg cgaccaccga aaaaaaaaaa aaaaaaaaaa aaaa          44

<210> SEQ ID NO 54
<211> LENGTH: 30
<212> TYPE: DNA
<213> ORGANISM: Artificial Sequence
<220> FEATURE:
<223> OTHER INFORMATION: oligonucleotides R of EGFR binder 1

<400> SEQUENCE: 54
tcgagtctta tcggtggtcg ccgtatcatt          30

<210> SEQ ID NO 55
<211> LENGTH: 69
<212> TYPE: DNA
<213> ORGANISM: Artificial Sequence

```
<220> FEATURE:
<223> OTHER INFORMATION: oligonucleotides L of EGFR binder 2

<400> SEQUENCE: 55
caagcagaag acggcatacg aacactcttt ccctacacga cgctcttccg atcttatatt    60
aatctgcac                                                            69

<210> SEQ ID NO 56
<211> LENGTH: 34
<212> TYPE: DNA
<213> ORGANISM: Artificial Sequence
<220> FEATURE:
<223> OTHER INFORMATION: oligonucleotides CP2 of EGFR binder 2

<400> SEQUENCE: 56
gagcgtcgtg tagggaaaga gtgttcgtat gccg                                34

<210> SEQ ID NO 57
<211> LENGTH: 20
<212> TYPE: DNA
<213> ORGANISM: Artificial Sequence
<220> FEATURE:
<223> OTHER INFORMATION: Connector (CNT) used in detection of EGFR

<400> SEQUENCE: 57
tttgactcga gtgcagaatt                                                20

<210> SEQ ID NO 58
<211> LENGTH: 20
<212> TYPE: DNA
<213> ORGANISM: Artificial Sequence
<220> FEATURE:
<223> OTHER INFORMATION: primer P5 used in qPCR detection of EGFR

<400> SEQUENCE: 58
aatgatacgg cgaccaccga                                                20

<210> SEQ ID NO 59
<211> LENGTH: 21
<212> TYPE: DNA
<213> ORGANISM: Artificial Sequence
<220> FEATURE:
<223> OTHER INFORMATION: primer P7 used in qPCR detection of EGFR

<400> SEQUENCE: 59
caagcagaag acggcatacg a                                              21

<210> SEQ ID NO 60
<211> LENGTH: 25
<212> TYPE: DNA
<213> ORGANISM: Artificial Sequence
<220> FEATURE:
<223> OTHER INFORMATION: primer SBS3 used in qPCR detection of EGFR

<400> SEQUENCE: 60
cactctttcc ctacacgacg ctctt                                          25
```

NUCLEIC ACID LINKED IMMUNE-SANDWICH ASSAY (NULISA)

CROSS REFERENCE TO RELATED APPLICATIONS

This application is a continuation of International Patent Application No. PCT/US2020/062791, filed Dec. 2, 2020, which claims the benefit of priority to U.S. Provisional Patent Application No. 62/943,135, filed Dec. 3, 2019, the disclosure of each of which is herein incorporated by reference in its entirety.

SEQUENCE LISTING

The present specification is being filed with a computer readable form (CRF) copy of the Sequence Listing. The CRF entitled 14582-003-999_SEQ_LISTING.txt, which was created on Dec. 1, 2020, is 13,463 bytes in size, and is incorporated herein by reference in its entirety.

1. FIELD

The present invention relates to the field of molecular biology. Specifically, the present disclosures relate to highly sensitive immunoassays for detection of target biological molecules or molecular complexes.

2. BACKGROUND

Detecting minute amount of target molecules or molecular complexes in biological samples is critically important for both scientific researches and clinical studies. With the invention and advancement of polymerase chain reaction (PCR), tremendous progresses have been made in recent decades in nucleic acid detection and analysis. However, the modest performance of current immunoassays for detection of other biological molecules, such as proteins, is still a technical bottleneck for many important applications. For example, it is estimated that early cancer detection requires effective detection of analytes at 4,000 molecules/mL or ~7 attomolar ("aM"), which is beyond the capacities of existing immunoassay technologies. Therefore, there is a great need to improve immunoassay performance. The present disclosures provide highly sensitive immunoassays that address these needs and provide related advantages.

3. SUMMARY OF INVENTION

Embodiment 1. An assay method for detecting an analyte in a sample, comprising:
(1) mixing a first binding moiety comprising a first binder and a first presenting group, a second binding moiety comprising a second binder, and the sample in a solution, wherein:
  (i) the first and second binders bind to the analyte and form an immunocomplex,
  (ii) the immunocomplex is captured on a first solid surface in contact with the solution via binding between the first presenting group and a first receiving group coupled to the first solid surface, and
  (iii) the first binding moiety further comprises a first target label and the second binding moiety further comprises a second target label;
(2) washing the first solid surface to remove unbound molecules;
(3) generating a reporter from the immunocomplex based on proximity between the first target label and the second target label; and
(4) detecting the reporter, thereby detecting the analyte.

Embodiment 2. The assay method of embodiment 1, wherein (i) the first target label comprises a first identity barcode ("ID") that is analyte-specific ("target ID"); (ii) the second target label comprises a second target ID; or (iii) both (i) and (ii).

Embodiment 3. The assay method of embodiment 1 or 2, wherein (i) the reporter comprises the first target ID; (ii) the reporter comprises the second target ID; or (iii) both (i) and (ii).

Embodiment 4. An assay method for detecting an analyte in a sample, comprising:
(1) mixing a first binding moiety comprising a first binder and a first presenting group, a second binding moiety comprising a second binder, and the sample in a solution, wherein:
  (i) the first and second binders bind to the analyte and form an immunocomplex,
  (ii) the immunocomplex is captured on a first solid surface in contact with the solution via binding between the first presenting group and a first receiving group coupled to the first solid surface, and
  (iii) the first binding moiety further comprises a first target label comprising a first identity barcode ("ID") that is analyte-specific ("target ID") and the second binding moiety further comprises a second target label comprising a second target ID;
(2) washing the first solid surface to remove unbound molecules;
(3) generating a reporter from the immunocomplex, wherein the reporter comprises (i) the first target ID, (ii) the second target ID, or (iii) both the first and the second target ID; and
(4) detecting the reporter, thereby detecting the analyte.

Embodiment 5. The assay method of embodiment 4, wherein the reporter is generated from the immunocomplex based on proximity between the first target label and the second target label.

Embodiment 6. The assay method of any one of embodiments 1 to 5, wherein the reporter is a nucleic acid reporter.

Embodiment 7. The assay method of embodiment 6, wherein:
  (i) the first target ID in the reporter is a complementary sequence of the first target ID in the first binding moiety;
  (ii) the second target ID in the reporter is a complementary sequence of the second target ID in the first binding moiety;
  (iii) both (i) and (ii).

Embodiment 8. The assay method of any one of embodiments 1 to 7, further comprising a step (2a) between step (2) and (3): releasing the immunocomplex from the first solid surface by disrupting the binding between the first presenting group and the first receiving group, wherein step (2a) is before, after or simultaneous of step (3).

Embodiment 9. The assay method of embodiment 8, wherein the second binding moiety further comprises a second presenting group.

Embodiment 10. The assay method of embodiment 9, wherein the method further comprises a step 2(b) between step 2(a) and step (3):
(2b) introducing a second solid surface and recapturing the immunocomplex on the second solid surface via binding between the second presenting group and the second receiving group coupled to the second solid surface.

Embodiment 11. The assay method of embodiment 10, wherein the method further comprises a step 2(c) between step 2(b) and step (3)

(2c) washing the second solid surface to remove unbound molecules.

Embodiment 12. The assay method of embodiment 10 or 11, further comprising a step (2d): releasing the immunocomplex from the second solid surface by disrupting the binding between the second presenting group and the second receiving group.

Embodiment 13. The assay method of embodiment 12, wherein step (2d) is before, after or simultaneous of step (3).

Embodiment 14. The assay method of any one of embodiments 2 to 13, wherein (i) the first target ID and the second target ID are identical; or (ii) the first target ID and the second target ID are different.

Embodiment 15. The assay method of any one of the preceding embodiments, further comprising a step (2e): binding a sample label comprising an ID that is sample-specific ("sample ID") (i) to the first target label, (ii) to the second target label, or (iii) to both the first target label and the second target label.

Embodiment 16. The assay method of embodiment 15, wherein the reporter formed in each sample comprises a sample ID.

Embodiment 17. The assay method of any one of the preceding embodiments, wherein the first presenting group is a polypeptide fused to the first binder, a polynucleotide conjugated to the first binder, or a chemical compound conjugated to the first binder.

Embodiment 18. The assay method of any one of embodiments 9 to 17, wherein the second presenting group is a polypeptide fused to the second binder, a polynucleotide conjugated to the second binder, or a chemical compound conjugated to the second binder.

Embodiment 19. The assay method of any one of the preceding embodiments, wherein the method further comprises releasing the reporter from the immunocomplex.

Embodiment 20. The assay method of any one of embodiments 6 to 19, wherein step (4) further comprises PCR amplification of the nucleic acid reporter.

Embodiment 21. The assay method of any one of embodiments 6 to 20, wherein the method further comprises purifying the nucleic acid reporter.

Embodiment 22. The assay method of any one of the preceding embodiments, wherein step (1) comprises forming the immunocomplex in the solution before capturing the immunocomplex on the first solid surface.

Embodiment 23. The assay method of any one of embodiments 1 to 21, wherein step (1) comprises pre-capturing the first binder on the first solid surface before forming the immunocomplex on the first solid surface.

Embodiment 24. The assay method of any one of embodiments 1 to 21, wherein the immunocomplex is formed in the solution and captured on the first solid surface simultaneously in step (1).

Embodiment 25. The assay method of any one of the preceding embodiments, wherein:
(i) the first binder binds to the analyte directly and the second binder binds to the analyte directly;
(ii) the first binder binds to the analyte directly and the second binder binds to the analyte indirectly;
(iii) the first binder binds to the analyte indirectly and the second binder binds to the analyte directly; or
(iv) the first binder binds to the analyte indirectly and the second binder binds to the analyte indirectly.

Embodiment 26. The assay method of any one of the preceding embodiments, wherein:
(i) the first binder binds to a first primary antibody or a fragment thereof that binds directly to the analyte;
(ii) the second binder binds to a second primary antibody or a fragment thereof that binds directly to the analyte; or
(iii) both (i) and (ii).

Embodiment 27. The assay method of any one of embodiments 1 to 25, wherein:
(i) the first and second binders bind to non-interfering epitopes on the analyte;
(ii) the first and second binders bind to non-overlapping epitopes on the analyte; or
(iii) the first and second binders bind to different epitopes on the analyte.

Embodiment 28. The assay method of any one of the preceding embodiments, further comprising:
(i) at least one additional cycle of recapture between steps (2) and (3), comprising: releasing the immunocomplex from the solid surface that it is captured on, recapturing the immunocomplex on an additional solid surface coupled with the first receiving group, and washing the additional solid surface to remove unbound molecules;
(ii) at least one additional cycle of recapture between steps (2c) and (2d), comprising: releasing the immunocomplex from the solid surface that it is captured on, recapturing the immunocomplex on an additional solid surface coupled with the first or the second receiving group, and washing the additional solid surface to remove unbound molecules; or
(iii) both (i) and (ii).

Embodiment 29. The assay method of any one of embodiments 8 to 28, wherein any of the releasing is by increasing temperature to 70° C.

Embodiment 30. The assay method of any one of preceding embodiments, wherein (i) the first presenting group binds the first receiving group via a thioester group, a disulfide linkage, or a cleavable linkage; (ii) the second presenting group binds the second receiving group via a thioester group, a disulfide linkage, or a cleavable linkage; or both (i) and (ii).

Embodiment 31. The assay method of embodiment 30, wherein (i) the first presenting group binds the first receiving group via a photocleavable linkage, a chemically cleavable linkage, or an enzymatically cleavable linkage; (ii) the second presenting group binds the second receiving group via a photocleavable linkage, a chemically cleavable linkage, or an enzymatically cleavable linkage; or both (i) and (ii).

Embodiment 32. The assay method of any one of embodiments 1 to 29, wherein (i) the first presenting group binds the first receiving group via a protein-protein interaction; (ii) the second presenting group binds the second receiving group via a protein-protein interaction; or both (i) and (ii).

Embodiment 33. The assay method of any one of embodiments 1 to 29, wherein (i) the first presenting group binds the first receiving group via biotin to streptavidin or avidin; (ii) the second presenting group binds the second receiving group via biotin to streptavidin or avidin; or both (i) and (ii).

Embodiment 34. The assay method of any one of embodiments 1 to 29, wherein
(i) the first presenting group is a first nucleic acid tag (the "first tag") and the first receiving group is a first nucleic acid capture probe (the "first probe"); or (ii) the second presenting group is a second nucleic acid tag (the "second tag") and the second receiving group is a second nucleic acid capture probe (the "second probe").

Embodiment 35. The assay method of any one of embodiments 9 to 29, wherein (i) the first presenting group is a first nucleic acid tag (the "first tag") and the first receiving group is a first nucleic acid capture probe (the "first probe"); and (ii) the second presenting group is a second nucleic acid tag (the "second tag") and the second receiving group is a second nucleic acid capture probe (the "second probe").

Embodiment 36. The assay method of embodiment 34 or 35, wherein:
(i) the first probe is a protein that specifically binds to the first tag;
(ii) the first probe is a protein and nucleic acid complex that specifically binds to the first tag;
(iii) the first probe is a nucleic acid molecule, wherein the first probe or a fragment thereof is complementary to the first tag or a fragment thereof; or
(iv) the first probe is a nucleic acid molecule, wherein the first probe or a fragment thereof hybridizes with the first tag or a fragment thereof.

Embodiment 37. The assay method of any one of embodiments 34 to 36, wherein:
(i) the second probe is a protein that specifically binds to the second tag;
(ii) the second probe is a protein and nucleic acid complex that specifically binds to the second tag;
(iii) the second probe is a nucleic acid molecule, wherein the second probe or a fragment thereof is complementary to the second tag or a fragment thereof; or
(iv) the second probe is a nucleic acid molecule, wherein the second probe or a fragment thereof hybridizes with the second tag or a fragment thereof.

Embodiment 38. The assay method of embodiment 36 or 37, wherein the complementarity is at least 80%, at least 81%, at least 82%, at least 83%, at least 84%, at least 85%, at least 86%, at least 87%, at least 88%, at least 89%, at least 90, at least 91%, at least 92%, at least 93%, at least 94%, at least 95%, at least 96%, at least 97%, at least 98%, or at least 99% complementation.

Embodiment 39. The assay method of any one of embodiments 34 to 38, wherein (i) the first probe is directly coupled to the first solid surface; or (ii) the second probe is directly coupled to the second solid surface.

Embodiment 40. The assay method of any one of embodiments 34 to 38, wherein (i) the first probe is directly coupled to the first solid surface; and (ii) the second probe is directly coupled to the second solid surface.

Embodiment 41. The assay method of any one of embodiments 34 to 38, wherein (i) the first probe hybridizes with a universal probe that is directly coupled to the first solid surface; or (ii) the second probe hybridizes with a universal probe that is directly coupled to the second solid surface.

Embodiment 42. The assay method of any one of embodiments 34 to 38, wherein (i) the first probe hybridizes with a universal probe that is directly coupled to the first solid surface; and (ii) the second probe hybridizes with a universal probe that is directly coupled to the second solid surface.

Embodiment 43. The assay method of any one of embodiments 34 to 38, wherein (i) the first probe is conjugated with biotin, which binds the streptavidin or avidin that is directly coupled to the first solid surface; or (ii) the second probe is conjugated with biotin, which binds the streptavidin or avidin that is directly coupled to the second solid surface.

Embodiment 44. The assay method of any one of embodiments 34 to 38, wherein
(i) the first probe is conjugated with biotin, which binds the streptavidin or avidin that is directly coupled to the first solid surface; and (ii) the second probe is conjugated with biotin, which binds the streptavidin or avidin that is directly coupled to the second solid surface.

Embodiment 45. The assay method of any one of embodiments 34 to 44, wherein the first tag and second tag are collaboratively captured on the first solid surface in step (1).

Embodiment 46. The assay method of embodiment 45, wherein a first fragment of the first probe is complementary to the first tag or a fragment thereof, and a second fragment of the first probe is complementary to the second tag or a fragment thereof, wherein the complementary region includes the unconjugated ends of the first and the second tags.

Embodiment 47. The assay method of embodiment 45, wherein a continuous fragment of the first probe consists of a first fragment and an immediately adjacent second fragment, wherein the first fragment is complementary to the first tag or a fragment thereof, and the second fragment is complementary to the second tag or a fragment thereof, such that when the first and second tags are linked to form a linked nucleic acid, a joint region of the linked nucleic acid is complementary to the continuous fragment of the first probe.

Embodiment 48. The assay method of embodiment 45, wherein a first fragment of the first probe is complementary to the first tag or a fragment thereof, and wherein a separate second fragment of the first probe is complementary to the second tag or a fragment thereof; and wherein the complementary region does not include the unconjugated ends of the first and the second tags.

Embodiment 49. The assay method of embodiment 45, wherein the first solid surface is coupled with both the first probe and an additional nucleic acid probe, and wherein the additional probe or a fragment thereof is complementary to the first tag or a fragment thereof.

Embodiment 50. The assay method of any one of embodiments 35 to 49, wherein the first tag and second tag are collaboratively captured on the second solid surface in step (2b).

Embodiment 51. The assay method of embodiment 50, wherein a first fragment of the second probe is complementary to the first tag or a fragment thereof, and a second fragment of the second probe is complementary to the second tag or a fragment thereof, wherein the complementary region includes the unconjugated ends of the first and the second tags.

Embodiment 52. The assay method of embodiment 50, wherein a continuous fragment of the second probe consists of a first fragment and an immediately adjacent second fragment, wherein the first fragment is complementary to the first tag or a fragment thereof, and the second fragment is complementary to the second tag or a fragment thereof, such that when the first and second tags are linked to form a linked nucleic acid, a joint region of the linked nucleic acid is complementary to the continuous fragment of the second probe.

Embodiment 53. The assay method of embodiment 50, wherein a first fragment of the second probe is complementary to the first tag or a fragment thereof, and wherein a separate second fragment of the second probe is complementary to the second tag or a fragment thereof; and wherein the complementary region does not include the unconjugated ends of the first and the second tags.

Embodiment 54. The assay method of embodiment 50, wherein the second solid surface is coupled with both the second probe and an additional nucleic acid probe, and wherein the additional probe or a fragment thereof is complementary to the second tag or a fragment thereof.

Embodiment 55. The assay method of any one of embodiments 34 to 54, wherein (i) the complementary fragments of the first tag and the first probe consist of 10 to 30 base pairs; (ii) the complementary fragments of the second tag and the second probe consist of 10 to 30 base pairs; or both (i) and (ii).

Embodiment 56. The assay method of any one of embodiments 34 to 55, wherein (i) the complementary fragments of the first tag and the first probe consist of 20 to 30 base pairs; (ii) the complementary fragments of the second tag and the second probe consist of 20 to 30 base pairs; or both (i) and (ii)

Embodiment 57. The assay method of any one of embodiments 34 to 56, wherein (i) the first tag comprises an A and/or T rich sequence and the first probe comprises a complementary A and/or T rich sequence; (ii) the second tag comprises an A and/or T rich sequence and the second probe comprises a complementary A and/or T rich sequence; or both (i) and (ii).

Embodiment 58. The assay method of embodiment 57, wherein the A and/or T rich sequence has a short length such that the binding from complementary A and/or T rich sequence is weaker than both the binding between first binder and the analyte and the binding between the second binder and the analyte, thereby keeping immunocomplex stable in releasing step (2a) and/or (2d).

Embodiment 59. The assay method of any one of the preceding embodiments, wherein the analyte is a binding pair of two molecules; wherein the first binder binds one molecule of the binding pair, and the second binder binds the other molecule of the binding pair.

Embodiment 60. The assay method of any one of the preceding embodiments, wherein the analyte is a nucleic acid, and the first and second binders for the nucleic acid analyte comprise nucleic acids that are complementary to different fragments of the nucleic acid analyte.

Embodiment 61. The assay method of any one of embodiments 1 or 59, wherein the analyte is a peptide or a protein, and (i) the first binder is an antibody or an antibody fragment that specifically binds the analyte; (ii) the second binder is an antibody or an antibody fragment that specifically binds the analyte; or both (i) and (ii).

Embodiment 62. The assay method of any one of the preceding embodiments, wherein the sample is a serum sample or a plasma sample.

Embodiment 63. The assay method of any one of embodiments 6 to 62, wherein:
  (i) in step (3) the nucleic acid reporter is generated while the immunocomplex is being captured on the first solid surface; or
  (ii) in step (3) the nucleic acid reporter is generated after the immunocomplex is released from the first solid surface.

Embodiment 64. The assay method of any one of embodiments 10 to 62, wherein:
  (i) in step (3) the nucleic acid reporter is generated while the immunocomplex is being captured on the second solid surface; or
  (ii) in step (3) the nucleic acid reporter is generated after the immunocomplex is released from the second solid surface.

Embodiment 65. The assay method of any one of embodiments 1 to 64, wherein: (i) the first target label is directly bound to the first binder; or (ii) the first target label is indirectly bound to the first binder.

Embodiment 66. The assay method of any one of embodiments 1 to 65, wherein: (i) the second target label is directly bound to the second binder; or (ii) the second target label is indirectly bound to the second binder.

Embodiment 67. The assay method of any one of embodiments 1 to 66, wherein:
  (i) the first target label is conjugated to the first binder;
  (ii) the first target label is non-covalently bound to the first binder;
  (iii) the first target label is conjugated to the first presenting group;
  (iv) the first target label is non-covalently bound to the first presenting group; or
  (v) the first target label is part of the first presenting group.

Embodiment 68. The assay method of any one of embodiments 1 to 67, wherein:
  (i) the second target label is conjugated to the second binder;
  (ii) the second target label is non-covalently bound to the second binder;
  (iii) the second target label is conjugated to the second presenting group;
  (iv) the second target label is non-covalently bound to the second presenting group; or
  (v) the second target label is part of the second presenting group.

Embodiment 69. The assay method of any one of embodiments 1 to 68, wherein: (i) the first presenting group is directly bound to the first binder; or (ii) the first presenting group is indirectly bound to the first binder.

Embodiment 70. The assay method of any one of embodiments 9 to 69, wherein: (i) the second presenting group is directly bound to the second binder; or (ii) the second presenting group is indirectly bound to the second binder.

Embodiment 71. The assay method of any one of embodiments 1 to 70, wherein:
  (i) the first presenting group is conjugated to the first binder;
  (ii) the first presenting group is non-covalently bound to the first binder;
  (iii) the first presenting group is conjugated to the first target label;
  (iv) the first presenting group is non-covalently bound to the first target label; or
  (v) the first presenting group is part of the first target label.

Embodiment 72. The assay method of any one of embodiments 9 to 71, wherein:
  (i) the second presenting group is conjugated to the second binder;
  (ii) the second presenting group is non-covalently bound to the second binder;
  (iii) the second presenting group is conjugated to the second target label;
  (iv) the second presenting group is non-covalently bound to the second target label; or
  (v) the second presenting group is part of the second target label.

Embodiment 73. The assay method of any one of embodiments 1 to 72, wherein:
(i) the first target label is a nucleic acid molecule;
(ii) the second target label is a nucleic acid molecule; or
(iii) both (i) and (ii).

Embodiment 74. The assay method of any one of embodiments 34 to 73, wherein:
(i) the first target label hybridizes with the first tag;
(ii) the second target label hybridizes with the second tag; or
(iii) both (i) and (ii).

Embodiment 75. The assay method of any one of embodiments 15 to 74, wherein the sample label is a single-stranded nucleic acid molecule ("single-stranded sample label").

Embodiment 76. The assay method of any one of embodiments 15 to 74, wherein the sample label is a double-stranded nucleic acid molecule ("double-stranded sample label").

Embodiment 77. The assay method of embodiment 76, wherein the sample label is:
(i) a double-stranded nucleic acid molecule comprising two 5' overhangs;
(ii) a double-stranded nucleic acid molecule comprising two 3' overhangs;
(iii) a double-stranded nucleic acid molecule comprising a 5' overhang and a 3' overhang;
(iv) a double-stranded nucleic acid molecule comprising a 5' overhang and a blunt end; or
(v) a double-stranded nucleic acid molecule comprising a 3' overhang and a blunt end.

Embodiment 78. The assay method of embodiment 77, wherein the sample label:
(i) hybridizes with the first target label via an overhang of the sample label;
(ii) hybridizes with the second target label via an overhang of the sample label; or
(iii) both (i) and (ii).

Embodiment 79. The assay method of any one of embodiments 34 to 78, wherein step (3) comprises generating the nucleic acid reporter by linking:
(a) the first tag and the second tag, and detecting the nucleic acid reporter composed of a fragment of the first tag and a fragment of the second tag;
(b) the first tag and a surrogate nucleic acid of the second tag (the "second surrogate"), and detecting the nucleic acid reporter composed of a fragment of the first tag and a fragment of the second surrogate;
(c) a surrogate nucleic acid of the first tag (the "first surrogate") and the second tag, and detecting the nucleic acid reporter composed of a fragment of the first surrogate and a fragment of the second tag; or
(d) the first surrogate and the second surrogate, and detecting the nucleic acid reporter composed of a fragment of the first surrogate and a fragment of the second surrogate; wherein the first tag or a fragment thereof is complementary to the first surrogate or a fragment thereof, and the second tag or a fragment thereof is complementary to the second surrogate or a fragment thereof.

Embodiment 80. The assay method of any one of embodiments 34 to 78, wherein step (3) comprises generating the nucleic acid reporter by linking:
(a) the first tag and the second target label, and detecting the nucleic acid reporter composed of a fragment of the first tag and a fragment of the second target label;
(b) the first tag and a surrogate nucleic acid of the second target label (the "second surrogate"), and detecting the nucleic acid reporter composed of a fragment of the first tag and a fragment of the second surrogate;
(c) a surrogate nucleic acid of the first tag (the "first surrogate") and the second target label, and detecting the nucleic acid reporter composed of a fragment of the first surrogate and a fragment of the second target label; or
(d) the first surrogate and the second surrogate, and detecting the nucleic acid reporter composed of a fragment of the first surrogate and a fragment of the second surrogate;
wherein the first tag or a fragment thereof is complementary to the first surrogate or a fragment thereof, and the second target label or a fragment thereof is complementary to the second surrogate or a fragment thereof.

Embodiment 81. The assay method of any one of embodiments 34 to 78, wherein step (3) comprises generating the nucleic acid reporter by linking:
(a) the first target label and the second tag, and detecting the nucleic acid reporter composed of a fragment of the first target label and a fragment of the second tag;
(b) the first target label and a surrogate nucleic acid of the second tag (the "second surrogate"), and detecting the nucleic acid reporter composed of a fragment of the first target label and a fragment of the second surrogate;
(c) a surrogate nucleic acid of the first target label (the "first surrogate") and the second tag, and detecting the nucleic acid reporter composed of a fragment of the first surrogate and a fragment of the second tag; or
(d) the first surrogate and the second surrogate, and detecting the nucleic acid reporter composed of a fragment of the first surrogate and a fragment of the second surrogate; wherein the first target label or a fragment thereof is complementary to the first surrogate or a fragment thereof, and the second tag or a fragment thereof is complementary to the second surrogate or a fragment thereof.

Embodiment 82. The assay method of any one of embodiments 34 to 78, wherein step (3) comprises generating the nucleic acid reporter by linking:
(a) the first target label and the second target label, and detecting the nucleic acid reporter composed of a fragment of the first target label and a fragment of the second target label;
(b) the first target label and a surrogate nucleic acid of the second target label (the "second surrogate"), and detecting the nucleic acid reporter composed of a fragment of the first target label and a fragment of the second surrogate;
(c) a surrogate nucleic acid of the first target label (the "first surrogate") and the second target label, and detecting the nucleic acid reporter composed of a fragment of the first surrogate and a fragment of the second target label; or
(d) the first surrogate and the second surrogate, and detecting the nucleic acid reporter composed of a fragment of the first surrogate and a fragment of the second surrogate; wherein the first target label or a fragment thereof is complementary to the first surrogate or a fragment thereof, and the second target label or a fragment thereof is complementary to the second surrogate or a fragment thereof.

Embodiment 83. The assay method of any one of embodiments 79 to 82, wherein the linking comprises linking:
(i) (a) the first tag or the first surrogate thereof, (b) the second tag or the second surrogate thereof, and (c) a surrogate nucleic acid of the single-stranded sample label ("sample surrogate") or one strand of the double-stranded sample label;
    (ii) (a) the first tag or the first surrogate thereof, (b) the second target label or the second surrogate thereof, and (c) a surrogate nucleic acid of the single-stranded sample label ("sample surrogate") or one strand of the double-stranded sample label;
    (iii) (a) the first target label or the first surrogate thereof, (b) the second tag or the second surrogate thereof, and (c) a surrogate nucleic acid of the single-stranded sample label ("sample surrogate") or one strand of the double-stranded sample label; or
    (iv) (a) the first target label or the first surrogate thereof, (b) the second target label or the second surrogate thereof, and (c) a surrogate nucleic acid of the single-stranded sample label ("sample surrogate") or one strand of the double-stranded sample label;
wherein the sample label or a fragment thereof is complementary to the sample surrogate or a fragment thereof.

Embodiment 84. The assay method of embodiment 83, wherein the linking in each of (i) to (iv) comprises linking (c) between (a) and (b).

Embodiment 85. The assay method of any one of embodiments 79 to 84, wherein the nucleic acid reporter is formed by proximity ligation.

Embodiment 86. The assay method of any one of embodiments 79 to 84, wherein the nucleic acid reporter is formed by proximity extension.

Embodiment 87. The assay method of any one of any one of embodiments 79 to 86, wherein the nucleic acid reporter comprises (a) the first target ID or a surrogate nucleic acid of the first target ID (the "first target ID surrogate"), (b) the second target ID or a surrogate nucleic acid of the second target ID (the "second target ID surrogate"), and (c) a sample ID.

Embodiment 88. The assay method of any one of embodiments 2 to 87, comprising simultaneously detecting at least two analytes in the sample by simultaneously detecting the unique target IDs associated with each analyte.

Embodiment 89. The assay method of embodiment 88, comprising proportionally reducing the signal from at least one of the analytes, by adding a non-functional binder to the solution in step (1), wherein the non-functional binder competes with the first binder for binding to the analyte but is either unconjugated or conjugated to a presenting group that does not bind the first receiving group.

Embodiment 90. The assay method of any one of embodiments 2 to 89, wherein in step (4), detecting the analyte comprises the co-detection of the first and the second target IDs.

Embodiment 91. The assay method of any one of the preceding embodiments, wherein in step (1) further comprising mixing a reference analyte.

Embodiment 92. The assay method of embodiment 91, wherein the reference analyte is an analyte that is absent in the sample.

Embodiment 93. The assay method of embodiment 91 or 92, wherein the reference analyte is a protein, a nucleic acid, or a chemical compound that is absent in the sample.

Embodiment 94. The assay method of embodiment 93, wherein the reference analyte is a viral protein, a bacterial protein, or an insect protein.

Embodiment 95. The assay method of any one of embodiments 15 to 94, comprising simultaneously detecting the analyte in at least two samples, by simultaneously detecting the unique sample IDs in the nucleic acid reporters associated with each sample.

Embodiment 96. The assay method of embodiment 95, further comprising pooling the nucleic acid reporters from the at least two samples before or simultaneously of the detection in step (4).

Embodiment 97. The assay method of any one of embodiments 15 to 95, comprising simultaneously detecting at least two analytes in at least two samples, by simultaneously detecting the unique sample IDs and unique target IDs in the nucleic acid reporters associated with each analyte in each sample.

Embodiment 98. The assay method of embodiment 97, further comprising pooling the nucleic acid reporters for the at least two analytes from the at least two samples before or simultaneously of the detection in step (4).

Embodiment 99. The assay method of any one of the preceding embodiments, wherein the nucleic acid reporters are detected by multiplexed qPCR, multiplexed digital PCR, or NGS.

Embodiment 100. The assay method of any one of the preceding embodiments, wherein the nucleic acid reporters are detected by NGS.

Embodiment 101. The assay method of any one of embodiments 91 to 100, wherein detecting further comprises normalizing the reporters generated from the analytes of the samples against the reporter generated from the reference analyte.

Embodiment 102. The assay method of any one of the preceding embodiments, wherein (i) the first solid surface is selected from the group consisting of a magnetic particle surface and a well of a microtiter plate; (ii) the second solid surface is selected from the group consisting of a magnetic particle surface and a well of a microtiter plate; or both (i) and (ii).

Embodiment 103. An assay method for detecting an analyte in a sample, comprising:
    (1) mixing a first binding moiety comprising a first binder and a first presenting group, a second binding moiety comprising a second binder and a second presenting group, and the sample in a solution, wherein:
        (i) the first and second binders bind to the analyte and form an immunocomplex,
        (ii) the immunocomplex is captured on a first solid surface in contact with the solution via binding between the first presenting group and a first receiving group coupled to the first solid surface, and
        (iii) the first binding moiety further comprises a first target label comprising a first identity barcode ("ID") that is analyte-specific ("target ID") and the second binding moiety further comprises a second target label comprising a second target ID;
    (2) washing the first solid surface to remove unbound molecules;
    (3) releasing the immunocomplex from the first solid surface by disrupting the binding between the first presenting group and the first receiving group;
    (4) introducing a second solid surface and recapturing the immunocomplex on the second solid surface via binding between the second presenting group and the second receiving group coupled to the second solid surface;
    (5) washing the second solid surface to remove unbound molecules;
    (6) binding a sample label comprising an ID that is sample-specific ("sample ID") (i) to the first target label, (ii) to the second target label, or (iii) to both the first target label and the second target label;
(7) generating a nucleic acid reporter from the immunocomplex based on proximity between the first target label and the second target label, wherein the nucleic acid reporter comprises the first target ID, the second target ID, and the sample ID;
(8) releasing the immunocomplex from the second solid surface by disrupting the binding between the second presenting group and the second receiving group; and
(9) detecting the nucleic acid reporter by qPCR, thereby detecting the analyte.

Embodiment 104. An assay method for detecting an analyte in at least two samples, comprising:
(1) mixing a first binding moiety comprising a first binder and a first presenting group, a second binding moiety comprising a second binder and a second presenting group, and the samples in a solution, wherein:
  (i) the first and second binders bind to the analyte and form an immunocomplex,
  (ii) the immunocomplex is captured on a first solid surface in contact with the solution via binding between the first presenting group and a first receiving group coupled to the first solid surface, and
  (iii) the first binding moiety further comprises a first target label comprising a first identity barcode ("ID") that is analyte-specific ("target ID") and the second binding moiety further comprises a second target label comprising a second target ID;
(2) washing the first solid surface to remove unbound molecules;
(3) releasing the immunocomplex from the first solid surface by disrupting the binding between the first presenting group and the first receiving group;
(4) introducing a second solid surface and recapturing the immunocomplex on the second solid surface via binding between the second presenting group and the second receiving group coupled to the second solid surface;
(5) washing the second solid surface to remove unbound molecules;
(6) binding a sample label comprising an ID that is sample-specific ("sample ID") (i) to the first target label, (ii) to the second target label, or (iii) to both the first target label and the second target label;
(7) generating a nucleic acid reporter from the immunocomplex based on proximity between the first target label and the second target label, wherein the nucleic acid reporter comprises the first target ID, the second target ID, and the sample ID;
(8) pooling the nucleic acid reporters from the at least two samples;
(9) releasing the immunocomplex from the second solid surface by disrupting the binding between the second presenting group and the second receiving group;
(9) amplifying the nucleic acid reporters;
(10) purifying the nucleic acid reporters; and
(11) detecting the nucleic acid reporters by next generation sequencing (NGS), thereby detecting the analyte.

Embodiment 105. A system for detecting an analyte in a sample comprising
(i) a first binding moiety comprising a first binder, a first presenting group, and a first target label;
(ii) a second binding moiety comprising a second binder and a second target label; and
(iii) a first receiving group;
and wherein
(i) the first and second binders bind epitopes on the analyte; and
(ii) the first presenting group binds the first receiving groups.

Embodiment 106. The system of embodiment 105, wherein (i) the first target label comprises a first identity barcode ("ID") that is analyte-specific ("target ID"); (ii) the second target label comprises a second target ID; or (iii) both (i) and (ii).

Embodiment 107. A system for detecting an analyte in a sample comprising
(i) a first binding moiety comprising a first binder, a first presenting group, and a first target label comprising a first identity barcode ("ID") that is analyte-specific ("target ID");
(ii) a second binding moiety comprising a second binder and a second target label comprising a second target ID; and
(iii) a first receiving group;
and wherein
(i) the first and second binders bind epitopes on the analyte; and
(ii) the first presenting group binds the first receiving groups.

Embodiment 108. The system of any one of embodiments 105 to 107, wherein the reporter is a nucleic acid reporter.

Embodiment 109. The system of any one of embodiments 105 to 108, wherein the second binding moiety further comprises a second presenting group, wherein the system further comprises a second receiving group, and wherein the second presenting group binds the second receiving groups.

Embodiment 110. The system of any one of embodiments 106 to 109, wherein (i) the first target ID and the second target ID are identical; or (ii) the first target ID and the second target ID are different.

Embodiment 111. The system of any one of embodiments 105 to 110, further comprising a sample label comprising an ID that is sample-specific ("sample ID"), where in the sample label binds (i) to the first target label, (ii) to the second target label, or (iii) to both the first target label and the second target label.

Embodiment 112. The system of any one of embodiments 106 to 111, further comprising reagents for proximity ligation or proximity extension to generate a nucleic acid reporter comprising (i) the first target ID and the second target ID, or (ii) the first target ID, the second target ID, and the sample ID.

Embodiment 113. The system of any one of embodiments 105 to 112, further comprising a first solid surface.

Embodiment 114. The system of any one of embodiments 109 to 113, further comprising a second solid surface.

Embodiment 115. The system of embodiment 113 or 114, wherein (i) the first solid surface is a magnetic particle surface or a well of a microtiter plate; (ii) the second solid surface is a magnetic particle surface or a well of a microtiter plate; or both (i) and (ii).

Embodiment 116. The system of embodiment 114 or 115, wherein the first solid surface is coupled with the first receiving group and the second solid surface is coupled with the second receiving group.

Embodiment 117. The system of any one of embodiments 105 to 116, wherein the first presenting group is a polypeptide fused to the first binder, a polynucleotide conjugated to the first binder, or a chemical compound conjugated to the first binder.

Embodiment 118. The system of any one of embodiments 109 to 117, wherein the second presenting group is a polypeptide fused to the second binder, a polynucleotide conjugated to the second binder, or a chemical compound conjugated to the second binder.

Embodiment 119. The system of any one of embodiments 108 to 118, further comprising reagents for PCR amplification of the nucleic acid reporter.

Embodiment 120. The system of any one of embodiments 108 to 119, further comprising reagents for purifying the nucleic acid reporter.

Embodiment 121. The system of any one of embodiments 105 to 120, wherein:
(i) the first binder binds to the analyte directly and the second binder binds to the analyte directly;
(ii) the first binder binds to the analyte directly and the second binder binds to the analyte indirectly;
(iii) the first binder binds to the analyte indirectly and the second binder binds to the analyte directly; or
(iv) the first binder binds to the analyte indirectly and the second binder binds to the analyte indirectly.

Embodiment 122. The system of any one of embodiments 105 to 121, wherein:
(i) the first binder binds to a first primary antibody or a fragment thereof that binds directly to the analyte;
(ii) the second binder binds to a second primary antibody or a fragment thereof that binds directly to the analyte; or
(iii) both (i) and (ii).

Embodiment 123. The system of any one of embodiments 105 to 122, wherein:
(i) the first and second binders bind to non-interfering epitopes on the analyte;
(ii) the first and second binders bind to non-overlapping epitopes on the analyte; or (iii) the first and second binders bind to different epitopes on the analyte.

Embodiment 124. The system of any one of embodiments 105 to 123, wherein (i) the first presenting group binds the first receiving group via a thioester group, a disulfide linkage, or a cleavable linkage; (ii) the second presenting group binds the second receiving group via a thioester group, a disulfide linkage, or a cleavable linkage; or both (i) and (ii).

Embodiment 125. The system of embodiment 124, wherein (i) the first presenting group binds the first receiving group via a photocleavable linkage, a chemically cleavable linkage, or an enzymatically cleavable linkage; (ii) the second presenting group binds the second receiving group via a photocleavable linkage, a chemically cleavable linkage, or an enzymatically cleavable linkage; or both (i) and (ii).

Embodiment 126. The system of any one of embodiments 105 to 123, wherein (i) the first presenting group binds the first receiving group via a protein-protein interaction; (ii) the second presenting group binds the second receiving group via a protein-protein interaction; or both (i) and (ii).

Embodiment 127. The system of any one of embodiments 105 to 123, wherein (i) the first presenting group binds the first receiving group via biotin to streptavidin or avidin; (ii) the second presenting group binds the second receiving group via biotin to streptavidin or avidin; or both (i) and (ii).

Embodiment 128. The system of any one of embodiments 105 to 123, wherein
(i) the first presenting group is a first nucleic acid tag (the "first tag") and the first receiving group is a first nucleic acid capture probe (the "first probe"); or (ii) the second presenting group is a second nucleic acid tag (the "second tag") and the second receiving group is a second nucleic acid capture probe (the "second probe").

Embodiment 129. The system of any one of embodiments 109 to 123, wherein (i) the first presenting group is a first nucleic acid tag (the "first tag") and the first receiving group is a first nucleic acid capture probe (the "first probe"); and (ii) the second presenting group is a second nucleic acid tag (the "second tag") and the second receiving group is a second nucleic acid capture probe (the "second probe").

Embodiment 130. The system of embodiments 128 or 129, wherein:
(i) the first probe is a protein that specifically binds to the first tag;
(ii) the first probe is a protein and nucleic acid complex that specifically binds to the first tag;
(iii) the first probe is a nucleic acid molecule, wherein the first probe or a fragment thereof is complementary to the first tag or a fragment thereof; or
(iv) the first probe is a nucleic acid molecule, wherein the first probe or a fragment thereof hybridizes with the first tag or a fragment thereof.

Embodiment 131. The system of embodiments 128 or 130, wherein:
(i) the second probe is a protein that specifically binds to the second tag;
(ii) the second probe is a protein and nucleic acid complex that specifically binds to the second tag;
(iii) the second probe is a nucleic acid molecule, wherein the second probe or a fragment thereof is complementary to the second tag or a fragment thereof; or
(iv) the second probe is a nucleic acid molecule, wherein the second probe or a fragment thereof hybridizes with the second tag or a fragment thereof.

Embodiment 132. The system of embodiments 130 or 131, wherein the complementarity is at least 80%, at least 81%, at least 82%, at least 83%, at least 84%, at least 85%, at least 86%, at least 87%, at least 88%, at least 89%, at least 90, at least 91%, at least 92%, at least 93%, at least 94%, at least 95%, at least 96%, at least 97%, at least 98%, or at least 99% complementation.

Embodiment 133. The system of any one of embodiments 128 to 132, wherein (i) the first probe is directly coupled to the first solid surface; or (ii) the second probe is directly coupled to the second solid surface.

Embodiment 134. The system of any one of embodiments 128 to 132, wherein (i) the first probe is directly coupled to the first solid surface; and (ii) the second probe is directly coupled to the second solid surface.

Embodiment 135. The system of any one of embodiments 128 to 132, wherein (i) the first probe hybridizes with a universal probe that is directly coupled to the first solid surface; or (ii) the second probe hybridizes with a universal probe that is directly coupled to the second solid surface.

Embodiment 136. The system of any one of embodiments 128 to 132, wherein (i) the first probe hybridizes with a universal probe that is directly coupled to the first solid surface; and (ii) the second probe hybridizes with a universal probe that is directly coupled to the second solid surface.

Embodiment 137. The system of any one of embodiments 128 to 132, wherein (i) the first probe is conjugated with biotin, which binds the streptavidin or avidin that is directly coupled to the first solid surface; or (ii) the second probe is conjugated with biotin, which binds the streptavidin or avidin that is directly coupled to the second solid surface.

Embodiment 138. The system of any one of embodiments 128 to 132, wherein (i) the first probe is conjugated with biotin, which binds the streptavidin or avidin that is directly coupled to the first solid surface; and (ii) the second probe is conjugated with biotin, which binds the streptavidin or avidin that is directly coupled to the second solid surface.

Embodiment 139. The system of any one of embodiments 128 to 138, wherein the first tag and second tag are collaboratively captured on the first solid surface.

Embodiment 140. The system of embodiment 139, wherein a first fragment of the first probe is complementary to the first tag or a fragment thereof, and a second fragment of the first probe is complementary to the second tag or a fragment thereof, wherein the complementary region includes the unconjugated ends of the first and the second tags.

Embodiment 141. The system of embodiment 139, wherein a continuous fragment of the first probe consists of a first fragment and an immediately adjacent second fragment, wherein the first fragment is complementary to the first tag or a fragment thereof, and the second fragment is complementary to the second tag or a fragment thereof, such that when the first and second tags are linked to form a linked nucleic acid, a joint region of the linked nucleic acid is complementary to the continuous fragment of the first probe.

Embodiment 142. The system of embodiment 139, wherein a first fragment of the first probe is complementary to the first tag or a fragment thereof, and wherein a separate second fragment of the first probe is complementary to the second tag or a fragment thereof; and wherein the complementary region does not include the unconjugated ends of the first and the second tags.

Embodiment 143. The system of embodiment 139, wherein the first solid surface is coupled with both the first probe and an additional nucleic acid probe, and wherein the additional probe or a fragment thereof is complementary to the first tag or a fragment thereof.

Embodiment 144. The system of any one of embodiments 128 to 143, wherein the first tag and second tag are collaboratively captured on the second solid surface.

Embodiment 145. The system of embodiment 144, wherein a first fragment of the second probe is complementary to the first tag or a fragment thereof, and a second fragment of the second probe is complementary to the second tag or a fragment thereof, wherein the complementary region includes the unconjugated ends of the first and the second tags.

Embodiment 146. The system of embodiment 144, wherein a continuous fragment of the second probe consists of a first fragment and an immediately adjacent second fragment, wherein the first fragment is complementary to the first tag or a fragment thereof, and the second fragment is complementary to the second tag or a fragment thereof, such that when the first and second tags are linked to form a linked nucleic acid, a joint region of the linked nucleic acid is complementary to the continuous fragment of the second probe.

Embodiment 147. The system of embodiment 144, wherein a first fragment of the second probe is complementary to the first tag or a fragment thereof, and wherein a separate second fragment of the second probe is complementary to the second tag or a fragment thereof; and wherein the complementary region does not include the unconjugated ends of the first and the second tags.

Embodiment 148. The system of embodiment 144, wherein the second solid surface is coupled with both the second probe and an additional nucleic acid probe, and wherein the additional probe or a fragment thereof is complementary to the second tag or a fragment thereof.

Embodiment 149. The system of any one of embodiments 128 to 148, wherein (i) the complementary fragments of the first tag and the first probe consist of 10 to 30 base pairs; (ii) the complementary fragments of the second tag and the second probe consist of 10 to 30 base pairs; or both (i) and (ii).

Embodiment 150. The system of any one of embodiments 128 to 149, wherein (i) the complementary fragments of the first tag and the first probe consist of 20 to 30 base pairs; (ii) the complementary fragments of the second tag and the second probe consist of 20 to 30 base pairs; or both (i) and (ii).

Embodiment 151. The system of any one of embodiments 128 to 150, wherein (i) the first tag comprises an A and/or T rich sequence and the first probe comprises a complementary A and/or T rich sequence; (ii) the second tag comprises an A and/or T rich sequence and the second probe comprises a complementary A and/or T rich sequence; or both (i) and (ii).

Embodiment 152. The system of embodiment 151, wherein the A and/or T rich sequence has a short length such that the binding from complementary A and/or T rich sequence is weaker than both the binding between first binder and the analyte and the binding between the second binder and the analyte.

Embodiment 153. The system of any one of embodiments 105 to 152, wherein the analyte is a binding pair of two molecules; wherein the first binder binds one molecule of the binding pair, and the second binder binds the other molecule of the binding pair.

Embodiment 154. The system of any one of embodiments 105 to 153, wherein the analyte is a nucleic acid, and the first and second binders for the nucleic acid analyte comprise nucleic acids that are complementary to different fragments of the nucleic acid analyte.

Embodiment 155. The system of any one of embodiments 105 to 153, wherein the analyte is a peptide or a protein, and (i) the first binder is an antibody or an antibody fragment that specifically binds the analyte; (ii) the second binder is an antibody or an antibody fragment that specifically binds the analyte; or both (i) and (ii).

Embodiment 156. The system of any one of embodiments 105 to 155, wherein the sample is a serum sample or a plasma sample.

Embodiment 157. The system of any one of embodiments 105 to 156, (i) the first target label is directly bound to the first binder; or (ii) the first target label is indirectly bound to the first binder.

Embodiment 158. The system of any one of embodiments 105 to 157, wherein: (i) the second target label is directly bound to the second binder; or (ii) the second target label is indirectly bound to the second binder.

Embodiment 159. The system of any one of embodiments 105 to 158, wherein:
(i) the first target label is conjugated to the first binder;
(ii) the first target label is non-covalently bound to the first binder;
(iii) the first target label is conjugated to the first presenting group;
(iv) the first target label is non-covalently bound to the first presenting group; or
(v) the first target label is part of the first presenting group.

Embodiment 160. The system of any one of embodiments 105 to 159, wherein:

(i) the second target label is conjugated to the second binder;
(ii) the second target label is non-covalently bound to the second binder;
(iii) the second target label is conjugated to the second presenting group;
(iv) the second target label is non-covalently bound to the second presenting group; or
(v) the second target label is part of the second presenting group.

Embodiment 161. The system of any one of embodiments 105 to 160, wherein: (i) the first presenting group is directly bound to the first binder; or (ii) the first presenting group is indirectly bound to the first binder.

Embodiment 162. The system of any one of embodiments 109 to 161, wherein: (i) the second presenting group is directly bound to the second binder; or (ii) the second presenting group is indirectly bound to the second binder.

Embodiment 163. The system of any one of embodiments 105 to 162, wherein:
(i) the first presenting group is conjugated to the first binder;
(ii) the first presenting group is non-covalently bound to the first binder;
(iii) the first presenting group is conjugated to the first target label;
(iv) the first presenting group is non-covalently bound to the first target label; or
(v) the first presenting group is part of the first target label.

Embodiment 164. The system of any one of embodiments 109 to 163, wherein:
(i) the second presenting group is conjugated to the second binder;
(ii) the second presenting group is non-covalently bound to the second binder;
(iii) the second presenting group is conjugated to the second target label;
(iv) the second presenting group is non-covalently bound to the second target label; or
(v) the second presenting group is part of the second target label.

Embodiment 165. The system of any one of embodiments 105 to 164, wherein:
(i) the first target label is a nucleic acid molecule;
(ii) the second target label is a nucleic acid molecule; or
(iii) both (i) and (ii).

Embodiment 166. The system of any one of embodiments 128 to 165, wherein:
(i) the first target label hybridizes with the first tag;
(ii) the second target label hybridizes with the second tag; or
(iii) both (i) and (ii).

Embodiment 167. The system of any one of embodiments 106 to 166, wherein the sample label is a single-stranded nucleic acid molecule ("single-stranded sample label").

Embodiment 168. The system of any one of embodiments 106 to 166, wherein the sample label is a double-stranded nucleic acid molecule ("double-stranded sample label").

Embodiment 169. The system of embodiment 168, wherein the sample label is:
(i) a double-stranded nucleic acid molecule comprising two 5' overhangs;
(ii) a double-stranded nucleic acid molecule comprising two 3' overhangs;
(iii) a double-stranded nucleic acid molecule comprising a 5' overhang and a 3' overhang;
(iv) a double-stranded nucleic acid molecule comprising a 5' overhang and a blunt end; or
(v) a double-stranded nucleic acid molecule comprising a 3' overhang and a blunt end.

Embodiment 170. The system of embodiment 169, wherein the sample label:
(i) hybridizes with the first target label via an overhang of the sample label;
(ii) hybridizes with the second target label via an overhang of the sample label; or (iii) both (i) and (ii).

Embodiment 171. The system of any one of embodiments 106 to 170, wherein the system is capable of simultaneously detecting at least two analytes in the sample by simultaneously detecting the unique target IDs associated with each analyte.

Embodiment 172. The system of any one of embodiments 105 to 171, wherein the system further comprises a reference analyte.

Embodiment 173. The system of embodiment 172, wherein the reference analyte is an analyte that is absent in the sample.

Embodiment 174. The system of embodiment 172 or 173, wherein the reference analyte is a protein, a nucleic acid, or a chemical compound that is absent in the sample.

Embodiment 175. The system of embodiment 174, wherein the reference analyte is viral protein, a bacterial protein, or an insect protein.

Embodiment 176. The system of any one of embodiments 111 to 175, wherein the system is capable of simultaneously detecting the analyte in at least two samples, by simultaneously detecting the unique sample IDs in the nucleic acid reporters associated with each sample.

Embodiment 177. The system of any one of embodiments 110 to 176, wherein the system is capable of simultaneously detecting at least two analytes in at least two samples, by simultaneously detecting the unique sample IDs and unique target IDs in the nucleic acid reporters associated with each analyte in each sample.

Embodiment 178. The system of any one of embodiments 105 to 177, comprising reagents and/or machines for multiplexed qPCR, multiplexed digital PCR, or NGS to detect nucleic acid reporters.

Embodiment 179. The system of any one of embodiments 105 to 177, comprising reagents and/or machines for NGS to detect the nucleic acid reporters.

Embodiment 180. The system of any one of embodiments 105 to 179, wherein the system is contained in a kit.

Embodiment 181. The system of embodiment 180, wherein the kit further comprises a binding buffer, an immobilization buffer, a washing buffer, a release buffer, or any combination thereof.

Embodiment 182. A system for detecting an analyte in a sample comprising (1) a first binding moiety comprising a first binder, a first presenting group, and a first target label comprising a first identity barcode ("ID") that is analyte-specific ("target ID"); (2) a second binding moiety comprising a second binder, a second presenting group, and a second target label comprising a second target ID; (3) a first receiving group, a first solid surface, a second receiving group, and a second solid surface; (4) reagents for ligation and a sample label comprising an ID that is sample-specific ("sample ID"); and (5) reagents for quantitative PCR; wherein:
(i) the first and second binders bind to the analyte and form an immunocomplex, (ii) the first receiving group is coupled to the first solid surface and is configured to capture the first presenting group;

(iii) the second receiving group is coupled to the second solid surface and is configured to capture the second presenting group;

(iv) the first target label is directly or indirectly bound to the first binder and the second target label is directly or indirectly bound to the second binder;

(v) the first presenting group is directly or indirectly bound to the first binder and the second presenting group is directly or indirectly bound to the second binder; and (vi) the sample label binds to both the first target label and the second target label.

Embodiment 183. The system of embodiment 182, wherein the system is contained in a kit.

Embodiment 184. The system of embodiment 183, wherein the kit further comprises a binding buffer, an immobilization buffer, a washing buffer, a release buffer, or any combination thereof.

Embodiment 185. A system for detecting an analyte in a sample comprising (1) a first binding moiety comprising a first binder, a first presenting group, and a first target label comprising a first identity barcode ("ID") that is analyte-specific ("target ID"); (2) a second binding moiety comprising a second binder, a second presenting group, and a second target label comprising a second target ID; (3) a first receiving group, a first solid surface, a second receiving group, and a second solid surface; and (4) reagents for ligation and a sample label comprising an ID that is sample-specific ("sample ID"); wherein:

(i) the first and second binders bind to the analyte and form an immunocomplex, (ii) the first receiving group is coupled to the first solid surface and is configured to capture the first presenting group;

(iii) the second receiving group is coupled to the second solid surface and is configured to capture the second presenting group;

(iv) the first target label is directly or indirectly bound to the first binder, and the second target label is directly or indirectly bound to the second binder;

(v) the first presenting group is directly or indirectly bound to the first binder, and the second presenting group is directly or indirectly bound to the second binder; and (vi) the sample label binds to both the first target label and the second target label.

Embodiment 186. The system of embodiment 185, wherein the system is contained in a kit.

Embodiment 187. The system of embodiment 186, wherein the kit further comprises a binding buffer, an immobilization buffer, a washing buffer, a release buffer, or any combination thereof.

Provided herein are assay methods that use two capture binders. In some embodiments, provided herein are assay methods for detecting an analyte in a sample, comprising:

(1) mixing a first binder, a second binder, and the sample in a solution, wherein the first and second binders bind non-interfering epitopes on the analyte and form an immunocomplex, and wherein the immunocomplex is captured on a first solid surface in contact with the solution via binding between a first presenting group conjugated to the first binder and a first receiving group coupled to the first surface;

(2) washing the first solid surface to remove unbound molecules;

(3) releasing the immunocomplex from the first solid surface by disrupting the binding between the first presenting group and the first receiving group;

(4) introducing a second solid surface and recapturing the immunocomplex via binding between a second presenting group conjugated to the second binder and the second receiving group coupled to the second solid surface;

(5) washing the second solid surface to remove unbound molecules; and (6) detecting the immunocomplex.

In some embodiments, step (1) comprises forming the immunocomplex in the solution before capturing the immunocomplex on the first solid surface. In some embodiments, step (1) comprises pre-capturing the first binder on the first solid surface before forming the immunocomplex on the first solid surface. In some embodiments, the immunocomplex is formed in the solution and captured on the first solid surface simultaneously in step (1).

In some embodiments, the assay methods provided herein further comprise at least one additional cycle of recapture between steps (5) and (6), comprising: releasing the immunocomplex from the solid surface that it is captured on, recapturing the immunocomplex on an additional solid surface coupled with the first or the second receiving group, and washing the additional solid surface to remove unbound molecules.

In some embodiments, (i) the first presenting group binds the first receiving group via a thioester group, a disulfide linkage, or a cleavable linkage; (ii) the second presenting group binds the second receiving group via a thioester group, a disulfide linkage, or a cleavable linkage; or both (i) and (ii).

In some embodiments, (i) the first presenting group binds the first receiving group via a photocleavable linkage, a chemically cleavable linkage, or an enzymatically cleavable linkage; (ii) the second presenting group binds the second receiving group via a photocleavable linkage, a chemically cleavable linkage, or an enzymatically cleavable linkage; or both (i) and (ii).

In some embodiments, (i) the first presenting group is a first nucleic acid tag (the "first tag") and the first receiving group is a first nucleic acid capture probe (the "first probe"), wherein the first probe or a fragment thereof is complementary to the first tag or a fragment thereof; or (ii) the second presenting group is a second nucleic acid tag (the "second tag") and the second receiving group is a second nucleic acid capture probe (the "second probe"), wherein the second probe or a fragment thereof is complementary to the second tag or a fragment thereof.

In some embodiments, (i) the first presenting group is the first tag and the first receiving group is the first probe; and (ii) the second presenting group is the second tag and the second receiving group is the second probe.

In some embodiments, (i) the first probe is directly coupled to the first solid surface; (ii) the second probe is directly coupled to the second solid surface; or both (i) and (ii).

In some embodiments, (i) the first probe hybridizes with a universal probe that is directed coupled to the first solid surface; (ii) the second probe hybridizes with a universal probe that is directed coupled to the second solid surface; or both (i) and (ii).

In some embodiments, (i) the first probe is conjugated with biotin, which binds the streptavidin or avidin that is directed coupled to the first solid surface; (ii) the second probe is conjugated with biotin, which binds the streptavidin or avidin that is directed coupled to the second solid surface; or both (i) and (ii).

In some embodiments, the first tag and second tag are collaboratively captured on the first solid surface in step (1).

In some embodiments, a first fragment of the first probe is complementary to the first tag or a fragment thereof, and a second fragment of the first probe is complementary to the second tag or a fragment thereof, wherein the complementary region includes the unconjugated ends of the first and the second tags.

In some embodiments, a continuous fragment of the first probe consists of a first fragment and an immediately adjacent second fragment, wherein the first fragment is complementary to the first tag or a fragment thereof, and the second fragment is complementary to the second tag or a fragment thereof, such that when the first and second tags are linked to form a linked nucleic acid, a joint region of the linked nucleic acid is complementary to the continuous fragment of the first probe.

In some embodiments, a first fragment of the first probe is complementary to the first tag or a fragment thereof, and a separate second fragment of the first probe is complementary to the second tag or a fragment thereof; wherein the complementary region does not include the unconjugated ends of the first and the second tags.

In some embodiments, the first solid surface is coupled with both the first probe and the second probe.

In some embodiments, (i) the complementary fragments of the first tag and the first probe consist of 10 to 25 base pairs; (ii) the complementary fragments of the second tag and the second probe consist of 10 to 25 base pairs; or both (i) and (ii).

Provided herein are also assay methods using one capture binder. In some embodiments, provided herein are assay methods for detecting an analyte in a sample, comprising:
(1) mixing a first binder, a second binder, and the sample in a solution; wherein the first and second binders bind non-interfering epitopes on the analyte and form an immunocomplex; and wherein the immunocomplex is captured on a first solid surface in contact with the solution via hybridization between a first nucleic acid tag (the "first tag") conjugated to the first binder and a first nucleic acid capture probe (the "first probe") coupled to the first solid surface;
(2) washing the first solid surface to remove unbound molecules;
(3) releasing the immunocomplex from the first solid surface via the dissolution of the hybridization between the first tag and the first probe;
(4) introducing a second solid surface coupled with a second nucleic acid probe (the "second probe") and recapturing the immunocomplex on the second solid surface via hybridization between the first tag and the second probe;
(5) washing the second solid surface to remove unbound molecules; and
(6) detecting the immunocomplex.

In some embodiments, the second probe is the same as the first probe.

In some embodiments, step (1) comprises forming the immunocomplex in the solution before capturing the immunocomplex on the first solid surface. In some embodiments, step (1) comprises pre-capturing the first binder on the first solid surface before forming the immunocomplex on the first solid surface. In some embodiments, the immunocomplex is formed in the solution and captured on the first solid surface simultaneously in step (1).

In some embodiments, assay methods provided herein comprise at least one additional cycle of recapture between steps (5) and (6), comprising: releasing the immunocomplex from the solid surface that it is captured on; recapturing the immunocomplex on an additional solid surface coupled with (a) the first probe, (b) the second probe, or (c) another nucleic acid probe that hybridizes with first tag; and washing the additional solid surface to remove unbound molecules.

In some embodiments, (i) the first probe is directly coupled to the first solid surface; (ii) the second probe is directly coupled to the second solid surface; or both (i) and (ii).

In some embodiments, (i) the first probe hybridizes with a universal probe that is directed coupled to the first solid surface; (ii) the second probe hybridizes with a universal probe that is directed coupled to the second solid surface; or both (i) and (ii).

In some embodiments, (i) the first probe is conjugated with biotin, which binds the streptavidin or avidin that is directed coupled to the first solid surface; (ii) the second probe is conjugated with biotin, which binds the streptavidin or avidin that is directed coupled to the second solid surface; or both (i) and (ii).

In some embodiments, the second binder is conjugated to a second nucleic acid tag (the "second tag").

In some embodiments, the first tag and second tag are collaboratively captured on the first solid surface in step (1).

In some embodiments, a first fragment of the first probe is complementary to the first tag or a fragment thereof, and a second fragment of the first probe is complementary to the second tag or a fragment thereof; wherein the complementary region includes the unconjugated ends of the first and the second tags.

In some embodiments, a continuous fragment of the first probe consists of a first fragment and an immediately adjacent second fragment, wherein the first fragment is complementary to the first tag or a fragment thereof, and the second fragment is complementary to the second tag or a fragment thereof, such that when the first and second tags are linked to form a linked nucleic acid, a joint region of the linked nucleic acid is complementary to the continuous fragment of the first probe.

In some embodiments, a first fragment of the first probe is complementary to the first tag or a fragment thereof, and a separate second fragment of the first probe is complementary to the second tag or a fragment thereof; wherein the complementary region does not include the unconjugated ends of the first and the second tags.

In some embodiments, the first solid surface is coupled with both the first probe and an additional nucleic acid probe, and the additional probe or a fragment thereof is complementary to the second tag or a fragment thereof.

In some embodiments, the first tag and second tag are collaboratively captured on the second solid surface in step (4).

In some embodiments, a first fragment of the second probe is complementary to the first tag or a fragment thereof, and a second fragment of the second probe is complementary to the second tag or a fragment thereof; wherein the complementary region includes the unconjugated ends of the first and the second tags.

In some embodiments, a continuous fragment of the second probe consists of a first fragment and an immediately adjacent second fragment, the first fragment is complementary to the first tag or a fragment thereof, and the second fragment is complementary to the second tag or a fragment thereof, such that when the first and second tags are linked to form a linked nucleic acid, a joint region of the linked nucleic acid is complementary to the continuous fragment of the second probe.

In some embodiments, a first fragment of the second probe is complementary to the first tag or a fragment thereof, and a separate second fragment of the second probe is complementary to the second tag or a fragment thereof; wherein the complementary region does not include the unconjugated ends of the first and the second tags.

In some embodiments, the second solid surface is coupled with both the second probe and an additional nucleic acid probe, and wherein the additional probe or a fragment thereof is complementary to the second tag or a fragment thereof.

In some embodiments, the complementary fragments of the first tag and the first probe consist of 10 to 25 base pairs.

The assay methods provided herein detect an analyte in a sample, which include detecting the immunocomplex in step (6).

In some embodiments, the sample is a serum sample or a plasma sample.

In some embodiments, the analyte is a binding pair of two molecules; wherein the first binder binds one molecule of the binding pair, and the second binder binds the other molecule of the binding pair.

In some embodiments, (i) the first binder is an antibody or an antibody fragment that specifically binds the analyte; (ii) the second binder is an antibody or an antibody fragment that specifically binds the analyte, or both (i) and (ii).

In some embodiments, in step (6): the immunocomplex is detected while being captured on a solid surface. In some embodiments, in step (6): the immunocomplex is detected after being released from a solid surface to a solution.

In some embodiments, either the first binder or the second binder is conjugated with a detectable marker. In some embodiments, the first binder is conjugated with a detectable marker. In some embodiments, the second binder is conjugated with a detectable marker. In some embodiments, the detectable marker is a nucleic acid.

In some embodiments, step (6) comprises generating a nucleic acid reporter by linking the first tag and the second tag, and detecting the nucleic acid reporter composed of a fragment of the first tag and a fragment of the second tag.

In some embodiments, step (6) comprises generating a nucleic acid reporter by linking: (a) the first tag and a surrogate nucleic acid of the second tag (the "second surrogate"), and detecting the nucleic acid reporter composed of a fragment of the first tag and a fragment of the second surrogate; (b) a surrogate nucleic acid of the first tag (the "first surrogate") and the second tag, and detecting the nucleic acid reporter composed of a fragment of the first surrogate and a fragment of the second tag; or (c) the first surrogate and the second surrogate, and detecting the nucleic acid reporter composed of a fragment of the first surrogate and a fragment of the second surrogate; wherein the first tag or a fragment thereof is complementary to the first surrogate or a fragment thereof, and the second tag or a fragment thereof is complementary to the second surrogate or a fragment thereof.

In some embodiments, the nucleic acid reporter is formed by proximity ligation. In some embodiments, the nucleic acid reporter is formed by proximity extension.

In some embodiments, the nucleic acid reporter is detected by qPCR, digital PCR, or next generating sequencing (NGS).

In some embodiments, the nucleic acid reporter is detected by Rolling Cycle Amplification (RCA), strand displacement amplification (SDA), Loop-Mediated Isothermal Amplification (LAMP), Recombinase Polymerase Amplification (RPA), or a QuantiGene assay.

In some embodiments, the nucleic acid reporter contains an identity barcode ("ID") fragment that is analyte-specific ("target ID") in the first tag or the first surrogate thereof, or in the second tag or the second surrogate thereof. In some embodiments, the nucleic acid reporter contains a first target ID in the first tag or the first surrogate, and a second target ID in the second tag or the second surrogate.

In some embodiments, assay methods provided herein comprise simultaneously detecting at least two analytes in the sample by simultaneously detecting the unique target IDs associated with each analyte.

In some embodiments, assay methods provided herein comprise proportionally reducing the signal from at least one of the analytes, by adding a non-functional binder to the solution in step (1), wherein the non-functional binder competes with the first binder for binding to the analyte but is either unconjugated or conjugated to a presenting group that does not bind the first receiving group.

In some embodiments, at least one analyte is a nucleic acid, and the first and second binders for the nucleic acid analyte comprise nucleic acids that are complementary to different fragments of the nucleic acid analyte.

In some embodiments, in step (6), detecting the analyte comprises the co-detection of the first and the second target IDs.

In some embodiments, the analyte is a binding pair of two molecules; wherein the first binder binds one molecule of the binding pair, and the second binder binds the other molecule of the binding pair.

In some embodiments, the nucleic acid reporter formed in each sample contains an ID that is sample-specific ("sample ID"), wherein the sample ID is (1) inserted between the first tag or surrogate thereof, and the second tag or surrogate thereof, (2) included in the first surrogate or the second surrogate, or (3) ligated to the first tag or surrogate thereof, or the second tag or surrogate thereof.

In some embodiments, assay methods provided herein comprise simultaneously detecting the analyte in at least two samples, by simultaneously detecting the unique sample IDs in the nucleic acid reporters associated with each sample.

In some embodiments, the nucleic acid reporter comprises (a) a target ID in the first tag or the first surrogate, or in the second tag or the second surrogate, and (b) a sample ID that is (1) inserted between the first tag or surrogate thereof, and the second tag or surrogate thereof, (2) included in the first surrogate or the second surrogate, or (3) ligated to the first tag or surrogate thereof, or the second tag or surrogate thereof.

In some embodiments, assay methods provided herein comprise simultaneously detecting at least two analytes in at least two samples, by simultaneously detecting the unique sample IDs and unique target IDs in the nucleic acid reporters associated with each analyte in each sample.

In some embodiments, the nucleic acid reporters are detected by multiplexed qPCR, multiplexed digital PCR, or NGS.

In some embodiments, (i) the first solid surface is a magnetic particle surface or a well of a microtiter plate; (ii)

the second solid surface is a magnetic particle surface or a well of a microtiter plate; or both (i) and (ii).

In some embodiments, provided herein are systems for detecting an analyte in a sample comprising a first binder, a second binder, a first presenting group, a second presenting group, a first receiving group, and a second receiving group; wherein (i) the first and second binders bind non-interfering epitopes on the analyte, and (ii) the first and second presenting groups bind the first and second receiving groups, respectively.

In some embodiments, systems provided herein further comprise a first solid surface and a second solid surface.

In some embodiments, (i) the first solid surface is a magnetic particle surface or a well of a microtiter plate; (ii) the second solid surface is a magnetic particle surface or a well of a microtiter plate; or both (i) and (ii).

In some embodiments, the first solid surface is coupled with the first receiving group, and the second first solid surface is coupled with the second receiving group.

In some embodiments, systems provided herein further comprise a detectable marker.

In some embodiments, the detectable marker is conjugated to the first binder or the second binder.

In some embodiments, the first binder is conjugated to the first presenting group, and the second binder is conjugated to the second presenting group.

In some embodiments, (i) the first presenting group binds the first receiving group via a thioester group, a disulfide linkage, or a cleavable linkage; (ii) the second presenting group binds the second receiving group via a thioester group, a disulfide linkage, or a cleavable linkage; or both (i) and (ii).

In some embodiments, (i) the first presenting group binds the first receiving group via a photocleavable linkage, a chemically cleavable linkage, or an enzymatically cleavable linkage; (ii) the second presenting group binds the second receiving group via a photocleavable linkage, a chemically cleavable linkage, or an enzymatically cleavable linkage; or both (i) and (ii).

In some embodiments, provided herein are systems for detecting an analyte in a sample comprising a first binder, a second binder, a first nucleic acid tag (the "first tag"), a second nucleic acid tag (the "second tag"), a first nucleic acid capture probe (the "first probe"), and a second nucleic acid capture probe (the "second probe"); wherein (i) the first and second binders bind non-interfering epitopes on the analyte; (ii) the first probe or a fragment thereof is complementary to the first tag or a fragment thereof; and (iii) the second probe or a fragment thereof is complementary to the second tag or a fragment thereof.

In some embodiments, systems provided herein further comprise a first solid surface and a second solid surface.

In some embodiments, (i) the first solid surface is a magnetic particle surface or a well of a microtiter plate; (ii) the second solid surface is a magnetic particle surface or a well of a microtiter plate; or both (i) and (ii).

In some embodiments, the first solid surface is coupled with the first probe, and the second first solid surface is coupled with the second probe.

In some embodiments, the first binder is conjugated to the first tag, and the second binder is conjugated to the second tag.

In some embodiments, (i) the complementary fragments of the first tag and the first probe consist of 10 to 25 base pairs; (ii) the complementary fragments of the second tag and the second probe consist of 10 to 25 base pairs; or both (i) and (ii).

In some embodiments, (i) the first binder is an antibody or an antibody fragment that specifically binds the analyte; (ii) the second binder is an antibody or an antibody fragment that specifically binds the analyte; or both (i) and (ii).

Provided herein are also systems for detecting an analyte in a sample comprising a first binder, a second binder, a first nucleic acid tag (the "first tag"), a first nucleic acid capture probe (the "first probe"), and a second nucleic acid capture probe (the "second probe"); wherein (i) the first and second binders bind non-interfering epitopes on the analyte; (ii) the first probe or a fragment thereof is complementary to the first tag or a fragment thereof; and (iii) the second probe or a fragment thereof is complementary to the first tag or a fragment thereof.

In some embodiments, the second probe is the same as the first probe.

In some embodiments, the first binder is conjugated to the first tag.

In some embodiments, systems provided herein further comprise a detectable marker. In some embodiments, either the first binder or the second binder is conjugated to the detectable marker.

In some embodiments, systems provided herein further comprise a second nucleic acid tag (the "second tag"). In some embodiments, the second tag is conjugated to the second binder.

In some embodiments, a fragment of the first probe is complementary to the second tag or a fragment thereof.

In some embodiments, systems provided herein further comprise a first solid surface and a second solid surface.

In some embodiments, (i) the first solid surface is a magnetic particle surface or a well of a microtiter plate; (ii) the second solid surface is a magnetic particle surface or a well of a microtiter plate; or both (i) and (ii).

In some embodiments, (1) the first solid surface is coupled with the first probe; (2) the second solid surface is coupled with the second probe; or both (1) and (2).

In some embodiments, systems provided herein further comprise an additional nucleic acid probe, wherein the additional probe or a fragment thereof is complementary to the second tag or a fragment thereof.

In some embodiments, systems provided herein further comprise a first solid surface and a second solid surface, wherein the first solid surface is coupled with the first probe and the additional probe, and the second solid surface is coupled with the second probe and the additional probe.

In some embodiments, (i) the first binder is an antibody or an antibody fragment that specifically binds the analyte; (ii) the second binder is an antibody or an antibody fragment that specifically binds the analyte; or both (i) and (ii).

In some embodiments, (i) the complementary fragments of the first tag and the first probe consist of 10 to 25 base pairs; (ii) the complementary fragments of the second tag and the second probe consist of 10 to 25 base pairs; or both (i) and (ii).

In some embodiments, the system is contained in a kit.

In some embodiments, the kit further comprises a binding buffer, an immobilization buffer, a washing buffer, a release buffer, or any combination thereof.

4. BRIEF DESCRIPTION OF DRAWINGS

FIG. 1 is a schematic diagram of SIngle MOlecular Array (SIMOA) assay work flow. As shown, the technology is based on sandwich ELISA, but, at the final readout stage of the assay, molecules carrying the signal generation moiety are isolated, detected and counted one at a time. The lower Limit of Detection (LOD) of the assay is limited to the range of two to single digit fM, depending on the quality of the antibody pair used (Yeung, *J. Imm. Meth.* 437: 53-63 (2016)).

FIG. 2 is a schematic diagram of Immuno-PCR work flow. As shown, a segment of the nucleic acid pre-conjugated to the detection antibody is used as the reporter of the immunocomplex, and PCR is used to amplify the reporter and generate a detectable signal. Despite the significant boost of signal strength resulted from the PCR amplification of reporters, the improvement to LOD has been modest, mostly by a factor of about 10 in comparison to sandwich ELISA (Potuckova, *J. Immu. Meth.* 371: 38-47 (2011)).

FIGS. 3A-3C are schematic diagrams of Proximity Ligation Assay ("PLA") (FIG. 3A), Proximity Extension Assay ("PEA") (FIG. 3B) and solid phase PLA (FIG. 3C). As shown, a nucleic acid reporter is generated when the two binders are in proximity so that their attached nucleic acids can be ligated (PLA; FIG. 3A) or extended (PEA; FIG. 3B). Proximity-based detection assays also have LOD in the mid-to-low fM range. In solid phase PLA, two binders to the target analyte are each conjugated with a nucleic acid and a third binder captures the analyte to solid surface (FIG. 3C). The solid phase proximity assay has demonstrated LODs in single digit fM range (Nong R Y, *Nature protocols,* 8 (6): 1234-1249 (2013)). However, the requirement of three non-interfering antibodies against the same target protein presents a significant challenge in assay development.

FIGS. 4A-4D are schematic diagrams of assay methods provided herein using capture-and-release mechanisms. FIG. 4A depicts assay methods involving two capture binders. FIG. 4B depicts assay methods that involve two capture binders and use nucleic acid tags and probes for capture-and-release. FIG. 4C depicts assay methods involving one capture binder that utilizes the renewable bond between the first presenting group and the first receiving group. FIG. 4D depicts assay methods that involve one capture binder that utilizes the hybridization between the same nucleic acid tag and probe pair for capture-and-release.

FIGS. 5A-5C are schematic diagrams of assay methods provided herein that use different nucleic acid reporter configurations. The nucleic acid reporters are generated by linking the surrogate of the first tag (the "first surrogate") to the second tag (FIG. 5A), by linking the first tag to the surrogate of the second tag (the "second surrogate") (FIG. 5B), or by linking the first surrogate to the second surrogate (FIG. 5C). Although ligation is depicted in the figure, the reporter can also be generated by extension.

FIGS. 6A-6D are schematic diagrams of exemplary capture configurations used in the assay methods provided herein. FIG. 6A depicts direct capture configuration. FIG. 6B depicts indirect capture configuration using a universal probe. FIG. 6C depicts indirect capture configuration using a biotin/streptavidin pair. FIG. 6D depicts direct collaborative capture configuration, wherein the first and second nucleic acid tags collaboratively bind the nucleic acid capture probe.

FIGS. 7A-7C are schematic diagrams of exemplary configurations of collaborative capture used in the assay methods provided herein. FIG. 7A depicts the collaborative capture wherein a continuous fragment of the probe hybridizes with a joint region of the first tag and a second tag. FIG. 7B depicts the collaborative capture wherein a fragment of the probe hybridizes with a fragment of the first tag and a separate fragment of the probe hybridizes with a fragment of the second tag. FIG. 7C depicts the collaborative capture wherein a solid surface is coupled with both the first and second probes, which capture the first and second tags, respectively.

FIGS. 8A-8G are schematic diagrams of embodiments of NULISA immunoassays. FIGS. 8A-8B depict the assay methods that involve two releasable, orthogonal bonds, wherein the capture/release process are performed at least once between each binder and their respective solid surfaces. FIG. 8A illustrates detection via the formation of a nucleic acid reporter using both nucleic acid tags conjugated to the binders; and FIG. 8B illustrates detection via iPCR of a nucleic acid molecule conjugated to the second binder. FIGS. 8C-8D depict the assay methods that involve one releasable and renewable bond on the first solid surface, wherein the capture/release are repeatedly performed between the first binder and more than one solid surfaces and the nucleic acid reporter. FIG. 8C illustrates detection via the formation of a nucleic acid reporter using both nucleic acid tags conjugated to the binders; FIG. 8D illustrates detection via iPCR of a nucleic acid molecule conjugated to the second binder; FIG. 8E illustrates detection of the first target label that is conjugated to the first binder after capture and release have been conducted at both the first binder and the second binder; FIG. 8F illustrates detection of non-nucleic acid reporter or label; and FIG. 8G illustrates an embodiment wherein binder 1 and binder 2 bind to a target indirectly, e.g. binder 1 and binder 2 bind to primary antibodies which bind directly to the analyte.

FIGS. 9A-9B are schematic diagrams of assay methods provided herein that incorporate identity barcodes (ID) into the nucleic acid reporters. In FIG. 9A, one ID is incorporated into one of the nucleic acid tags conjugated to one of the binders. In FIG. 9B, two IDs are separately incorporated in the two tags of both binders.

FIGS. 10A-10B are schematic diagrams of assay methods provided herein using an indirect ID barcoding approach. In FIG. 10A, the nucleic acid reporter is formed by linking a first nucleic acid surrogate (the "first surrogate"), which can hybridize with the first tag, and the second tag, and one ID is incorporated into the first surrogate. In FIG. 10B, the nucleic acid reporter is formed by linking the first surrogate and a second nucleic acid surrogate (the "second surrogate") that can hybridize with the second tag; and each surrogate is incorporated with an ID.

FIG. 11 is a schematic diagram of multiplexing assay methods provided herein, which can detect multiple analytes in parallel by detecting the unique IDs incorporated in the tags conjugated to the binders for each analyte.

FIG. 12 is a schematic diagram of assay methods provided herein that use unique IDs to achieve enhanced specificity. As shown, by requiring the co-detection of ID 1 and ID 2 that are incorporated into tags conjugated to Binder 1 and Binder 2, respectively, as the detection of a "true signal," the methods reduce false positive signals associated with the detection of only ID 1 or ID 2, but not both.

FIG. 13 is a schematic diagram of assay methods provided herein for detecting protein-protein interactions, wherein each protein in the binding pair is captured by a binder associated with a unique ID, and interaction of the two proteins are reflected by the co-detection of both IDs in a single immunocomplex.

FIGS. 14A-14C are schematic diagrams of assay methods provided herein that incorporate sample-specific IDs ("sample IDs") and can detect multiple samples in parallel. FIG. 14A depicts the incorporation of a sample ID between the first and second nucleic acid tags in forming the reporter for detection. FIG. 14B depicts the incorporation of a sample ID in either the first or second surrogate nucleic acid that is part of the reporter for detection. FIG. 14C depicts the ligation of a sample ID to the first or second nucleic acid tags or the surrogates thereof in forming the reporter for detection.

FIGS. 15A-15J are schematic diagrams of assay methods provided herein for detecting nucleic acid analytes, including the formation of analyte-binder complex in solution (FIG. 15A), the capture of the immunocomplex to the first solid surface (FIG. 15B), the release of the immunocomplex from the first surface (FIG. 15C), the recapture of the immunocomplex to the second surface (FIG. 15D), the reporter generation (FIG. 15E); FIGS. 15F-15J illustrate an alternative workflow for nucleic acid detection, including formation of analyte-binder complex in the solution (FIG. 15F), capturing the analyte-binder complex to the first surface (FIG. 15G), release of the analyte-binder complex (FIG. 15H), recapturing the analyte-binder complex to the second surface (FIG. 15I), and the generation of reporter (FIG. 15J).

FIG. 16 is a schematic diagram of an exemplary NULISA immunoassay configuration. As shown, two binders for the analyte are each conjugated with a nucleic acid tag ("CP" and "L", respectively), wherein CP is indirectly coupled to the first solid surface (paramagnetic beads 1) via a universal probe (poly T), and L is indirectly coupled to the second solid surface (paramagnetic beads 2) via streptavidin/biotin binding. After the formation of the immunoassay and the reduction of nonspecific binding via the capture/release mechanism disclosed herein, a nucleic acid reporter of the immunocomplex is formed through the ligation of L, CP's surrogate R (which hybridizes with part of CP) and a short oligo SI service as the Sample ID. The Target ID (TI) is incorporated as a segment of L. Connector (CNT) is a bridging probe deployed for ligation.

Figure 19A:
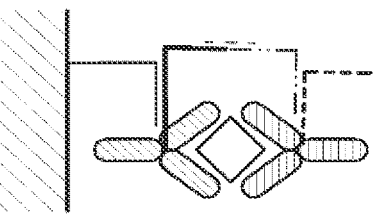
Figure 19B:
Figure 19C:
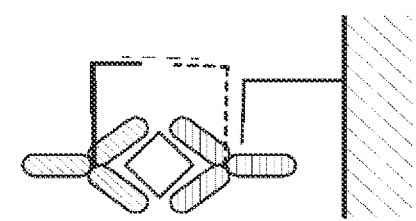
Figure 19D:
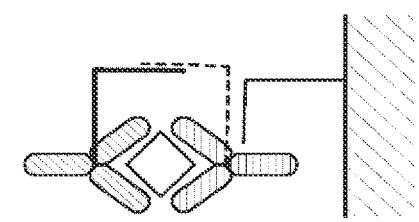
Figure 20E:
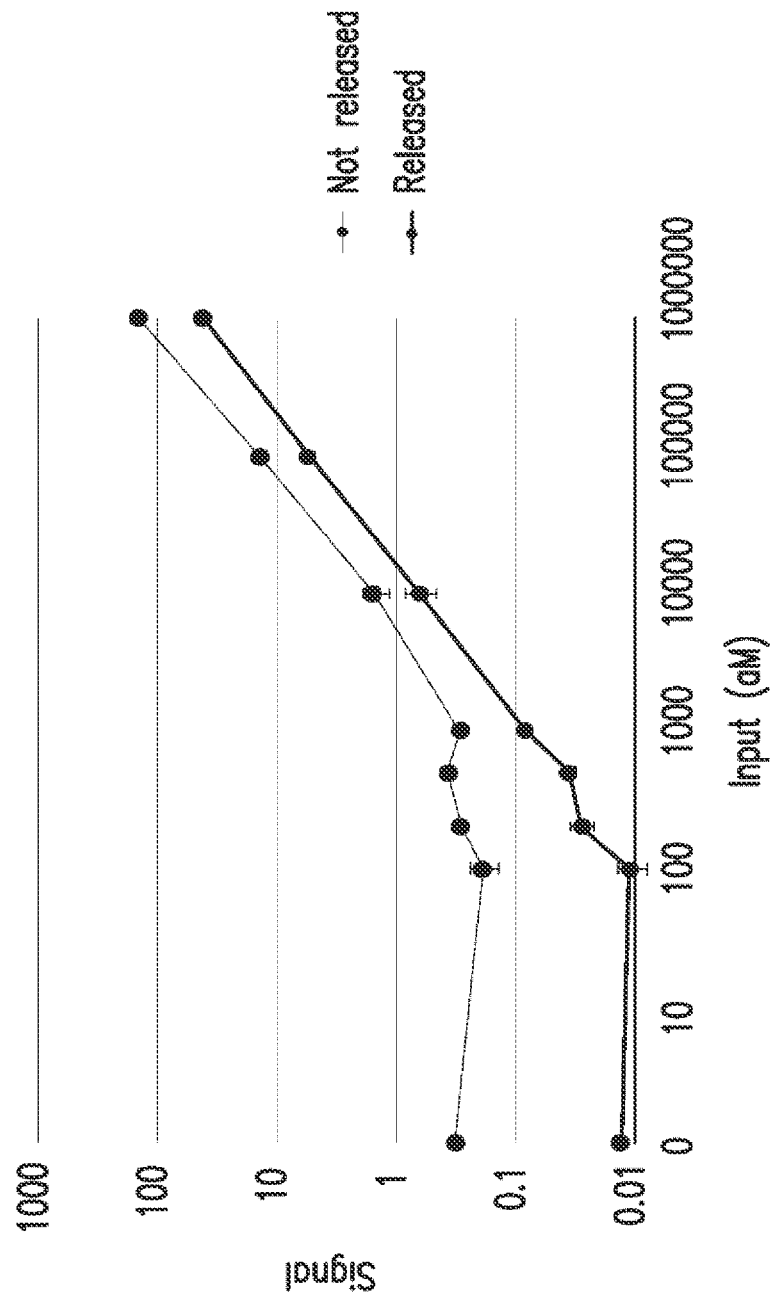

FIGS. 19A-19D illustrates some additional configurations of the nucleic acid linked immunocomplex provided herein FIGS. 20A-20E illustrate a NULISA alternative workflow, including the formation of immunocomplex in the solution (FIG. 20A), capturing the binder 1 to the first solid surface via the first nucleic acid capture probe molecules ("CP1" or the "first probe") (FIG. 20B), releasing of the immunocomplex from the first surface (FIG. 20C), and the generation of a nucleic acid reporter (FIG. 20D), and a comparison of signals generated when the immunocomplex is released to the solution (the right bar in each pair) or not (the left bar in each pair) (FIG. 20E).

Figure 21A:
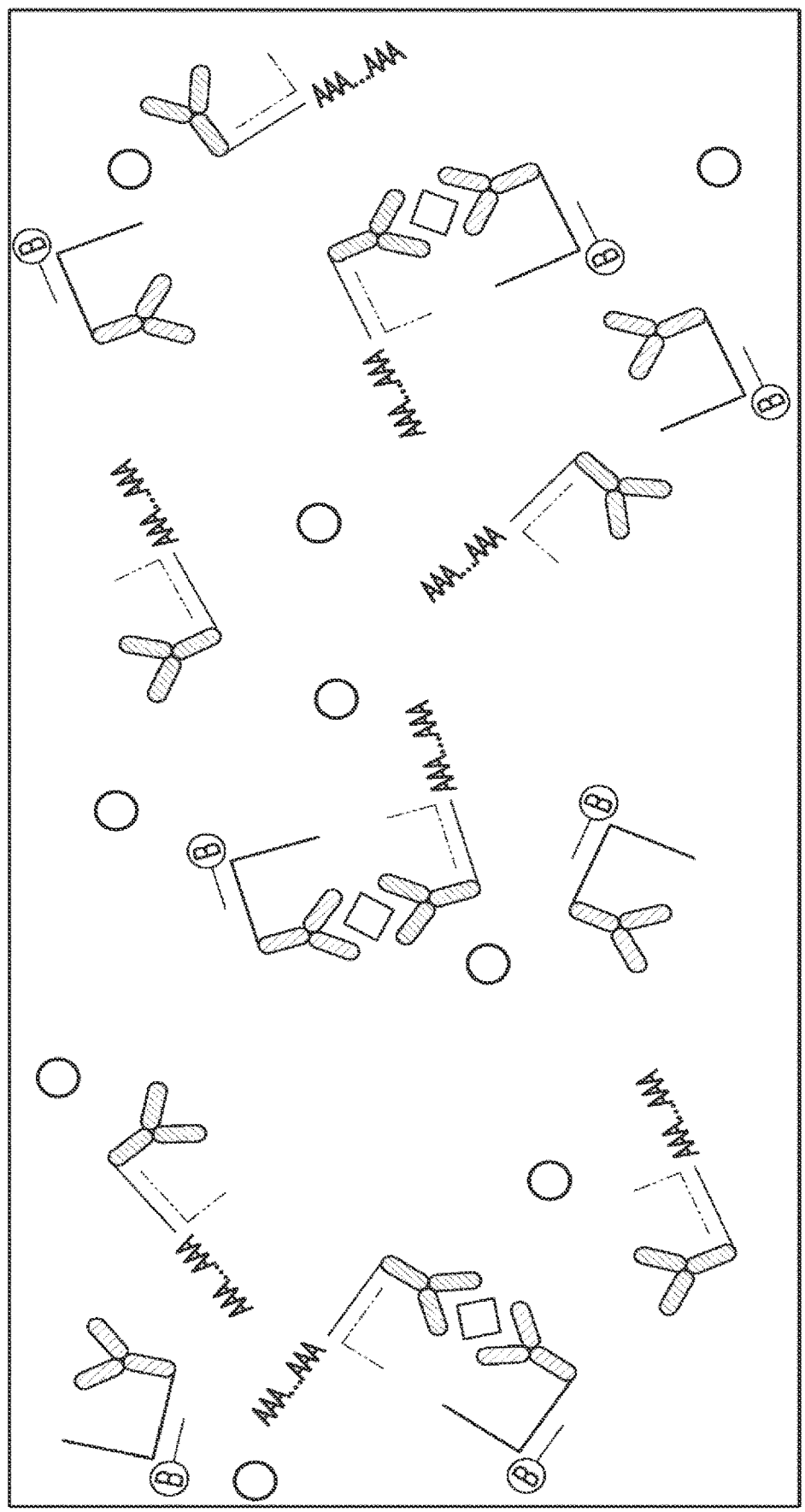
Figure 21B:
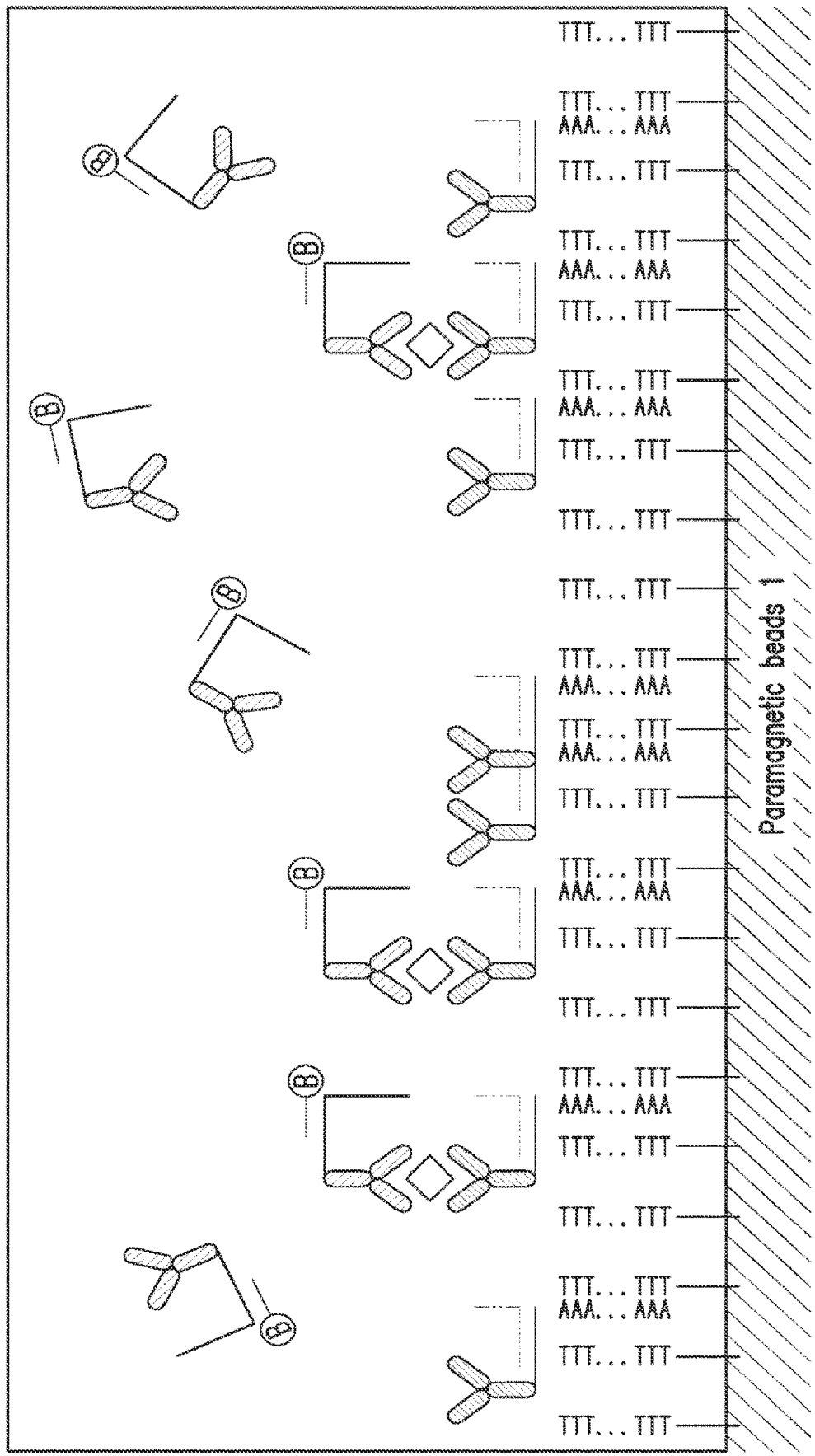
Figure 21C:
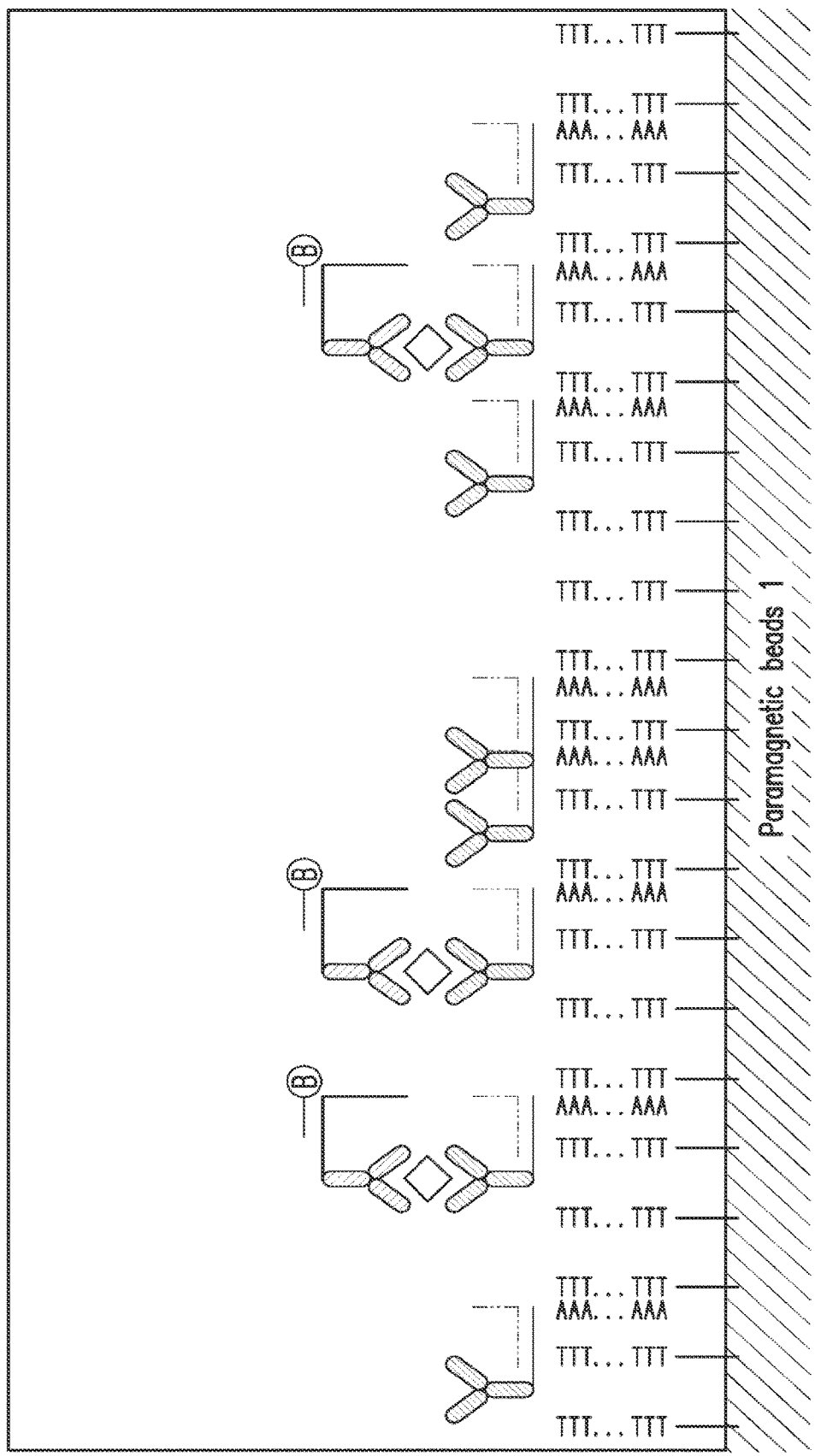
Figure 21D:
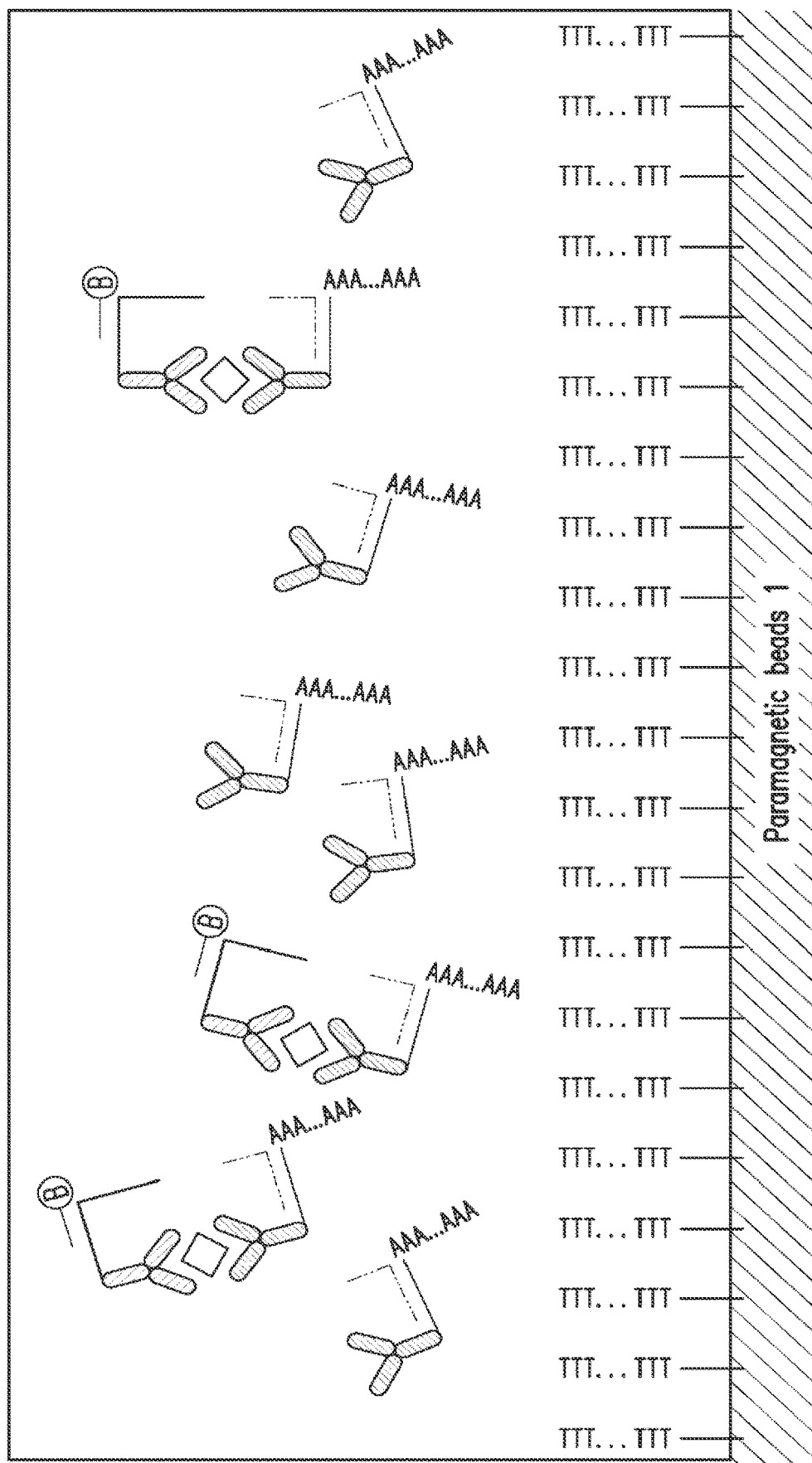
Figure 21E:
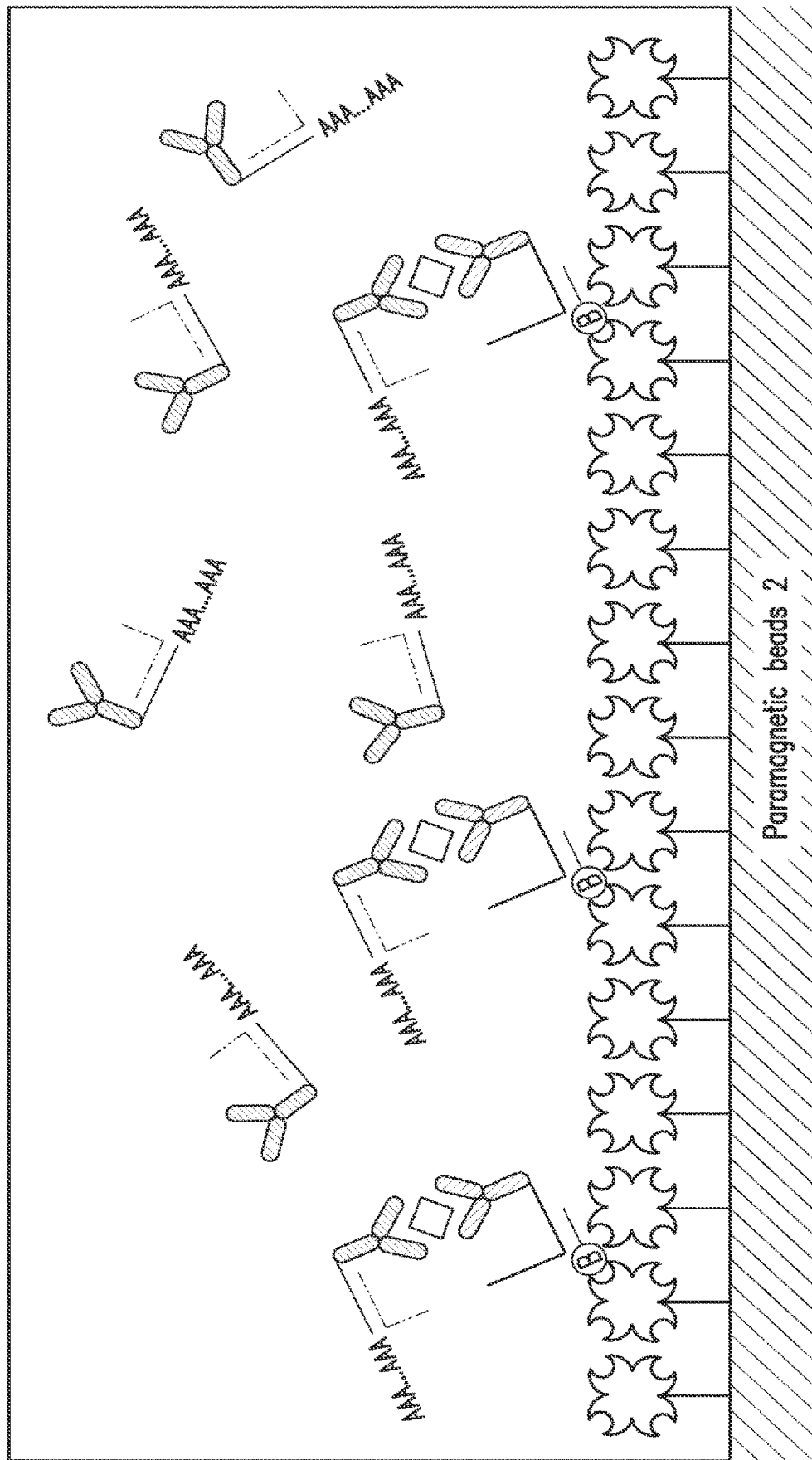
Figure 21F:
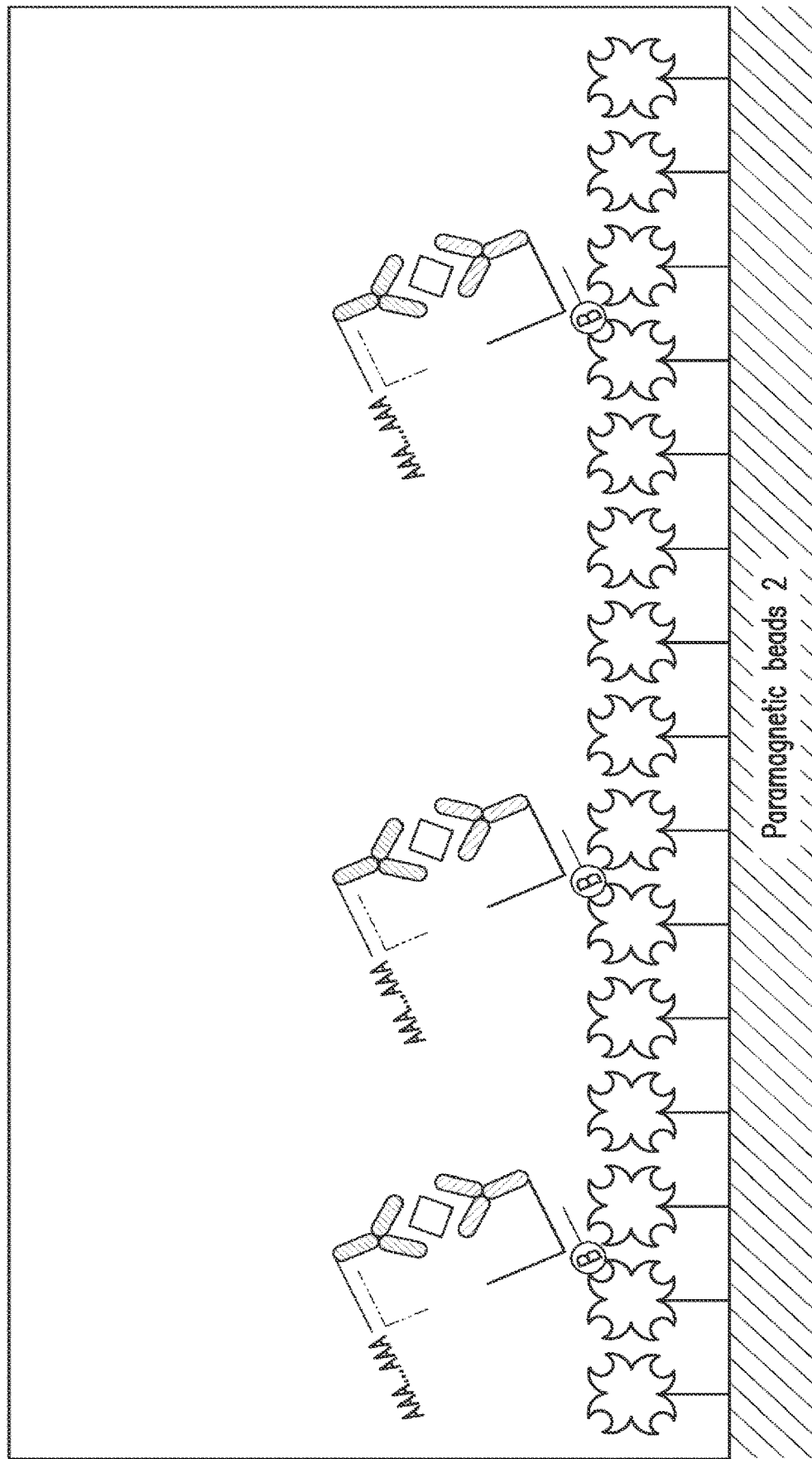
Figure 21G:
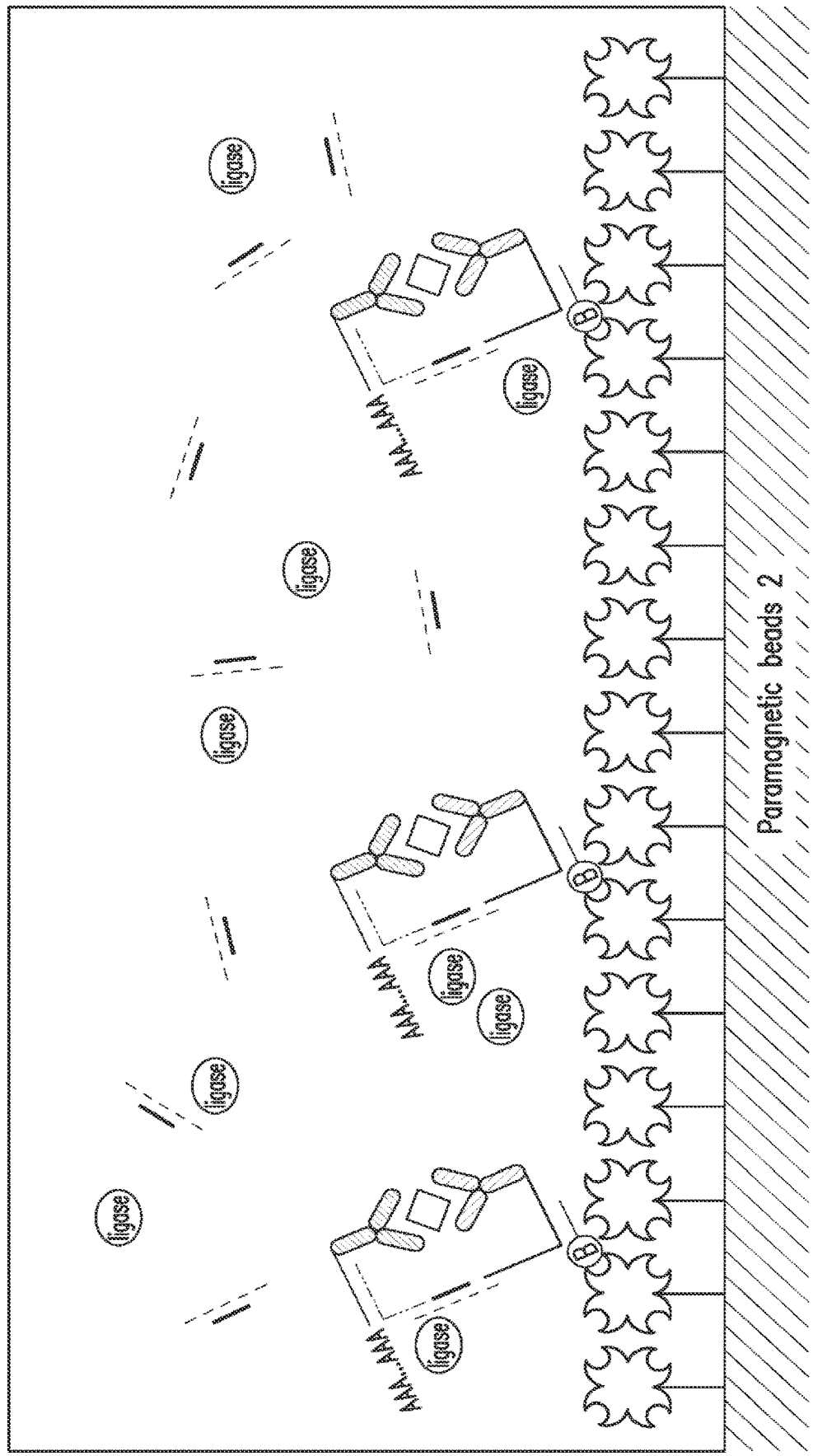
Figure 21H:
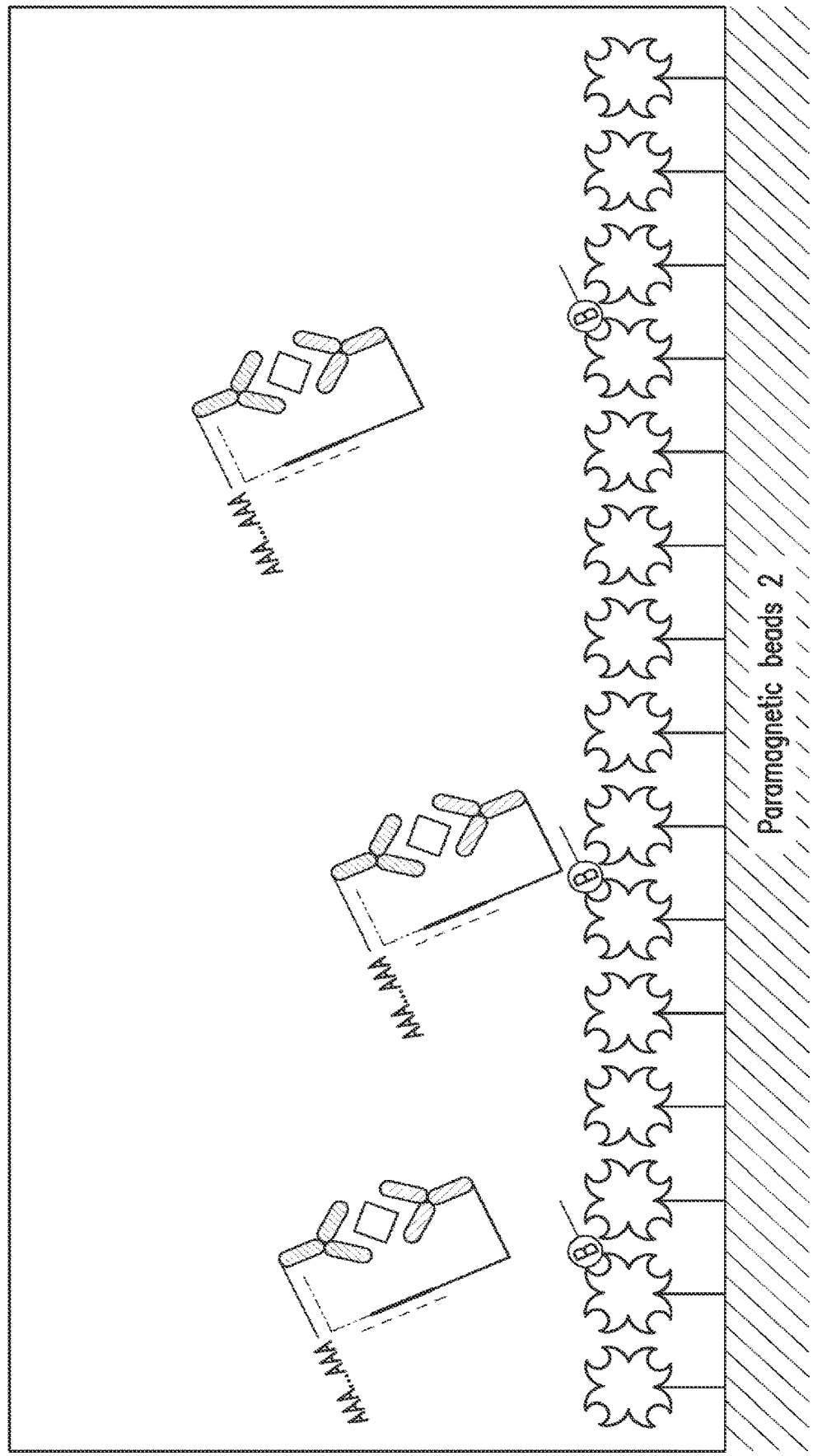
Figure 21I:
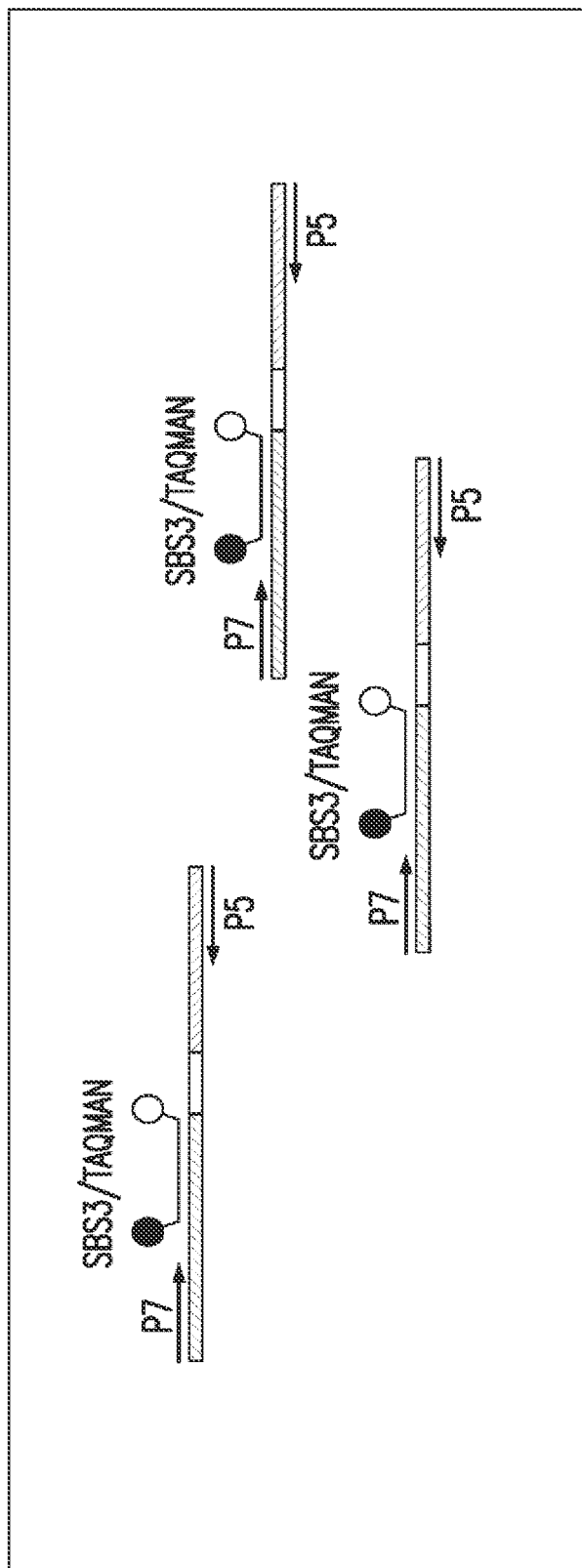

FIGS. 21A-21I illustrate steps of a Multi-plex NULISA, including incubation (FIG. 21A), the capture of immunocomplex to the first solid surface (FIG. 21B), the first wash (FIG. 21C), the release of immunocomplex from the first solid surface (FIG. 21D), the capture of immunocomplex to the second solid surface (FIG. 21E), the second wash (FIG. 21F), binding of the sample label and ligation to generate nucleic acid reporters containing two analyte-specific identity barcodes ("target ID") and one sample-specific identity barcode ("sample ID") (FIG. 21G), final wash and elution (FIG. 21H), and PCR amplification and detection (FIG. 21I). Alternatively, ligation products with Target ID and Sample ID can be pooled for sequencing with or without preamplification.

Figure 22:
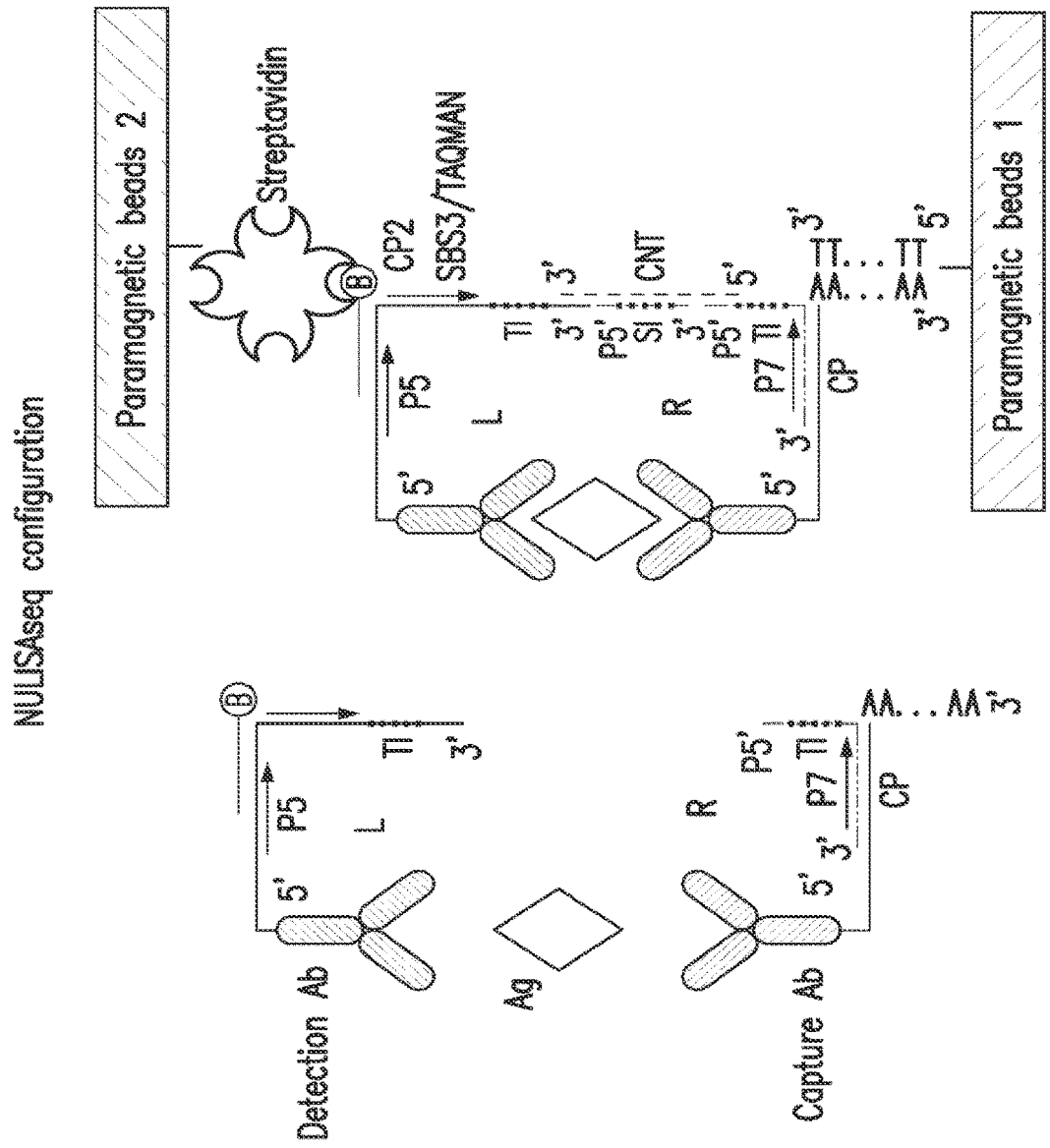

FIG. 22 illustrates an exemplary configuration of NULISAseq. In this configuration, CP can be the first presenting group (first tag), the poly-T coupled to the paramagnetic beads can be the first receiving group (first probe), R can be the first target label comprising the first target ID (TI), L can be the second target label comprising the second target ID (TI), biotinylated CP2 can be the second presenting group, streptavidin can be the second receiving group, and CNT (short for "connector") can be the sample label with a 3' overhang binding to the second target label and a 5' overhang binding to the first target label, SI can be the sample ID within the sample label (CNT), paramagnetic beads 1 can be the first solid surface, and the paramagnetic beads 2 can be the second solid surface.

Figure 23A:
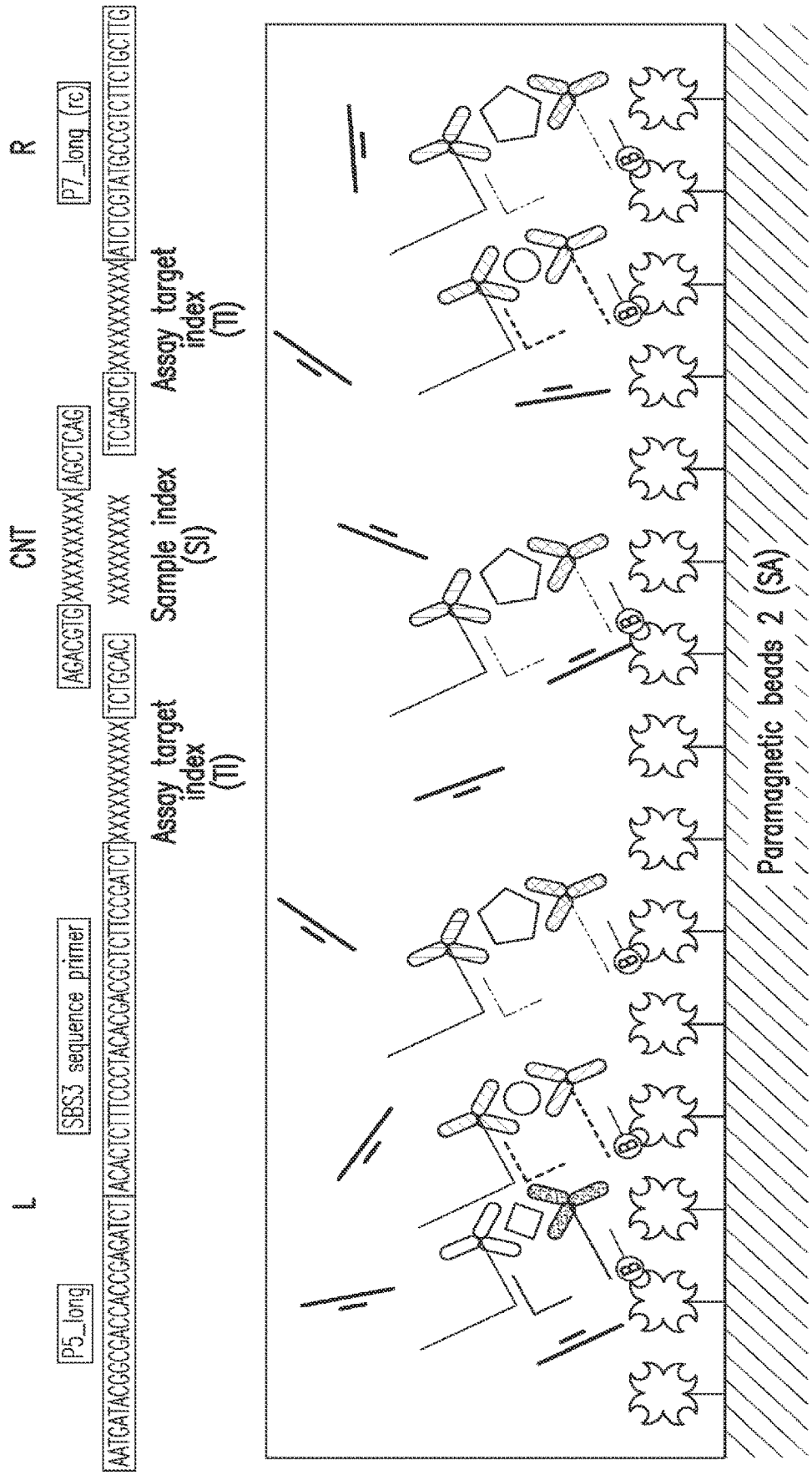
Figure 23B:
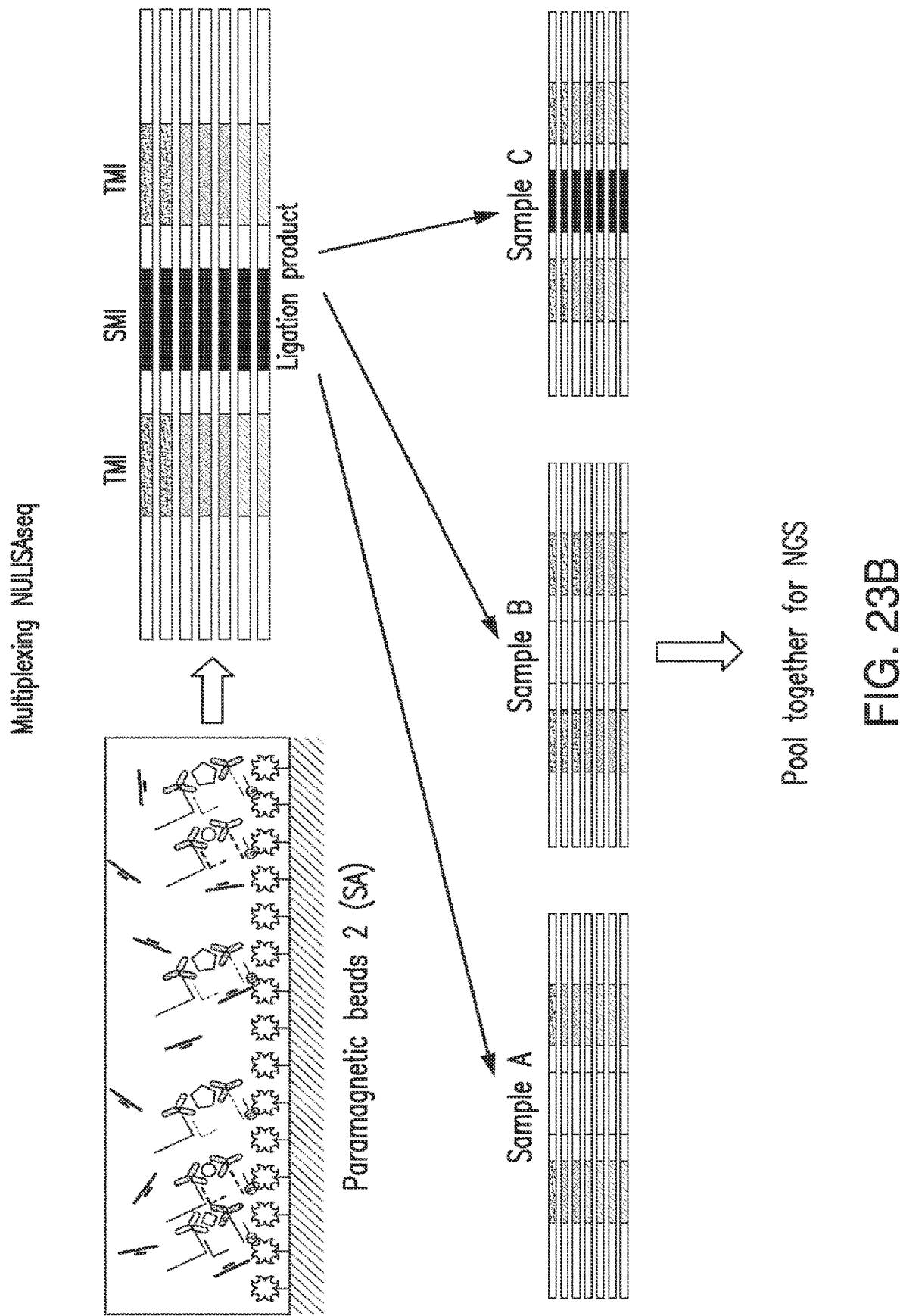

FIGS. 23A-23B illustrate the mechanisms for the high sensitivity and multiplexing of NULISAseq, including (FIG. 23A) an exemplary sequence of a fragment of "L" from FIG. 22, a bridging probe for ligation ("CNT" from FIG. 22), and an exemplary sequence of a fragment of "R" from FIG. 22; and (FIG. 23B) exemplary ligation products for a multiplexing NULISAseq with 3 analytes and 3 samples.

Figure 24A:
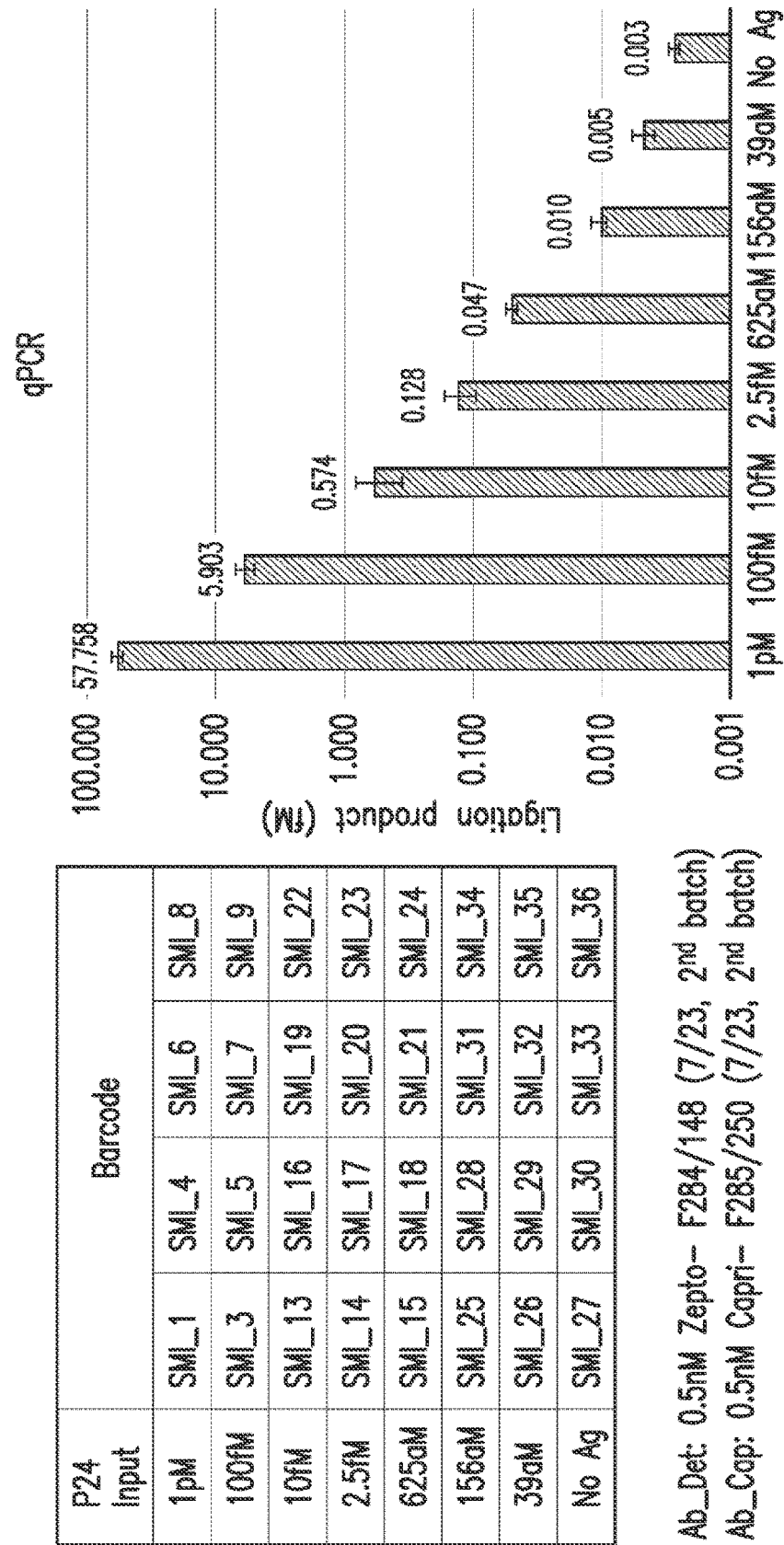
Figure 24B:
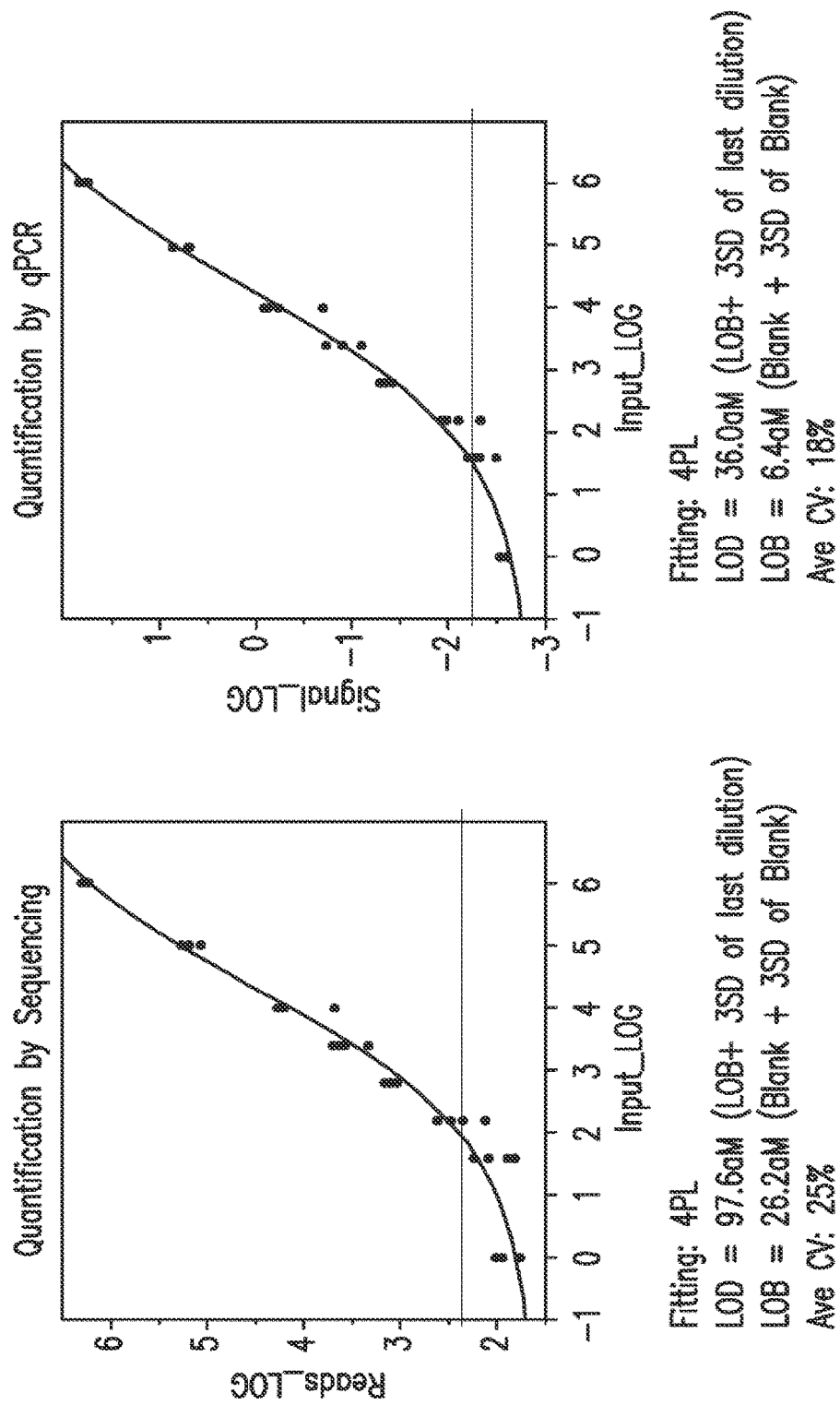

FIGS. 24A-24B illustrate quantification of qPCR and sequencing of an analyte P24, including barcode assignment and qPCR results across different concentrations of P24 (FIG. 24A), and a comparison between quantification by sequencing versus qPCR (FIG. 24B).

Figure 25A:
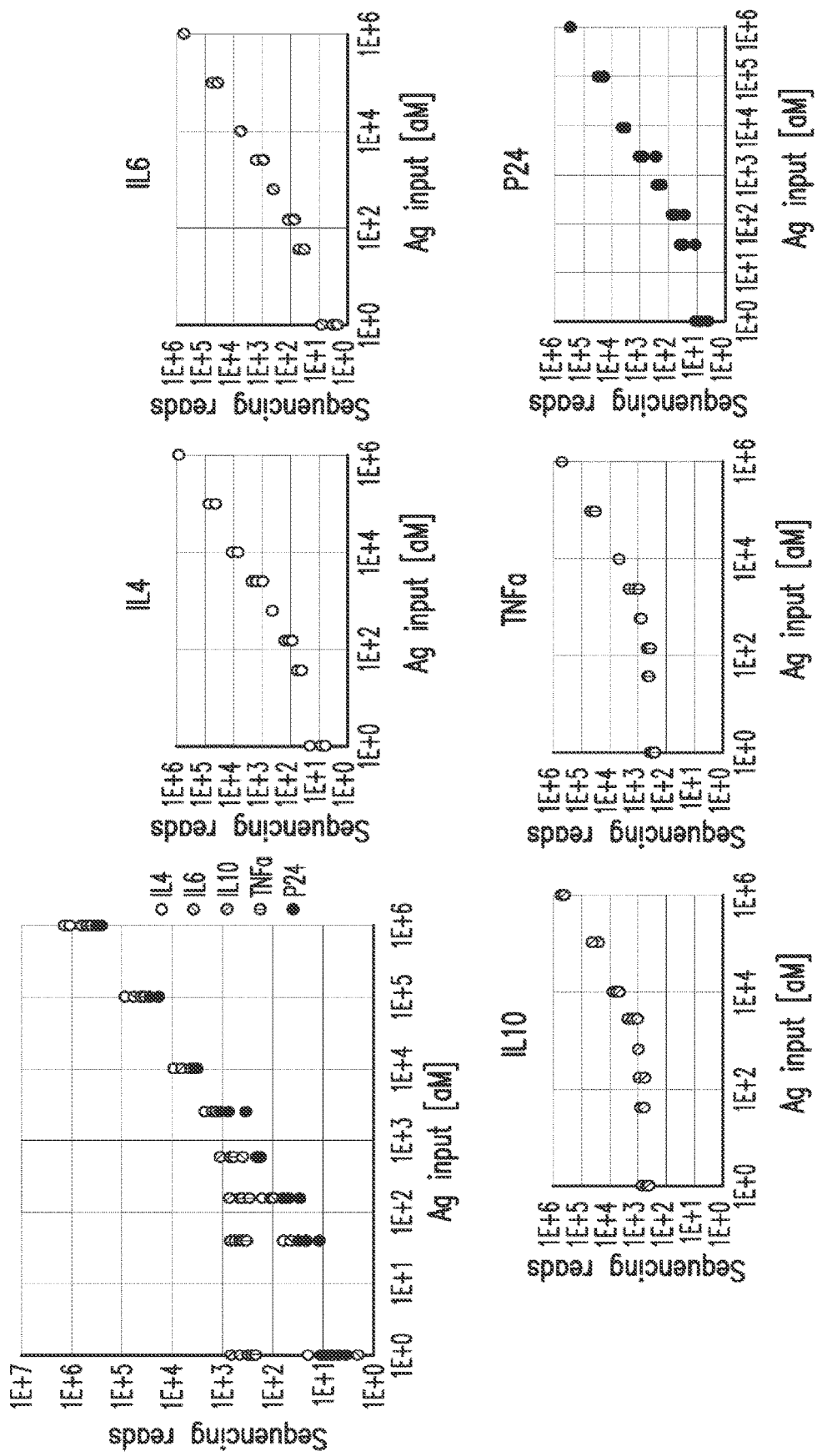
Figure 25B:
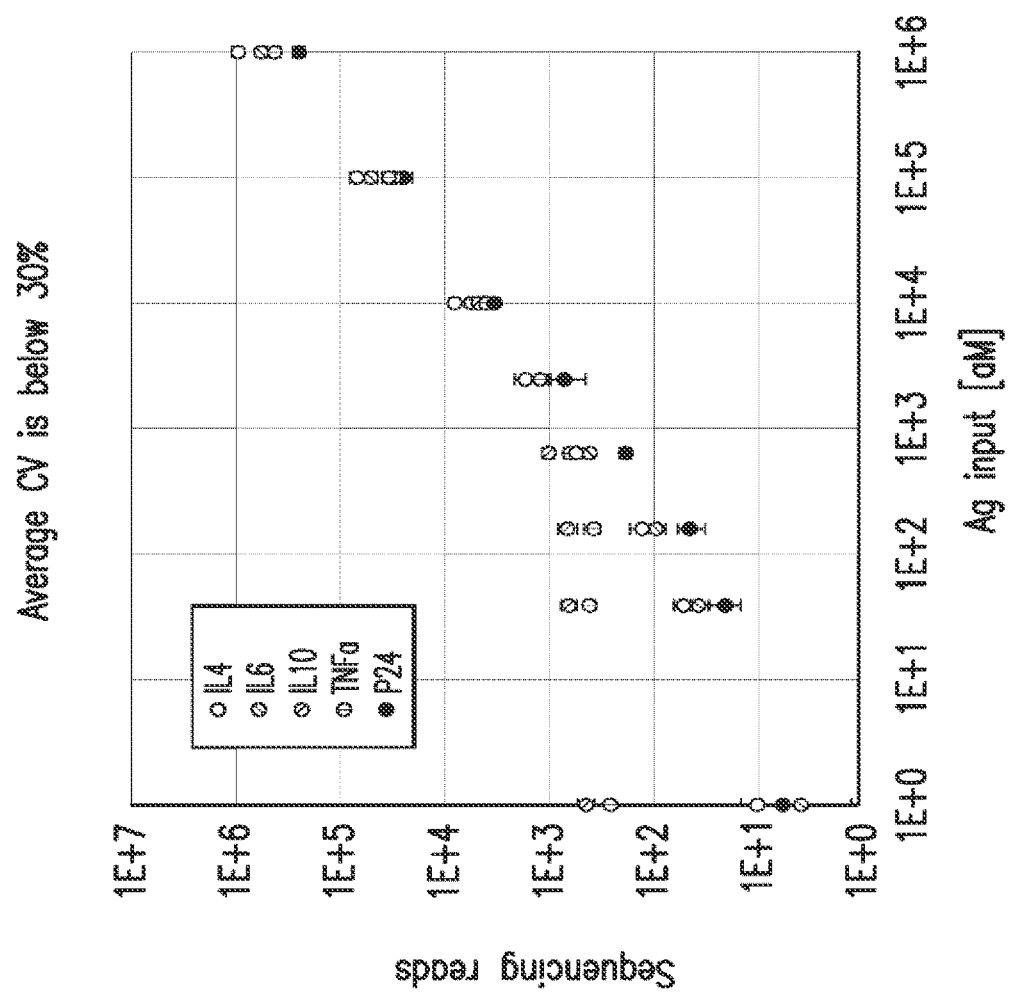
Figure 25C:
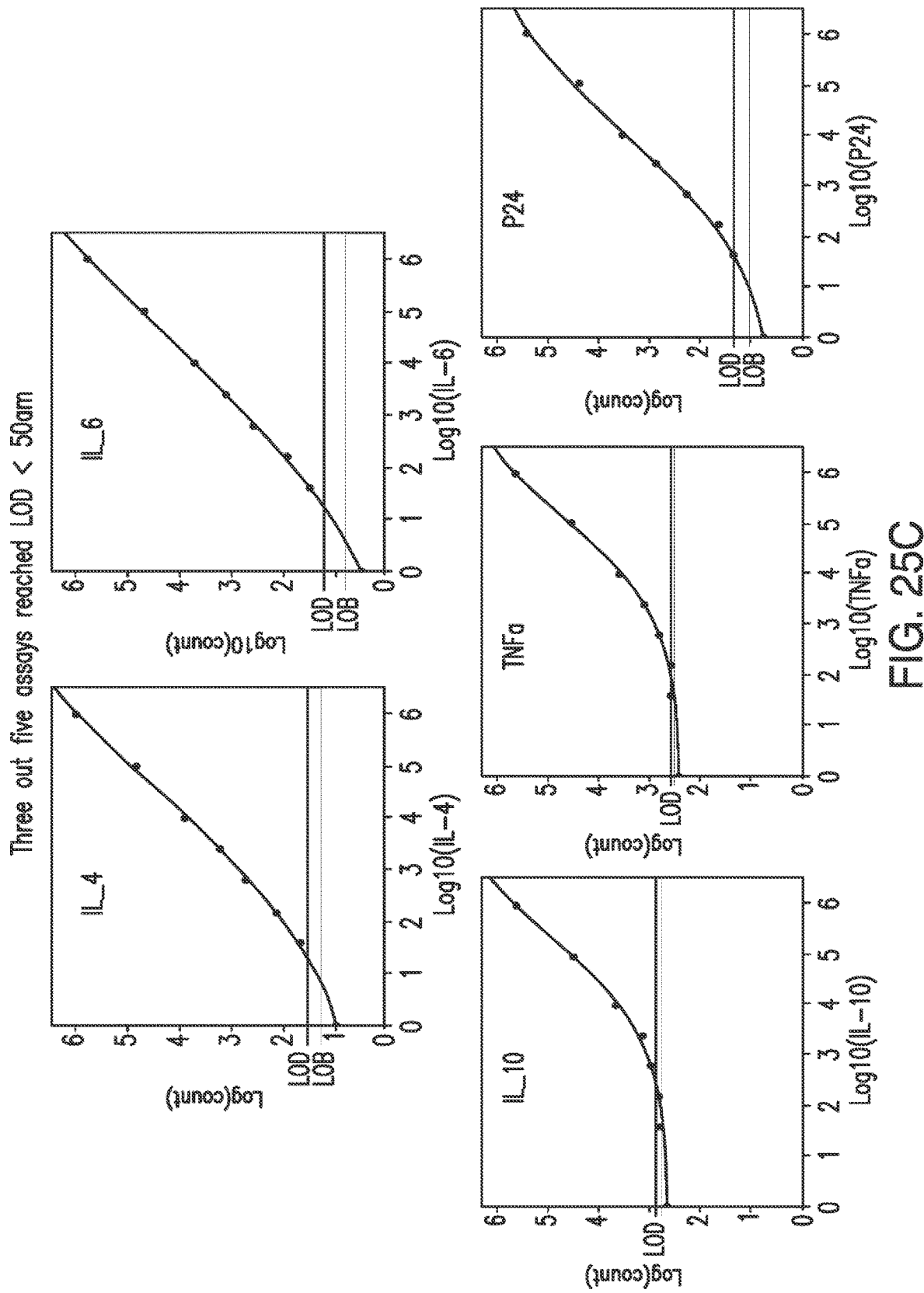

FIGS. 25A-25C illustrate results of a 5-plex NILISAseq, including sequencing results in each of the 5 repeating assays (FIG. 25A), average of coefficient of variation (CV) (FIG. 25B), and limit of detection (LOD) for each assay (FIG. 25C).

5. DETAILED DESCRIPTION

Before the present disclosure is further described, it is to be understood that the disclosure is not limited to the particular embodiments set forth herein, and it is also to be understood that the terminology used herein is for the purpose of describing particular embodiments only, and is not intended to be limiting.

5.1 Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, molecular biology, immunology, genetics and protein and nucleic acid chemistry and hybridization described herein are those well-known and commonly used in the art.

As used herein, the term "detect" or its grammatical equivalents are used broadly to include any means of determining the presence of the analyte (i.e. if it is present or not) or any form of measurement of the analyte. Thus, "detecting" can include determining, measuring, or assessing the presence or absence or amount or location of analyte. Quantitative, semi-quantitative and qualitative determinations, measurements or assessments are included. Such determinations, measurements or assessments can be relative, for example, when two or more different analytes in a sample are being detected, or absolute. As such, the term "quantifying" when used in the context of quantifying a target analyte(s) in a sample can refer to absolute or to relative quantification. Absolute quantification can be accomplished by inclusion of known concentration(s) of one or more control analytes and/or referencing the detected level of the target analyte with known control analytes (e.g., through generation of a standard curve). Alternatively, relative quantification can be accomplished by comparison of detected levels or amounts between two or more different target analytes to provide a relative quantification of each of the two or more different analytes, i.e., relative to each other.

As used herein, the term "analyte" can be any substance (e.g. molecule) or entity to be detected by the assay methods provided herein. The analyte is the target of the assay method provided herein. Accordingly, the analyte can be any biomolecule or chemical compound that need to be detected, for example a peptide or protein, a nucleic acid molecule or a small molecule, including organic and inorganic molecules. The analyte can be a cell or a microorganism, including a virus, or a fragment or product thereof. The analyte can be any substance or entity for which a specific binder can be developed, and which is capable of simultaneously binding at least two "binders." In some embodiments, the analytes are proteins or polypeptides. As such, analytes of interest include proteinaceous molecules such as polypeptides, proteins or prions or any molecule which contains a protein or polypeptide component, or fragments thereof. In some embodiments, the analyte is a wholly or partially proteinaceous molecule. The analyte can also be a single molecule or a complex that contains two or more molecular subunits, which may or may not be covalently bound to one another, and which may be the same or different. Thus, the analyte that can be detected by assay methods described herein can be a complex analyte, which can be a protein complex. Such a complex can thus be a homo- or hetero-multimer. Aggregates of molecules (e.g. proteins) can also be target analytes. The aggregate analytes can be aggregates of the same protein or different proteins. The analyte can also be a complex composed of proteins or peptides, or nucleic acid molecules such as DNA or RNA. In some embodiments, the analyte is a complex composed of both proteins and nucleic acids, e.g. regulatory factors, such as transcription factors.

As used herein, the term "sample" can be any biological and clinical samples, included, e.g. any cell or tissue sample of an organism, or any body fluid or preparation derived therefrom, as well as samples such as cell cultures, cell preparations, cell lysates, etc. Environmental samples, e.g. soil and water samples or food samples are also included. The samples can be freshly prepared or prior-treated in any convenient way (e.g. for storage).

Representative samples thus include any material that contains a biomolecule, or any other desired or target analyte, including, for example, foods and allied products, clinical and environmental samples. The sample can be a biological sample, including viral or cellular materials, including prokaryotic or eukaryotic cells, viruses, bacteriophages, mycoplasmas, protoplasts and organelles. Such biological material comprise all types of mammalian and non-mammalian animal cells, plant cells, algae including blue-green algae, fungi, bacteria, protozoa etc. Representative samples also include whole blood and blood-derived products such as plasma, serum and buffy coat, blood cells, urine, faeces, cerebrospinal fluid or any other body fluids (e.g. respiratory secretions, saliva, milk, etc.), tissues, biopsies, cell cultures, cell suspensions, conditioned media or other samples of cell culture constituents, etc. The sample can be pre-treated in any convenient or desired way to prepare for use in the method disclosed herein. For example, the sample can be treated by cell lysis or purification, isolation of the analyte, etc.

As used herein, the term "bind" or its grammatical equivalents refer to an interaction between molecules (e.g. a binder and an analyte, or a presenting group and a receiving group) to form a complex. Interactions can be, for example, non-covalent interactions including hydrogen bonds, ionic bonds, hydrophobic interactions, and/or van der Waals interactions. A "binder," as used herein in connection with an analyte, is any molecule or entity capable of binding to the analyte. In some embodiments, a binder binds specifically to its target analyte, namely, the binder binds to the target analyte with greater affinity than to other components in the sample. In some embodiments, the binder's binding to the target analyte can be distinguished from that to non-target analytes in that the binder either does not bind to non-target analytes or does so negligibly or non-detectably, or any such non-specific binding, if it occurs, is at a relatively low level that can be distinguished. The binding between the target analyte and its binder is typically non-covalent. The binder used in methods provided herein can be covalently conjugated to a presenting group (e.g. a nucleic acid tag) without substantially abolishing the binding affinity of the binder to its target analyte.

The binder can be selected to have a high binding affinity for a target analyte. In some embodiments, the binder can have a binding affinity to the target analyte of at least about $10^{-4}$ M, at least about $10^{-6}$ M, or at least $10^{-9}$ M or higher. The binder can be a variety of different types of molecules, so long as it exhibits the requisite binding affinity for the target analyte. In other embodiments, the binder can have a medium or even low affinity for its target analyte, e.g., less than about $10^{-4}$ M.

The binder can be a large molecule. In some embodiments, the binders are antibodies, or binding fragments, derivatives or mimetics thereof. Where antibodies are the binder, they can be derived from polyclonal compositions, such that a heterogeneous population of antibodies differing by specificity are each conjugated with the same presenting group, or monoclonal compositions, in which a homogeneous population of identical antibodies that have the same specificity for the target analyte are each conjugated with the same presenting group. As such, the binder can be either a monoclonal or polyclonal antibody.

In some embodiments, the binder is an antibody fragment, derivative or mimetic thereof, where these fragments, derivatives and mimetics have the requisite binding affinity for the target analyte. Such antibody fragments or derivatives generally include at least the $V_H$ and $V_L$ domains of the subject antibodies, so as to retain the binding characteristics of the subject antibodies. In some embodiments, the binder is an antibody fragment that binds the analyte. An antibody fragment as used herein refers to a molecule other than an intact antibody that comprises a portion of an antibody and generally an antigen-binding site. Examples of antibody fragments include, but are not limited to, Fab, Fab', F(ab')2, Fv, single chain antibody molecules (e.g., scFv), disulfide-linked scFv (dsscFv), diabodies, tribodies, tetrabodies, minibodies, dual variable domain antibodies (DVD), single variable domain antibodies (e.g., camelid antibodies, alpaca antibodies), single variable domain of heavy chain antibodies (VHH), and multispecific antibodies formed from antibody fragments. In some embodiments, the binder is an Fab. In some embodiments, the binder is a scFv. In some embodiments, the binder is a single variable domain antibody.

In some embodiments, the binder is an antibody mimetic. An antibody mimetic can be molecules that, like antibodies, can specifically bind antigens, but that are not structurally related to antibodies. The antibody mimetics are usually artificial peptides within a molar mass of about 2 to 20 kDa. Nucleic acids and small molecules are sometimes considered antibody mimetics as well. Antibody mimetics known in the art include affibodies, affilins, affimers, affitins, alphabodies, anticalins, aptamers, avimers, DARPins, Fynomers, Kunitz domain peptides, monobodies, and nanoCLAMPs.

In some embodiments, suitable for use as binders are polynucleic acid aptamers.

Polynucleic acid aptamers can be RNA oligonucleotides which can act to selectively bind proteins, much in the same manner as a receptor or antibody (Conrad et al., Methods Enzymol. (1996), 267(Combinatorial Chemistry), 336-367). The above described antibodies, fragments, derivatives and mimetics thereof can be obtained from commercial sources and/or prepared using any convenient technology, where methods of producing polyclonal antibodies, monoclonal antibodies, fragments, derivatives and mimetics thereof, including recombinant derivatives thereof, are known to those of the skill in the art (e.g. U.S. Pat. Nos. 5,851,829 and 5,965,371).

In addition to antibody-based peptide/polypeptide or protein-based binding domains, the binder can also be a lectin, a soluble cell-surface receptor or derivative thereof, an affibody or any combinatorically derived protein or peptide from phage display or ribosome display or any type of combinatorial peptide or protein library.

The binder can also be a ligand. The ligand binder can have different sizes. In some embodiments, the ligand binder has a size from about 50 to about 10,000 daltons, from about 50 to about 5,000 daltons, or from about 100 to about 1000 daltons. In some embodiments, the ligand binder has a size of about 10,000 daltons or greater in molecular weight.

In some embodiments, the binder is a small molecule that is capable of binding with the requisite affinity to the target analyte. The small molecule can be a small organic molecule. The small molecule can include one or more functional groups necessary for structural interaction with the target analyte, e.g. groups necessary for hydrophobic, hydrophilic, electrostatic or even covalent interactions. Where the target analyte is a protein, the small molecule binder can include functional groups necessary for structural interaction with proteins, such as hydrogen bonding, hydrophobic-hydrophobic interactions, electrostatic interactions, etc., and typically include at least an amine, amide, sulfhydryl, carbonyl, hydroxyl or carboxyl group. In some embodiments, at least two of the functional groups are included. The small molecule binder can also comprise a region that can be modified and/or participate in covalent linkage to a presenting group (e.g. a nucleic acid tag), without substantially adversely affecting the small molecules ability to bind to its target analyte.

Small molecule binders can also comprise cyclical carbon or heterocyclic structures and/or aromatic or polyaromatic structures substituted with one or more of the above functional groups. Small molecule binders can also contain structures found among biomolecules, including peptides, saccharides, fatty acids, steroids, purines, pyrimidines, derivatives, structural analogs or combinations thereof. Such compounds can be screened to identify those of interest. A variety of different screening protocols are known in the art.

The small molecule binder can also be derived from a naturally occurring or synthetic compound that can be obtained from a wide variety of sources, including libraries of synthetic or natural compounds. For example, numerous means are available for random and directed synthesis of a wide variety of organic compounds and biomolecules. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known small molecules can be subjected to directed or random chemical modifications, such as acylation, alkylation, esterification, amidification, etc., to produce structural analogs. As such, the small molecule binders can be obtained from a library of naturally occurring or synthetic molecules, including a library of compounds produced through combinatorial means, i.e. a compound diversity combinatorial library. When obtained from such libraries, the small molecule binders are selected for demonstrating some desirable affinity for the protein target in a convenient binding affinity assay.

The assay methods provided herein use a first binder and a second binder that bind non-interfering "epitopes" of an analyte. An epitope of an analyte, as understood in the art, refers to a site on the surface of an analyte to which a binder binds. An epitope can be a localized region on the surface of an analyte. An epitope can consist of chemically active surface groupings of molecules such as amino acids or sugar side chains. An epitope can have specific three dimensional structural characteristics and specific charge characteristics. An epitope can be a continuous fragment of the analyte molecule. An epitope can also be a molecule having more than one non-continuous fragments of the antigen linked together. If the analyte is a polypeptide or a protein, its epitope can include continuous or non-continuous sequence along the primary sequence of the polypeptide chain. In some embodiments, the first and the second binders used in the assay methods disclosed herein are of the same type of molecule. For example, the first and second binders can both be monoclonal antibodies that bind non-interfering epitopes of the analyte. In some embodiments, the first and the second binders can be different. For example, the first binder can be an antibody, and the second binder can be a small molecule.

The term "binding moiety," when used in reference to an analyte, refers to a moiety including a molecule or a collection of more than one molecules, such that the moiety as a whole is capable of binding specifically to an analyte. The binding moiety can include one or more binder, one or more target label, one or more sample label, and/or one or more presenting group. The binding moiety can also include a binder, a target label, a sample label, and/or a presenting group. Alternatively, the binding moiety can include a binder, a target label, and/or a presenting group. The molecules in the binding moiety can be held together as a moiety by covalent, non-covalent, or a combination of covalent or non-covalent intermolecular interactions. Alternatively, the molecules in the binding moiety can be held together via interactions with a molecule that is not part of the binding moiety, for example the analyte or one or more receiving groups. Additionally, the molecules in the binding moiety can be held together as a moiety via (i) intermolecular interactions among the molecules within the binding moiety and (ii) via interactions with a molecule that is not part of the binding moiety, for example the analyte or one or more receiving groups. In one embodiment, the binding moiety comprises or consists of a binder. In some embodiments, the binding moiety comprises or consists of a target label. In certain embodiments, the binding moiety comprises or consists of a presenting group. In other embodiments, the binding moiety comprises or consists of a sample label. In one embodiment, the binding moiety comprises or consists of a binder and a target label. In some embodiments, the binding moiety comprises or consists of a binder and a presenting group. In certain embodiments, the binding moiety comprises or consists of a binder and a sample label. In further embodiments, the binding moiety comprises or consists of a target label and a presenting group. In one embodiment, the binding moiety comprises or consists of a target label and a sample label. In other embodiments, the binding moiety comprises or consists of a presenting group and a sample label. In yet other embodiments, the binding moiety comprises or consists of a binder, a target label, and a presenting group. In some embodiments, the binding moiety comprises or consists of a binder, a target label and a sample label. In certain embodiments, the binding moiety comprises or consists of a binder, a presenting group and a sample label. In some embodiments, the binding moiety comprises or consists of a target label, a presenting group and a sample label. In other embodiments, the binding moiety comprises or consists of a binder, a target label, a presenting group, and a sample label. In some embodiments, the binding moiety comprises or consists of any one of a binder, a target label, a presenting group, and a sample label. In some embodiments, the binding moiety comprises or consists of any two of a binder, a target label, a presenting group, and a sample label, in any combination or permutation. In some embodiments, the binding moiety comprises or consists of any three of a binder, a target label, a presenting group, and a sample label, in any combination or permutation. In some embodiments, the binding moiety comprises or consists of all four of a binder, a target label, a presenting group, and a sample label.

The terms "presenting group" and "receiving group" are used herein in reference to each other, which refer to a binding pair that can form, a complex under appropriate conditions. As used in the assay methods disclosed herein, presenting groups can be conjugated to binders for the target analyte, and receiving groups can be coupled to a solid surface. Therefore, the binding between presenting group and receiving group allows the analyte to be captured on the solid surface. In some embodiments, the bond formed between the presenting group and receiving group is "releasable," allowing the captured binder to be released from the solid surface. In some embodiments, the bond formed between the presenting group and receiving group is "renewable," allowing the binder to be recaptured to another solid surface coupled with the same receiving group. Same as the binding pair of a "binder" and its "analyte" discussed above, the binding pair of "presenting group" and "receiving group" can take a variety of forms. Examples of binding pairs of "presenting groups" and "receiving groups" include, but are not limited to, an antigen and an antibody against the antigen (including its fragments, derivatives or mimetics), a ligand and its receptor, complementary strands of nucleic acids, biotin and avidin (or streptavidin or neutravidin), lectin and carbohydrates, and vice versa. Additional binding pairs of "presenting groups" and "receiving groups" include fluorescein and anti-fluorescein, digioxigenin/anti-digioxigenin, and DNP (dinitrophenol)/anti-DNP, and vice versa. In some embodiments, binding pairs of "presenting groups" and "receiving groups" are complementary strands of nucleic acids, and are referred to as "tags" and "probes." In some embodiments, binding pairs of "presenting groups" and "receiving groups" are antigens and antibodies, or antigens and antibody fragments.

The term "target label" refers to a moiety that facilitates detection and identification of a target molecule. The term "sample label" refers to a moiety that facilitates detection and identification of sample origin of the target. Suitable labels for target label and sample label include labels that can provide identifiers that can be correlated with the particular target or sample. A common label that can be used for target label and/or sample label in the context of the present disclosure is sequences of nucleotides which can be correlated with the target or sample via sequencing. In some embodiments, a target label comprises a target ID. In certain embodiments, a target label consists of a target ID. In other embodiments, the target label is the target ID. In some embodiments, a sample label comprises a sample ID. In certain embodiments, a sample label consists of a sample ID. In other embodiments, the sample label is the sample ID. Additional labels suitable for target label and sample label of the present disclosure include other identifiable or correlative information containing molecules, such as fluorescent molecules or the combination or sequences of fluorescent molecules, and/or colorimetric moieties or the combination or sequences of colorimetric moieties. Other labels contemplated for the present disclosure include luminescent, light-scattering, radionuclides, substrates, cofactors, inhibitors, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Many labels are commercially available and can be used in the context of the invention.

The term "identity barcode" or "ID," when used in reference with target or sample, refers to a molecule or a series of molecules that can be used to identify, directly or indirectly through the identification information contained in the molecule or the series of the molecules, the target or the sample. Such an ID can be a nucleic acid molecule with a given sequence, a unique fluorescent label, a unique colorimetric label, a sequence of the fluorescent labels, a sequence of the colorimetric label, or any other molecules or combination of molecules, so long as molecules or the combination of molecules used as IDs can identify or otherwise distinguish a particular target or sample from other targets or samples and be correlated with the intended target or sample. Nucleic acid molecules used as such IDs are also known as barcode sequences. Such an ID can also be a further derivative molecule that contains the information derived from but is non-identical to the original ID, so long as such derived molecules or the derived information can identify or otherwise distinguish a particular target or sample from other targets or samples and be correlated with the intended target or sample. For example, a nucleic acid ID can include both the original nucleic acid barcode sequence and/or the reverse complement of the original nucleic acid barcode sequence, as both can distinguish and be correlated with the intended target or sample. The barcode sequence can be any sequences, natural or non-natural, that are not present without being introduced as barcode sequences in the intended sample, the intended target, or any part of the intended sample or target, so that the barcode sequence can identify and be correlated with the sample or target. A barcode sequence can be unique to a single nucleic acid species in a population or a barcode sequence can be shared by several different nucleic acid species in a population. Each nucleic acid probe in a population can include different barcode sequences from all other nucleic acid probes in the population. Alternatively, each nucleic acid probe in a population can include different barcode sequences from some or most other nucleic acid probes in a population. For a specific example, all the reporters generated from immunocomplexes from one sample can have the same sample barcode sequence (sample ID). For another example, all the reporters generated from immunocomplexes from the same sample can have different target barcode sequences (target IDs). Furthermore, all the reporters generated from immunocomplexes from the same sample, for the same target, and with the same binders can have the same target barcode sequences (target IDs).

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

5.2 Immunoassays

Provided herein are assay methods that address the limitations of existing immunoassays and enable single molecule detection of immunocomplex through nucleic acid-based signal amplification. The methods provided herein reduce background signal through a capture-and-release mechanism. Accordingly, provided herein are assay methods for detecting an analyte in a sample comprising the capture-and-release mechanism. In some embodiments, the capture-and-release mechanism is based on the hybridization and dissociation of nucleic acid pairs.

5.2.1 Capture-and-Release Mechanisms

Assay methods provided herein use a capture-and-release mechanism to reduce non-specific background signals. The processes of capturing the immunocomplex onto solid surface and releasing it back to solution can be applied to different assay formats as disclosed herein (e.g. FIGS. 4A-4D and FIGS. 8A-8D).

5.2.1.1 Capture-and-Release with Two Capture Binders

Figure 4A:
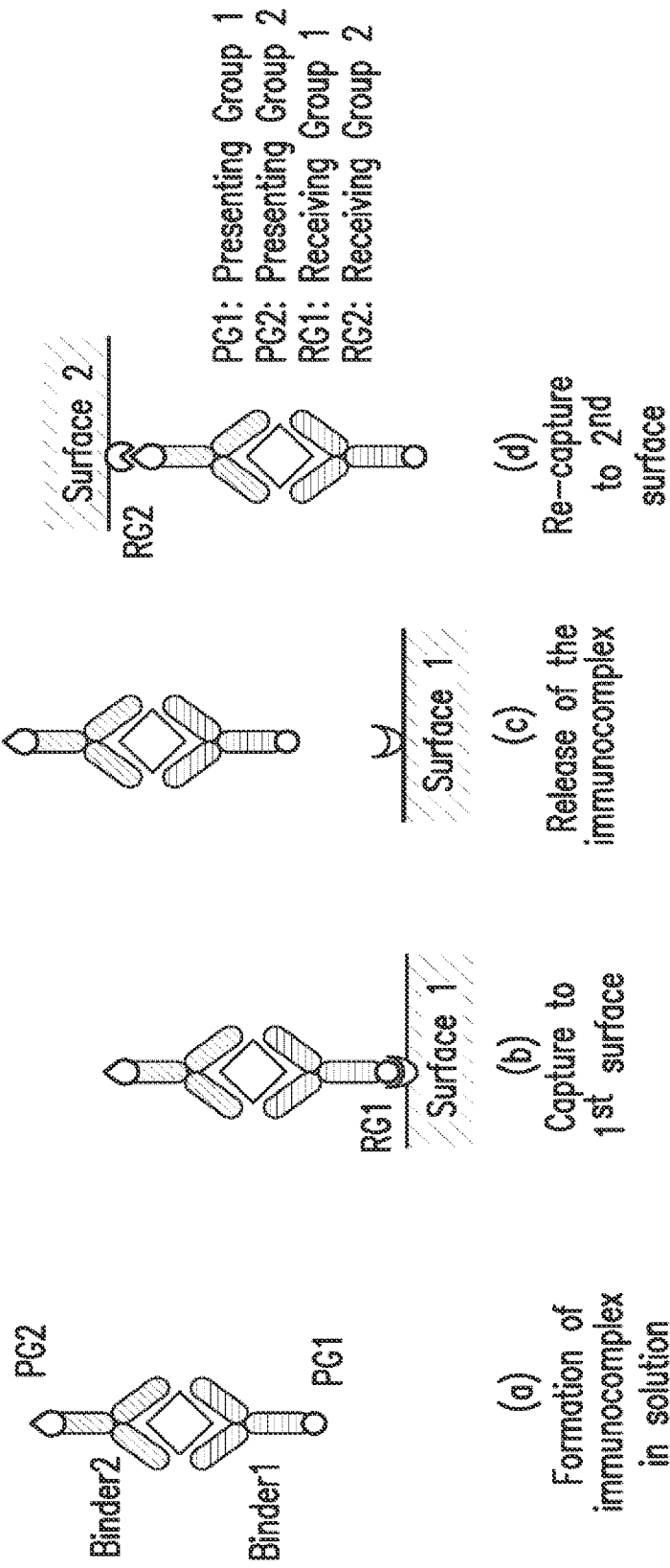
Figures 8A, 8B:
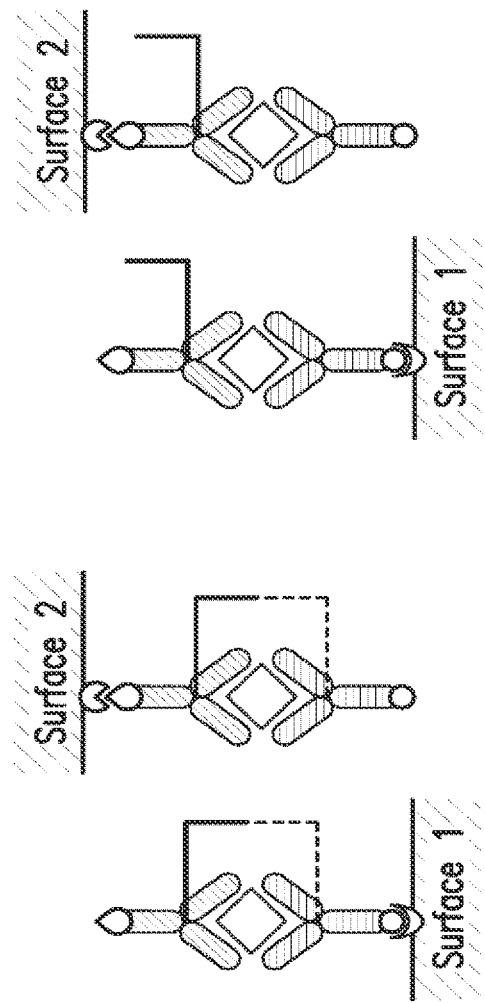

In some embodiments, as depicted in FIGS. 4A, 8A, and 8B, assay methods provided herein use a capture-and-release mechanism that involves two binders, which can be captured by two receiving groups on two solid surfaces, respectively. In some embodiments, provided herein are assay methods for detecting an analyte in a sample comprising the following steps:
(1) mixing a first binder, a second binder, and the sample in a solution, wherein the first and second binders bind non-interfering epitopes on the analyte and form an immunocomplex, and wherein the immunocomplex is captured on a first solid surface in contact with the solution via binding between a first presenting group conjugated to the first binder and a first receiving group coupled to the first surface;
(2) washing the first solid surface to remove unbound molecules;
(3) releasing the immunocomplex from the first solid surface by disrupting the binding between the first presenting group and the first receiving group;
(4) introducing a second solid surface and recapturing the immunocomplex via binding between a second presenting group conjugated to the second binder and the second receiving group coupled to the second solid surface;
(5) washing the second solid surface to remove unbound molecules; and
(6) detecting the immunocomplex.

In FIGS. 4A, 8A and 8B, the capture/release of the first binder ("Binder 1") to/from the first solid surface ("Surface 1") and the capture/release of the second binder ("Binder 2") to/from the second solid surface ("Surface 2") are achieved through two bonds between the presenting groups ("PG") and the receiving groups ("RG") that are bio-orthogonal (i.e. each independent and specific). The bond between the first Presenting Group ("PG1") and the first Receiving Group ("RG1"), namely, the first bond ("Bond 1"), is releasable. In some embodiments, the bond between the second Presenting Group ("PG2") and the second Receiving Group ("RG2"), namely, the second bond ("Bond 2"), is also releasable, and the immunocomplex can be detected either on Surface 2, or after being released from Surface 2. In some embodiments, Bond 2 is not releasable, and the immunocomplex can be detected on Surface 2.

As a person of ordinary skill in the art would understand, additional round(s) of capture/release would further reduce nonspecific background signal. In some embodiments, Bond 1 is renewable, and at least one additional round of capture/release can be performed via Binder 1. Specifically, the immunocomplex released from Surface 2 can be recaptured by a new Surface 1 by forming another bond between PG1 on Binder 1 and RG1 on the new Surface 1. In some embodiments, Bond 2 is renewable, and at least one additional round of capture/release can be performed via Binder 2. Specifically, the immunocomplex released from either Surface 1 or Surface 2 can be recaptured by a new Surface 2 by forming another bond between PG2 on Binder 2 and RG2 on the new Surface 2. In some embodiments, both Bond 1 and Bond 2 are renewable, and more than one cycle of recapture can be performed Bond 1, Bond 2, or both. In some embodiments, neither Bond 1 nor Bond 2 is renewable, and only one cycle of capture/release is performed.

Accordingly, in some embodiments, assay methods provided herein further comprise at least one additional cycle of recapture between steps (5) and (6), comprising: releasing the immunocomplex from the solid surface that it is captured on, recapturing the immunocomplex on an additional solid surface coupled with the first receiving group, and washing the additional solid surface to remove unbound molecules. In some embodiments, assay methods provided herein further comprise at least one additional cycle of recapture between steps (5) and (6), comprising: releasing the immunocomplex from the solid surface that it is captured on, recapturing the immunocomplex on an additional solid surface coupled with the second receiving group, and washing the additional solid surface to remove unbound molecules. Additional cycles of recapture can be included.

Releasable bond can be achieved through many different approaches known by an artisan in the field of protein immobilization. For example, in some embodiments, the releasable bond is an attachment via thioester groups (e.g. U.S. Pat. No. 4,284,553). In some embodiments, the releasable bond is a cleavable bond (e.g. Leriche, *Bioorganic & Med. Chem.* 20(2): 571-581 (2012)). In some embodiments, the releasable bond is disulfide linkages (e.g. Chan, *Biochemistry* 15 (19): 4215-4222 (1976)). In some embodiments, the releasable bond is photocleavable linkages (e.g. Photo-cleavable spacer, available at Integrated DNA Technologies, Inc.; Wan, *PLOS ONE* 13(2): e0191987 (2018)). In some embodiments, the releasable bond is a linkage that can be cleaved with appropriate enzymatic activities, including for example, phosphodiester, phospholipid, ester or b-galactose. In some embodiments, the releasable bond is a linkage that can be cleaved by chemoenzymatic reactions, such as Staphy-eSrtA pair (e.g. Ham et al., *Nature Communications*

7:11140 (2016)), and others (Rabuka, *Curr. Opin. Chem. Biol.* 14, 790-796 (2010); Rashidian, *J. Am. Chem. Soc.* 134:8455-8467 (2012)), Kosa, *Nat. Methods* 9, 981-984 (2012)). In some embodiments, the releasable bond is formed between arginine residues and a sorbent derivatized with 4-(oxoacetyl) phenoxyacetic acid (e.g. Duerksen-Hughes, *Biochemistry*, 28 (21):8530-6 (1989)). In some embodiments, the releasable bond is noncovalent bonds disrupted through binding competition (e.g. Nguyen, *Biomol. Eng.* 22 (2005) 147-150). Renewable bond can also be achieved through many different approaches known by an artisan in the field of protein immobilization. For example, noncovalent bonds, including hydrogen bonds, formed between binding pairs (e.g. antigen and antibody, ligand and receptor, complementary nucleic acids, etc.) can be renewable. The releasable and renewable bond can also be achieved through, for example, use of metal-affinity (e.g. Cheung, *Appl. Microbiol. Biotechnol.* 96, 1411-1420 (2012)), N-halamine structures (e.g. Hui, *Biomacromolecules* 14 585-601 (2013)), or disulfide bonds (e.g. Boitieux, *Anal. Chim. Acta* 197: 229-237 (1987)).

In some embodiments, in step (3), the immunocomplex is released from the first solid surface via binding competition by adding an excessive amount of either free first presenting group or free first receiving group to the solution. A "free" presenting group refers to a presenting group that is unconjugated to a binder. A "free" receiving group refers to a receiving group that is uncoupled to a solid surface.

In some embodiments, the releasable and renewable bond is formed via nucleic acid hybridization, wherein the presenting group and the receiving group include nucleic acids that are complementary to each other. In some embodiments, the presenting group is a nucleic acid, which can bind a receiving group that is a DNA/RNA specific protein or aptamer binding partner (e.g. U.S. Pat. No. 5,312,730). In some embodiments, the receiving group is a nucleic acid, which can bind a presenting group that is a DNA/RNA specific protein or aptamer binding partner.

In some embodiments, the first presenting group is a first nucleic acid tag (the "first tag") and the first receiving group is a first nucleic acid capture probe (the "first probe"), wherein the first probe or a fragment thereof is complementary to the first tag or a fragment thereof. In some embodiments, the second presenting group is a second nucleic acid tag (the "second tag") and the second receiving group is a second nucleic acid capture probe (the "second probe"), wherein the second probe or a fragment thereof is complementary to the second tag or a fragment thereof.

Figure 4B:
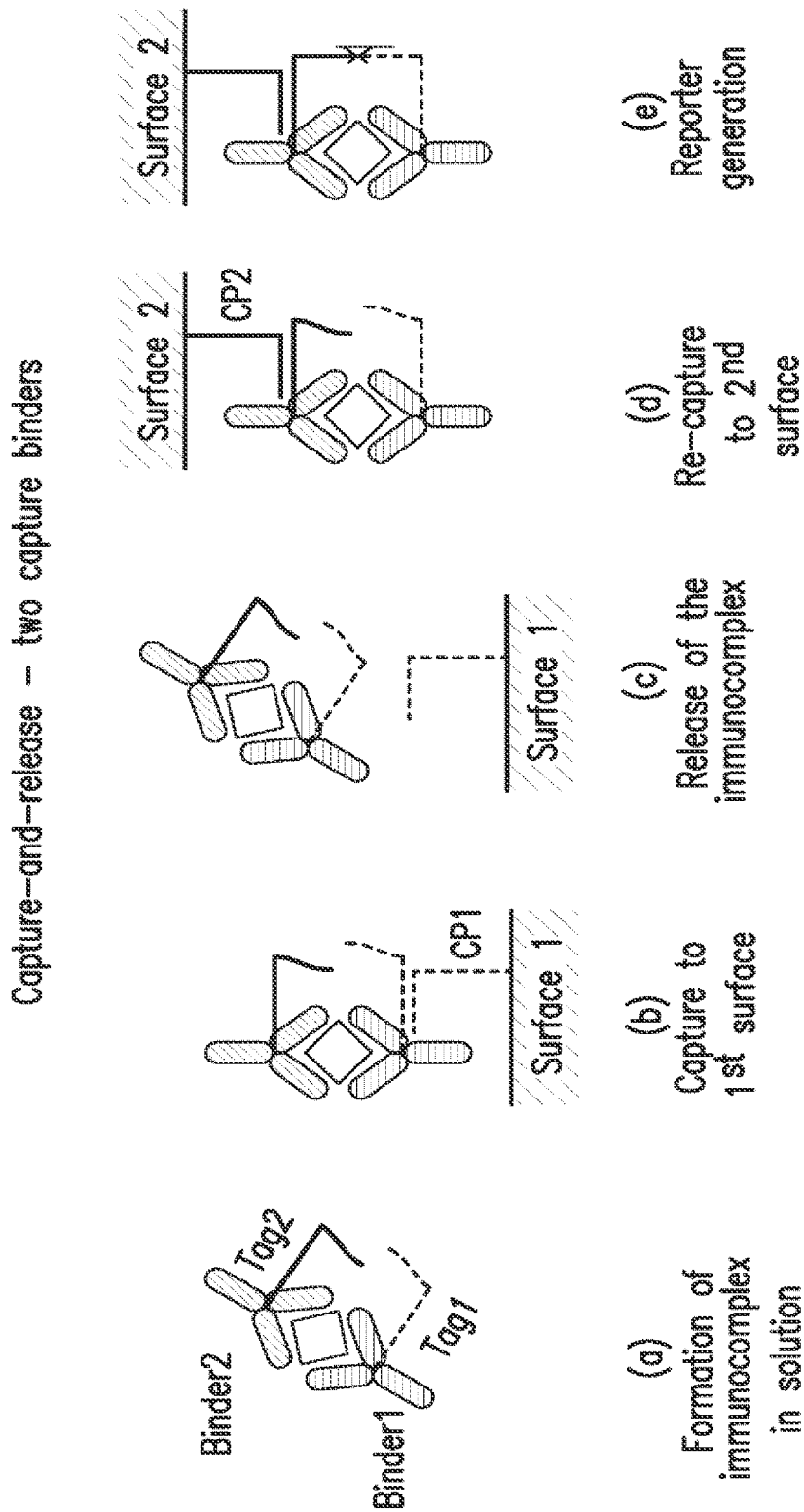

In some embodiments, as depicted in FIG. 4B, the first presenting group is the first tag and the first receiving group is the first probe, wherein the first probe or a fragment thereof is complementary to the first tag or a fragment thereof; and the second presenting group is the second tag and the second receiving group is the second probe, wherein the second probe or a fragment thereof is complementary to the second tag or a fragment thereof. Accordingly, provided herein are assay methods for detecting an analyte in a sample comprising the following steps:
  (1) mixing a first binder, a second binder, and the sample in a solution, wherein the first and second binders bind non-interfering epitopes on the analyte and form an immunocomplex, and wherein the immunocomplex is captured on a first solid surface in contact with the solution via hybridization between a first tag conjugated to the first binder and a first probe coupled to the first surface;
  (2) washing the first solid surface to remove unbound molecules;
  (3) releasing the immunocomplex from the first solid surface via the dissolution of the hybridization between the first tag and the first probe;
  (4) introducing a second solid surface and recapturing the immunocomplex on the second solid surface via hybridization between a second tag conjugated to the second binder and the second probe coupled to the second solid surface;
  (5) washing the second solid surface to remove unbound molecules; and
  (6) detecting the immunocomplex.

In some embodiments, assay methods provided herein further comprise at least one additional cycle of recapture between steps (5) and (6), comprising: releasing the immunocomplex from the solid surface that it is captured on via the dissolution of the hybridization between the second tag and the second probe, recapturing the immunocomplex on an additional solid surface coupled with the first receiving group, and washing the additional solid surface to remove unbound molecules. In some embodiments, assay methods provided herein further comprise at least one additional cycle of recapture between steps (5) and (6), comprising: releasing the immunocomplex from the solid surface that it is captured on via the dissolution of the hybridization between the first tag and the first probe, recapturing the immunocomplex on an additional solid surface coupled with the second receiving group, and washing the additional solid surface to remove unbound molecules.

5.2.1.2 Capture-and-Release with One Capture Binder

Figure 4C:
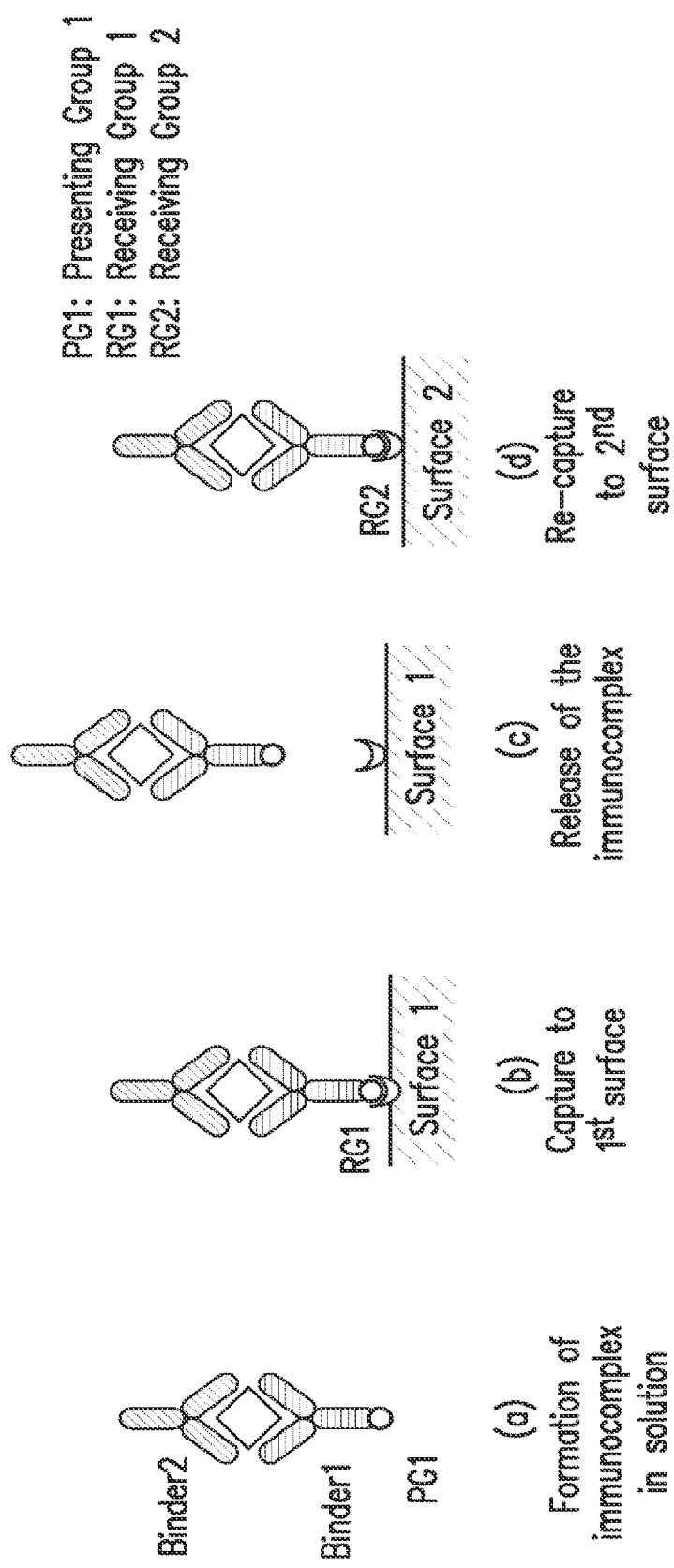

In some embodiments, as depicted in FIGS. 4C, 8C and 8D, assay methods provided herein use a capture-and-release mechanism that involves only one binder, which is captured by the solid surface via one releasable and renewable bond, although two binders are used to form the immunocomplex. In some embodiments, the first binder is captured sequentially by two solid surfaces. In some embodiments, provided herein are assay methods for detecting an analyte in a sample comprising the following steps:
  (1) mixing a first binder, a second binder, and the sample in a solution; wherein the first and second binders bind non-interfering epitopes on the analyte and form an immunocomplex; and wherein the immunocomplex is captured on a first solid surface in contact with the solution via binding between a first presenting group conjugated to the first binder and a first receiving group coupled to the first solid surface;
  (2) washing the first solid surface to remove unbound molecules;
  (3) releasing the immunocomplex from the first solid surface by disrupting the binding between the first presenting group and the first receiving group;
  (4) introducing a second solid surface and recapturing the immunocomplex via binding between the first presenting group and the second receiving group coupled to the second solid surface;
  (5) washing the second solid surface to remove unbound molecules; and
  (6) detecting the immunocomplex The exact same capture/release mechanism can be repeated on the second solid surface. Accordingly, in some embodiments, the second receiving group is the same as the first receiving group.

As depicted in FIGS. 4C, 8C and 8D, the captures/releases can be achieved via the releasable and renewable bond between the first one ("Bond 1") between the first presenting group ("PG1") of the first binder ("Binder 1") and the first receiving group ("RG1") of the first solid surface ("Surface 1"). The same presenting group (PG1) can then form a second bond ("Bond 2") with the second receiving group ("RG2") of the second solid surface ("Surface 2"). RG2 can be the same as RG1. In some embodiments, Bond 2 is also releasable, and the immunocomplex can be detected either on Surface 2, or after being released from Surface 2. In some embodiments, Bond 2 is not releasable, and the immunocomplex can be detected on Surface 2.

As a person of ordinary skill in the art would understand, additional round(s) of capture/release would further reduce nonspecific background signal. As Bond 1 is renewable, at least one additional round of capture/release can be performed via Binder 1. Specifically, the immunocomplex released from Surface 2 can be recaptured by a new Surface 1 by forming another bond between PG1 on Binder 1 and RG1 on the new Surface 1. In some embodiments, Bond 2 is also renewable, and the immunocomplex released from Surface 1 or 2 can be recaptured by a new Surface 2 by forming another bond between PG1 on Binder 1 and RG2 on the new Surface 2. In some embodiments, both Bond 1 and Bond 2 are renewable, and more than one cycle of capture/release can be performed via Bond 1, Bond 2, or both.

Accordingly, in some embodiments, assay methods provided herein further comprise at least one additional cycle of recapture between steps (5) and (6), comprising: releasing the immunocomplex from the solid surface that it is captured on, recapturing the immunocomplex on an additional solid surface coupled with the first receiving group, and washing the additional solid surface to remove unbound molecules. In some embodiments, assay methods provided herein further comprise at least one additional cycle of recapture between steps (5) and (6), comprising: releasing the immunocomplex from the solid surface that it is captured on, recapturing the immunocomplex on an additional solid surface coupled with the second receiving group, and washing the additional solid surface to remove unbound molecules. Additional cycles of recapture can be included.

As described above, releasable bond and renewable bond can be achieved through many different approaches known by an artisan in the field of protein immobilization, including those disclosed herein. In some embodiments, the releasable and renewable bond is formed via nucleic acid hybridization, wherein the presenting group and the receiving group include nucleic acids that are complementary to each other.

Figure 4D:
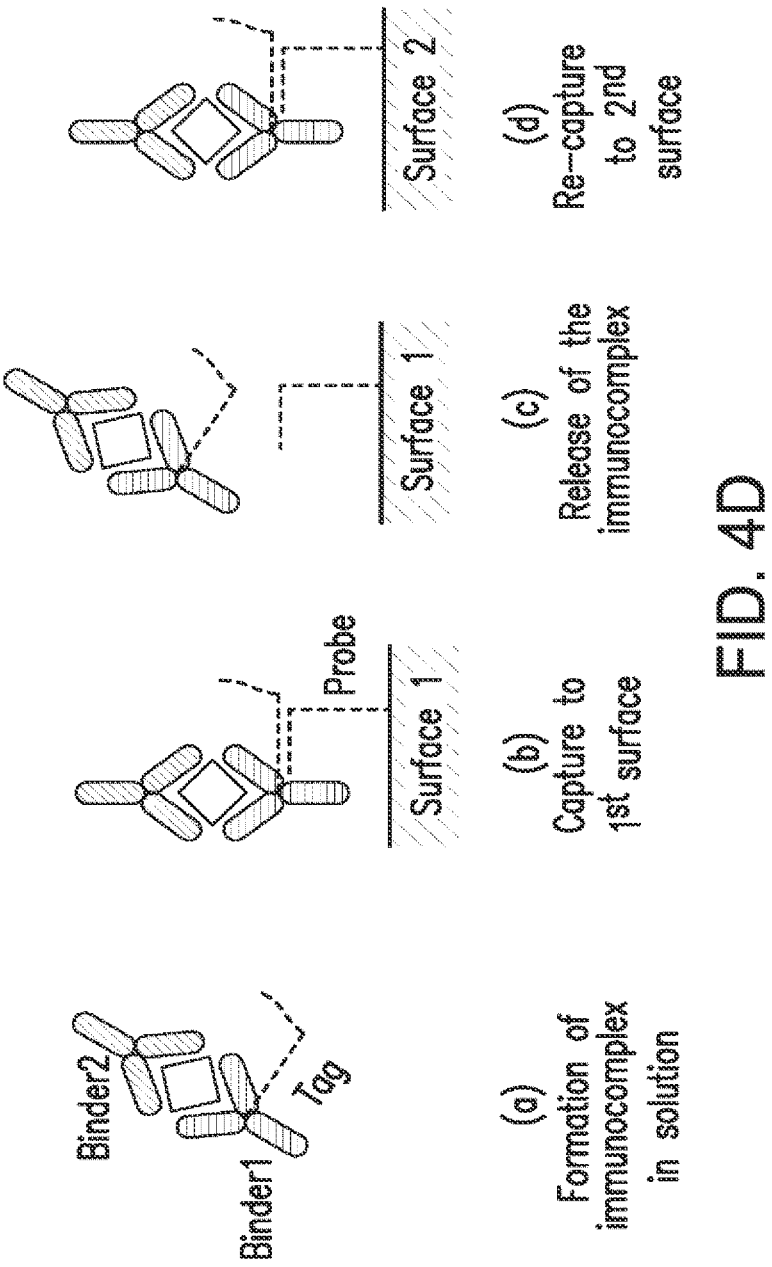

In some embodiments, the first presenting group is a nucleic acid tag (the "first tag") and the first receiving group is a nucleic acid capture probe (the "first probe"), wherein the first probe or a fragment thereof is complementary to the first tag or a fragment thereof. Accordingly, as depicted in FIG. 4D, provided herein are also assay methods for detecting an analyte in a sample, comprising:
  (1) mixing a first binder, a second binder, and the sample in a solution; wherein the first and second binders bind non-interfering epitopes on the analyte and form an immunocomplex; and wherein the immunocomplex is captured on a first solid surface in contact with the solution via hybridization between a first nucleic acid tag (the "first tag") conjugated to the first binder and a first nucleic acid capture probe (the "first probe") coupled to the first solid surface;
  (2) washing the first solid surface to remove unbound molecules;
  (3) releasing the immunocomplex from the first solid surface via the dissolution of the hybridization between the first tag and the first probe;
  (4) introducing a second solid surface coupled with a second nucleic acid probe (the "second probe") and recapturing the immunocomplex on the second solid surface via hybridization between the first tag and the second probe;
  (5) washing the second solid surface to remove unbound molecules; and
  (6) detecting the immunocomplex.

In some embodiments, the second probe is the same as the first probe.

In some embodiments, assay methods provided herein further comprise at least one additional cycle of recapture between steps (5) and (6), comprising: releasing the immunocomplex from the solid surface that it is captured on; recapturing the immunocomplex on an additional solid surface coupled with the probe, which can be either the first probe, the second probe, or another nucleic acid probe that hybridizes with the first tag; and washing the additional solid surface to remove unbound molecules.

The use of nucleic acid hybridization as the capture/release mechanism brings several advantages to the assay methods disclosed herein, at least because that the conditions of nucleic acid hybridization is quite different from that of protein binding. First, binding to target analyte by the first binder and the second binder can be conducted in solution which enables fast binding kinetics and allow large volume of sample input. Second, capture of the immunocomplex to solid surface through nucleic acid hybridization is generally more efficient, specific and predictable. The sequence of capture probe can be designed to specifically targeting an intended immunocomplex, which is useful in multiplexed assay formats. Third, the dissociation of the hybridization as the release mechanism can be realized through the change of salt concentration in buffer, which helps to maximize the efficiency of the release while maintaining the integrity of the immunocomplex. By purposefully designing a relatively weaker hybridization link between the capture probe and the tag, through either shorter segment or A, T rich sequence, an appropriate release buffer condition can be identified in which the designated hybridization link dissociates to release the immunocomplex, while the immunocomplex and other hybridizations between longer or stronger complementary sequences remain stable. Fourth, capture/release through hybridization can be renewed and repeated multiple cycles without deterioration of efficiency and selectivity. Therefore, additional rounds of capture/release can be implemented in the assay until the desired level of low background is reached. The robust capture/release mechanism ensures the unprecedented predictability and reliability of the assay methods. Another unexpected benefit is that, the nucleic acid capture probes coupled to the first and second surfaces help further reduce non-specific entrapment of the first binder and the second binder due to their negatively charged oligonucleotide tags.

5.2.2 Formation of Immunocomplex

The assay methods disclosed herein include step (1): formation of an immunocomplex by mixing a first binder, a second binder, and a sample in a solution, wherein the first and second binders bind non-interfering epitopes on the analyte, and wherein the immunocomplex is captured on a first solid surface in contact with the solution via the binding between a first presenting group conjugated to the first binder and a first receiving group coupled to the first surface. In some embodiments, the first presenting group is a nucleic acid tag, and the first receiving group is a nucleic acid capture probe, wherein the probe or a fragment thereof is complementary to the tag or a fragment thereof.

As disclosed herein, the binders used in the assay methods can be any molecule or a portion of a molecule which binds a specific target analyte. As such, a binder can comprise any protein, peptide, nucleic acid, carbohydrate, lipid, or small molecule. In some embodiments, a binder comprises an antibody. In some embodiments, a binder comprises an antibody fragment. In some embodiments, a binder comprises an antibody mimetic. In some embodiments, a binder comprises a small molecule.

The binders used in assay methods disclosed herein can be conjugated to presenting groups (e.g. nucleic acid tags). The binder and presenting group can be joined together either directly through a bond or indirectly through a linking group. Where linking groups are employed, such groups can be chosen to provide for covalent attachment of the presenting groups and binders, as well as to maintain the desired binding affinity of the binder for its target analyte. Linking groups can vary depending on the binder. The linking group, when present, is typically biologically inert. A variety of linking groups are known to those of skill in the art and can be used in the assay methods disclosed herein. In some embodiments, a linking group comprises a spacer group terminated at either end with a reactive functionality capable of covalently bonding to the presenting group or the binder.

Spacer groups can include aliphatic and unsaturated hydrocarbon chains, spacers containing heteroatoms such as oxygen (ethers such aspolyethylene glycol) or nitrogen (polyamines), peptides, carbohydrates, cyclic or acyclic systems that can contain heteroatoms. Spacer groups can also comprise ligands that bind to metals such that the presence of a metal ion coordinates two or more ligands to form a complex. Specific spacer elements include: 1,4-diaminohexane, xylylenediamine, terephthalic acid, 3,6-dioxaoctanedioic acid, ethylenediamine-N,N-diacetic acid, 1, 1'-ethylenebis(5-oxo-3-pyrrolidinecarboxylic acid), 4,4'-ethylenedipiperidine. Potential reactive functionalities include nucleophilic functional groups (amines, alcohols, thiols, hydrazides), electrophilic functional groups (aldehydes, esters, vinyl ketones, epoxides, isocyanates, maleimides), functional groups capable of cycloaddition reactions, forming disulfide bonds, or binding to metals. Specific examples include primary and secondary amines, hydroxamic acids, N-hydroxysuccinimidyl esters, N-hydroxysuccinimidyl carbonates, oxycarbonylimidazoles, nitrophenylesters, trifluoroethyl esters, glycidyl ethers, vinylsulfones, and maleimides. Specific linker groups that can be used herein also include heterofunctional compounds, such as azidobenzoyl hydrazide, N-[4-(p-azidosalicylamino)butyl]-3'-[2'-pyridyldithio)propionamid), bis-sulfosuccinimidyl suberate, dimethyladipimidate, disuccinimidyltartrate, N-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl]aminobenzoate, glutaraldehyde, and succinimidyl-4-[N-maleimidomethyl]cyclohexane-1-carboxylate, 3-(2-pyridyldithio)propionic acid N-hydroxysuccinimide ester (SPDP), 4-(N-maleimidomethyl)-cyclohexane-1-carboxylic acid N-hydroxysuccinimide ester (SMCC), and the like.

The binder/presenting group conjugates employed in the assay methods disclosed herein can be prepared using any methods known in the art. In some embodiments, the presenting groups (e.g. nucleic acid tags) can be conjugated to the binder, either directly or through a linking group. The components can be covalently bound to one another through functional groups, as is known in the art, where such functional groups can be present on the components or introduced onto the components using one or more steps, e.g. oxidation reactions, reduction reactions, cleavage reactions and the like. Functional groups that can be used in covalently bonding the components together include: hydroxy, sulfhydryl, amino, and the like. The particular portion of the different components that are modified to provide for covalent linkage can be chosen so as not to substantially adversely interfere with that component's desired binding affinity for the target analyte. Where necessary and/or desired, certain moieties on the components can be protected using blocking groups, as is known in the art, see e.g. Green & Wuts, Protective Groups in Organic Synthesis (John Wley & Sons) (1991); U.S. Pat. No. 5,733, 523.

When the nucleic acid tags are used as presenting groups, the binder/presenting group conjugates can also be produced using in vitro protocols that yield nucleic acid-protein conjugates. Examples of such in vitro protocols of interest include: RepA based protocols (see e.g., Fitzgerald, *Drug Discov. Today* (2000) 5:253-258 and WO 98/37186), ribosome display based protocols (see e.g., Hanes et al., *Proc. Natl Acad. Sci. USA* (1997) 94:4937-42; Roberts, *Curr Opin Chem Biol* (1999) June; 3: 268-73; Schaffitzel et al., *J Immunol Methods* (1999) December 10; 231:1 19-35; and WO 98/54312).

As used in the assay methods disclosed herein, the receiving groups (e.g. nucleic acid capture probes) can be "coupled" to solid surfaces by any means known in the art, which can be either direct or indirect e.g. via a linking group as described above for linking the presenting groups and the binders. For example, the receiving groups can be coupled to solid surfaces by covalent linkage (e.g. chemical cross-linking) or by non-covalent association e.g., via streptavidin-biotin based coupling (biotin being provided on one domain and streptavidin on the other). In some embodiments, for example, the solid surface is the surface of a magnetic bead, which can be coupled with a nucleic acid capture probe as the presenting group via, for example, the binding between the carboxylic acid on the magnetic bead and the nucleic acid capture probe. In some embodiments, the solid surface can be covalently coupled with protein A/G as the presenting group.

The presenting groups and receiving groups can be any binding pairs disclosed herein or otherwise known in the art, which include, but are not limited to, an antigen and an antibody against the antigen (including its fragments, derivatives or mimetics), a ligand and its receptor, complementary strands of nucleic acids, biotin and avidin (or streptavidin or neutravidin), lectin and carbohydrates, and vice versa. Additional binding pairs of "presenting groups" and "receiving groups" include fluorescein and anti-fluorescein, digioxigenin/anti-digioxigenin, and DNP (dinitrophenol)/anti-DNP, and vice versa. In some embodiments, binding pairs of "presenting groups" and "receiving groups" are complementary strands of nucleic acids, and are referred to as "tags" and "probes." In some embodiments, binding pairs of "presenting groups" and "receiving groups" are antigens and antibodies, or antigens and antibody fragments.

As described above, the sample that can be assayed in the assay methods disclosed herein can be a material or mixture of materials containing one or more components of interest. In some embodiments, the sample is derived from a biological source. For example, the sample can be obtained from a subject, which can be a biological tissue or fluid, obtained, reached, or collected in vivo or in situ. Exemplary samples include a biological fluid, such as a blood sample, a urine sample, a plasma sample, a saliva sample, a cerebrospinal fluid sample, a semen sample, a sputum sample, a mucus sample, a dialysis fluid sample, an intestinal fluid sample, a synovial fluid sample, a serous fluid sample. In some embodiments, the sample is a blood sample. In some embodiments, the sample is a urine sample. In some embodiments, the sample is a saliva sample. In some embodiments, the sample is a plasma sample. In some embodiments, the sample is a cerebrospinal fluid sample. Exemplary samples include a tissue sample. The tissue sample can be a liquid tissue sample. The tissue sample can be a homogenized tissue sample. The tissue sample can be obtained from a diseased tissue. In some embodiments, the sample is a cancer sample.

The solid surface can also include any support known in the art on which can be used for immobilization of molecules. In some embodiments, the solid surface can be any surfaces suitable of attaching nucleic acid and facilitates the assay step. Examples of solid surfaces include beads (e.g., magnetic beads, xMAPR beads), particles, colloids, single surfaces, tubes, chips, multiwell plates, microtiter plates, slides, membranes, cuvettes, gels, and resins. Exemplary solid surfaces can include surfaces of magnetic particles, and wells of microtiter plates. When the solid phase is a particulate material (e.g., beads), it can be distributed in the wells of multi-well plates to allow for parallel processing. In some embodiments, the solid surface is the surface of a magnetic bead. The magnetic beads can be coupled with a presenting group. In some embodiments, the magnet beads can be carboxylate-modified magnetic beads, amine-blocked magnetic beads, Oligo(dT)-coated magnetic beads, streptavidin-coated magnetic beads, Protein A/G coated magnetic beads, or silica-coated magnetic beads. In some embodiments, the solid surface is a well of a microtiter plate. In some embodiments, the first and second solid surfaces are the same. In some embodiments, the first and the second solid surfaces are different. In some embodiments, both the first and second solid surfaces used in the assay methods disclosed herein are surfaces of magnetic particles. In some embodiments, both the first and second surfaces used in the assay methods disclosed herein are surfaces of microtiter plates.

As described above, the analyte measured in assay methods disclosed herein can be any biological molecule. In some embodiments, the analyte is a protein analyte. In some embodiments, the analyte is a peptide analyte. In some embodiments, the analyte is a complex that includes at least two molecules. In some embodiments, the analyte is a protein complex that includes at least two proteins. In some embodiments, the analyte is a binding pair of two proteins. In some embodiments, the analyte is a macromolecular complex that includes at least a protein and at least a nucleic acid. In some embodiments, the analyte is a nucleic acid analyte.

In some embodiments, the analyte is a binding pair of two different molecules, the first binder binds one molecule of the binding pair, and the second binder binds the other molecule of the binding pair.

In some embodiments, the analyte is a binding pair of two different proteins, the first binder binds one protein of the binding pair, and the second binder binds the other protein of the binding pair. Accordingly, provided herein are assay methods for detecting protein-protein interaction in a sample comprising the following steps:

(1) mixing a first binder, a second binder, and the sample in a solution, wherein the first binder binds one protein of the binding pair, and the second binder binds the other protein of the binding pair and form an immunocomplex, and wherein the immunocomplex is captured on a first solid surface in contact with the solution via binding between a first presenting group conjugated to the first binder and a first receiving group coupled to the first surface;

(2) washing the first solid surface to remove unbound molecules;

(3) releasing the immunocomplex from the first solid surface by disrupting the binding between the first presenting group and the first receiving group;

(4) introducing a second solid surface and recapturing the immunocomplex via binding between a second presenting group conjugated to the second binder and the second receiving group coupled to the second solid surface;

(5) washing the second solid surface to remove unbound molecules; and (6) detecting the immunocomplex.

In some embodiments, the first presenting group is a first nucleic acid tag (the "first tag") and the first receiving group is a first nucleic acid capture probe (the "first probe"), wherein the first probe or a fragment thereof is complementary to the first tag or a fragment thereof. In some embodiments, the second presenting group is a second nucleic acid tag (the "second tag") and the second receiving group is a second nucleic acid capture probe (the "second probe"), wherein the second probe or a fragment thereof is complementary to the second tag or a fragment thereof.

In some embodiments, provided herein are assay methods for detecting protein-protein interaction in a sample comprising the following steps:

(1) mixing a first binder, a second binder, and the sample in a solution;

wherein the first binder binds one protein of the binding pair, and the second binder binds the other protein of the binding pair and form an immunocomplex; and wherein the immunocomplex is captured on a first solid surface in contact with the solution via binding between a first presenting group conjugated to the first binder and a first receiving group coupled to the first surface;

(2) washing the first solid surface to remove unbound molecules;

(3) releasing the immunocomplex from the first solid surface by disrupting the binding between the first presenting group and the first receiving group;

(4) introducing a second solid surface coupled with a second receiving group and recapturing the immunocomplex on the second solid surface via binding between the first presenting group and the second receiving group;

(5) washing the second solid surface to remove unbound molecules; and (6) detecting the immunocomplex.

In some embodiments, the first presenting group is a first nucleic acid tag (the "first tag") and the first receiving group is a first nucleic acid capture probe (the "first probe"), wherein the probe or a fragment thereof is complementary to the tag or a fragment thereof. In some embodiments, the second receiving group is a second nucleic acid capture probe (the "second probe"), wherein the probe or a fragment thereof is complementary to the tag or a fragment thereof.

Figure 15:
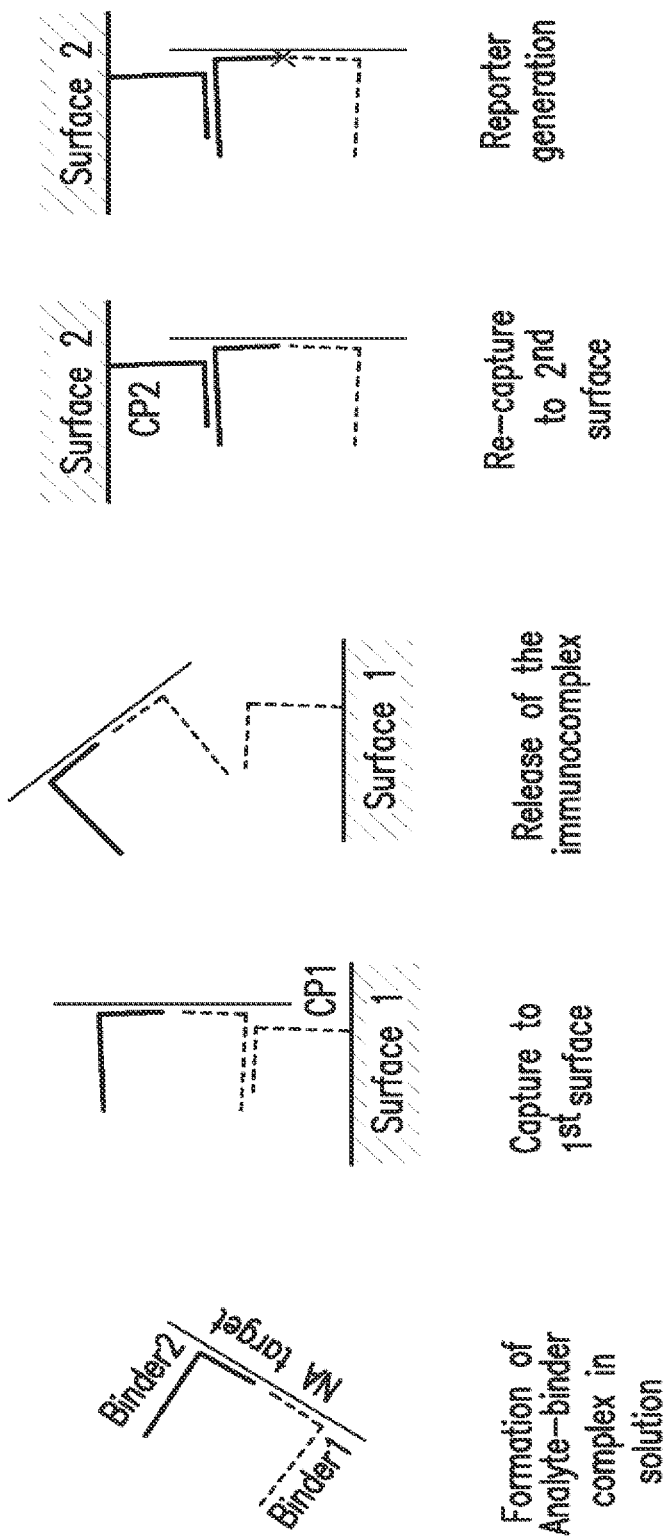

The analyte can be a nucleic acid molecule (e.g. DNA & RNA). In some embodiments, the analyte is a DNA molecule. In some embodiments, the analyte is a RNA molecule. Assay methods provided herein can detect nucleic acid molecules directly in samples such as plasma and urine without the need for nucleic acid isolation. As shown in FIG. 15, nucleic acid analyte can be hybridized and captured onto the first surface, released into solution, and recaptured on the second surface while the target-probe complex remains intact throughout the assay procedure. Accordingly, in some embodiments, assay methods provided herein can be used for detecting a nucleic acid analyte. For example, provided herein are assay methods for detecting a nucleic acid analyte in a sample comprising the following steps:

(1) mixing a first binder, a second binder, and the sample in a solution, wherein the first and second binders bind non-interfering epitopes on the nucleic acid analyte and form an immunocomplex, and wherein the immunocomplex is captured on a first solid surface in contact with the solution via binding between a first presenting group conjugated to the first binder and a first receiving group coupled to the first surface; wherein the first and second binders for the nucleic acid analyte are nucleic acids that are complementary to different fragments of the nucleic acid analyte;

(2) washing the first solid surface to remove unbound molecules;

(3) releasing the immunocomplex from the first solid surface by disrupting the binding between the first presenting group and the first receiving group;

(4) introducing a second solid surface and recapturing the immunocomplex via binding between a second presenting group conjugated to the second binder and the second receiving group coupled to the second solid surface;

(5) washing the second solid surface to remove unbound molecules; and (6) detecting the immunocomplex.

In some embodiments, provided herein are assay methods for detecting a nucleic acid analyte in a sample comprising the following steps:

(1) mixing a first nucleic acid tag (the "first tag"), a second nucleic acid tag (the "second tag"), and the sample in a solution, wherein a fragment of the first tag and a fragment of the second tags are each complementary to different fragments of the nucleic acid analyte and form an immunocomplex;

wherein the immunocomplex is captured on a first solid surface in contact with the solution via hybridization between the first tag and a first nucleic acid capture probe (the "first probe") coupled to the first solid surface, wherein the first probe or a fragment thereof is complementary to the first tag or a fragment thereof;

(2) washing the first solid surface to remove unbound molecules;

(3) releasing the immunocomplex from the first solid surface via the dissolution of the hybridization between the first tag and the first probe;

(4) introducing a second solid surface and recapturing the immunocomplex on the second solid surface via hybridization between the second tag and a second nucleic acid capture probe (the "second probe") coupled to the second solid surface; wherein the second probe or a fragment thereof is complementary to the second tag or a fragment thereof;

(5) washing the second solid surface to remove unbound molecules; and (6) detecting the immunocomplex.

The methods can be used for high throughput analysis of a large number of targets by Next Generation Sequencing (NGS), including analysis of mutation, methylation, translocation, fusion, and/or copy number variation, etc. Alternatively, selected targets can be analyzed by qPCR, digital PCR or other nucleic acid analysis technologies.

Step 1 in the assay methods provided herein can be conducted in various different approaches. For example, in some embodiments, the first binder can be pre-bound to the first surface, which, upon contacting the sample, captures the analyte. In some other embodiments, the second binder can be added subsequently or concurrently with sample to form the immunocomplex on the surface through multiple rounds of addition/incubation/washing steps.

Accordingly, in some embodiments, step (1) comprises forming the immunocomplex in the solution before capturing the immunocomplex on the first solid surface. In some embodiments, step (1) comprises pre-capturing the first binder on the first solid surface before forming the immunocomplex on the first solid surface. In some embodiments, the immunocomplex is formed in the solution and captured on the first solid surface simultaneously in step (1).

In some embodiments, the first binder is pre-bound to the first surface, the sample is added to the solution to allow the analyte to bind the first binder, and subsequently, the second binder is added to bind the analyte and form the immunocomplex composed of the analyte and the binders. In some embodiments, the first binder is pre-bound to the first surface, and the sample and the second binder are concurrently added to form the immunocomplex. A person of ordinary skill in the art would understand that the immunocomplexes can be formed using different approaches as disclosed herein, or variants with different sequences of addition/incubation/washing.

5.2.3 Alternative Capture Probe Configurations

As described above, provided herein are assay methods for detecting an analyte in a sample comprising the following steps:

(1) mixing a first binder, a second binder, and the sample in a solution, wherein the first and second binders bind non-interfering epitopes on the analyte and form an immunocomplex, and wherein the immunocomplex is captured on a first solid surface in contact with the solution via hybridization between a first tag conjugated to the first binder and a first probe coupled to the first surface;

(2) washing the first solid surface to remove unbound molecules;

(3) releasing the immunocomplex from the first solid surface via the dissolution of the hybridization between the first tag and the first probe;

(4) introducing a second solid surface and recapturing the immunocomplex via binding between a second tag conjugated to the second binder and the second probe coupled to the second solid surface;

(5) washing the second solid surface to remove unbound molecules; and (6) detecting the immunocomplex.

Provided herein are also assay methods for detecting an analyte in a sample, comprising:

(1) mixing a first binder, a second binder, and the sample in a solution; wherein the first and second binders bind non-interfering epitopes on the analyte and form an immunocomplex; and wherein the immunocomplex is captured on a first solid surface in contact with the solution via hybridization between a first nucleic acid tag (the "first tag") conjugated to the first binder and a first nucleic acid capture probe (the "first probe") coupled to the first solid surface;

(2) washing the first solid surface to remove unbound molecules;

(3) releasing the immunocomplex from the first solid surface via the dissolution of the hybridization between the first tag and the first probe;

(4) introducing a second solid surface coupled with a second nucleic acid probe (the "second probe") and recapturing the immunocomplex on the second solid surface via hybridization between the first tag and the second probe;

(5) washing the second solid surface to remove unbound molecules; and (6) detecting the immunocomplex.

In addition to the direct capture configuration shown in FIGS. 4A-4D and FIG. 6A, FIG. 6B shows an example of indirect capture where the capture probe comprises two segments: one complementary to the tag of binder and the other complementary to another capture probe linked to the surface. The advantages of indirect capture approach, include, for example, that the sequences on the capture probe that is directly coupled to the solid surface can be universal (poly T or A for example) thus providing flexibility in a multiplex assay. FIG. 6C shows another exemplary approach of indirect capture, where the capture probe is biotinylated, and the surface is coated with streptavidin or avidin. The capture probe is therefore coupled onto surface through the highly specific binding of biotin-streptavidin/avidin.

Accordingly, in some embodiments, direct capture is used in the assay methods provided herein, wherein the first probe is directly coupled to the first solid surface (FIG. 6A). In some embodiments, the second probe is directly coupled to the second solid surface. In some embodiments, the first probe is directly coupled to the first solid surface, and the second probe is directly coupled to the second solid surface.

In some embodiments, indirect capture is used in the assay methods provided herein, wherein the first probe hybridizes with a universal probe that is directed coupled to the first solid surface, wherein a fragment of the first probe is complementary to the universal probe or a fragment thereof (FIG. 6B). In some embodiments, the second probe hybridizes with a universal probe that is directed coupled to the second solid surface, wherein a fragment of the second probe is complementary to the universal probe or a fragment thereof. In some embodiments, the first probe hybridizes with a universal probe that is directed coupled to the first solid surface, and the second probe hybridizes with a universal probe that is directed coupled to the second solid surface.

In some embodiments, indirect capture is used in the assay methods provided herein, wherein the first probe is conjugated with a biotin, which binds the streptavidin or avidin that is directed coupled to the first solid surface (FIG. 6C). In some embodiments, the second probe is conjugated with a biotin, which binds the streptavidin or avidin that is directed coupled to the second solid surface. In some embodiments, the first probe is conjugated with a biotin, which binds the streptavidin or avidin that is directed coupled to the first solid surface, and the second probe is conjugated with a biotin, which binds the streptavidin or avidin that is directed coupled to the second solid surface.

In some embodiments, collaborative capture can be used in the assay methods described herein. As depicted in FIG. 6D, the capture probe hybridizes to a shorter segment of the nucleic acid tags of Binder 1 and 2, simultaneously. The assay conditions can be set such that tags of individual binders cannot be stably hybridized to the capture probe alone due to the relatively short complementary segments. When both binders bind to the target protein and form the immunocomplex, the tags of the two binders are hybridized to the capture probe collaboratively with sufficient strength to be stably captured to surface. This approach further reduces non-specific binders that are not part of immunocomplex, which reduces or even eliminates the need for release/re-capture rounds.

Accordingly, in some embodiments, direct collaborative capture is used in the assay methods provided herein, wherein the first tag and second tag are collaboratively captured on the solid surface in step (1) (FIG. 6D). Provided herein are assay methods for detecting an analyte in a sample comprising the following steps:

(1) mixing a first binder, a second binder, and the sample in a solution, wherein the first and second binders bind non-interfering epitopes on the analyte and form an immunocomplex, and wherein the immunocomplex is captured on a solid surface in contact with the solution via hybridization between a first nucleic acid tag (the "first tag") conjugated to the first binder and a nucleic acid capture probe ("the probe") coupled to the surface and between a second nucleic acid tag (the "second tag") conjugated to the second binder and the probe;

(2) washing the solid surface to remove unbound molecules; and (3) detecting the immunocomplex.

The collaborative capture can also be repeated to further reduce nonspecific binding. In some embodiments, the immunocomplex is released from the first solid surface by dissolving the collaborative hybridization between the first and second tags and the probe and is collaboratively recaptured on the second solid surface, and wherein the second solid surface is also coupled with the probe.

Figure 7A:
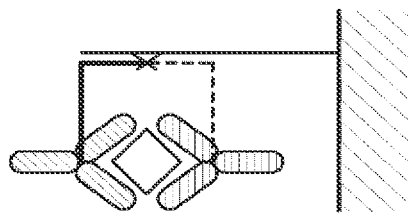

The collaborative capture can take different formats. In some embodiments, a continuous fragment of the probe consists of a first fragment and an immediately adjacent second fragment, wherein the first fragment is complementary to the first tag or a fragment thereof, and the second fragment is complementary to the second tag or a fragment thereof, such that when the first and second tags are linked to form a linked nucleic acid, a joint region of the linked nucleic acid is complementary to the continuous fragment of the first probe (FIG. 7A). In some embodiments, the first tag and second tag are also collaboratively captured on the second solid surface. In some embodiments, a continuous fragment of the second probe consists of a first fragment and an immediately adjacent second fragment, wherein the first fragment is complementary to the first tag or a fragment thereof, and the second fragment is complementary to the second tag or a fragment thereof, such that when the first and second tags are linked to form a linked nucleic acid, a joint region of the linked nucleic acid is complementary to the continuous fragment of the second probe. In some embodiments, the second probe is the same as the first probe. In some embodiments, the immunocomplex is captured on the second solid surface via a different mechanism. For example, the second surface can be coupled with an antibody that binds the first binder or the second binder.

Figure 7B:
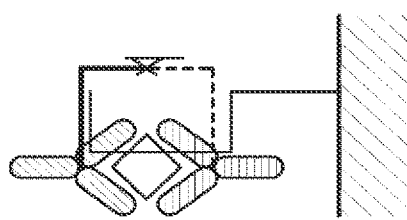

In some embodiments, a first fragment of the first probe is complementary to the first tag or a fragment thereof, and a separate second fragment of the first probe is complementary to the second tag or a fragment thereof (FIGS. 6D and 7B). In some embodiments, the first tag and second tag are also collaboratively recaptured on the second solid surface. In some embodiments, a first fragment of the second probe is complementary to the first tag or a fragment thereof, and a separate second fragment of the second probe is complementary to the second tag or a fragment thereof. In some embodiments, the second probe is the same as the first probe. In some embodiments, the complementary region includes the unconjugated ends, or "free" ends, of the first and the second tags, namely, the ends that are not conjugated with the respective binders (FIG. 6D). In some embodiments, the complementary region does not include the unconjugated ends of the first and the second tags (FIG. 7B). In some embodiments, the complementary region includes the conjugated ends of the first and the second tags (FIG. 7B). In some embodiments, the second probe is the same as the first probe. In some embodiments, the immunocomplex is captured on the second solid surface via a different mechanism. For example, the second surface can be coupled with an antibody that binds the first binder or the second binder.

Figure 7C:
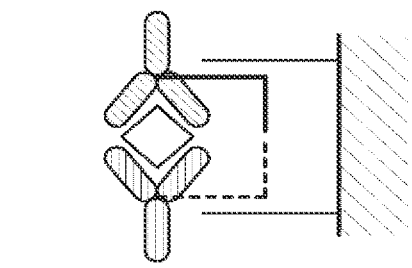

In some embodiments, direct collaborative capture is used in the assay methods provided herein wherein the first solid surface is coupled with both the first probe and the second probe (FIG. 7C). Provided herein are assay methods for detecting an analyte in a sample comprising the following steps:
  (1) mixing a first binder, a second binder, and the sample in a solution, wherein the first and second binders bind non-interfering epitopes on the analyte and form an immunocomplex, and wherein the immunocomplex is captured on a solid surface in contact with the solution via hybridization between a first nucleic acid tag (the "first tag") conjugated to the first binder and a first nucleic acid capture probe (the "first probe") coupled to the surface, and the hybridization between a second nucleic acid tag (the "second tag") conjugated to the second binder and a second nucleic acid capture probe (the "second probe") coupled to the surface;
  (2) washing the solid surface to remove unbound molecules; and
  (3) detecting the immunocomplex.

In some embodiments, the first tag and second tag are also collaboratively recaptured on the second solid surface, and wherein the second solid surface is also coupled with both the first probe and the second probe. In some embodiments, the first solid surface is coupled with a first probe and an additional probe, and the second solid surface is coupled with a second probe an additional probe, wherein both the first and second probes can hybridize with the first tag and the additional probe and hybridize with the second tag. In some embodiments, the second probe is the same as the first probe. In some embodiments, the immunocomplex is captured on the second solid surface via a different mechanism. For example, the second surface can be coupled with an antibody that binds the first binder or the second binder.

The complementary sequences between a nucleic acid tag and a nucleic acid capture probe are designed to facilitate the specific hybridization between the tag to the probe as well as the later dissociation of the hybridized immunocomplex. In one embodiment, sequences with low or no G/C can be used which, with appropriate length, can provide sufficient strength in hybridization, and which can be dissolved under low salt condition during release without disruption to the immunocomplex. In some embodiments, sequences that only include poly T/A or poly "TA"/"AT" can be used. As a person of ordinary skill in the art would understand, any sequence with appropriate hybridization strength can be utilized.

In some embodiments, more than 80%, more than 85%, more than 90%, more than 95%, or more than 98% of the complementary fragments of a nucleic acid tag and a nucleic acid capture probe used in the assay methods provided herein are adenine ("A") and thymine ("T") pairs. In some embodiments, more than 80%, more than 85%, more than 90%, more than 95%, or more than 98% of the complementary fragments of the first tag and the first probe are A and T pairs. In some embodiments, more than 80%, more than 85%, more than 90%, more than 95%, or more than 98% of the complementary fragments of the second tag and the second probe are A and T pairs. In some embodiments, more than 80% of the complementary fragments of the first tag and the first probe are A and T pairs, and more than 80% of the complementary fragments of the second tag and the second probe are A and T pairs. In some embodiments, complementary fragments of the first tag and the first probe comprise A and T pairs, and complementary fragments of the second tag and the second probe comprise A and T pairs.

In some embodiments, more than 80%, more than 85%, more than 90%, more than 95%, or more than 98% of the complementary fragments of a universal probe and a nucleic acid capture probe used in the assay methods provided herein are adenine ("A") and thymine ("T") pairs. In some embodiments, more than 80%, more than 85%, more than 90%, more than 95%, or more than 98% of the complementary fragments of the universal probe and the first probe are A and T pairs. In some embodiments, more than 80%, more than 85%, more than 90%, more than 95%, or more than 98% of the complementary fragments of the universal probe and the second capture probe are A and T pairs. In some embodiments, more than 80% of the complementary fragments of the universal probe and the first probe are A and T pairs, and more than 80% of the complementary fragments of the universal probe and the second probe are A and T pairs. In some embodiments, complementary fragments of the universal probe and the first probe comprise A and T pairs, and complementary fragments of the universal probe and the second probe comprise A and T pairs.

In some embodiments, the complementary fragments of a nucleic acid tag and a nucleic acid capture probe used in the assay methods provided herein consist of 10 to 30 base pairs, 10 to 25 base pairs, 12 to 20 base pairs, or 10 to 16 base pairs. In some embodiments, the complementary fragments of a nucleic acid tag and a nucleic acid capture probe used in the assay methods provided herein consist of 10 to 25 base pairs. In some embodiments, the complementary fragments of a nucleic acid tag and a nucleic acid capture probe used in the assay methods provided herein consist of 12 to 20 base pairs. In some embodiments, the complementary fragments of a nucleic acid tag and a nucleic acid capture probe used in the assay methods provided herein consist of 12 to 16 base pairs. In some embodiments, the complementary fragments of a nucleic acid tag and a nucleic acid capture probe used in the assay methods provided herein consist of 12 to 14 base pairs. In some embodiments, the complementary fragments of the first tag and the first probe consist of 10 to 25 base pairs. In some embodiments, the complementary fragments of the second tag and the second probe consist of 10 to 25 base pairs. In some embodiments, the complementary fragments of the first tag and the first probe consist of 12 to 20 base pairs. In some embodiments, the complementary fragments of the second tag and the second probe consist of 12 to 20 base pairs. In some embodiments, the complementary fragments of the first tag and the first probe consist of 12 to 16 base pairs. In some embodiments, the complementary fragments of the second tag and the second probe consist of 12 to 16 base pairs.

5.2.4 Detection

After sufficient depletion of non-specific binders that are not part of the immunocomplex through the capture/release mechanism, the immunocomplex can be detected. As such, the assay methods provided herein include step (6), detecting the immunocomplex.

In some embodiments, the immunocomplex is detected while being captured on a solid surface. The solid surface can be the second surface. The solid surface can also be another solid surface if at least one additional capture/release cycle is included between steps (5) and (6). In some embodiments, the immunocomplex is released from the solid surface into a solution and detected in the solution.

In some embodiments, the assay methods provided herein include detecting the first binder of the immunocomplex. In some embodiments, the assay methods provided herein include detecting the second binder of the immunocomplex. In some embodiments, the assay methods provided herein include detecting the first presenting group that is conjugated to the first binder of the immunocomplex. In some embodiments, the assay methods provided herein include detecting the second presenting group that is conjugated to either the first binder or the second binder of the immunocomplex. In some embodiments, the immunocomplex is detected via a detectable marker conjugated to the first binder. In some embodiments, the immunocomplex is detected via a detectable marker conjugated to the second binder.

Figure 1:
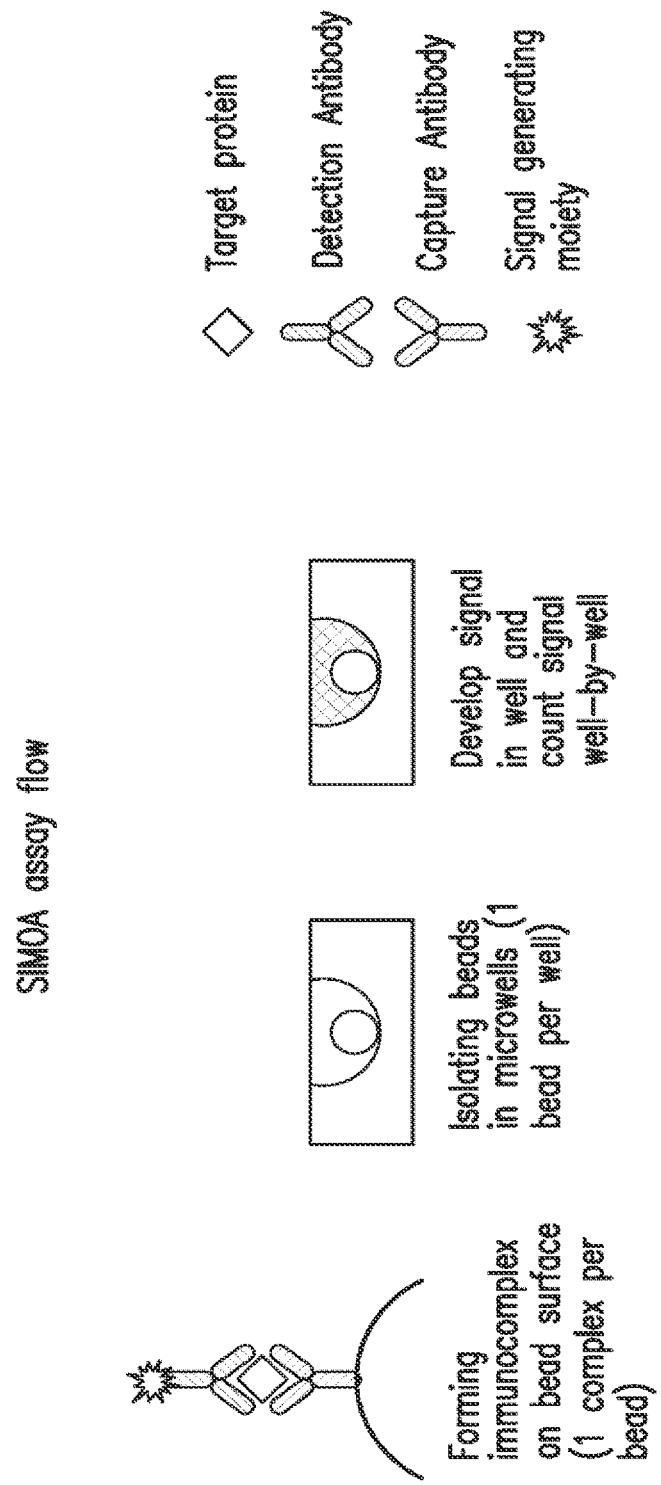
Figure 2:
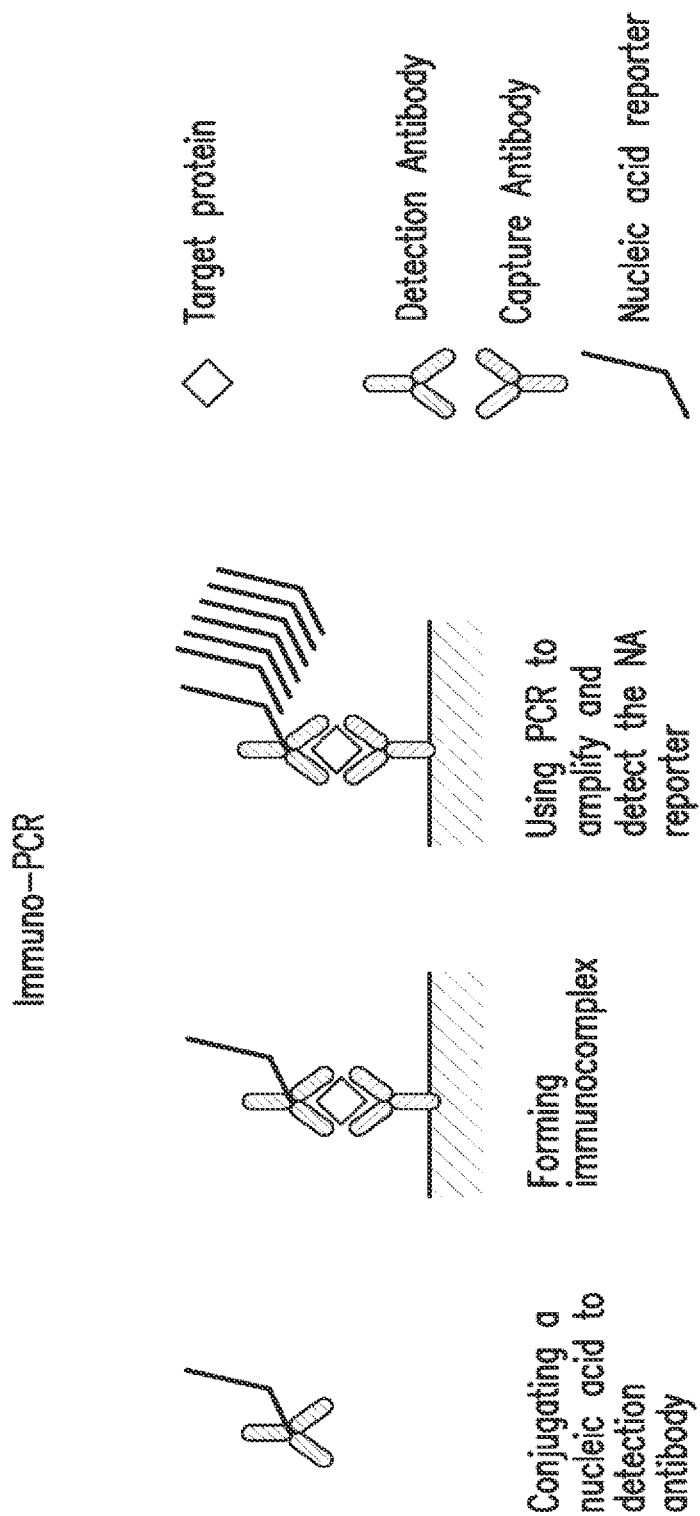

In some embodiments, the detectable marker is a nucleic acid, which can be amplified and detected by Polymerase Chain Reaction (PCR) (FIG. 2). Immuno-PCR technology can be used, which harasses the power of nucleic acid technology for protein detection by converting protein analyte detection into a nucleic acid reporter (e.g. U.S. Pat. No. 5,665,539). As depicted in FIGS. 8B and 8D, a segment of nucleic acid pre-conjugated to the detection binder can be used as the reporter of the immunocomplex and PCR is used to amplify the reporter and generate detectable signal. In some embodiments, the nucleic acid tags used for capture/release can be detected, and no additional detectable marker is needed. In some embodiments, the first tag is used for detection by PCR. In some embodiments, the second tag is used for detection by PCR.

The immunocomplex can be detected by any methods known in the art. For example, the detection of immunocomplex can be achieved using antibodies which specifically bind to the first binder, the second binder, the first presenting group, or the second presenting group. The antibodies for detection can be labeled with an enzyme, including for example, horseradish peroxidase, alkaline phosphatase, or beta-galactosidase, which is capable of converting a colorless or nearly colorless substrate or co-substrate into a highly colored product or a product capable of forming a colored complex with a chromogen. Alternatively, the detection system can employ an enzyme which, in the presence of the proper substrate(s), emits light. The amount of product formed can be detected either visually, spectrophotometrically, electrochemically, fluorescently or luminometrically, and can be compared to a similarly treated control. The detection system can also employ radioactively labeled antibodies, in which case the amount of immune complex is quantified by scintillation counting or gamma counting. Other detection systems which may be used include those based on the use of protein A derived from *Staphylococcus aureus* Cowan strain I, protein G from group C *Staphylococcus* sp. (strain 26RP66).

In some embodiments, the immunocomplex is detected by immunofluorescence. In some embodiments, the immunocomplex is detected by measuring a detectable marker conjugated to a binder. The detectable marker can be a fluorescent-labeled agent. The labeled agent can be a secondary antibody. The detectable marker can be a colorimetric detection reagent, a fluorescent detection reagent, or a chemiluminescent detection reagent. The colorimetric detectable marker can include PNPP (p-nitrophenyl phosphate), ABTS (2,2'-azino-bis(3-ethylbenzothiazoline-6-sulphonic acid)) or OPD (o-phenylenediamine). The fluorescent detectable marker includes QuantaBlu™ or QuantaRed™ (Thermo Scientific, Waltham, MA). The luminescent detectable marker includes luminol or luciferin. In some embodiments, the detectable marker can include a trigger (e.g., $H_2O_2$) and a tracer (e.g., isoluminol-conjugate).

The secondary antibody can be, for example, an anti-human IgA, anti-human IgD, anti-human IgE, anti-human IgG, or anti-human IgM antibody. The secondary antibody can be a monoclonal or polyclonal antibody. The secondary antibody can be derived from any mammalian organism, including mice, rats, hamsters, goats, camels, chicken, rabbit, and others. The secondary antibody can also be recombinant. Secondary antibodies can be conjugated to enzymes (e.g., horseradish peroxidase (HRP), alkaline phosphatase (AP), luciferase, and the like) or dyes (e.g., colorimetric dyes, fluorescent dyes, fluorescence resonance energy transfer (FRET)-dyes, time-resolved (TR)-FRET dyes, and the like). In some embodiment, the secondary antibody can be conjugated to a fluorescein (FITC) based dye, such as fluorescein isothiocyanate. In some embodiment, the secondary antibody can be conjugated to Alexa Fluor® 488 (Life technologies).

Methods and protocols for conducting immunoassays and biophysical protein-interaction assays are well known in the art. See, e.g., Wild D., *The Immunoassay Handbook*, Elsevier Science, $4^{th}$ Edition (2013); Fu H., Protein-Protein Interactions, Humana Press, $4^{th}$ Edition (2004).

5.2.4.1 Generation of Nucleic Acid Reporters

As depicted in FIGS. 8A and 8C, in some embodiments, nucleic acid tags can be conjugated to the binders used in the assay methods disclosed herein. The nucleic acid tags can be used for generation of nucleic acid reporters that allows highly sensitive detection. As described above, provided herein are two-capture binder assay methods for detecting an analyte in a sample comprising:

(1) mixing a first binder, a second binder, and the sample in a solution, wherein the first and second binders bind non-interfering epitopes on the analyte and form an immunocomplex, and wherein the immunocomplex is captured on a first solid surface in contact with the solution via hybridization between a first tag conjugated to the first binder and a first probe coupled to the first surface;

(2) washing the first solid surface to remove unbound molecules;

(3) releasing the immunocomplex from the first solid surface via the dissolution of the hybridization between the first tag and the first probe;
(4) introducing a second solid surface and recapturing the immunocomplex via binding between a second tag conjugated to the second binder and the second probe coupled to the second solid surface;
(5) washing the second solid surface to remove unbound molecules; and
(6) detecting the immunocomplex.

Provided herein are also one-capture binder assay methods for detecting an analyte in a sample, comprising:
(1) mixing a first binder, a second binder, and the sample in a solution; wherein the first and second binders bind non-interfering epitopes on the analyte and form an immunocomplex; and wherein the immunocomplex is captured on a first solid surface in contact with the solution via hybridization between a first nucleic acid tag (the "first tag") conjugated to the first binder and a first nucleic acid capture probe (the "first probe") coupled to the first solid surface;
(2) washing the first solid surface to remove unbound molecules;
(3) releasing the immunocomplex from the first solid surface via the dissolution of the hybridization between the first tag and the first probe;
(4) introducing a second solid surface coupled with a second nucleic acid probe (the "second probe") and recapturing the immunocomplex on the second solid surface via hybridization between the first tag and the second probe;
(5) washing the second solid surface to remove unbound molecules; and
(6) detecting the immunocomplex.

In some embodiments of one-capture binder assay methods, the second binder is also conjugated to a second nucleic acid tag (the "second tag").

In both the two-capture binder assay methods and the one-capture binder assay methods, after sufficient depletion of non-specific first binder and second binder that are not part of the immunocomplex through the capture/release mechanism, a nucleic acid reporter can be generated using the first tag and the second tag. The nucleic acid reporters can take various forms. For example, as depicted in FIG. 4B(e), the first tag and the second tag can be ligated to generate the nucleic acid reporter. As a person of ordinary skill in the art would understand, any of the reporter generation methods disclosed herein or otherwise known in the art can be deployed in this step, including such as ligation, polymerization extension or collaborative hybridization.

In some embodiments, the second capture does not have to be releasable, and the nucleic acid reporter can be generated with the immunocomplex captured on the second surface. Alternatively, the immunocomplex can first be released back to solution before the nucleic acid reporters are generated.

Proximity Ligation Assay (PLA) and Proximity Extension Assay (PEA) are known in the art (e.g. U.S. Pat. Nos. 6,511,809, 6,878,515, 7,306,904, 9,777,315, 10,174,366, WO9700446, Greenwood C, *Biomol. Det. & Quan.* 4 (2015) 10-16). Proximity-based detection differ from immuno-PCR in that they depend on the simultaneous recognition of target analyte by two nucleic acid-conjugated binders in order to trigger the formation of amplifiable products. Therefore, individual nucleic acid-conjugated binders that are not part of the immunocomplex will not generate reports, thus avoiding background from single nonspecifically bound binder. In some embodiments, proximity ligation is used to generate the nucleic acid reporter (FIG. 3A), wherein, upon the formation of the immunocomplex, the first tag and the second tag are brought into sufficient proximity to be ligated, and a fragment of the ligation product, which composes a fragment of the first tag and a fragment of the second tag, is used as an amplicon to generate the signal for detection. In some embodiments, proximity extension is used to generate the nucleic acid reporter (FIG. 3B), wherein, upon the formation of the immunocomplex, the first tag and the second tag are brought into sufficient proximity to interact with each other and form a duplex, such that the 3' end of at least one nucleic acid tag of the duplex can be extended to generate an extension product, which can be used as an amplicon to generate the signal for detection. In some embodiments, collaborative hybridization is used to generate the nucleic acid reporter, wherein, upon the formation of the immunocomplex, the first tag and the second tag are brought into sufficient proximity to interact each other and form a hybridization product, which can be used as an amplicon to generate the signal for detection.

The nucleic acid reporters can be generated using the nucleic acid tags in step (1) of the assay methods provided herein. As shown in FIG. 4B(e), the reporter can be generated by linking the first tag and the second tag together directly via proximity ligation, proximity extension, or collaborative hybridization. Alternatively, as shown in FIGS. 5A-5C, the nucleic acid reporters can be generated using nucleic acid surrogates that can hybridize with the nucleic acid tags. For example, in some embodiments, surrogate nucleic acids are used, wherein the first surrogate or a fragment thereof is complementary to the first tag or a fragment thereof, and the second surrogate or a fragment thereof is complementary to the second tag or a fragment thereof. In some embodiments, the reporter can be generated by linking the first surrogate to the second tag via proximity ligation, proximity extension, or collaborative hybridization (FIG. 5A). In some embodiments, the reporter can be generated by linking the first tag to the second surrogate via proximity ligation, proximity extension, or collaborative hybridization (FIG. 5B). Alternatively, the reporter can be generated by linking the first surrogate with the second surrogate via proximity ligation, proximity extension, or collaborative hybridization (FIG. 5C). In some embodiments, the first surrogate and/or the second surrogate can be added after the immunocomplex is formed. In another embodiment, the first surrogate and the second surrogate are pre-hybridized to the first tag and the second tag, respectively, prior to the immunocomplex formation.

Accordingly, in some embodiments, step (6) of the assay methods provided herein comprises generating a nucleic acid reporter by linking the first tag and the second tag by proximity ligation, proximity extension, or collaborative hybridization, and detecting the nucleic acid reporter composed of a fragment of the first tag and a fragment of the second tag. In some embodiments, surrogate nucleic acids are used, wherein the first tag or a fragment thereof is complementary to the first surrogate or a fragment thereof, and the second tag or a fragment thereof is complementary to the second surrogate or a fragment thereof. In some embodiments, step (6) of the assay methods provided herein comprises generating a nucleic acid reporter by linking the first tag and the second surrogate via proximity ligation, proximity extension, or collaborative hybridization, and detecting the nucleic acid reporter composed of a fragment of the first tag and a fragment of the second surrogate. In some embodiments, step (6) of the assay methods provided herein comprises generating a nucleic acid reporter by linking the first surrogate and the second tag via proximity ligation, proximity extension, or collaborative hybridization, and detecting the nucleic acid reporter composed of a fragment of the first surrogate and a fragment of the second tag. In some embodiments, step (6) of the assay methods provided herein comprises generating a nucleic acid reporter by linking the first surrogate and the second surrogate via proximity ligation, proximity extension, or collaborative hybridization, and detecting the nucleic acid reporter composed of a fragment of the first surrogate and a fragment of the second surrogate.

Although assay methods exemplified in FIGS. 5A-5C and 8A-8B use proximity ligation, as described above, proximity extension, collaborative hybridization, or other methods known in the art can also be used for generating the nucleic acid reporter for detection.

5.2.4.2 Detection of Nucleic Acid Reporters

The reporters generated in the last step can be detected using any existing nucleic acid detection technologies, which include, but are not limited to, PCR, quantitative PCR (qPCR), digital PCR (dPCR) or next-generation sequencing (NGS). In some embodiments, the detection is qualitative detection. In some embodiments, the detection is quantitative detection. In some embodiments, the nucleic acid reporter is detected by qPCR. In some embodiments, the nucleic acid reporter is detected by dPCR. In some embodiments, the nucleic acid reporter is detected by NGS.

In addition to these common technologies, other nucleic acid amplification/detection methods can also be used, which include, but not limited to, Rolling Cycle Amplification (RCA), strand displacement amplification (SDA), Loop-Mediated Isothermal Amplification (LAMP) and Recombinase Polymerase Amplification (RPA). Additional technologies capable of highly sensitive nucleic acid detection without the need for target amplification can also be adopted for the detection of nucleic acid reporters in the assay methods disclosed herein. These include, but are not limited to, QuantiGene assay from ThermoFisher Scientific (ThermoFisher (2019)), SIMOA assay from Quanterix (Rissin D M (2010)) and SMCxPRO™ from MilliporeSigma (MilliporeSigma (2019)). Accordingly, in some embodiments, the nucleic acid reporter is detected by Rolling Cycle Amplification (RCA), strand displacement amplification (SDA), Loop-Mediated Isothermal Amplification (LAMP), Recombinase Polymerase Amplification (RPA), or a QuantiGene assay.

5.2.5 Multiplexing

Since the reporter generated in assay methods disclosed herein is a nucleic acid molecule, a unique sequence can be incorporated as an identity barcode (ID) that can be decoded by DNA sequencing or other methods. A segment of ID comprising N base nucleotides can generate up to $4^N$ unique identity codes. One approach, as shown in FIGS. 9A-9B, is to directly incorporate the ID into the tag of one binder (FIG. 9A) or the tags of both binders (FIG. 9B). In some embodiments, the nucleic acid reporter contains an ID in the first tag. In some embodiments, the nucleic acid reporter contains an ID in the second tag. In some embodiments, the nucleic acid reporter contains a first ID in the first tag and a second ID in the second tag.

FIG. 10 shows an indirect ID barcoding approach, where the IDs are on a separate single-strand nucleic acid molecule hybridized on the corresponding tag of the binder (i.e. the nucleic acid surrogate). In some embodiments, surrogate nucleic acids are used, wherein the first tag or a fragment thereof is complementary to the first surrogate or a fragment thereof, and the second tag or a fragment thereof is complementary to the second surrogate or a fragment thereof. In FIG. 10A, only the first binder is IDed indirectly through a first surrogate. The nucleic acid reporter is generated through ligating the first surrogate with the second tag. In FIG. 10B, both the first and the second binders are IDed indirectly. Although ligation is exemplified in FIGS. 9A-9B and 10A-10B, the reporter can also be generated through proximity extension, collaborative hybridization, and other methods known in the art as disclosed above. In addition, the annealing of the ID carrying nucleic acid surrogates with its associated binder tags can be done in reagent manufacturing process before the assay. Alternatively, it can be conducted as part of the assay.

In some embodiments, provided herein are assay methods wherein the nucleic acid reporter contains an ID in the first tag, the first surrogate, the second tag or the second surrogate. In some embodiments, the nucleic acid reporter is composed of a fragment of the first tag and a fragment of the second surrogate, and contains an ID in the first tag or the second surrogate. In some embodiments, the nucleic acid reporter contains a first ID in the first tag and a second ID in in the second surrogate. In some embodiments, the nucleic acid reporter is composed of a fragment of the first surrogate and a fragment of the second tag, and contains an ID in the first surrogate or the second tag. In some embodiments, the nucleic acid reporter contains a first ID in the first surrogate and a second ID in the second surrogate. In some embodiments, the nucleic acid reporter is composed of a fragment of the first surrogate and a fragment of the second surrogate, and contains an ID in the first surrogate or the second surrogate. In some embodiments, the nucleic acid reporter contains a first ID in the first surrogate and the second ID in the second surrogate.

One application of the ID methods described above is to detect and measure multiple different analytes in the same sample in parallel. In some embodiments, the nucleic acid reporters as disclosed herein contain an analyte-specific ID (the "target ID"). Each analyte is assigned with a unique ID. As such, provided herein are assay methods comprising simultaneously detecting at least two analytes in the sample by simultaneously detecting the unique target IDs associated with each analyte. In some embodiments, the assay methods provided herein simultaneously detect at least three, at least four, at least five, at least six, at least seven, at least eight, at least nine, at least ten, at least twelve, at least fifteen, at least twenty, at least thirty, at least forty, at least fifty, at least sixty, at least seventy, at least eighty, at least ninety, or at least one hundred analytes in the sample by simultaneously detecting the unique target IDs associated with each analyte.

In some embodiments, the analytes are proteins. In some embodiments, the analytes include at least one protein and at least one nucleic acid. The nucleic acid can be DNA or RNA. The fact that the assay methods provided herein can be used for analysis of protein, DNA and RNA makes it an ideal platform for multi-omic analysis.

Figure 11:
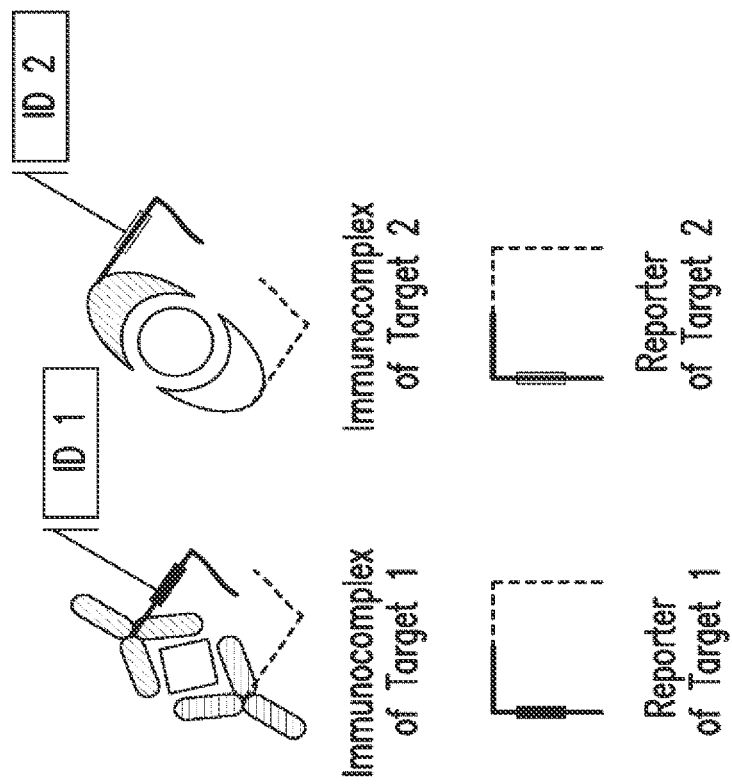

As illustrated in FIG. 11, one ID is sufficient to represent the identity of the target analyte or the immunocomplex formed with the analyte. Once the ID is incorporated into the reporter, it can be detected and quantified by existing multiplexed nucleic acid detection technologies, such as multiplexed qPCR, multiplexed digital PCR or next generating sequencing (NGS).

Figure 12:
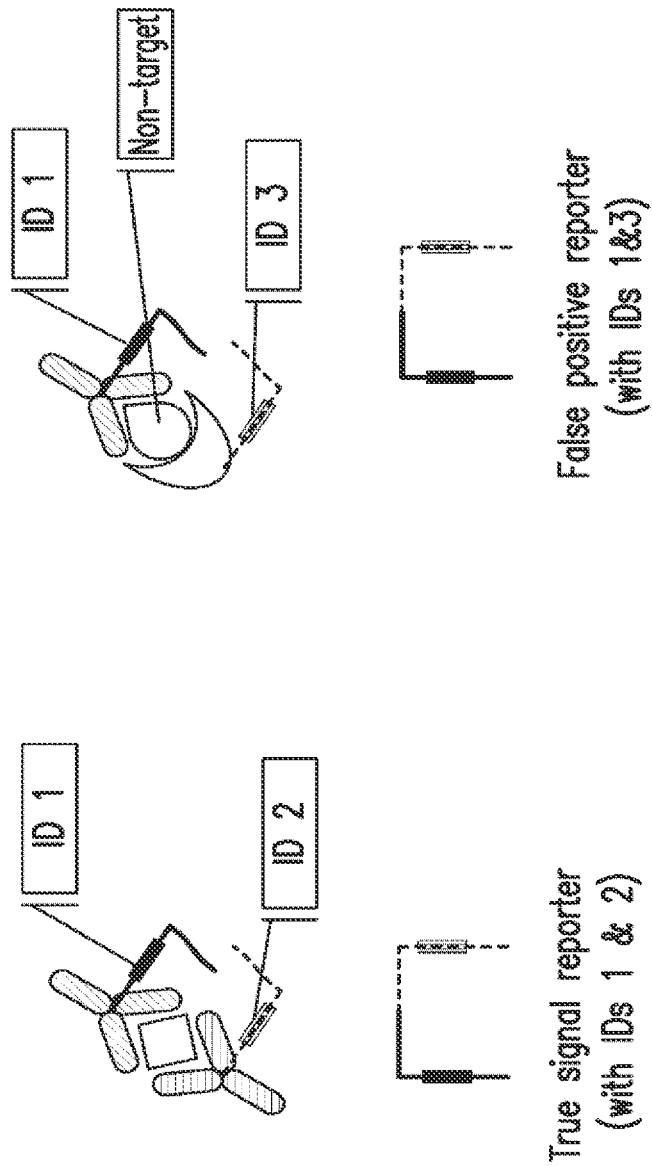

Incorporation of IDs in the nucleic acid reporters in the assay methods provided herein can also help improve the specificity of the assay. As illustrated in FIG. 12, each of the first binder and the second binder is associated with a unique ID, and only the signals generated from reporter containing the IDs of both binders are counted as true signal. This scheme can be used to reduce or eliminate false positive signal generated by cross-reactivity or non-specific binding among different binding pairs. Accordingly, provided herein are assay methods for detecting analyte in a sample by the co-detection of the first and the second target IDs each associated with the first and second binders, respectively.

Figure 13:
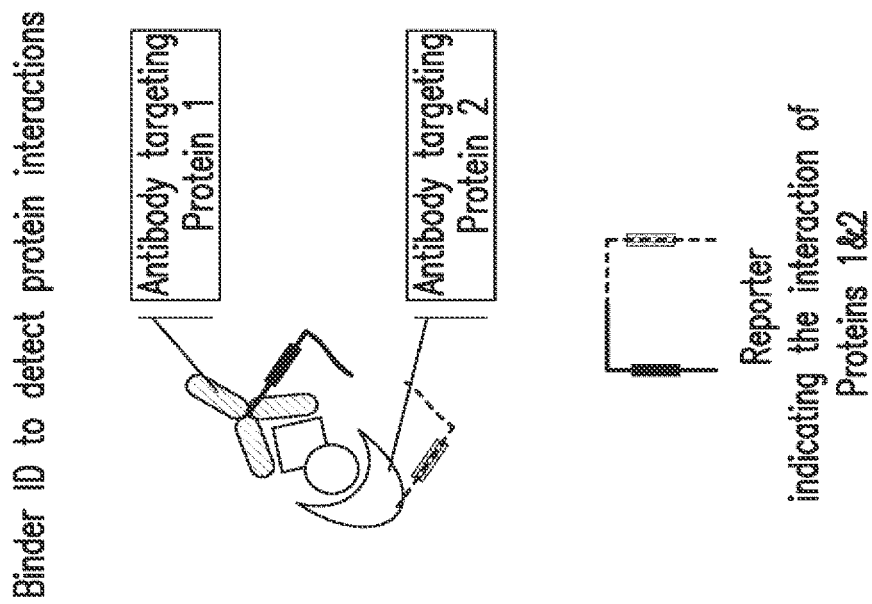

Incorporation of IDs in the nucleic acid reporters in the assay methods provided herein can also be used to detect interactions between molecules, for example, protein-protein interactions. As depicted in FIG. 13, the co-detection and quantification of reporters containing IDs of two binders designed for different molecules would indicate the interaction and affinity of these two associated molecules under the assay condition. In some embodiments, the assay methods provided herein detect protein-protein interactions. Accordingly, provided herein are assay methods for detecting analyte in a sample, wherein the analyte is a binding pair of two different proteins; wherein the first binder binds one protein, and the second binder binds the other protein of the binding pair; and wherein the binding pair is detected by the co-detection of the first and the second target IDs.

Figure 14:
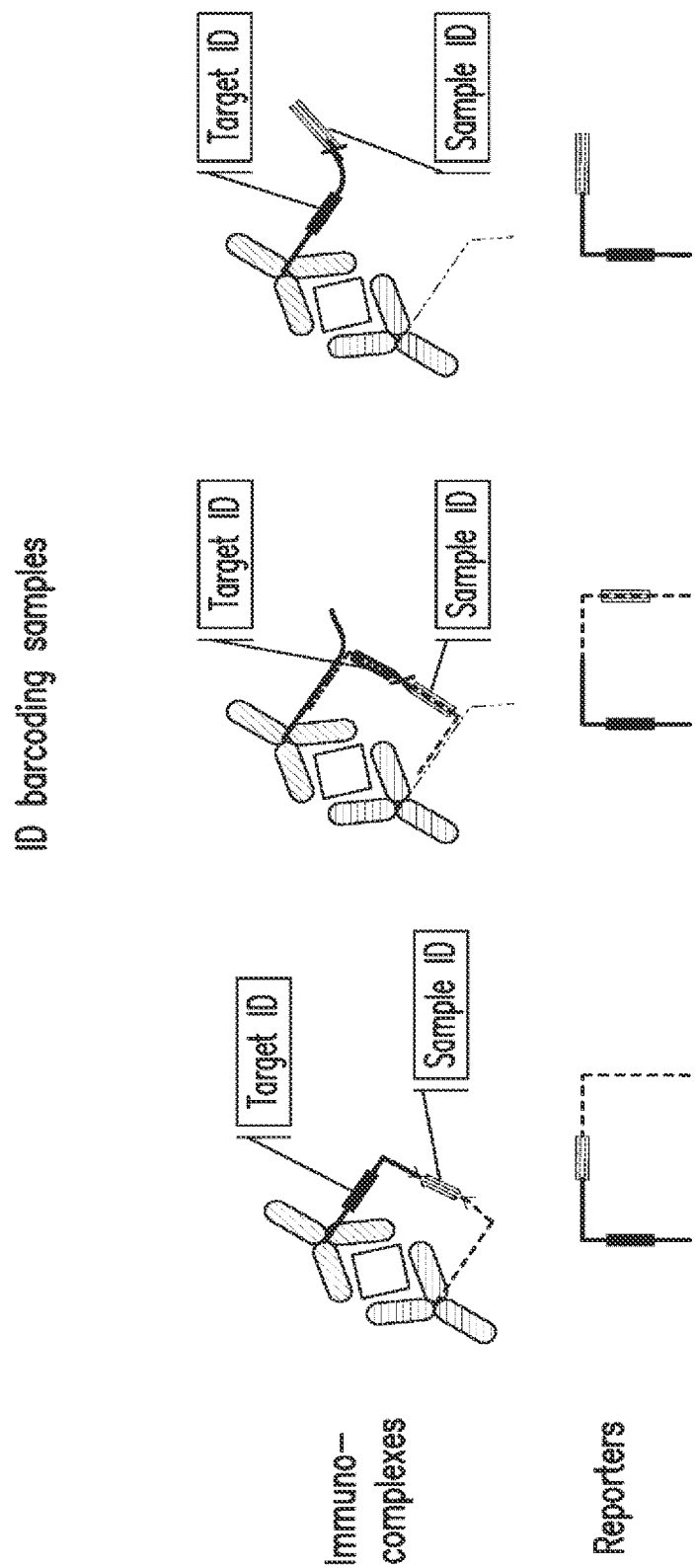

In addition to analyte-specific "target IDs," the nucleic acid reporters generated in the assay methods provided herein can also include sample-specific "sample IDs." As depicted in FIGS. 14A-14C, when the assay method provided herein is performed on a particular sample, a sample ID can be introduced during the assay at or before reporter generation step to identify the sample. With such sample ID incorporated into the reporter, reporters from many samples can be pooled together and read by NGS in parallel. In some embodiments, the sample ID can be carried on a nucleic acid independent of the binder tags and incorporated into the reporter at the ligation step as shown in FIG. 14A. Accordingly, in some embodiments, the nucleic acid reporter formed in each sample contains an ID that is a sample ID, wherein the sample ID is inserted between the first tag or surrogate, and the second tag or surrogate.

In some embodiments, the nucleic acid reporter is composed of a fragment of the first tag and a fragment of the second tag, and contains a sample ID inserted between the first tag and the second tag. In some embodiments, the nucleic acid reporter is composed of a fragment of the first tag and a fragment of the second surrogate, and contains a sample ID inserted between the first tag and the second surrogate. In some embodiments, the nucleic acid reporter is composed of a fragment of the first surrogate and a fragment of the second tag, and contains a sample ID inserted between the first surrogate and the second tag. In some embodiments, the nucleic acid reporter is composed of a fragment of the first surrogate and a fragment of the second surrogate, and contains a sample ID inserted between the first surrogate and the second surrogate.

Alternatively, the sample ID can be incorporated on a nucleic acid surrogate that is hybridized to a tag during an assay step as shown in FIG. 14B. Accordingly, in some embodiments, the nucleic acid reporter formed in each sample contains sample ID in the first surrogate or the second surrogate. In some embodiments, the nucleic acid reporter is composed of a fragment of the first tag and a fragment of the second surrogate, and contains a sample ID in the second surrogate. In some embodiments, the nucleic acid reporter is composed of a fragment of the first surrogate and a fragment of the second tag, and contains a sample ID in the first surrogate. In some embodiments, the nucleic acid reporter is composed of a fragment of the first surrogate and a fragment of the second surrogate, and contains a sample ID in the first surrogate or the second surrogate.

Alternatively, the sample ID can be incorporated by ligation to a nucleic acid tag or its surrogate during an assay step as shown in FIG. 14C. Accordingly, in some embodiments, the nucleic acid reporter formed in each sample contains sample ID ligated to the first tag or the second tag, or their respective surrogate. In some embodiments, the nucleic acid reporter is composed of a fragment of the first tag and a fragment of the second tag, and contains a sample ID ligated to the first tag or the second tag. In some embodiments, the nucleic acid reporter is composed of a fragment of the first tag and a fragment of the second surrogate, and contains a sample ID ligated to the first tag or the second surrogate. In some embodiments, the nucleic acid reporter is composed of a fragment of the first surrogate and a fragment of the second tag, and contains a sample ID ligated to the first surrogate or the second tag. In some embodiments, the nucleic acid reporter is composed of a fragment of the first surrogate and a fragment of the second surrogate, and contains a sample ID ligated to the first surrogate or the second surrogate.

As such, also provided herein are assay methods comprising simultaneously detecting an analyte in at least two samples, by incorporating a unique sample ID in the nucleic acid reporter formed in each sample, and simultaneously detecting the unique sample IDs in the nucleic acid reporters associated with each sample. In some embodiments, the assay methods provided herein simultaneously detect an analyte in at least three, at least four, at least five, at least six, at least seven, at least eight, at least nine, at least ten, at least 15, at least 20, at least 30, at least 40, at least 50, at least 60, at least 70, at least 80, at least 90, at least 100, at least 150, at least 200, at least 250, at least 300, at least 350, at least 400, at least 450, or at least 500 samples by simultaneously detecting the unique sample IDs associated with each sample.

In some embodiments, the nucleic acid reporters generated in the assay methods provided herein can comprise both a target ID and a sample ID. In some embodiments, the nucleic acid reporter comprises (a) a target ID in the first tag or the first surrogate, or in the second tag or the second surrogate, and (b) a sample ID that is (1) inserted between the first tag or surrogate thereof, and the second tag or surrogate thereof, (2) included in the first surrogate or the second surrogate or (3) ligated to the first tag or surrogate thereof, or the second tag or surrogate thereof.

In some embodiments, the nucleic acid reporter is composed of a fragment of the first tag and a fragment of the second tag, and contains a target ID and a sample ID. The nucleic acid reporter can contain a target ID in the first tag or the second tag. The nucleic acid reporter can contain a first target ID in the first tag and a second target ID in the second tag. The nucleic acid reporter can contain a sample ID inserted between the first tag or the second tag.

In some embodiments, the nucleic acid reporter is composed of a fragment of the first tag and a fragment of the second surrogate, and contains a target ID and a sample ID. The nucleic acid reporter can contain a target ID in the first tag or the second surrogate. The nucleic acid reporter can contain a first target ID in the first tag and a second target ID in the second surrogate. The nucleic acid reporter can contain a sample ID inserted between the first tag and the second surrogate. The nucleic acid reporter can also contain a sample ID in the second surrogate.

In some embodiments, the nucleic acid reporter is composed of a fragment of the first surrogate and a fragment of the second tag, and contains a target ID and a sample ID. The nucleic acid reporter can contain a target ID in the first surrogate or the second tag. The nucleic acid reporter can contain a first target ID in the first surrogate and a second target ID in the second tag. The nucleic acid reporter can contain a sample ID inserted between the first surrogate and the second tag. The nucleic acid reporter can also contain a sample ID in the first surrogate.

In some embodiments, the nucleic acid reporter is composed of a fragment of the first surrogate and a fragment of the second surrogate, and contains a target ID and a sample ID. The nucleic acid reporter can contain a target ID in the first surrogate or the second surrogate. The nucleic acid reporter can contain a first target ID in the first surrogate and a second target ID in the second surrogate. The nucleic acid reporter can contain a sample ID inserted between the first surrogate and the second surrogate. The nucleic acid reporter can also contain a sample ID in the first surrogate or the second surrogate.

As such, provided herein are also assay methods comprising simultaneously detecting at least two analytes in at least two samples, by simultaneously detecting the unique sample IDs and unique target IDs associated with each analyte and the unique sample IDs associated with each sample.

In some embodiments, the assay methods provided herein simultaneously detect at least two analytes in at least three, at least four, at least five, at least six, at least seven, at least eight, at least nine, at least ten, at least 15, at least 20, at least 30, at least 40, at least 50, at least 60, at least 70, at least 80, at least 90, at least 100, at least 150, at least 200, at least 250, at least 300, at least 350, at least 400, at least 450, or at least 500 samples by simultaneously detecting unique sample IDs and unique target IDs in the nucleic acid reporters with each sample.

In some embodiments, the assay methods provided herein simultaneously detect at least three analytes in at least three, at least four, at least five, at least six, at least seven, at least eight, at least nine, at least ten, at least 15, at least 20, at least 30, at least 40, at least 50, at least 60, at least 70, at least 80, at least 90, at least 100, at least 150, at least 200, at least 250, at least 300, at least 350, at least 400, at least 450, or at least 500 samples by simultaneously detecting unique sample IDs and unique target IDs in the nucleic acid reporters with each sample.

In some embodiments, the assay methods provided herein simultaneously detect at least five analytes in at least three, at least four, at least five, at least six, at least seven, at least eight, at least nine, at least ten, at least 15, at least 20, at least 30, at least 40, at least 50, at least 60, at least 70, at least 80, at least 90, at least 100, at least 150, at least 200, at least 250, at least 300, at least 350, at least 400, at least 450, or at least 500 samples by simultaneously detecting unique sample IDs and unique target IDs in the nucleic acid reporters with each sample.

In some embodiments, the assay methods provided herein simultaneously detect at least ten analytes in at least three, at least four, at least five, at least six, at least seven, at least eight, at least nine, at least ten, at least 15, at least 20, at least 30, at least 40, at least 50, at least 60, at least 70, at least 80, at least 90, at least 100, at least 150, at least 200, at least 250, at least 300, at least 350, at least 400, at least 450, or at least 500 samples by simultaneously detecting unique sample IDs and unique target IDs in the nucleic acid reporters with each sample.

In some embodiments, the assay methods provided herein simultaneously detect at least twenty analytes in at least three, at least four, at least five, at least six, at least seven, at least eight, at least nine, at least ten, at least 15, at least 20, at least 30, at least 40, at least 50, at least 60, at least 70, at least 80, at least 90, at least 100, at least 150, at least 200, at least 250, at least 300, at least 350, at least 400, at least 450, or at least 500 samples by simultaneously detecting unique sample IDs and unique target IDs in the nucleic acid reporters with each sample.

In some embodiments, the assay methods provided herein simultaneously detect at least fifty analytes in at least three, at least four, at least five, at least six, at least seven, at least eight, at least nine, at least ten, at least 15, at least 20, at least 30, at least 40, at least 50, at least 60, at least 70, at least 80, at least 90, at least 100, at least 150, at least 200, at least 250, at least 300, at least 350, at least 400, at least 450, or at least 500 samples by simultaneously detecting unique sample IDs and unique target IDs in the nucleic acid reporters with each sample.

In some embodiments, the assay methods provided herein simultaneously detect at least eighty analytes in at least three, at least four, at least five, at least six, at least seven, at least eight, at least nine, at least ten, at least 15, at least 20, at least 30, at least 40, at least 50, at least 60, at least 70, at least 80, at least 90, at least 100, at least 150, at least 200, at least 250, at least 300, at least 350, at least 400, at least 450, or at least 500 samples by simultaneously detecting unique sample IDs and unique target IDs in the nucleic acid reporters with each sample.

In some embodiments, the assay methods provided herein simultaneously detect at least one hundred analytes in at least three, at least four, at least five, at least six, at least seven, at least eight, at least nine, at least ten, at least 15, at least 20, at least 30, at least 40, at least 50, at least 60, at least 70, at least 80, at least 90, at least 100, at least 150, at least 200, at least 250, at least 300, at least 350, at least 400, at least 450, or at least 500 samples by simultaneously detecting unique sample IDs and unique target IDs in the nucleic acid reporters with each sample.

As a person of ordinary skill in the art would understand, different permutations and combinations of the nucleic acid-based capture and ID configurations as described above and shown in FIGS. 4A to 7C and 9A-14 can be used in the assay methods disclosed herein.

The nucleic acid reporters in the multiplexing assay methods disclosed herein can be detected by multiplexed qPCR, multiplexed digital PCR, or NGS. For example, in some embodiments, the nucleic acid reporters in the multiplexing assay methods disclosed herein can be detected by NGS. The use of NGS to detect the nucleic acid reporters generated by assay methods disclosed herein include at least the following advantages. First, NGS is capable of detecting and reading the sequences of nucleic acid molecules in the sample. By incorporating target and sample ID tags into the reporter, as described herein, NGS is capable of multiplexed detection at a very large scale. For example, NGS can read a pool of 100 samples, each comprising 10 targets (i.e. 1000-plex) in a single run. This significantly reduces the per data point cost. Second, NGS can count and aggregate the number of molecules of the same sequence, providing digital quantification at single molecule resolution. Since the sequences of reporters are pre-designed and short, NGS as a reporter detection method can be completed much faster with reduced cost compared to de novo sequencing. Additionally, a wide range of error correction algorithms, such as parity check, Hamming codes (e.g. Bystrykh, *PLOS ONE* 7(5): e36852 (2012)), and Levenshtein codes (e.g. Buschmann, *BMC Bioinformatics*. 2013; 14: 272 (2013)) can be used from communication theory and applied herein to reduce false positive counts so that NGS based quantification can achieve high precision without repeated sequencing.

Since NGS is a single molecule detection and counting method, the sequencing instrument imposes an upper limit on the total number of molecules that can be sequenced. The MiSeq system from Illumina, for example, is capable of 25 million reads per run, which limits the total number of molecules to be sequenced in a run to 25 million. This limit is not restrictive in most applications where the target is present at low concentration or even near limit-of-detection ("LOD"). In multiplexed tests, however, some targets are known to express at a level that is many magnitudes higher than others, consuming the sequencing bandwidth without providing useful clinical/biological information. Therefore, there is a need to purposefully reducing the signal generated from these abundant analytes, while maintaining sensitivity for the rest of the analytes in a multiplexed assay format.

This T assay methods provided herein additionally address this need and provide related advantages. In some embodiments, provided herein are assay methods wherein the number of reporter molecules generated from a high-concentration target analyte is reduced in a precise and known proportion so that the limited bandwidth of detection can be efficiently assigned to different target analytes. The assay methods disclosed herein capture the immunocomplexes on a solid surface using a receiving group (e.g. a nucleic acid capture probe) before the reporter is generated, which provides a unique opportunity to reduce the signal of highly abundant analytes by selectively capturing only a portion of the immunocomplexes generated therefrom to the surface.

For example, in some embodiments, the binders can be conjugated with and without their presenting groups (e.g. nucleic acid tags) in a known proportion. If, for example, binders conjugated with a presenting group are mixed with the same binder without the presenting group at 1% concentration, then only 1% immunocomplex can be captured onto the surface and the reporter to target analyte ratio will be 1%. Nonfunctional presenting groups, namely, presenting groups that do not bind receiving groups, can also be used. For example, if only 0.1% of first binder is conjugated to a first presenting group (e.g. the first tag) that is functional, and the rest 99.9% of the first binders are conjugated to a first presenting group (e.g. the first tag) that that cannot be captured by the first receiving group (e.g. the first probe), the reporter to immunocomplex ratio will be 1:1000, effectively reducing the signals generated by this analyte by 1000 fold.

An alternative approach for such partial capture can be used, which introduces a known portion of nonfunctional receiving groups (e.g. nucleic acid capture probes). In the indirect capture methods shown in FIGS. 6B and 6C, for example, a certain proportion of the first capture probe can be included that does not have the segment complementary to the universal capture probe (FIG. 6B) or is not biotinylated (FIG. 6C). As a result, the same proportion of immunocomplexes cannot be captured on the surface and thus cannot generate nucleic acid reporters for detection. For example, if the receiving group contains only 0.1% functional molecule that can be coupled to the solid surface (the rest 99.9% are non-functional dummy molecules), the reporter to immunocomplex ratio will also be 1:1000, reducing the signals generated by this analyte by 1000 fold.

Accordingly, provided herein are also assay methods that include proportionally reducing the amount of an analyte detected by the assay, by adding a non-functional binder to the solution in step (1), wherein the non-functional binder competes with the first binder for binding to the analyte but is either unconjugated, or conjugated to a presenting group that does not bind the first receiving group. In some embodiments, the non-functional binder is unconjugated. In some embodiments, the non-functional binder is conjugated to a presenting group that does not bind the first receiving group. In some embodiments, the non-functional binder is conjugated to a nucleic acid tag that cannot hybridize with the first probe coupled to the first solid surface.

Accordingly, provided herein are also assay methods that include proportionally reducing the amount of an analyte detected by the assay, by adding a non-functional receiver to the solution in step (1), wherein the non-functional receiver competes with the first receiving for binding to the first presenting group but cannot be coupled with the first solid surface.

In some embodiments, provided herein are also assay methods that include proportionally reducing the amount of an analyte detected by the assay, by adding a non-functional binder to the solution in step (1), wherein the non-functional binder competes with either the first binder or the second binder for binding to the analyte but forms a immunocomplex that cannot be detected. In some embodiments, the assay methods provided herein detect the immunocomplex by detecting a detectable marker conjugated to either the first binder or the second binder, and the non-functional binder is either unconjugated to the detectable marker, or is conjugated to a defective detectable marker that cannot produce the signal for detection. In some embodiments, the immunocomplex is detected via the nucleic acid reporter, and the non-functional binder can be conjugated to a nucleic acid tag that lacks the proper segment for generating the nucleic acid reporter. A person of ordinary skill in the art would understand that different approaches that are variants of the methods disclosed herein can be taken to proportionally reduce the signal generated by highly-abundant analytes in the sample, therefore allowing the concurrent detection of multiple analytes that may be present at concentrations that differ by even orders of magnitude.

In addition to NGS, many other single molecule detection technologies, such as digital PCR, SIMOA, have a limit on the total number of target molecules that can be read by the system in a single run (instrument bandwidth). The method described above of precisely controlling report/immunocomplex ratio can be applicable to all of these technologies in order to maximize the efficient use of the system resources.

5.2.6 Assay Method with Target ID and/or Sample ID

In one aspect, provided herein is an assay method for detecting an analyte in a sample, comprising:
(1) mixing a first binding moiety comprising a first binder and a first presenting group, a second binding moiety comprising a second binder, and the sample in a solution, wherein:
  (i) the first and second binders bind to the analyte and form an immunocomplex,
  (ii) the immunocomplex is captured on a first solid surface in contact with the solution via binding between the first presenting group and a first receiving group coupled to the first solid surface, and (iii) the first binding moiety further comprises a first target label and the second binding moiety further comprises a second target label;

(2) washing the first solid surface to remove unbound molecules;

(3) generating a reporter from the immunocomplex based on proximity between the first target label and the second target label; and (4) detecting the reporter, thereby detecting the analyte.

As described in Section 5.1, target label can provide identifiers that can be correlated with the particular target to facilitate the detection and identification of a target molecule. As such, in some embodiments of the methods provided herein including those in this section (Section 5.2.6) and in the preceding paragraph, each target label can comprises one or more target IDs. In one specific embodiment, the first target label comprises a first target ID. In another embodiment, the second target label comprises a second target ID. In yet another embodiment, the first target label comprises a first target ID and the second target label comprises a second target ID.

As described further above in Section 5.2.4, in some embodiments of the methods provided herein, including those of this section (Section 5.2.6), the reporter can be generated based on proximity between the first target label and the second target label. Accordingly, in one embodiment, the reporter comprises the first target ID. In another embodiment, the reporter comprises the second target ID. In yet another embodiment, the reporter comprises the first target ID the second target ID. In a further embodiment, the reporter comprises the first target ID and the second target ID. In one embodiment, the reporter comprises the first target ID and the sample ID. In another embodiment, the reporter comprises the second target ID and the sample ID. In a further embodiment, the reporter comprises the first target ID, the second target ID, and the sample ID.

In one aspect, provided herein is an assay method for detecting an analyte in a sample, comprising:

(1) mixing a first binding moiety comprising a first binder and a first presenting group, a second binding moiety comprising a second binder, and the sample in a solution, wherein:
  (i) the first and second binders bind to the analyte and form an immunocomplex,
  (ii) the immunocomplex is captured on a first solid surface in contact with the solution via binding between the first presenting group and a first receiving group coupled to the first solid surface, and
  (iii) the first binding moiety further comprises a first target label comprising a first identity barcode ("ID") that is analyte-specific ("target ID") and the second binding moiety further comprises a second target label comprising a second target ID;

(2) washing the first solid surface to remove unbound molecules;

(3) generating a reporter from the immunocomplex, wherein the reporter comprises (i) the first target ID, (ii) the second target ID, or (iii) both the first and the second target ID; and (4) detecting the reporter, thereby detecting the analyte.

Figure 3A:
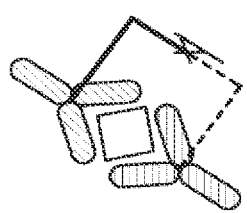
Figure 3B:
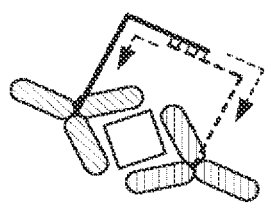
Figure 3C:
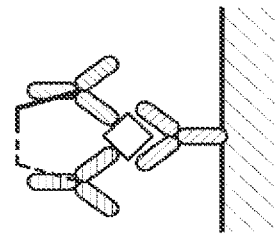

As is clear from the description in Section 5.2.4.1 and FIGS. 3A-3C among others, in various embodiments of the methods provided herein, the reporter can be generated based on the properties of the immunocomplex that correlates with the specificity of the binding between both binders and the analyte. In one embodiment of the methods provided herein including in this Section 5.2.6, the reporter is generated based on proximity between the first target label and the second target label. In another embodiment, the reporter is generated based on proximity between the first target ID and the second target ID. In yet another embodiment, the reporter is generated based on proximity between the first binder and the second binder.

In one aspect, provided herein is an assay method for detecting an analyte in a sample, comprising:

(1) mixing a first binding moiety comprising a first binder, a second binding moiety comprising a second binder, and the sample in a solution, wherein:
  (i) the first and second binders bind to the analyte and form an immunocomplex; and
  (ii) the first binding moiety further comprises a first target label comprising a first identity barcode ("ID") that is analyte-specific ("target ID") and the second binding moiety further comprises a second target label comprising a second target ID;

(2) generating a reporter from the immunocomplex, wherein the reporter is generated based on proximity between the first target label and the second target label and wherein the reporter comprises (i) the first target ID, (ii) the second target ID, or (iii) both the first and the second target ID; and (3) detecting the reporter, thereby detecting the analyte.

Figure 8G:
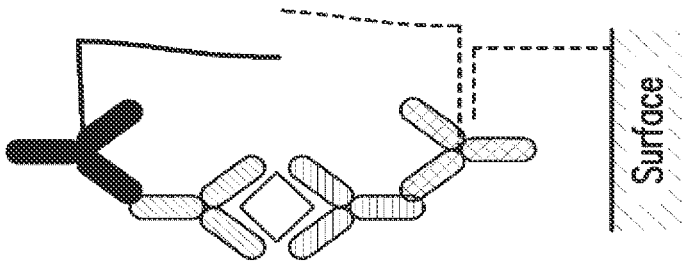
Figure 8F:
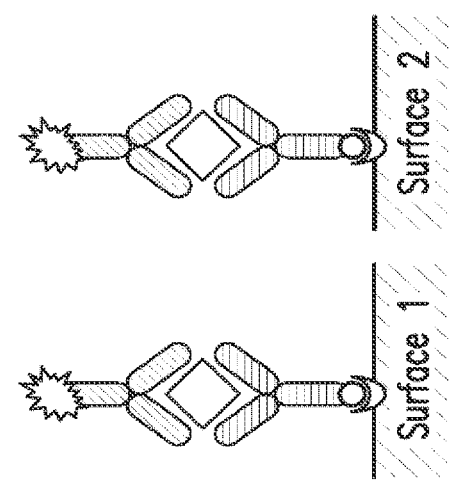
Figure 8E:
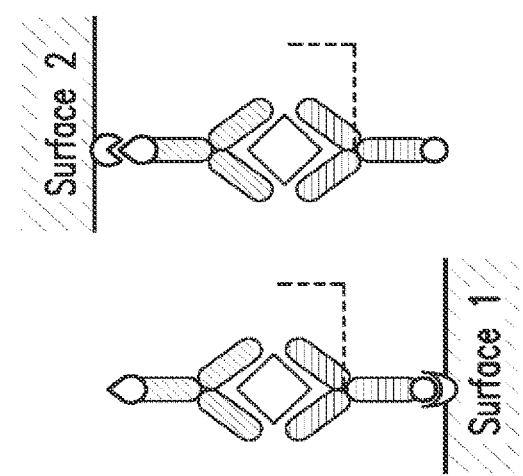

As disclosed in Section 5.2.4 and FIG. 8F, in some embodiments of the methods provided herein, including those of this section (Section 5.2.6), the reporter is a non-nucleic acid reporter. In other embodiments, the reporter is a nucleic acid reporter. As such, in one specific embodiment, the method provided herein comprises:

(1) mixing a first binding moiety comprising a first binder and a first presenting group, a second binding moiety comprising a second binder, and the sample in a solution, wherein:
  (i) the first and second binders bind to the analyte and form an immunocomplex,
  (ii) the immunocomplex is captured on a first solid surface in contact with the solution via binding between the first presenting group and a first receiving group coupled to the first solid surface, and
  (iii) the first binding moiety further comprises a first target label and the second binding moiety further comprises a second target label;

(2) washing the first solid surface to remove unbound molecules;

(3) generating a nucleic acid reporter from the immunocomplex based on proximity between the first target label and the second target label; and (4) detecting the reporter, thereby detecting the analyte.

In another specific embodiment, the method provided herein comprises:

(1) mixing a first binding moiety comprising a first binder and a first presenting group, a second binding moiety comprising a second binder, and the sample in a solution, wherein:
  (i) the first and second binders bind to the analyte and form an immunocomplex,
  (ii) the immunocomplex is captured on a first solid surface in contact with the solution via binding between the first presenting group and a first receiving group coupled to the first solid surface, and
  (iii) the first binding moiety further comprises a first target label comprising a first identity barcode ("ID") that is analyte-specific ("target ID") and the second binding moiety further comprises a second target label comprising a second target ID;
(2) washing the first solid surface to remove unbound molecules;
(3) generating a nucleic acid reporter from the immunocomplex, wherein the nucleic acid reporter comprises (i) the first target ID, (ii) the second target ID, or (iii) both the first and the second target ID; and
(4) detecting the reporter, thereby detecting the analyte.

Additionally, as described above in Section 5.2.1.1, the immunocomplex can be released from the first surface and recaptured in the second surface to further increase the signal to noise ratio. Therefore, in one embodiment, methods provided herein comprises:
(1) mixing a first binding moiety comprising a first binder and a first presenting group, a second binding moiety comprising a second binder, and the sample in a solution, wherein:
  (i) the first and second binders bind to the analyte and form an immunocomplex,
  (ii) the immunocomplex is captured on a first solid surface in contact with the solution via binding between the first presenting group and a first receiving group coupled to the first solid surface, and
  (iii) the first binding moiety further comprises a first target label and the second binding moiety further comprises a second target label;
(2) washing the first solid surface to remove unbound molecules;
(2a) releasing the immunocomplex from the first solid surface by disrupting the binding between the first presenting group and the first receiving group;
(3) generating a reporter from the immunocomplex based on proximity between the first target label and the second target label; and
(4) detecting the reporter, thereby detecting the analyte.

In another embodiment, methods provided herein comprise:
(1) mixing a first binding moiety comprising a first binder and a first presenting group, a second binding moiety comprising a second binder, and the sample in a solution, wherein:
  (i) the first and second binders bind to the analyte and form an immunocomplex,
  (ii) the immunocomplex is captured on a first solid surface in contact with the solution via binding between the first presenting group and a first receiving group coupled to the first solid surface, and
  (iii) the first binding moiety further comprises a first target label and the second binding moiety further comprises a second target label;
(2) washing the first solid surface to remove unbound molecules;
(3) releasing the immunocomplex from the first solid surface by disrupting the binding between the first presenting group and the first receiving group, simultaneously generating a reporter from the immunocomplex based on proximity between the first target label and the second target label; and
(4) detecting the reporter, thereby detecting the analyte.

In yet another embodiment, methods provided herein comprise:
(1) mixing a first binding moiety comprising a first binder and a first presenting group, a second binding moiety comprising a second binder, and the sample in a solution, wherein:
  (i) the first and second binders bind to the analyte and form an immunocomplex,
  (ii) the immunocomplex is captured on a first solid surface in contact with the solution via binding between the first presenting group and a first receiving group coupled to the first solid surface, and
  (iii) the first binding moiety further comprises a first target label and the second binding moiety further comprises a second target label;
(2) washing the first solid surface to remove unbound molecules;
(3) generating a reporter from the immunocomplex based on proximity between the first target label and the second target label; and
(3a) releasing the immunocomplex from the first solid surface by disrupting the binding between the first presenting group and the first receiving group; and
(4) detecting the reporter, thereby detecting the analyte.

In still another embodiment, methods provided herein comprise:
(1) mixing a first binding moiety comprising a first binder and a first presenting group, a second binding moiety comprising a second binder, and the sample in a solution, wherein:
  (i) the first and second binders bind to the analyte and form an immunocomplex,
  (ii) the immunocomplex is captured on a first solid surface in contact with the solution via binding between the first presenting group and a first receiving group coupled to the first solid surface, and
  (iii) the first binding moiety further comprises a first target label comprising a first identity barcode ("ID") that is analyte-specific ("target ID") and the second binding moiety further comprises a second target label comprising a second target ID;
(2) washing the first solid surface to remove unbound molecules;
(2a) releasing the immunocomplex from the first solid surface by disrupting the binding between the first presenting group and the first receiving group;
(3) generating a reporter from the immunocomplex, wherein the reporter comprises (i) the first target ID, (ii) the second target ID, or (iii) both the first and the second target ID; and
(4) detecting the reporter, thereby detecting the analyte.

In still yet another embodiment, methods provided herein comprise:
(1) mixing a first binding moiety comprising a first binder and a first presenting group, a second binding moiety comprising a second binder, and the sample in a solution, wherein:
  (i) the first and second binders bind to the analyte and form an immunocomplex,
  (ii) the immunocomplex is captured on a first solid surface in contact with the solution via binding between the first presenting group and a first receiving group coupled to the first solid surface, and
  (iii) the first binding moiety further comprises a first target label comprising a first identity barcode ("ID") that is analyte-specific ("target ID") and the second binding moiety further comprises a second target label comprising a second target ID;
(2) washing the first solid surface to remove unbound molecules;
(3) releasing the immunocomplex from the first solid surface by disrupting the binding between the first presenting group and the first receiving group, and simultaneously generating a reporter from the immunocomplex, wherein the reporter comprises (i) the first target ID, (ii) the second target ID, or (iii) both the first and the second target ID; and (4) detecting the reporter, thereby detecting the analyte.

In a further embodiment, methods provided herein comprise:

(1) mixing a first binding moiety comprising a first binder and a first presenting group, a second binding moiety comprising a second binder, and the sample in a solution, wherein:
  (i) the first and second binders bind to the analyte and form an immunocomplex,
  (ii) the immunocomplex is captured on a first solid surface in contact with the solution via binding between the first presenting group and a first receiving group coupled to the first solid surface, and
  (iii) the first binding moiety further comprises a first target label comprising a first identity barcode ("ID") that is analyte-specific ("target ID") and the second binding moiety further comprises a second target label comprising a second target ID;

(2) washing the first solid surface to remove unbound molecules;

(3) generating a reporter from the immunocomplex, wherein the reporter comprises (i) the first target ID, (ii) the second target ID, or (iii) both the first and the second target ID;

(3a) releasing the immunocomplex from the first solid surface by disrupting the binding between the first presenting group and the first receiving group; and (4) detecting the reporter, thereby detecting the analyte.

Additionally, as described above in Section 5.2.1.1, the immunocomplex can be released from the first surface and recaptured in the second surface to further increase the signal to noise ratio. FIGS. 21A-21F depict exemplary schematic representations of an assay method including such two captures. Accordingly, in one embodiment of the method provided herein, the second binding moiety further comprises a second presenting group. In another embodiment, the method further comprises a step 2(b) between step 2(a) and step (3): (2b) introducing a second solid surface and recapturing the immunocomplex on the second solid surface via binding between the second presenting group and the second receiving group coupled to the second solid surface. As such, in some embodiments, the methods provided herein comprise:

(1) mixing a first binding moiety comprising a first binder and a first presenting group, a second binding moiety comprising a second binder, and the sample in a solution, wherein:
  (i) the first and second binders bind to the analyte and form an immunocomplex,
  (ii) the immunocomplex is captured on a first solid surface in contact with the solution via binding between the first presenting group and a first receiving group coupled to the first solid surface, and
  (iii) the first binding moiety further comprises a first target label and the second binding moiety further comprises a second target label;

(2) washing the first solid surface to remove unbound molecules;

(2a) releasing the immunocomplex from the first solid surface by disrupting the binding between the first presenting group and the first receiving group;

(2b) introducing a second solid surface and recapturing the immunocomplex on the second solid surface via binding between the second presenting group and the second receiving group coupled to the second solid surface;

(3) generating a reporter from the immunocomplex based on proximity between the first target label and the second target label; and (4) detecting the reporter, thereby detecting the analyte.

In other embodiments, the methods provided herein comprise:

(1) mixing a first binding moiety comprising a first binder and a first presenting group, a second binding moiety comprising a second binder, and the sample in a solution, wherein:
  (i) the first and second binders bind to the analyte and form an immunocomplex,
  (ii) the immunocomplex is captured on a first solid surface in contact with the solution via binding between the first presenting group and a first receiving group coupled to the first solid surface, and
  (iii) the first binding moiety further comprises a first target label comprising a first identity barcode ("ID") that is analyte-specific ("target ID") and the second binding moiety further comprises a second target label comprising a second target ID;

(2) washing the first solid surface to remove unbound molecules;

(2a) releasing the immunocomplex from the first solid surface by disrupting the binding between the first presenting group and the first receiving group;

(2b) introducing a second solid surface and recapturing the immunocomplex on the second solid surface via binding between the second presenting group and the second receiving group coupled to the second solid surface;

(3) generating a reporter from the immunocomplex, wherein the reporter comprises (i) the first target ID, (ii) the second target ID, or (iii) both the first and the second target ID; and (4) detecting the reporter, thereby detecting the analyte.

Additionally, the methods provided herein further comprise a step 2(c) between step 2(b) and step (3): (2c) washing the second solid surface to remove unbound molecules. As such, in some embodiments, the methods provided herein comprise:

(1) mixing a first binding moiety comprising a first binder and a first presenting group, a second binding moiety comprising a second binder, and the sample in a solution, wherein:
  (i) the first and second binders bind to the analyte and form an immunocomplex,
  (ii) the immunocomplex is captured on a first solid surface in contact with the solution via binding between the first presenting group and a first receiving group coupled to the first solid surface, and
  (iii) the first binding moiety further comprises a first target label and the second binding moiety further comprises a second target label;

(2) washing the first solid surface to remove unbound molecules;

(2a) releasing the immunocomplex from the first solid surface by disrupting the binding between the first presenting group and the first receiving group;

(2b) introducing a second solid surface and recapturing the immunocomplex on the second solid surface via binding between the second presenting group and the second receiving group coupled to the second solid surface;

(2c) washing the second solid surface to remove unbound molecules;
(3) generating a reporter from the immunocomplex based on proximity between the first target label and the second target label; and
(4) detecting the reporter, thereby detecting the analyte.

In other embodiments, the methods provided herein comprise:
(1) mixing a first binding moiety comprising a first binder and a first presenting group, a second binding moiety comprising a second binder, and the sample in a solution, wherein:
  (i) the first and second binders bind to the analyte and form an immunocomplex,
  (ii) the immunocomplex is captured on a first solid surface in contact with the solution via binding between the first presenting group and a first receiving group coupled to the first solid surface, and
  (iii) the first binding moiety further comprises a first target label comprising a first identity barcode ("ID") that is analyte-specific ("target ID") and the second binding moiety further comprises a second target label comprising a second target ID;
(2) washing the first solid surface to remove unbound molecules;
(2a) releasing the immunocomplex from the first solid surface by disrupting the binding between the first presenting group and the first receiving group;
(2b) introducing a second solid surface and recapturing the immunocomplex on the second solid surface via binding between the second presenting group and the second receiving group coupled to the second solid surface;
(2c) washing the second solid surface to remove unbound molecules;
(3) generating a reporter from the immunocomplex, wherein the reporter comprises (i) the first target ID, (ii) the second target ID, or (iii) both the first and the second target ID; and
(4) detecting the reporter, thereby detecting the analyte.

Additionally, the methods provided herein further comprise a step 2(d): releasing the immunocomplex from the second solid surface by disrupting the binding between the second presenting group and the second receiving group. As such, in some embodiments, the methods provided herein comprise:
(1) mixing a first binding moiety comprising a first binder and a first presenting group, a second binding moiety comprising a second binder, and the sample in a solution, wherein:
  (i) the first and second binders bind to the analyte and form an immunocomplex,
  (ii) the immunocomplex is captured on a first solid surface in contact with the solution via binding between the first presenting group and a first receiving group coupled to the first solid surface, and
  (iii) the first binding moiety further comprises a first target label and the second binding moiety further comprises a second target label;
(2) washing the first solid surface to remove unbound molecules;
(2a) releasing the immunocomplex from the first solid surface by disrupting the binding between the first presenting group and the first receiving group;
(2b) introducing a second solid surface and recapturing the immunocomplex on the second solid surface via binding between the second presenting group and the second receiving group coupled to the second solid surface;
(2c) washing the second solid surface to remove unbound molecules;
(2d) releasing the immunocomplex from the second solid surface by disrupting the binding between the second presenting group and the second receiving group;
(3) generating a reporter from the immunocomplex based on proximity between the first target label and the second target label; and
(4) detecting the reporter, thereby detecting the analyte.

In other embodiments, the methods provided herein comprise:
(1) mixing a first binding moiety comprising a first binder and a first presenting group, a second binding moiety comprising a second binder, and the sample in a solution, wherein:
  (i) the first and second binders bind to the analyte and form an immunocomplex,
  (ii) the immunocomplex is captured on a first solid surface in contact with the solution via binding between the first presenting group and a first receiving group coupled to the first solid surface, and
  (iii) the first binding moiety further comprises a first target label comprising a first identity barcode ("ID") that is analyte-specific ("target ID") and the second binding moiety further comprises a second target label comprising a second target ID;
(2) washing the first solid surface to remove unbound molecules;
(2a) releasing the immunocomplex from the first solid surface by disrupting the binding between the first presenting group and the first receiving group;
(2b) introducing a second solid surface and recapturing the immunocomplex on the second solid surface via binding between the second presenting group and the second receiving group coupled to the second solid surface;
(2c) washing the second solid surface to remove unbound molecules;
(2d) releasing the immunocomplex from the second solid surface by disrupting the binding between the second presenting group and the second receiving group;
(3) generating a reporter from the immunocomplex, wherein the reporter comprises (i) the first target ID, (ii) the second target ID, or (iii) both the first and the second target ID; and
(4) detecting the reporter, thereby detecting the analyte.

In yet other embodiments, the methods provided herein comprise:
(1) mixing a first binding moiety comprising a first binder and a first presenting group, a second binding moiety comprising a second binder, and the sample in a solution, wherein:
  (i) the first and second binders bind to the analyte and form an immunocomplex,
  (ii) the immunocomplex is captured on a first solid surface in contact with the solution via binding between the first presenting group and a first receiving group coupled to the first solid surface, and
  (iii) the first binding moiety further comprises a first target label and the second binding moiety further comprises a second target label;
(2) washing the first solid surface to remove unbound molecules;

(2a) releasing the immunocomplex from the first solid surface by disrupting the binding between the first presenting group and the first receiving group;

(2b) introducing a second solid surface and recapturing the immunocomplex on the second solid surface via binding between the second presenting group and the second receiving group coupled to the second solid surface;

(2c) washing the second solid surface to remove unbound molecules;

(3) releasing the immunocomplex from the second solid surface by disrupting the binding between the second presenting group and the second receiving group, and generating a reporter from the immunocomplex based on proximity between the first target label and the second target label; and (4) detecting the reporter, thereby detecting the analyte.

In yet other embodiments, the methods provided herein comprise:

(1) mixing a first binding moiety comprising a first binder and a first presenting group, a second binding moiety comprising a second binder, and the sample in a solution, wherein:
  (i) the first and second binders bind to the analyte and form an immunocomplex,
  (ii) the immunocomplex is captured on a first solid surface in contact with the solution via binding between the first presenting group and a first receiving group coupled to the first solid surface, and
  (iii) the first binding moiety further comprises a first target label comprising a first identity barcode ("ID") that is analyte-specific ("target ID") and the second binding moiety further comprises a second target label comprising a second target ID;

(2) washing the first solid surface to remove unbound molecules;

(2a) releasing the immunocomplex from the first solid surface by disrupting the binding between the first presenting group and the first receiving group;

(2b) introducing a second solid surface and recapturing the immunocomplex on the second solid surface via binding between the second presenting group and the second receiving group coupled to the second solid surface;

(2c) washing the second solid surface to remove unbound molecules;

(3) releasing the immunocomplex from the second solid surface by disrupting the binding between the second presenting group and the second receiving group, and generating a reporter from the immunocomplex, wherein the reporter comprises (i) the first target ID, (ii) the second target ID, or (iii) both the first and the second target ID; and (4) detecting the reporter, thereby detecting the analyte.

As such, in some embodiments, the methods provided herein comprise:

(1) mixing a first binding moiety comprising a first binder and a first presenting group, a second binding moiety comprising a second binder, and the sample in a solution, wherein:
  (i) the first and second binders bind to the analyte and form an immunocomplex,
  (ii) the immunocomplex is captured on a first solid surface in contact with the solution via binding between the first presenting group and a first receiving group coupled to the first solid surface, and
  (iii) the first binding moiety further comprises a first target label and the second binding moiety further comprises a second target label;

(2) washing the first solid surface to remove unbound molecules;

(2a) releasing the immunocomplex from the first solid surface by disrupting the binding between the first presenting group and the first receiving group;

(2b) introducing a second solid surface and recapturing the immunocomplex on the second solid surface via binding between the second presenting group and the second receiving group coupled to the second solid surface;

(2c) washing the second solid surface to remove unbound molecules;

(3) generating a reporter from the immunocomplex based on proximity between the first target label and the second target label;

(4) releasing the immunocomplex from the second solid surface by disrupting the binding between the second presenting group and the second receiving group; and (5) detecting the reporter, thereby detecting the analyte.

In other embodiments, the methods provided herein comprise:

(1) mixing a first binding moiety comprising a first binder and a first presenting group, a second binding moiety comprising a second binder, and the sample in a solution, wherein:
  (i) the first and second binders bind to the analyte and form an immunocomplex,
  (ii) the immunocomplex is captured on a first solid surface in contact with the solution via binding between the first presenting group and a first receiving group coupled to the first solid surface, and
  (iii) the first binding moiety further comprises a first target label comprising a first identity barcode ("ID") that is analyte-specific ("target ID") and the second binding moiety further comprises a second target label comprising a second target ID;

(2) washing the first solid surface to remove unbound molecules;

(2a) releasing the immunocomplex from the first solid surface by disrupting the binding between the first presenting group and the first receiving group;

(2b) introducing a second solid surface and recapturing the immunocomplex on the second solid surface via binding between the second presenting group and the second receiving group coupled to the second solid surface;

(2c) washing the second solid surface to remove unbound molecules;

(3) generating a reporter from the immunocomplex, wherein the reporter comprises (i) the first target ID, (ii) the second target ID, or (iii) both the first and the second target ID; and (4) releasing the immunocomplex from the second solid surface by disrupting the binding between the second presenting group and the second receiving group; and (5) detecting the reporter, thereby detecting the analyte.

In one aspect, provided herein is an assay method for detecting an analyte in a sample, comprising:

(1) mixing a first binding moiety comprising a first binder and a first presenting group, a second binding moiety comprising a second binder, and the sample in a solution, wherein:

(i) the first and second binders bind non-interfering epitopes on the analyte and form an immunocomplex, (ii) the immunocomplex is captured on a first solid surface in contact with the solution via binding between the first presenting group and a first receiving group coupled to the first solid surface, and (iii) the first binding moiety further comprises a first target label comprising a first identity barcode ("ID") that is analyte-specific ("target ID") and the second binding moiety further comprises a second target label comprising a second target ID;

(2) washing the first solid surface to remove unbound molecules;

(3) generating a nucleic acid reporter comprising the first target ID and the second target ID; and (4) detecting the nucleic acid reporter, thereby detecting the analyte.

As described above in Section 5.2.1.1 and 5.2.1.2, the immunocomplex can be detected and the nucleic acid reporter generated either on a solid surface, or after being released from a solid surface. FIGS. 20A-20D provide exemplary schematic representations of generating a nucleic acid reporter after being released from a solid surface (indicated as 1st surface in FIGS. 20B-20C) and FIG. 20E provides confirmatory data showing from such an exemplary capture and release assay, in which the analyte is detected by signals determined via the target ID in the target label as generated in the nucleic acid reporter. As such, in one embodiment, the method provided herein further comprises a step (2a) between step (2) and (3): releasing the immunocomplex from the first solid surface by disrupting the binding between the first presenting group and the first receiving group. In one specific embodiment, the method provided herein comprises:

(1) mixing a first binding moiety comprising a first binder and a first presenting group, a second binding moiety comprising a second binder, and the sample in a solution, wherein:

(i) the first and second binders bind non-interfering epitopes on the analyte and form an immunocomplex, (ii) the immunocomplex is captured on a first solid surface in contact with the solution via binding between the first presenting group and a first receiving group coupled to the first solid surface, and (iii) the first binding moiety further comprises a first target label comprising a first identity barcode ("ID") that is analyte-specific ("target ID") and the second binding moiety further comprises a second target label comprising a second target ID;

(2) washing the first solid surface to remove unbound molecules;

(2a) releasing the immunocomplex from the first solid surface by disrupting the binding between the first presenting group and the first receiving group;

(3) generating a nucleic acid reporter comprising the first target ID and the second target ID; and (4) detecting the nucleic acid reporter, thereby detecting the analyte.

Additionally, as described above in Section 5.2.1.1, the immunocomplex can be released from the first surface and recaptured in the second surface to further increase the signal to noise ratio. FIGS. 21A-21F depict exemplary schematic representations of an assay method including such two captures. Accordingly, in one embodiment of the method provided herein, the second binding moiety further comprises a second presenting group. In another embodiment, the method further comprises a step 2(b) and a step 2(c) between step 2(a) and step (3): (2b) introducing a second solid surface and recapturing the immunocomplex on the second solid surface via binding between the second presenting group and the second receiving group coupled to the second solid surface; and (2c) washing the second solid surface to remove unbound molecules. As such, in some embodiments, the methods provided herein comprises:

(1) mixing a first binding moiety comprising a first binder and a first presenting group, a second binding moiety comprising a second binder and a second presenting group, and the sample in a solution, wherein:

(i) the first and second binders bind non-interfering epitopes on the analyte and form an immunocomplex, (ii) the immunocomplex is captured on a first solid surface in contact with the solution via binding between the first presenting group and a first receiving group coupled to the first solid surface, and (iii) the first binding moiety further comprises a first target label comprising a first identity barcode ("ID") that is analyte-specific ("target ID") and the second binding moiety further comprises a second target label comprising a second target ID;

(2) washing the first solid surface to remove unbound molecules;

(2a) releasing the immunocomplex from the first solid surface by disrupting the binding between the first presenting group and the first receiving group;

(2b) introducing a second solid surface and recapturing the immunocomplex on the second solid surface via binding between the second presenting group and the second receiving group coupled to the second solid surface;

(2c) washing the second solid surface to remove unbound molecules;

(3) generating a nucleic acid reporter comprising the first target ID and the second target ID; and (4) detecting the nucleic acid reporter, thereby detecting the analyte Similarly, as described above in this section and in Section 5.2.1.1 and 5.2.1.2, the immunocomplex can be detected and the nucleic acid reporter generated either on a solid surface, or after being released from a solid surface. FIGS. 21G-21I provide exemplary schematic representations of generating a nucleic acid reporter after being captured and released from 1st and 2nd solid surface and FIGS. 24A-24B and 25A-25C provide confirmatory data showing such an exemplary capture and release assay, in which the analyte is detected by signals determined via the target ID in the target label as generated in the nucleic acid reporter. Accordingly, in one embodiment, the method provided herein further comprises a step (2d): releasing the immunocomplex from the second solid surface by disrupting the binding between the second presenting group and the second receiving group. In one specific embodiment, the method provided herein comprises:

(1) mixing a first binding moiety comprising a first binder and a first presenting group, a second binding moiety comprising a second binder and a second presenting group, and the sample in a solution, wherein:

(i) the first and second binders bind non-interfering epitopes on the analyte and form an immunocomplex, (ii) the immunocomplex is captured on a first solid surface in contact with the solution via binding between the first presenting group and a first receiving group coupled to the first solid surface, and (iii) the first binding moiety further comprises a first target label comprising a first identity barcode ("ID") that is analyte-specific ("target ID") and the second binding moiety further comprises a second target label comprising a second target ID;

(2) washing the first solid surface to remove unbound molecules;

(2a) releasing the immunocomplex from the first solid surface by disrupting the binding between the first presenting group and the first receiving group;

(2b) introducing a second solid surface and recapturing the immunocomplex on the second solid surface via binding between the second presenting group and the second receiving group coupled to the second solid surface;

(2c) washing the second solid surface to remove unbound molecules;

(2d) releasing the immunocomplex from the second solid surface by disrupting the binding between the second presenting group and the second receiving group;

(3) generating a nucleic acid reporter comprising the first target ID and the second target ID; and (4) detecting the nucleic acid reporter, thereby detecting the analyte.

As described further above in Section 5.2.5, in addition to analyte-specific "target IDs," the nucleic acid reporters generated in the assay methods provided herein can also include sample-specific "sample IDs." FIGS. 22 and FIGS. 23A-23B provide exemplary schematic representations for generating a nucleic acid reporter with sample IDs and FIGS. 24A-24B and 25A-25C provide confirmatory data showing such multiplexing assays, wherein the analyte is detected by signals determined via the target ID in the target label and the sample ID as generated in the nucleic acid reporter, thereby parsing out the samples via the sample IDs and analyte via the target IDs. Accordingly, in one embodiment, the method provided herein further comprises a step (2e): binding a sample label comprising an ID that is sample-specific ("sample ID") (i) to the first target label, (ii) to the second target label, or (iii) to both the first target label and the second target label. In one specific embodiment, the method provided herein comprises:

(1) mixing a first binding moiety comprising a first binder and a first presenting group, a second binding moiety comprising a second binder and a second presenting group, and the sample in a solution, wherein:
  (i) the first and second binders bind non-interfering epitopes on the analyte and form an immunocomplex,
  (ii) the immunocomplex is captured on a first solid surface in contact with the solution via binding between the first presenting group and a first receiving group coupled to the first solid surface, and
  (iii) the first binding moiety further comprises a first target label comprising a first identity barcode ("ID") that is analyte-specific ("target ID") and the second binding moiety further comprises a second target label comprising a second target ID;

(2) washing the first solid surface to remove unbound molecules;

(2a) releasing the immunocomplex from the first solid surface by disrupting the binding between the first presenting group and the first receiving group;

(2b) introducing a second solid surface and recapturing the immunocomplex on the second solid surface via binding between the second presenting group and the second receiving group coupled to the second solid surface;

(2c) washing the second solid surface to remove unbound molecules;

(2d) releasing the immunocomplex from the second solid surface by disrupting the binding between the second presenting group and the second receiving group;

(2e) binding a sample label comprising an ID that is sample-specific ("sample ID") (i) to the first target label, (ii) to the second target label, or (iii) to both the first target label and the second target label (3) generating a nucleic acid reporter comprising the first target ID and the second target ID; and (4) detecting the nucleic acid reporter, thereby detecting the analyte.

Each binding moiety can comprise one or more target labels. In one embodiment, the first binding moiety comprises one target label. In another embodiment, the first binding moiety comprises two target labels. In a further embodiment, the first binding moiety comprises three target labels. In yet another embodiment, the first binding moiety comprises four target labels. In yet another embodiment, the first binding moiety comprises five or more target labels. In one embodiment, the second binding moiety comprises one target label. In another embodiment, the second binding moiety comprises two target labels. In a further embodiment, the second binding moiety comprises three target labels. In yet another embodiment, the second binding moiety comprises four target labels. In yet another embodiment, the second binding moiety comprises five or more target labels. In some embodiments, the target labels between the first binding moiety and the second binding moiety are different. In certain embodiments, the target labels between the first binding moiety and the second binding moiety are identical. In some further embodiments, the target labels within the first binding moiety are different. In other embodiments, the target labels within the first binding moiety are identical. In some further embodiments, the target labels within the second binding moiety are different. In other embodiments, the target labels within the second binding moiety are identical. In some embodiments, the first binding moiety have any target labels as provided in this paragraph and the second binding moiety have any target labels as provided in this paragraph in any combination. In one specific embodiment, the first binding moiety comprises a first target label and the second binding moiety comprises a second target label, wherein the first target label and the second target label are different. In another specific embodiment, the first binding moiety comprises a first target label and the second binding moiety comprises a second target label, wherein the first target label and the second target label are identical.

Alternatively, one of the two binding moieties can have no target label. In one embodiment of the methods provided herein including in this Section 5.2.6, the first binding moiety lacks a target label. In another embodiment, the second binding moiety lacks a target label. In a further embodiment, the first binding moiety comprises no target label. In yet another embodiment, the second binding moiety comprises no target label. In one embodiment, the first binding moiety comprises no target label and the second binding moiety comprises one target label. In another embodiment, the first binding moiety comprises one target label and the second binding moiety comprises no target label. In yet another embodiment, the first binding moiety comprises no target label and the second binding moiety comprises two, three, four, five, or more target labels. In another embodiment, the first binding moiety comprises two, three, four, five, or more target labels and the second binding moiety comprises no target label. In one embodiment, the first binding moiety lacks a target label and the second binding moiety comprises one target label. In another embodiment, the first binding moiety comprises one target label and the second binding moiety lacks a target label. In yet another embodiment, the first binding moiety lacks a target label and the second binding moiety comprises two, three, four, five, or more target labels. In another embodiment, the first binding moiety comprises two, three, four, five, or more target labels and the second binding moiety lacks a target label.

Similarly, one of the two binding moieties can have no presenting group. In one embodiment of the methods provided herein including in this Section 5.2.6, the first binding moiety lacks a presenting group. In another embodiment, the second binding moiety lacks a presenting group. In a further embodiment, the first binding moiety comprises no presenting group. In yet another embodiment, the second binding moiety comprises no presenting group. In one embodiment, the first binding moiety comprises no presenting group and the second binding moiety comprises one presenting group. In another embodiment, the first binding moiety comprises one presenting group and the second binding moiety comprises no presenting group. In one embodiment, the first binding moiety lacks a presenting group and the second binding moiety comprises one presenting group. In another embodiment, the first binding moiety comprises one presenting group and the second binding moiety lacks a presenting group.

Additionally, in some embodiments of the methods provided herein including those in this section (Section 5.2.6) and in the preceding paragraph, each target label can comprises one or more target IDs. In one embodiment, the first target label comprises a first target ID. In another embodiment, the second target label comprises a second target ID. In some embodiments, the target IDs between the first target label and the second target label are different. In certain embodiments, the target IDs between the first target label and the second target label are identical. In one specific embodiment, the first target label comprises a first target ID and the second target label comprises a second target ID, wherein the first target ID and the second target ID are different. In another specific embodiment, the first target label comprises a first target ID and the second target label comprises a second target ID, wherein the first target ID and the second target ID are identical.

Similarly as described further above in Section 5.2.5, in some embodiments of the methods provided herein, including those of this section (Section 5.2.6), each nucleic acid reporter can comprise one or more target IDs and/a sample ID. In one embodiment, the nucleic acid reporter formed in each sample contains a sample ID. In another embodiment, the nucleic acid reporter formed in each sample contains a target ID. In a further embodiment, the nucleic acid reporter formed in each sample contains the first target ID. In still another embodiment, the nucleic acid reporter formed in each sample contains the second target ID. In yet another embodiment, the nucleic acid reporter formed in each sample contains a sample ID and the first target ID. In one embodiment, the nucleic acid reporter formed in each sample contains a sample ID and the second target ID. In another embodiment, the nucleic acid reporter formed in each sample contains the first target ID and the second target ID. In a further embodiment, the nucleic acid reporter formed in each sample contains the first target ID and the second target ID, wherein the nucleic acid reporter lacks a sample ID. In yet another embodiment, the nucleic acid reporter formed in each sample contains the first target ID, the second target ID, and a sample ID.

As the nucleic acid reporter is generated from the immunocomplex that is formed from the first binding moiety comprising the first target label, the second binding moiety comprising the second target label, the analyte, and/or the sample label, such immunocomplex formed in the methods provided herein (including in this section (Section 5.2.6)) can similarly comprise one or more target IDs and/a sample ID. In one embodiment, the immunocomplex formed in each sample contains a sample ID. In another embodiment, the immunocomplex formed in each sample contains a target ID. In a further embodiment, the immunocomplex formed in each sample contains the first target ID. In still another embodiment, the immunocomplex formed in each sample contains the second target ID. In yet another embodiment, the immunocomplex formed in each sample contains a sample ID and the first target ID. In one embodiment, the immunocomplex formed in each sample contains a sample ID and the second target ID. In another embodiment, the immunocomplex formed in each sample contains the first target ID and the second target ID. In a further embodiment, the immunocomplex formed in each sample contains the first target ID and the second target ID, wherein the immunocomplex lacks a sample ID. In yet another embodiment, the immunocomplex formed in each sample contains the first target ID, the second target ID, and a sample ID.

Furthermore, as the sample ID is contained in the sample label and the target ID is contained in the target label, the immunocomplex formed in the methods provided herein (including in this section (Section 5.2.6)) can comprise one or more target labels and/a sample label. In one embodiment, the immunocomplex formed in each sample contains a sample label. In another embodiment, the immunocomplex formed in each sample contains a target label. In a further embodiment, the immunocomplex formed in each sample contains the first target label. In still another embodiment, the immunocomplex formed in each sample contains the second target label. In yet another embodiment, the immunocomplex formed in each sample contains a sample label and the first target label. In one embodiment, the immunocomplex formed in each sample contains a sample label and the second target label. In another embodiment, the immunocomplex formed in each sample contains the first target label and the second target label. In a further embodiment, the immunocomplex formed in each sample contains the first target label and the second target label, wherein the immunocomplex lacks a sample label. In yet another embodiment, the immunocomplex formed in each sample contains the first target label, the second target label, and a sample label.

As Section 5.1 provides, IDs include both the original ID molecules and derivative ID molecules that contain the information derived from but is non-identical to the original ID, so long as such derived molecules or the derived information can identify or otherwise distinguish a particular target or sample from other targets or samples and be correlated with the intended target or sample. Specifically, when IDs are nucleic acid barcode sequences, the nucleic acid ID can include both the original nucleic acid barcode sequence and/or the reverse complement of the original nucleic acid barcode sequence, as both can distinguish and be correlated with the intended target or sample. Accordingly, in some embodiments, the first target ID in the reporter comprises or consists of the original sequence of the first target ID in the first binding moiety. In certain embodiments, the first target ID in the reporter comprises or consists of a complementary sequence of the first target ID in the first binding moiety. In one embodiment, the second target ID in the reporter comprises or consists of the original sequence of the second target ID in the second binding moiety. In other embodiments, the second target ID in the reporter comprises or consists of a complementary sequence of the second target ID in the second binding moiety. In one embodiment, the sample ID in the reporter comprises or consists of the original sequence of the sample ID in the sample label. In another embodiment, the sample ID in the reporter comprises or consists of a complementary sequence of the sample ID in sample label.

In one embodiment, the first target ID in the reporter comprises or consists of the original sequence of the first target ID in the first binding moiety and the second target ID in the reporter comprises or consists of the original sequence of the second target ID in the second binding moiety. In one embodiment, the first target ID in the reporter comprises or consists of the original sequence of the first target ID in the first binding moiety and the sample ID in the reporter comprises or consists of the original sequence of the sample ID in the sample label. In one embodiment, the second target ID in the reporter comprises or consists of the original sequence of the second target ID in the second binding moiety and the sample ID in the reporter comprises or consists of the original sequence of the sample ID in the sample label.

In one embodiment, the first target ID in the reporter comprises or consists of a complementary sequence of the first target ID in the first binding moiety and the second target ID in the reporter comprises or consists of a complementary sequence of the second target ID in the second binding moiety. In one embodiment, the first target ID in the reporter comprises or consists of a complementary sequence of the first target ID in the first binding moiety and the sample ID in the reporter comprises or consists of a complementary sequence of the sample ID in the sample label. In one embodiment, the second target ID in the reporter comprises or consists of a complementary sequence of the second target ID in the second binding moiety and the sample ID in the reporter comprises or consists of a complementary sequence of the sample ID in the sample label.

In one embodiment, the first target ID in the reporter comprises or consists of the original sequence of the first target ID in the first binding moiety and the second target ID in the reporter comprises or consists of a complementary sequence of the second target ID in the second binding moiety. In one embodiment, the first target ID in the reporter comprises or consists of the original sequence of the first target ID in the first binding moiety and the sample ID in the reporter comprises or consists of a complementary sequence of the sample ID in the sample label. In one embodiment, the second target ID in the reporter comprises or consists of the original sequence of the second target ID in the second binding moiety and the sample ID in the reporter comprises or consists of a complementary sequence of the sample ID in the sample label. In one embodiment, the first target ID in the reporter comprises or consists of a complementary sequence of the first target ID in the first binding moiety and the second target ID in the reporter comprises or consists of the original sequence of the second target ID in the second binding moiety. In one embodiment, the first target ID in the reporter comprises or consists of a complementary sequence of the first target ID in the first binding moiety and the sample ID in the reporter comprises or consists of the original sequence of the sample ID in the sample label. In one embodiment, the second target ID in the reporter comprises or consists of a complementary sequence of the second target ID in the second binding moiety and the sample ID in the reporter comprises or consists of the original sequence of the sample ID in the sample label.

In one embodiment, the first target ID in the reporter comprises or consists of the original sequence of the first target ID in the first binding moiety, the second target ID in the reporter comprises or consists of the original sequence of the second target ID in the second binding moiety, and the sample ID in the reporter comprises or consists of the original sequence of the sample ID in the sample label.

In one embodiment, the first target ID in the reporter comprises or consists of a complementary sequence of the first target ID in the first binding moiety, the second target ID in the reporter comprises or consists of the original sequence of the second target ID in the second binding moiety, and the sample ID in the reporter comprises or consists of the original sequence of the sample ID in the sample label. In one embodiment, the first target ID in the reporter comprises or consists of the original sequence of the first target ID in the first binding moiety, the second target ID in the reporter comprises or consists of a complementary sequence of the second target ID in the second binding moiety, and the sample ID in the reporter comprises or consists of the original sequence of the sample ID in the sample label. In one embodiment, the first target ID in the reporter comprises or consists of the original sequence of the first target ID in the first binding moiety, the second target ID in the reporter comprises or consists of the original sequence of the second target ID in the second binding moiety, and the sample ID in the reporter comprises or consists of a complementary sequence of the sample ID in the sample label.

In one embodiment, the first target ID in the reporter comprises or consists of a complementary sequence of the first target ID in the first binding moiety, the second target ID in the reporter comprises or consists of a complementary sequence of the second target ID in the second binding moiety, and the sample ID in the reporter comprises or consists of the original sequence of the sample ID in the sample label. In one embodiment, the first target ID in the reporter comprises or consists of a complementary sequence of the first target ID in the first binding moiety, the second target ID in the reporter comprises or consists of the original sequence of the second target ID in the second binding moiety, and the sample ID in the reporter comprises or consists of a complementary sequence of the sample ID in the sample label. In one embodiment, the first target ID in the reporter comprises or consists of the original sequence of the first target ID in the first binding moiety, the second target ID in the reporter comprises or consists of a complementary sequence of the second target ID in the second binding moiety, and the sample ID in the reporter comprises or consists of a complementary sequence of the sample ID in the sample label.

In one embodiment, the first target ID in the reporter comprises or consists of a complementary sequence of the first target ID in the first binding moiety, the second target ID in the reporter comprises or consists of the original sequence of the second target ID in the second binding moiety, and the sample ID in the reporter comprises or consists of a complementary sequence of the sample ID in the sample label. In one embodiment, the first target ID in the reporter comprises or consists of the original sequence of the first target ID in the first binding moiety, the second target ID in the reporter comprises or consists of a complementary sequence of the second target ID in the second binding moiety, and the sample ID in the reporter comprises or consists of a complementary sequence of the sample ID in the sample label.

In one embodiment, the first target ID in the reporter comprises or consists of a complementary sequence of the first target ID in the first binding moiety, the second target ID in the reporter comprises or consists of a complementary sequence of the second target ID in the second binding moiety, and the sample ID in the reporter comprises or consists of a complementary sequence of the sample ID in the sample label.

As is clear from the disclosure, in the methods provided herein including those provided in this section (Section 5.2.6), the presenting group in the first binding moiety and the presenting group in the second binding moiety each can be any embodiments of presenting group provided in the disclosure including those provided in Sections 3, 5.1, 5.2.1 to 5.2.6, 5.3.1 to 5.3.3, and 6. The combination of the presenting group in the first binding moiety and the presenting group in the second binding moiety can be any combination of any embodiments of presenting group provided in the disclosure including those provided in Sections 3, 5.1, 5.2.1 to 5.2.6, 5.3.1 to 5.3.3, and 6. In one embodiment of the methods provided herein, the first presenting group is a polypeptide fused to the first binder. In another embodiment of the methods provided herein, the first presenting group is a polynucleotide conjugated to the first binder. In yet another embodiment of the methods provided herein, the first presenting group is a chemical compound conjugated to the first binder. In one embodiment of the methods provided herein, the second presenting group is a polypeptide fused to the second binder. In another embodiment of the methods provided herein, the second presenting group is a polynucleotide conjugated to the second binder. In yet another embodiment of the methods provided herein, the second presenting group is or a chemical compound conjugated to the second binder.

In some embodiments of the methods provided herein, the first presenting group is selected from the group consisting of a polypeptide fused to the first binder, a polynucleotide conjugated to the first binder, or a chemical compound conjugated to the first binder; and the second presenting group is selected from the group consisting of a polypeptide fused to the second binder, a polynucleotide conjugated to the second binder, or a chemical compound conjugated to the second binder. In one embodiment, the first presenting group is a polypeptide fused to the first binder and the second presenting group is a polypeptide fused to the second binder. In one embodiment, the first presenting group is a polypeptide fused to the first binder and the second presenting group is a polynucleotide conjugated to the second binder. In one embodiment, the first presenting group is a polypeptide fused to the first binder and the second presenting group is a chemical compound conjugated to the second binder. In one embodiment, the first presenting group is a polynucleotide conjugated to the first binder and the second presenting group is a polypeptide fused to the second binder. In one embodiment, the first presenting group is a polynucleotide conjugated to the first binder and the second presenting group is a polynucleotide conjugated to the second binder. In one embodiment, the first presenting group is a polynucleotide conjugated to the first binder and the second presenting group is a chemical compound conjugated to the second binder. In one embodiment, the first presenting group is a chemical compound conjugated to the first binder and the second presenting group is a polypeptide fused to the second binder. In one embodiment, the first presenting group is a chemical compound conjugated to the first binder and the second presenting group is a polynucleotide conjugated to the second binder. In one embodiment, the first presenting group is a chemical compound conjugated to the first binder and the second presenting group is a chemical compound conjugated to the second binder.

The disclosure further provides that the methods provided herein including in this Section 5.2.6 further comprises releasing the reporter from the immunocomplex. As is clear from the description including the description in Section 6, the reporter can be released from the immunocomplex to the solution for detection. In one embodiment, the methods provided herein comprises releasing the reporter from the immunocomplex before detecting the reporter. In another embodiment, the methods provided herein comprises releasing the reporter from the immunocomplex simultaneously detecting the reporter. In another embodiment, the reporter is not released from the immunocomplex before detecting the reporter. In yet another embodiment, the reporter released from the immunocomplex after detecting the reporter.

The disclosure further provides that the step (4) of the methods provided in this Section 5.2.6 further comprises PCR amplification of the nucleic acid reporter. As is clear from the disclosure, such PCR can be any PCR as provided in this and other sections, such as Sections 5.2.4 (including 5.2.4.1 and 5.2.4.2), 5.2.5 and 6, as well as any suitable PCR known and practiced in the field.

The disclosure further provides that the methods provided in this Section 5.2.6 further comprises purifying the nucleic acid reporter. In some embodiments, the methods provided herein further comprise purifying the nucleic acid reporter by selecting fragments of a given size of nucleic acids that is known and practiced in the field. In one embodiment, the methods provided herein further comprise purifying the nucleic acid reporter by affinity purification. In one embodiment, the methods provided herein further comprise purifying the nucleic acid reporter by affinity purification with a nucleic acid affinity tag that is complementary to the nucleic acid reporter or a fragment thereof. In one embodiment, the methods provided herein further comprise purifying the nucleic acid reporter by affinity purification with a nucleic acid affinity tag that hybridizes to the nucleic acid reporter or a fragment thereof. In other embodiment, the methods provided herein further comprise purifying the nucleic acid reporter by binding to an affinity tag and eluting in low-salt buffer or water after proper wash, which results in the nucleic acid reporter free of contaminating nucleotides, primers, adapters, adapter dimers, enzymes, buffer additives, or salts.

As is clear from the disclosures provided herein, including those of Sections 3, 5.2.2, and 6, the formation of the immunocomplex and the capturing of immunocomplex in the methods provided herein can be simultaneous or in order of one after the other, such as formation before capturing or capturing before formation. In one embodiment of the methods provided herein, including the methods of this Section (Section 5.2.6), the step (1) of the methods comprises forming the immunocomplex in the solution before capturing the immunocomplex on the first solid surface. In another embodiment, the step (1) of the methods provided herein comprises pre-capturing the first binder on the first solid surface before forming the immunocomplex on the first solid surface. In yet another embodiment, the immunocomplex is formed in the solution and captured on the first solid surface simultaneously in step (1) of the methods provided herein.

The disclosure further provides that the various steps of the methods provided here, including those in this Section (Section 5.2.6), the steps can be performed in any order that permits reporter to be generated from the immunocomplex formed in the methods. Accordingly, in one embodiment, the step of releasing the immunocomplex from the first solid surface by disrupting the binding between the first presenting group and the first receiving group can be performed before the step of generating a reporter from the immunocomplex. In another embodiment, the step of releasing the immunocomplex from the first solid surface by disrupting the binding between the first presenting group and the first receiving group can be performed after the step of generating a reporter from the immunocomplex. In a further embodiment, the step of releasing the immunocomplex from the first solid surface by disrupting the binding between the first presenting group and the first receiving group can be performed simultaneously of the step of generating a reporter from the immunocomplex. In one embodiment, the step of releasing the immunocomplex from the second solid surface by disrupting the binding between the second presenting group and the second receiving group can be performed before the step of generating a reporter from the immunocomplex. In another embodiment, the step of releasing the immunocomplex from the second solid surface by disrupting the binding between the second presenting group and the second receiving group can be performed after the step of generating a reporter from the immunocomplex. In a further embodiment, the step of releasing the immunocomplex from the second solid surface by disrupting the binding between the second presenting group and the second receiving group can be performed simultaneously of the step of generating a reporter from the immunocomplex.

As illustrated in FIGS. 8A-8G, the binders provided herein for the methods can bind directly or indirectly to analyte. As such, in some embodiments of the methods provided herein, including the methods of this Section (Section 5.2.6), the binder binds to the analyte directly. In other embodiments of the methods provided herein, the binder binds to the analyte indirectly. Accordingly, in some embodiments, the first binder binds to the analyte directly. In other embodiments, the second binder binds to the analyte directly. In yet other embodiments, the first binder binds to the analyte indirectly. In still yet other embodiments, the second binder binds to the analyte indirectly. Furthermore, any embodiments of binding relationship between the first binder and the analyte can be combined with any embodiments of binding relationship between the second binder and the analyte. In one specific embodiment, the first binder binds to the analyte directly and the second binder binds to the analyte directly. In another embodiment, the first binder binds to the analyte directly and the second binder binds to the analyte indirectly. In yet another embodiment, the first binder binds to the analyte indirectly and the second binder binds to the analyte directly. In still yet another embodiment, the first binder binds to the analyte indirectly and the second binder binds to the analyte indirectly.

As illustrated in FIG. 8G, the binders can bind to an analyte indirectly through an intermediary, e.g. a primary antibody against the analyte. As such, in some embodiments of the method provided herein, including the methods of this Section (Section 5.2.6), the binder binds to a primary antibody or a fragment thereof that binds directly to the analyte. Therefore, in some embodiments, the first binder binds to a first primary antibody or a fragment thereof that binds directly to the analyte. In other embodiments, the second binder binds to a second primary antibody or a fragment thereof that binds directly to the analyte. In yet other embodiment, the first binder binds to a first primary antibody or a fragment thereof that binds directly to the analyte, and the second binder binds to a second primary antibody or a fragment thereof that binds directly to the analyte. In a further embodiment, the first binder binds directly to the analyte, and the second binder binds to a second primary antibody or a fragment thereof that binds directly to the analyte. In some other embodiments, the first binder binds to a first primary antibody or a fragment thereof that binds directly to the analyte, and the second binder binds directly to the analyte.

As is clear from the disclosure that the two binders can simultaneously bind to an analyte, in some embodiments of the methods provided herein, including the methods of Sections 5.1 and 5.2, the first and second binders can bind epitopes on the analyte that permit simultaneous binding, thereby increasing the specificity of the detection. In some embodiments, the first and second binders bind to non-interfering epitopes on the analyte. In other embodiments, the first and second binders bind to non-overlapping epitopes on the analyte. In other embodiments, the first and second binders bind to different epitopes on the analyte. In yet other embodiments, the first and second binders bind to separate epitopes on the analyte. In still yet other embodiments, the first and second binders bind to two epitopes on the analyte to which the two binders can simultaneously and separately bind without having any steric hindrance.

The disclosure provides and a person of ordinary skill reading the disclosure would understand that the methods provided herein, including the methods of this Section (Section 5.2.6), can comprise additional cycles of releasing, washing, and/or capturing to further enrich or purify the immunocomplex and increase the signal to noise ratio. In one embodiment of the method provided herein, including the methods of this Section (Section 5.2.6), the method further comprises 1, 2, 3, 4, or 5, or at least 1, at least 2, at least 3, at least 4, or at least 5 additional cycles of recapture between steps (2) and (3), comprising: releasing the immunocomplex from the solid surface that it is captured on, recapturing the immunocomplex on an additional solid surface coupled with the first receiving group, and washing the additional solid surface to remove unbound molecules. In another embodiment of the method provided herein, the method further comprises 1, 2, 3, 4, or 5, or at least 1, at least 2, at least 3, at least 4, or at least 5 additional cycles of recapture between steps (2) and (2a), comprising: releasing the immunocomplex from the solid surface that it is captured on, recapturing the immunocomplex on an additional solid surface coupled with the first or the second receiving group, and washing the additional solid surface to remove unbound molecules. In another embodiment of the method provided herein, the method further comprises 1, 2, 3, 4, or 5, or at least 1, at least 2, at least 3, at least 4, or at least 5 additional cycles of recapture between steps (2c) and (2d), comprising:

releasing the immunocomplex from the solid surface that it is captured on, recapturing the immunocomplex on an additional solid surface coupled with the first or the second receiving group, and washing the additional solid surface to remove unbound molecules. In yet another embodiment of the method provided herein, the method further comprises 1, 2, 3, 4, or 5, or at least 1, at least 2, at least 3, at least 4, or at least 5 additional cycles of recapture between steps (2) and (3), comprising: releasing the immunocomplex from the solid surface that it is captured on, recapturing the immunocomplex on an additional solid surface coupled with the first receiving group, and washing the additional solid surface to remove unbound molecules; and 1, 2, 3, 4, or 5, or at least 1, at least 2, at least 3, at least 4, or at least 5 additional cycles of recapture between steps (2c) and (2d), comprising: releasing the immunocomplex from the solid surface that it is captured on, recapturing the immunocomplex on an additional solid surface coupled with the first or the second receiving group, and washing the additional solid surface to remove unbound molecules. In a further embodiment of the method provided herein, the method further comprises 1, 2, 3, 4, or 5, or at least 1, at least 2, at least 3, at least 4, or at least 5 additional cycles of recapture between steps (2) and (2a), comprising: releasing the immunocomplex from the solid surface that it is captured on, recapturing the immunocomplex on an additional solid surface coupled with the first receiving group, and washing the additional solid surface to remove unbound molecules; and 1, 2, 3, 4, or 5, or at least 1, at least 2, at least 3, at least 4, or at least 5 additional cycles of recapture between steps (2c) and (2d), comprising: releasing the immunocomplex from the solid surface that it is captured on, recapturing the immunocomplex on an additional solid surface coupled with the first or the second receiving group, and washing the additional solid surface to remove unbound molecules.

Various suitable means for the releasing steps of the methods provided herein, including those exemplified in Sections 6.2.2 and 6.4, are provided for the methods. As described in the disclosure including in this Section 5.2.6, such releasing include releasing bindings between different components of binding moiety, between the reporter and the immunocomplex, between presenting group and receiving group, or between receiving group and solid surface can be achieved by increasing temperature while maintaining the reporter intact. Accordingly, in some embodiments, in the methods provided herein including methods provided in this Section (Section 5.2.6), any of the releasing is releasing by increasing temperature to at least 50° C., at least 55° C., at least 60° C., at least 65° C., at least 70° C., at least 75° C., at least 80° C., at least 85° C., at least 90° C. In other embodiments, any of the releasing is releasing by increasing temperature to about 50° C., about 55° C., about 60° C., about 65° C., about 70° C., about 75° C., about 80° C., about 85° C., about 90° C. In some further embodiments, any of the releasing is releasing by increasing the salt concentration to at least 1M, at least 1.5M, at least 2M, at least 2.5M, at least 3M, at least 3.5M, or at least 4M of salt. In certain embodiments, any of the releasing is releasing by increasing the salt concentration to about 1M, about 1.5M, about 2M, about 2.5M, about 3M, about 3.5M, or about 4M of salt. In one embodiment, the any of the releasing is releasing by increasing the pH to at least 10, at least 10.1, at least 10.2, at least 10.3, at least 10.4, at least 10.5, at least 10.6, at least 10.7, at least 10.8, at least 10.9, at least 11, at least 11.1, at least 11.2, at least 11.3, at least 11.4, at least 11.5, at least 11.6, at least 11.7, at least 11.8, at least 11.9, at least 12, at least 12.1, at least 12.2, at least 12.3, at least 12.4, at least 12.5, at least 13, at least 13.5, or at least 14. In another embodiment, any of the releasing is releasing by increasing the pH to about 10, about 10.1, about 10.2, about 10.3, about 10.4, about 10.5, about 10.6, about 10.7, about 10.8, about 10.9, about 11, about 11.1, about 11.2, about 11.3, about 11.4, about 11.5, about 11.6, about 11.7, about 11.8, about 11.9, about 12, about 12.1, about 12.2, about 12.3, about 12.4, about 12.5, about 13, about 13.5, or about 14.

The presenting group and the receiving group can be bound, linked, coupled, or otherwise connected together for the methods provided herein, including methods provided in this Section (Section 5.2.6), via various embodiments of binding, linking, coupling or otherwise connecting the presenting group and the receiving group provided anywhere in the disclosure, including in Sections 3, 5.3.1, 5.3.2, and 6. In one embodiment of the method provided herein, the first presenting group binds the first receiving group via a thioester group, a disulfide linkage, or a cleavable linkage. In another embodiment of the method provided herein, the second presenting group binds the second receiving group via a thioester group, a disulfide linkage, or a cleavable linkage. In yet another embodiment of the method provided herein, the first presenting group binds the first receiving group via a thioester group, a disulfide linkage, or a cleavable linkage; and the second presenting group binds the second receiving group via a thioester group, a disulfide linkage, or a cleavable linkage. In one embodiment of the method provided herein, the first presenting group binds the first receiving group via a photocleavable linkage, a chemically cleavable linkage, or an enzymatically cleavable linkage. In another embodiment of the method provided herein, the second presenting group binds the second receiving group via a photocleavable linkage, a chemically cleavable linkage, or an enzymatically cleavable linkage. In yet another embodiment of the method provided herein, the first presenting group binds the first receiving group via a photocleavable linkage, a chemically cleavable linkage, or an enzymatically cleavable linkage; and the second presenting group binds the second receiving group via a photocleavable linkage, a chemically cleavable linkage, or an enzymatically cleavable linkage. In one embodiment of the method provided herein, the first presenting group binds the first receiving group via a protein-protein interaction. In another embodiment of the method provided herein, the second presenting group binds the second receiving group via a protein-protein interaction. In yet another embodiment of the method provided herein, the first presenting group binds the first receiving group via a protein-protein interaction; and the second presenting group binds the second receiving group via a protein-protein interaction. In one embodiment of the method provided herein, the first presenting group binds the first receiving group via biotin to streptavidin or avidin. In another embodiment of the method provided herein, the second presenting group binds the second receiving group via biotin to streptavidin or avidin. In yet another embodiment of the method provided herein, the first presenting group binds the first receiving group via biotin to streptavidin or avidin; and the second presenting group binds the second receiving group via biotin to streptavidin or avidin. In some embodiments, the first presenting group binds the first receiving group via any one of the embodiments provided in this paragraph and the second presenting group binds the second receiving group via any one of the embodiments provided in this paragraph. As such, the disclosure provides that any embodiment provided in this paragraph for the binding between the first presenting group and the first receiving group can be combined with any other embodiment provided in this paragraph for the binding between the second presenting group and the second receiving group.

As provided in the disclosure, including the disclosure of Sections 3, 5.1, 5.2.1 to 5.2.6, 5.3.1 to 5.3.3, and 6, in some embodiments of the methods provided herein, including those provided in this Section 5.2.6, the presenting group can be nucleic acid. Similarly, in some embodiments of the methods provided herein, including those provided in this Section 5.2.6, the receiving group can be nucleic acid. In one embodiment, the presenting group that is nucleic acid binds the receiving group. In another embodiment, the first presenting group is a first nucleic acid tag (the "first tag") and the first receiving group is a first nucleic acid capture probe (the "first probe"). In a further embodiment, the second presenting group is a second nucleic acid tag (the "second tag") and the second receiving group is a second nucleic acid capture probe (the "second probe"). In yet another embodiment, (i) the first presenting group is a first nucleic acid tag (the "first tag") and the first receiving group is a first nucleic acid capture probe (the "first probe"); and (ii) the second presenting group is a second nucleic acid tag (the "second tag") and the second receiving group is a second nucleic acid capture probe (the "second probe"). In one embodiment, the first probe is a protein that specifically binds to the first tag. In another embodiment, the first probe is a protein and nucleic acid complex that specifically binds to the first tag. In yet another embodiment, the first probe is a nucleic acid molecule, wherein the first probe or a fragment thereof is complementary to the first tag or a fragment thereof. In a further embodiment, the first probe is a nucleic acid molecule, wherein the first probe or a fragment thereof hybridizes with the first tag or a fragment thereof. In one embodiment, the second probe is a protein that specifically binds to the second tag. In another embodiment, the second probe is a protein and nucleic acid complex that specifically binds to the second tag. In yet another embodiment, the second probe is a nucleic acid molecule, wherein the second probe or a fragment thereof is complementary to the second tag or a fragment thereof. In a further embodiment, the second probe is a nucleic acid molecule, wherein the second probe or a fragment thereof hybridizes with the second tag or a fragment thereof.

Additionally, such first tag, first probe, second tag, and second probe can be combined as provided in the preceding paragraph in various ways. Accordingly, in one embodiment, the first probe is a protein that specifically binds to the first tag and the second probe is a protein that specifically binds to the second tag. In another embodiment, the first probe is a protein that specifically binds to the first tag and the second probe is a protein and nucleic acid complex that specifically binds to the second tag. In yet another embodiment, the first probe is a protein that specifically binds to the first tag and the second probe is a nucleic acid molecule, wherein the second probe or a fragment thereof is complementary to the second tag or a fragment thereof. In a further embodiment, the first probe is a protein that specifically binds to the first tag and the second probe is a nucleic acid molecule, wherein the second probe or a fragment thereof hybridizes with the second tag or a fragment thereof.

Additionally, in one embodiment, the first probe is a protein and nucleic acid complex that specifically binds to the first tag and the second probe is a protein that specifically binds to the second tag. In another embodiment, the first probe is a protein and nucleic acid complex that specifically binds to the first tag and the second probe is a protein and nucleic acid complex that specifically binds to the second tag. In yet another embodiment, the first probe is a protein and nucleic acid complex that specifically binds to the first tag and the second probe is a nucleic acid molecule, wherein the second probe or a fragment thereof is complementary to the second tag or a fragment thereof. In a further embodiment, the first probe is a protein and nucleic acid complex that specifically binds to the first tag and the second probe is a nucleic acid molecule, wherein the second probe or a fragment thereof hybridizes with the second tag or a fragment thereof.

Alternatively, in one embodiment, the first probe is a nucleic acid molecule, wherein the first probe or a fragment thereof is complementary to the first tag or a fragment thereof, and the second probe is a protein that specifically binds to the second tag. In another embodiment, the first probe is a nucleic acid molecule, wherein the first probe or a fragment thereof is complementary to the first tag or a fragment thereof, and the second probe is a protein and nucleic acid complex that specifically binds to the second tag. In yet another embodiment, the first probe is a nucleic acid molecule, wherein the first probe or a fragment thereof is complementary to the first tag or a fragment thereof, and the second probe is a nucleic acid molecule, wherein the second probe or a fragment thereof is complementary to the second tag or a fragment thereof. In a further embodiment, the first probe is a nucleic acid molecule, wherein the first probe or a fragment thereof is complementary to the first tag or a fragment thereof, and the second probe is a nucleic acid molecule, wherein the second probe or a fragment thereof hybridizes with the second tag or a fragment thereof.

In addition, in one embodiment, the first probe is a nucleic acid molecule, wherein the first probe or a fragment thereof hybridizes with the first tag or a fragment thereof, and the second probe is a protein that specifically binds to the second tag. In another embodiment, the first probe is a nucleic acid molecule, wherein the first probe or a fragment thereof hybridizes with the first tag or a fragment thereof, and the second probe is a protein and nucleic acid complex that specifically binds to the second tag. In yet another embodiment, the first probe is a nucleic acid molecule, wherein the first probe or a fragment thereof hybridizes with the first tag or a fragment thereof, and the second probe is a nucleic acid molecule, wherein the second probe or a fragment thereof is complementary to the second tag or a fragment thereof. In a further embodiment, the first probe is a nucleic acid molecule, wherein the first probe or a fragment thereof hybridizes with the first tag or a fragment thereof, and the second probe is a nucleic acid molecule, wherein the second probe or a fragment thereof hybridizes with the second tag or a fragment thereof.

The complementarity provided in the preceding paragraphs can be complementarity of various levels so long as the binding of the complementary fragment provides sufficient binding for the capture, washing and/or release for the various methods provided herein. In one embodiment of the methods provided herein including in this Section 5.2.6, the complementarity is at least 80%, at least 81%, at least 82%, at least 83%, at least 84%, at least 85%, at least 86%, at least 87%, at least 88%, at least 89%, at least 90, at least 91%, at least 92%, at least 93%, at least 94%, at least 95%, at least 96%, at least 97%, at least 98%, or at least 99% complementation. In another embodiment, the complementarity is about 80%, about 81%, about 82%, about 83%, about 84%, about 85%, about 86%, about 87%, about 88%, about 89%, about 90, about 91%, about 92%, about 93%, about 94%, about 95%, about 96%, about 97%, about 98%, or about 99% complementation.

In certain embodiments, the presenting group that is nucleic acid binds or hybridizes to the receiving group that is nucleic acid. Accordingly, in some embodiments, the first presenting group is a first nucleic acid tag (the "first tag") and the first receiving group is a first nucleic acid capture probe (the "first probe"), wherein the first probe or a fragment thereof is complementary to the first tag or a fragment thereof. In certain embodiments, the second presenting group is a second nucleic acid tag (the "second tag") and the second receiving group is a second nucleic acid capture probe (the "second probe"), wherein the second probe or a fragment thereof is complementary to the second tag or a fragment thereof. In one embodiment, the first presenting group is a first nucleic acid tag (the "first tag") and the first receiving group is a first nucleic acid capture probe (the "first probe"), wherein the first probe or a fragment thereof is complementary to the first tag or a fragment thereof; and the second presenting group is a second nucleic acid tag (the "second tag") and the second receiving group is a second nucleic acid capture probe (the "second probe"), wherein the second probe or a fragment thereof is complementary to the second tag or a fragment thereof.

Accordingly, in some specific embodiment of the methods provided herein, the method comprises:

(1) mixing a first binding moiety comprising a first binder and a first tag, a second binding moiety comprising a second binder and a second tag, and the sample in a solution, wherein:
  (i) the first and second binders bind non-interfering epitopes on the analyte and form an immunocomplex,
  (ii) the immunocomplex is captured on a first solid surface in contact with the solution via binding between the first tag and a first probe coupled to the first solid surface, and
  (iii) the first binding moiety further comprises a first target label comprising a first identity barcode ("ID") that is analyte-specific ("target ID") and the second binding moiety further comprises a second target label comprising a second target ID;
(2) washing the first solid surface to remove unbound molecules;
(2a) releasing the immunocomplex from the first solid surface by disrupting the binding between the first tag and the first probe;
(2b) introducing a second solid surface and recapturing the immunocomplex on the second solid surface via binding between the second tag and the second probe coupled to the second solid surface;
(2c) washing the second solid surface to remove unbound molecules;
(2d) releasing the immunocomplex from the second solid surface by disrupting the binding between the second tag and the second probe;
(2e) binding a sample label comprising an ID that is sample-specific ("sample ID") (i) to the first target label, (ii) to the second target label, or (iii) to both the first target label and the second target label
(3) generating a nucleic acid reporter comprising the first target ID and the second target ID; and
(4) detecting the nucleic acid reporter, thereby detecting the analyte.

The disclosure further provides and a person of ordinary skill in the art reading the disclosure would understand that the receiving group can be bound, linked, coupled, or otherwise connected to the solid surface for the methods provided herein, including methods provided in this Section (Section 5.2.6), via various embodiments of binding, linking, coupling or otherwise connecting the receiving group and the solid surface provided anywhere in the disclosure, including in Sections 3, 5.2.3, and 6. As the receiving group could be nucleic acid capture probes, the disclosure thus provides that the nucleic acid capture probe (e.g. first probe and/or second probe) can be bound, linked, coupled, or otherwise connected to the solid surface for the methods provided herein, including methods provided in this Section (Section 5.2.6), via various embodiments of binding, linking, coupling or otherwise connecting the nucleic acid capture probe (e.g. first probe and/or second probe) and the solid surface provided anywhere in the disclosure, including in Sections 3, 5.2.3, and 6. In one embodiment of the methods provided herein, including methods provided in this Section (Section 5.2.6), the first probe is directly coupled to the first solid surface. In another embodiment, the first probe hybridizes with a universal probe that is directly coupled to the first solid surface. In a further embodiment, the first probe is conjugated with biotin, which binds the streptavidin or avidin that is directly coupled to the first solid surface. In yet another embodiment, the first probe is conjugated with a chemical compound (e.g. FITC), which binds an antibody that specifically binds such compound (e.g. FITC) and is directly coupled to the first solid surface. In one embodiment of the methods provided herein, including methods provided in this Section (Section 5.2.6), the second probe is directly coupled to the second solid surface. In another embodiment, the second probe hybridizes with a universal probe that is directly coupled to the second solid surface. In a further embodiment, the second probe is conjugated with biotin, which binds the streptavidin or avidin that is directly coupled to the second solid surface. In yet another embodiment, the second probe is conjugated with a chemical compound (e.g. FITC), which binds an antibody that specifically binds such compound (e.g. FITC) and is directly coupled to the second solid surface.

In certain embodiments, any embodiment provided in the preceding paragraph for the binding, linking, coupling, or otherwise connection between the first probe and the first solid surface can be combined with any other embodiment provided in the preceding paragraph for the binding, linking, coupling, or otherwise connection between the second probe and the second solid surface. Accordingly, in one embodiment of the methods provided herein, including methods provided in this Section (Section 5.2.6), the first probe is directly coupled to the first solid surface and the second probe is directly coupled to the second solid surface. In another embodiment, the first probe is directly coupled to the first solid surface and the second probe hybridizes with a universal probe that is directly coupled to the second solid surface. In a further embodiment, the first probe is directly coupled to the first solid surface and the second probe is conjugated with biotin, which binds the streptavidin or avidin that is directly coupled to the second solid surface. In yet another embodiment, the first probe is directly coupled to the first solid surface and the second probe is conjugated with a chemical compound (e.g. FITC), which binds an antibody that specifically binds such compound (e.g. FITC) and is directly coupled to the second solid surface. In one embodiment, the first probe hybridizes with a universal probe that is directly coupled to the first solid surface and the second probe is directly coupled to the second solid surface. In another embodiment, the first probe hybridizes with a universal probe that is directly coupled to the first solid surface and the second probe hybridizes with a universal probe that is directly coupled to the second solid surface. In a further embodiment, the first probe hybridizes with a universal probe that is directly coupled to the first solid surface and the second probe is conjugated with biotin, which binds the streptavidin or avidin that is directly coupled to the second solid surface. In yet another embodiment, the first probe hybridizes with a universal probe that is directly coupled to the first solid surface and the second probe is conjugated with a chemical compound (e.g. FITC), which binds an antibody that specifically binds such compound (e.g. FITC) and is directly coupled to the second solid surface. In one embodiment, the first probe is conjugated with biotin, which binds the streptavidin or avidin that is directly coupled to the first solid surface and the second probe is directly coupled to the second solid surface. In another embodiment, the first probe is conjugated with biotin, which binds the streptavidin or avidin that is directly coupled to the first solid surface and the second probe hybridizes with a universal probe that is directly coupled to the second solid surface. In a further embodiment, the first probe is conjugated with biotin, which binds the streptavidin or avidin that is directly coupled to the first solid surface and the second probe is conjugated with biotin, which binds the streptavidin or avidin that is directly coupled to the second solid surface. In yet another embodiment, the first probe is conjugated with biotin, which binds the streptavidin or avidin that is directly coupled to the first solid surface and the second probe is conjugated with a chemical compound (e.g. FITC), which binds an antibody that specifically binds such compound (e.g. FITC) and is directly coupled to the second solid surface. In one embodiment, the first probe is conjugated with a chemical compound (e.g. FITC), which binds an antibody that specifically binds such compound (e.g. FITC) and is directly coupled to the first solid surface and the second probe is directly coupled to the second solid surface. In another embodiment, the first probe is conjugated with a chemical compound (e.g. FITC), which binds an antibody that specifically binds such compound (e.g. FITC) and is directly coupled to the first solid surface and the second probe hybridizes with a universal probe that is directly coupled to the second solid surface. In a further embodiment, the first probe is conjugated with a chemical compound (e.g. FITC), which binds an antibody that specifically binds such compound (e.g. FITC) and is directly coupled to the first solid surface and the second probe is conjugated with biotin, which binds the streptavidin or avidin that is directly coupled to the second solid surface. In yet another embodiment, the first probe is conjugated with a chemical compound (e.g. FITC), which binds an antibody that specifically binds such compound (e.g. FITC) and is directly coupled to the first solid surface and the second probe is conjugated with a chemical compound (e.g. FITC), which binds an antibody that specifically binds such compound (e.g. FITC) and is directly coupled to the second solid surface.

As described above in Sections 3, 5.2.3, 5.2.4, and 5.2.5, the nucleic acid capture probes can be collaboratively captured on the solid surface. In one embodiment of the methods provided herein, including in this Section (Section 5.2.6), the first tag and second tag are collaboratively captured on the first solid surface. In another embodiment of the methods provided herein, the first tag and second tag are collaboratively captured on the second solid surface. In a further embodiment of the methods provided herein, the first tag and second tag are collaboratively captured on the first solid surface in step (1). In yet another embodiment of the methods provided herein, the first tag and second tag are collaboratively captured on the second solid surface in step (2b). In some embodiments, the collaborative capture of this Section (Section 5.2.6) including this paragraph for the methods provided herein can take different formats, including any embodiments described in Sections 3, 5.2.3, 5.2.4, and 5.2.5. In one specific embodiment, the first tag and second tag are collaboratively captured on the first solid surface in any format embodied in Sections 3, 5.2.3, 5.2.4, and 5.2.5. In another specific embodiment, the first tag and second tag are collaboratively captured on the first solid surface in step (1) in any format embodied in Sections 3, 5.2.3, 5.2.4, and 5.2.5. In a further embodiment, the first tag and second tag are collaboratively captured on the second solid surface in any format embodied in Sections 3, 5.2.3, 5.2.4, and 5.2.5. In yet another embodiment, the first tag and second tag are collaboratively captured on the second solid surface in step (2b) in any format embodied in Sections 3, 5.2.3, 5.2.4, and 5.2.5. In some embodiments, the first tag and second tag are collaboratively captured on the first solid surface in any format embodied in Sections 3, 5.2.3, 5.2.4, and 5.2.5 and the first tag and second tag are collaboratively captured on the second solid surface in any format embodied in Sections 3, 5.2.3, 5.2.4, and 5.2.5. In certain embodiments, the first tag and second tag are collaboratively captured on the first solid surface in step (1) in any format embodied in Sections 3, 5.2.3, 5.2.4, and 5.2.5 and the first tag and second tag are collaboratively captured on the second solid surface in step (2b) in any format embodied in Sections 3, 5.2.3, 5.2.4, and 5.2.5. In some embodiments, the first solid surface is coupled with both the first probe and an additional nucleic acid probe, and wherein the additional probe or a fragment thereof is complementary to the first tag or a fragment thereof. In certain embodiments, the second solid surface is coupled with both the second probe and an additional nucleic acid probe, and wherein the additional probe or a fragment thereof is complementary to the second tag or a fragment thereof. In other embodiments, the first solid surface is coupled with both the first probe and an additional nucleic acid probe, and wherein the additional probe or a fragment thereof is complementary to the first tag or a fragment thereof, and the second solid surface is coupled with both the second probe and an additional nucleic acid probe, and wherein the additional probe or a fragment thereof is complementary to the second tag or a fragment thereof.

In any of the embodiments of the methods provided herein that involves nucleic acid binding or hybridization, the complementary fragments of two nucleic acids can be of any length that provides sufficient interaction for the purpose of binding the presenting group (e.g. the first tag and/or the second tag) and the receiving group (e.g. the first probe and/or the second probe) or binding the receiving group (e.g. the first probe and/or the second probe) and the solid surface (e.g. the first solid surface and/or the second solid surface). In some embodiments of the methods provided herein, such complementary fragments can be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, or more base pairs. In one embodiment of the methods provided herein, the complementary fragments of the first tag and the first probe consist of 10 to 30 base pairs. In another embodiment of the methods provided herein, the complementary fragments of the first tag and the first probe consist of 20 to 30 base pairs. In yet another embodiment of the methods provided herein, the complementary fragments of the first tag and the first probe consist of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs. In one embodiment of the methods provided herein, the complementary fragments of the second tag and the second probe consist of 10 to 30 base pairs. In another embodiment of the methods provided herein, the complementary fragments of the second tag and the second probe consist of 20 to 30 base pairs. In yet another embodiment of the methods provided herein, the complementary fragments of the second tag and the second probe consist of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs. In one embodiment of the methods provided herein, the complementary fragments of the first tag and the first probe consist of 10 to 30 base pairs and the complementary fragments of the second tag and the second probe consist of 10 to 30 base pairs. In another embodiment of the methods provided herein, the complementary fragments of the first tag and the first probe consist of 20 to 30 base pairs and the complementary fragments of the second tag and the second probe consist of 20 to 30 base pairs. In yet another embodiment of the methods provided herein, the complementary fragments of the first tag and the first probe consist of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs and complementary fragments of the second tag and the second probe consist of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs.

For any of the embodiments of the methods provided herein that involves nucleic acid binding or hybridization, the complementary fragments of two nucleic acid can be a pair of complementary A and/or T rich sequences or a pair of complementary G and/or C rich sequences for the purpose of binding the presenting group (e.g. the first tag and/or the second tag) and the receiving group (e.g. the first probe and/or the second probe) or binding the receiving group (e.g. the first probe and/or the second probe) and the solid surface (e.g. the first solid surface and/or the second solid surface). In one embodiment of the methods provided herein, the first tag comprises an A and/or T rich sequence and the first probe comprises a complementary T and/or A rich sequence. In another embodiment, the first tag comprises a poly-A and/or poly-T sequence and the first probe comprises a complementary poly-T and/or poly-A sequence. In a further embodiment, the first tag comprises an G and/or C rich sequence and the first probe comprises a complementary C and/or G rich sequence. In yet another embodiment, the first tag comprises a poly-G and/or poly-C sequence and the first probe comprises a complementary poly-C and/or poly-G sequence. In one embodiment of the methods provided herein, the second tag comprises an A and/or T rich sequence and the second probe comprises a complementary T and/or A rich sequence. In another embodiment, the second tag comprises a poly-A and/or poly-T sequence and the second probe comprises a complementary poly-T and/or poly-A sequence. In a further embodiment, the second tag comprises an G and/or C rich sequence and the second probe comprises a complementary C and/or G rich sequence. In yet another embodiment, the second tag comprises a poly-G and/or poly-C sequence and the second probe comprises a complementary poly-C and/or poly-G sequence.

In one embodiment of the methods provided herein, the first tag comprises an A and/or T rich sequence and the first probe comprises a complementary T and/or A rich sequence, and the second tag comprises an A and/or T rich sequence and the second probe comprises a complementary T and/or A rich sequence. In another embodiment, the first tag comprises an A and/or T rich sequence and the first probe comprises a complementary T and/or A rich sequence, and the second tag comprises a poly-A and/or poly-T sequence and the second probe comprises a complementary poly-T and/or poly-A sequence. In a further embodiment, the first tag comprises an A and/or T rich sequence and the first probe comprises a complementary T and/or A rich sequence, and the second tag comprises an G and/or C rich sequence and the second probe comprises a complementary C and/or G rich sequence. In yet another embodiment, the first tag comprises an A and/or T rich sequence and the first probe comprises a complementary T and/or A rich sequence, and the second tag comprises a poly-G and/or poly-C sequence and the second probe comprises a complementary poly-C and/or poly-G sequence.

In one embodiment of the methods provided herein, the first tag comprises a poly-A and/or poly-T sequence and the first probe comprises a complementary poly-T and/or poly-A sequence, and the second tag comprises an A and/or T rich sequence and the second probe comprises a complementary T and/or A rich sequence. In another embodiment, the first tag comprises a poly-A and/or poly-T sequence and the first probe comprises a complementary poly-T and/or poly-A sequence, and the second tag comprises a poly-A and/or poly-T sequence and the second probe comprises a complementary poly-T and/or poly-A sequence. In a further embodiment, the first tag comprises a poly-A and/or poly-T sequence and the first probe comprises a complementary poly-T and/or poly-A sequence, and the second tag comprises an G and/or C rich sequence and the second probe comprises a complementary C and/or G rich sequence. In yet another embodiment, the first tag comprises a poly-A and/or poly-T sequence and the first probe comprises a complementary poly-T and/or poly-A sequence, and the second tag comprises a poly-G and/or poly-C sequence and the second probe comprises a complementary poly-C and/or poly-G sequence.

In one embodiment of the methods provided herein, the first tag comprises an G and/or C rich sequence and the first probe comprises a complementary C and/or G rich sequence, and the second tag comprises an A and/or T rich sequence and the second probe comprises a complementary T and/or A rich sequence. In another embodiment, the first tag comprises an G and/or C rich sequence and the first probe comprises a complementary C and/or G rich sequence, and the second tag comprises a poly-A and/or poly-T sequence and the second probe comprises a complementary poly-T and/or poly-A sequence. In a further embodiment, the first tag comprises an G and/or C rich sequence and the first probe comprises a complementary C and/or G rich sequence, and the second tag comprises an G and/or C rich sequence and the second probe comprises a complementary C and/or G rich sequence. In yet another embodiment, the first tag comprises an G and/or C rich sequence and the first probe comprises a complementary C and/or G rich sequence, and the second tag comprises a poly-G and/or poly-C sequence and the second probe comprises a complementary poly-C and/or poly-G sequence.

In one embodiment of the methods provided herein, the first tag comprises a poly-G and/or poly-C sequence and the first probe comprises a complementary poly-C and/or poly-G sequence, and the second tag comprises an A and/or T rich sequence and the second probe comprises a complementary T and/or A rich sequence. In another embodiment, the first tag comprises a poly-G and/or poly-C sequence and the first probe comprises a complementary poly-C and/or poly-G sequence, and the second tag comprises a poly-A and/or poly-T sequence and the second probe comprises a complementary poly-T and/or poly-A sequence. In a further embodiment, the first tag comprises a poly-G and/or poly-C sequence and the first probe comprises a complementary poly-C and/or poly-G sequence, and the second tag comprises an G and/or C rich sequence and the second probe comprises a complementary C and/or G rich sequence. In yet another embodiment, the first tag comprises a poly-G and/or poly-C sequence and the first probe comprises a complementary poly-C and/or poly-G sequence, and the second tag comprises a poly-G and/or poly-C sequence and the second probe comprises a complementary poly-C and/or poly-G sequence.

In certain embodiments of the methods provided herein, including those provided in the preceding 5 paragraphs, the complementary sequences have a short length such that the binding from complementary sequences is weaker than both the binding between first binder and the analyte and the binding between the second binder and the analyte, thereby keeping immunocomplex stable in any releasing steps, for example, releasing step (2a) and/or (2d). In some specific embodiments, the A and/or T rich sequence has a short length such that the binding from complementary A and/or T rich sequence is weaker than both the binding between first binder and the analyte and the binding between the second binder and the analyte, thereby keeping immunocomplex stable in any releasing steps, for example, releasing step (2a) and/or (2d). In other specific embodiments, the poly-A and/or poly-T sequence has a short length such that the binding from complementary poly-A and/or poly-T sequence is weaker than both the binding between first binder and the analyte and the binding between the second binder and the analyte, thereby keeping immunocomplex stable in any releasing steps, for example, releasing step (2a) and/or (2d). In yet other specific embodiments, the G and/or C rich sequence has a short length such that the binding from complementary G and/or C rich sequence is weaker than both the binding between first binder and the analyte and the binding between the second binder and the analyte, thereby keeping immunocomplex stable in any releasing steps, for example, releasing step (2a) and/or (2d). In some further specific embodiments, the poly-G and/or poly-C sequence has a short length such that the binding from complementary poly-G and/or poly-C sequence is weaker than both the binding between first binder and the analyte and the binding between the second binder and the analyte, thereby keeping immunocomplex stable in any releasing steps, for example, releasing step (2a) and/or (2d).

The T analyte detected in the methods provided herein, including the methods provided in this Section 5.2.6, can be various molecules as described in Sections 3, 5.2.2, and 6. In one specific embodiment, the analyte is a binding pair of two molecules; wherein the first binder binds one molecule of the binding pair, and the second binder binds the other molecule of the binding pair. In another embodiment, the analyte is a nucleic acid, and the first and second binders for the nucleic acid analyte comprise nucleic acids that are complementary to different fragments of the nucleic acid analyte. In yet another embodiment, the analyte is a peptide or a protein, and (i) the first binder is an antibody or an antibody fragment that specifically binds the analyte; (ii) the second binder is an antibody or an antibody fragment that specifically binds the analyte; or both (i) and (ii).

The analyte detected in the methods provided herein, including the methods provided in this Section 5.2.6, can be from various samples as described in Sections 3 and 6. In some specific embodiment of the methods provided herein, the sample is a bodily fluid sample. In one embodiment, the sample is a tissue sample. In one embodiment, the sample is a cell sample. In one embodiment, the sample is a blood sample. In one embodiment, the sample is a bone marrow sample. In one embodiment, the sample is a plasma sample. In one embodiment, the sample is a serum sample. In one embodiment, the sample is a urine sample. In one embodiment, the sample is a cerebrospinal fluid sample.

In various embodiments of the methods provided herein, the nucleic acid reporter can be generated while the immunocomplex is being captured on a solid surface or after the immunocomplex is released from the solid surface, as described in Sections 3, 5.2.4 (including 5.2.4.1 and 5.2.4.2), 5.2.5, and 6. In one specific embodiment, the nucleic acid reporter is generated (e.g. in step (3)) while the immunocomplex is being captured on the first solid surface. In another specific embodiment, the nucleic acid reporter is generated (e.g. in step (3)) after the immunocomplex is released from the first solid surface. In another specific embodiment, the nucleic acid reporter is generated (e.g. in step (3)) while the immunocomplex is being captured on the second solid surface. In yet another specific embodiment, the nucleic acid reporter is generated (e.g. in step (3)) after the immunocomplex is released from the second solid surface.

The disclosure provides that the target label, the binder, and the presenting group can have various configurations in each binding moiety for various embodiments of the methods provided herein, including those of this Section 5.2.6 and Sections 3, 5.2.1 to 5.2.5 and 6. In one embodiment of the methods provided herein, including those of this Section 5.2.6, the target label is directly bound to the binder. In another embodiment, the target label is indirectly bound to the binder. In yet another embodiment, the first target label is directly bound to the first binder. In a further embodiment, the first target label is indirectly bound to the first binder. In some embodiments, the second target label is directly bound to the second binder. In certain embodiments, the second target label is indirectly bound to the second binder. In one embodiment, the first target label is directly bound to the first binder and the second target label is directly bound to the second binder. In another embodiment, the first target label is directly bound to the first binder and the second target label is indirectly bound to the second binder. In yet another embodiment, the first target label is indirectly bound to the first binder and the second target label is directly bound to the second binder. In a further embodiment, the first target label is indirectly bound to the first binder and the second target label is indirectly bound to the second binder. In one embodiment of the methods provided herein, including those of this Section 5.2.6, the target label is conjugated to the binder. In another embodiment, the target label is non-covalently bound to the binder. In a further embodiment, the target label is conjugated to the presenting group. In another embodiment, the target label is non-covalently bound to the presenting group. In yet another embodiment, the target label is part of the presenting group, for example, the target label and the presenting group are both nucleic acid and the target label is a nucleic acid fragment within the sequence of the presenting group. In one embodiment of the methods provided herein, including those of this Section 5.2.6, the first target label is conjugated to the first binder. In another embodiment, the first target label is non-covalently bound to the first binder. In a further embodiment, the first target label is conjugated to the first presenting group. In another embodiment, the first target label is non-covalently bound to the first presenting group. In yet another embodiment, the first target label is part of the first presenting group, for example, the first target label and the first presenting group are both nucleic acid molecules and the first target label is a nucleic acid fragment within the sequence of the first presenting group. In one embodiment of the methods provided herein, including those of this Section 5.2.6, the second target label is conjugated to the second binder. In another embodiment, the second target label is non-covalently bound to the second binder. In a further embodiment, the second target label is conjugated to the second presenting group. In another embodiment, the second target label is non-covalently bound to the second presenting group. In yet another embodiment, the second target label is part of the second presenting group, for example, the second target label and the second presenting group are both nucleic acid molecules and the second target label is a nucleic acid fragment within the sequence of the second presenting group.

The configuration among the first target label, the first binder, and the first presenting group in the first binding moiety can be any embodiment provided herein including in this Section 5.2.6 and in the preceding paragraph and such embodiment can be combined with any embodiment of configuration among the second target label, the second binder, and the second presenting group in the second binding moiety provided herein including in this Section 5.2.6 and in the preceding paragraph. In one specific embodiment of the methods provided herein, including those of this Section 5.2.6, the first target label is conjugated to the first binder and the second target label is conjugated to the second binder. In another embodiment, the first target label is conjugated to the first binder and the second target label is non-covalently bound to the second binder. In a further embodiment, the first target label is conjugated to the first binder and the second target label is conjugated to the second presenting group. In another embodiment, the first target label is conjugated to the first binder and the second target label is non-covalently bound to the second presenting group. In yet another embodiment, the first target label is conjugated to the first binder and the second target label is part of the second presenting group, for example, the second target label and the second presenting group are both nucleic acid molecules and the second target label is a nucleic acid fragment within the sequence of the second presenting group.

In some specific embodiments of the methods provided herein, including those of this Section 5.2.6, the first target label is non-covalently bound to the first binder and the second target label is conjugated to the second binder. In another embodiment, the first target label is non-covalently bound to the first binder and the second target label is non-covalently bound to the second binder. In a further embodiment, the first target label is non-covalently bound to the first binder and the second target label is conjugated to the second presenting group. In another embodiment, the first target label is non-covalently bound to the first binder and the second target label is non-covalently bound to the second presenting group. In yet another embodiment, the first target label is non-covalently bound to the first binder and the second target label is part of the second presenting group, for example, the second target label and the second presenting group are both nucleic acid molecules and the second target label is a nucleic acid fragment within the sequence of the second presenting group.

In some specific embodiments of the methods provided herein, including those of this Section 5.2.6, the first target label is conjugated to the first presenting group and the second target label is conjugated to the second binder. In another embodiment, the first target label is conjugated to the first presenting group and the second target label is non-covalently bound to the second binder. In a further embodiment, the first target label is conjugated to the first presenting group and the second target label is conjugated to the second presenting group. In another embodiment, the first target label is conjugated to the first presenting group and the second target label is non-covalently bound to the second presenting group. In yet another embodiment, the first target label is conjugated to the first presenting group and the second target label is part of the second presenting group, for example, the second target label and the second presenting group are both nucleic acid molecules and the second target label is a nucleic acid fragment within the sequence of the second presenting group.

In some specific embodiments of the methods provided herein, including those of this Section 5.2.6, the first target label is non-covalently bound to the first presenting group and the second target label is conjugated to the second binder. In another embodiment, the first target label is non-covalently bound to the first presenting group and the second target label is non-covalently bound to the second binder. In a further embodiment, the first target label is non-covalently bound to the first presenting group and the second target label is conjugated to the second presenting group. In another embodiment, the first target label is non-covalently bound to the first presenting group and the second target label is non-covalently bound to the second presenting group. In yet another embodiment, the first target label is non-covalently bound to the first presenting group and the second target label is part of the second presenting group, for example, the second target label and the second presenting group are both nucleic acid molecules and the second target label is a nucleic acid fragment within the sequence of the second presenting group.

In some specific embodiments of the methods provided herein, including those of this Section 5.2.6, the first target label is part of the first presenting group, for example, the first target label and the first presenting group are both nucleic acid molecules and the first target label is a nucleic acid fragment within the sequence of the first presenting group, and the second target label is conjugated to the second binder. In another embodiment, the first target label is part of the first presenting group, for example, the first target label and the first presenting group are both nucleic acid molecules and the first target label is a nucleic acid fragment within the sequence of the first presenting group, and the second target label is non-covalently bound to the second binder. In a further embodiment, the first target label is part of the first presenting group, for example, the first target label and the first presenting group are both nucleic acid molecules and the first target label is a nucleic acid fragment within the sequence of the first presenting group, and the second target label is conjugated to the second presenting group. In another embodiment, the first target label is part of the first presenting group, for example, the first target label and the first presenting group are both nucleic acid molecules and the first target label is a nucleic acid fragment within the sequence of the first presenting group, and the second target label is non-covalently bound to the second presenting group. In yet another embodiment, the first target label is part of the first presenting group, for example, the first target label and the first presenting group are both nucleic acid molecules and the first target label is a nucleic acid fragment within the sequence of the first presenting group, and the second target label is part of the second presenting group, for example, the second target label and the second presenting group are both nucleic acid molecules and the second target label is a nucleic acid fragment within the sequence of the second presenting group.

Similarly, the binder and the presenting group can have various configurations in each binding moiety for various embodiments of the methods provided herein, including those of this Section 5.2.6 and Sections 3, 5.2.1 to 5.2.5 and 6. In one embodiment of the methods provided herein, including those of this Section 5.2.6, the presenting group is directly bound to the binder. In another embodiment, the presenting group is indirectly bound to the binder. In yet another embodiment, the first presenting group is directly bound to the first binder. In a further embodiment, the first presenting group is indirectly bound to the first binder. In some embodiments, the second presenting group is directly bound to the second binder. In certain embodiments, the second presenting group is indirectly bound to the second binder. In one embodiment, the first presenting group is directly bound to the first binder and the second presenting group is directly bound to the second binder. In another embodiment, the first presenting group is directly bound to the first binder and the second presenting group is indirectly bound to the second binder. In yet another embodiment, the first presenting group is indirectly bound to the first binder and the second presenting group is directly bound to the second binder. In a further embodiment, the first presenting group is indirectly bound to the first binder and the second presenting group is indirectly bound to the second binder. In one embodiment of the methods provided herein, including those of this Section 5.2.6, the presenting group is conjugated to the binder. In another embodiment, the presenting group is non-covalently bound to the binder. In a further embodiment, the presenting group is conjugated to the presenting group. In another embodiment, the presenting group is non-covalently bound to the presenting group. In yet another embodiment, the presenting group is part of the presenting group, for example, the presenting group and the presenting group are both nucleic acid and the presenting group is a nucleic acid fragment within the sequence of the presenting group. In one embodiment of the methods provided herein, including those of this Section 5.2.6, the first presenting group is conjugated to the first binder. In another embodiment, the first presenting group is non-covalently bound to the first binder. In a further embodiment, the first presenting group is conjugated to the first presenting group. In another embodiment, the first presenting group is non-covalently bound to the first presenting group. In yet another embodiment, the first presenting group is part of the first target label, for example, the first presenting group and the first target label are both nucleic acid molecules and the first presenting group is a nucleic acid fragment within the sequence of the first target label. In one embodiment of the methods provided herein, including those of this Section 5.2.6, the second presenting group is conjugated to the second binder. In another embodiment, the second presenting group is non-covalently bound to the second binder. In a further embodiment, the second presenting group is conjugated to the second presenting group. In another embodiment, the second presenting group is non-covalently bound to the second presenting group. In yet another embodiment, the second presenting group is part of the second target label, for example, the second presenting group and the second target label are both nucleic acid molecules and the second presenting group is a nucleic acid fragment within the sequence of the second target label.

The configuration among the first presenting group, the first binder, and the first presenting group in the first binding moiety can be any embodiment provided herein including in this Section 5.2.6 and in the preceding paragraph and such embodiment can be combined with any embodiment of configuration among the second presenting group, the second binder, and the second presenting group in the second binding moiety provided herein including in this Section 5.2.6 and in the preceding paragraph. In one specific embodiment of the methods provided herein, including those of this Section 5.2.6, the first presenting group is conjugated to the first binder and the second presenting group is conjugated to the second binder. In another embodiment, the first presenting group is conjugated to the first binder and the second presenting group is non-covalently bound to the second binder. In a further embodiment, the first presenting group is conjugated to the first binder and the second presenting group is conjugated to the second presenting group. In another embodiment, the first presenting group is conjugated to the first binder and the second presenting group is non-covalently bound to the second presenting group. In yet another embodiment, the first presenting group is conjugated to the first binder and the second presenting group is part of the second target label, for example, the second presenting group and the second target label are both nucleic acid molecules and the second presenting group is a nucleic acid fragment within the sequence of the second target label.

In some specific embodiments of the methods provided herein, including those of this Section 5.2.6, the first presenting group is non-covalently bound to the first binder and the second presenting group is conjugated to the second binder. In another embodiment, the first presenting group is non-covalently bound to the first binder and the second presenting group is non-covalently bound to the second binder. In a further embodiment, the first presenting group is non-covalently bound to the first binder and the second presenting group is conjugated to the second presenting group. In another embodiment, the first presenting group is non-covalently bound to the first binder and the second presenting group is non-covalently bound to the second presenting group. In yet another embodiment, the first presenting group is non-covalently bound to the first binder and the second presenting group is part of the second target label, for example, the second presenting group and the second target label are both nucleic acid molecules and the second presenting group is a nucleic acid fragment within the sequence of the second target label.

In some specific embodiments of the methods provided herein, including those of this Section 5.2.6, the first presenting group is conjugated to the first presenting group and the second presenting group is conjugated to the second binder. In another embodiment, the first presenting group is conjugated to the first presenting group and the second presenting group is non-covalently bound to the second binder. In a further embodiment, the first presenting group is conjugated to the first presenting group and the second presenting group is conjugated to the second presenting group. In another embodiment, the first presenting group is conjugated to the first presenting group and the second presenting group is non-covalently bound to the second presenting group. In yet another embodiment, the first presenting group is conjugated to the first presenting group and the second presenting group is part of the second target label, for example, the second presenting group and the second target label are both nucleic acid molecules and the second presenting group is a nucleic acid fragment within the sequence of the second target label.

In some specific embodiments of the methods provided herein, including those of this Section 5.2.6, the first presenting group is non-covalently bound to the first presenting group and the second presenting group is conjugated to the second binder. In another embodiment, the first presenting group is non-covalently bound to the first presenting group and the second presenting group is non-covalently bound to the second binder. In a further embodiment, the first presenting group is non-covalently bound to the first presenting group and the second presenting group is conjugated to the second presenting group. In another embodiment, the first presenting group is non-covalently bound to the first presenting group and the second presenting group is non-covalently bound to the second presenting group. In yet another embodiment, the first presenting group is non-covalently bound to the first presenting group and the second presenting group is part of the second target label, for example, the second presenting group and the second target label are both nucleic acid molecules and the second presenting group is a nucleic acid fragment within the sequence of the second target label.

In some specific embodiments of the methods provided herein, including those of this Section 5.2.6, the first presenting group is part of the first target label, for example, the first presenting group and the first target label are both nucleic acid molecules and the first presenting group is a nucleic acid fragment within the sequence of the first target label, and the second presenting group is conjugated to the second binder. In another embodiment, the first presenting group is part of the first target label, for example, the first presenting group and the first target label are both nucleic acid molecules and the first presenting group is a nucleic acid fragment within the sequence of the first target label, and the second presenting group is non-covalently bound to the second binder. In a further embodiment, the first presenting group is part of the first target label, for example, the first presenting group and the first target label are both nucleic acid molecules and the first presenting group is a nucleic acid fragment within the sequence of the first target label, and the second presenting group is conjugated to the second presenting group. In another embodiment, the first presenting group is part of the first target label, for example, the first presenting group and the first target label are both nucleic acid molecules and the first presenting group is a nucleic acid fragment within the sequence of the first target label, and the second presenting group is non-covalently bound to the second presenting group. In yet another embodiment, the first presenting group is part of the first target label, for example, the first presenting group and the first target label are both nucleic acid molecules and the first presenting group is a nucleic acid fragment within the sequence of the first target label, and the second presenting group is part of the second target label, for example, the second presenting group and the second target label are both nucleic acid molecules and the second presenting group is a nucleic acid fragment within the sequence of the second target label.

As is clear from the disclosure, in some embodiments of the methods provided herein, including the methods of this Section 5.2.6 and Sections 3, 5.2.1 to 5.2.5 and 6, the target label (e.g. the first target label and/or the second target label) can be a nucleic acid molecule. In one embodiment, the first target label is a nucleic acid molecule. In another embodiment, the second target label is a nucleic acid molecule. In a further embodiment, the first target label is a nucleic acid molecule and the second target label is a nucleic acid molecule. The disclosure further provides that in some embodiments of the methods provided herein, including the methods of this Section 5.2.6 and Sections 3, 5.2.1 to 5.2.5 and 6, when the target label is a nucleic acid molecule, the target label hybridizes with the receiving group that is also a nucleic acid molecule. In one embodiment, the first target label hybridizes with the first tag. In another embodiment, the second target label hybridizes with the second tag. In a further embodiment, the first target label hybridizes with the first tag and the second target label hybridizes with the second tag.

Additionally, the disclosure provides sample label comprising sample ID, wherein the sample label binds to the immunocomplex for various embodiments of the methods provided herein, including the methods of this Section 5.2.6 and Sections 3, 5.2.1 to 5.2.5 and 6. The sample label can bind to any component of the binding moiety, the immunocomplex formed by the two binding moieties (e.g. the first binding moiety and the second binding moiety), the receiving group, or a component coupled to the solid surface. In one embodiment, the sample label binds to a target label. In another embodiment, the sample label binds to the presenting group (e.g. presenting group that is a nucleic acid molecule). In a further embodiment, the sample label binds to a binder. In yet another embodiment, the sample label binds to a receiving group. In one embodiment, the sample label binds to the first target label. In another embodiment, the sample label binds to the first presenting group (e.g. presenting group that is a nucleic acid molecule). In still another embodiment, the sample label binds to the first tag. In a further embodiment, the sample label binds to the first binder. In yet another embodiment, the sample label binds to the first receiving group. In one embodiment, the sample label binds to the second target label. In another embodiment, the sample label binds to the second presenting group (e.g. presenting group that is a nucleic acid molecule). In still another embodiment, the sample label binds to the second tag. In a further embodiment, the sample label binds to the second binder. In yet another embodiment, the sample label binds to the second receiving group.

Furthermore, any embodiment of the binding between the sample label and the component of the first binding moiety or the first receiving group can be combined with any embodiment of the binding between the sample label and the component of the second binding moiety or the second receiving group. Accordingly, in one embodiment, the sample label binds to the first target label and the second target label. In another embodiment, the sample label binds to the first target label and the second presenting group (e.g. presenting group that is a nucleic acid molecule). In still another embodiment, the sample label binds to the first target label and the second tag. In a further embodiment, the sample label binds to the first target label and the second binder. In yet another embodiment, the sample label binds to the first target label and the second receiving group.

In one embodiment, the sample label binds to the first presenting group (e.g. presenting group that is a nucleic acid molecule) and the second target label. In another embodiment, the sample label binds to the first presenting group (e.g. presenting group that is a nucleic acid molecule) and the second presenting group (e.g. presenting group that is a nucleic acid molecule). In still another embodiment, the sample label binds to the first presenting group (e.g. presenting group that is a nucleic acid molecule) and the second tag. In a further embodiment, the sample label binds to the first presenting group (e.g. presenting group that is a nucleic acid molecule) and the second binder. In yet another embodiment, the sample label binds to the first presenting group (e.g. presenting group that is a nucleic acid molecule) and the second receiving group.

In one embodiment, the sample label binds to the first tag and the second target label. In another embodiment, the sample label binds to the first tag and the second presenting group (e.g. presenting group that is a nucleic acid molecule). In still another embodiment, the sample label binds to the first tag and the second tag. In a further embodiment, the sample label binds to the first tag and the second binder. In yet another embodiment, the sample label binds to the first tag and the second receiving group.

In one embodiment, the sample label binds to the first binder and the second target label. In another embodiment, the sample label binds to the first binder and the second presenting group (e.g. presenting group that is a nucleic acid molecule). In still another embodiment, the sample label binds to the first binder and the second tag. In a further embodiment, the sample label binds to the first binder and the second binder. In yet another embodiment, the sample label binds to the first binder and the second receiving group.

In one embodiment, the sample label binds to the first receiving group and the second target label. In another embodiment, the sample label binds to the first receiving group and the second presenting group (e.g. presenting group that is a nucleic acid molecule). In still another embodiment, the sample label binds to the first receiving group and the second tag. In a further embodiment, the sample label binds to the first receiving group and the second binder. In yet another embodiment, the sample label binds to the first receiving group and the second receiving group.

The sample label can be a nucleic acid molecules and the sample ID in the sample label can be a nucleic acid sequence that identifies or correlates with a sample in various embodiments provided herein including in this Section 5.2.6 and Sections 3, 5.2.1 to 5.2.5 and 6. In one embodiment, the sample label is a single-stranded nucleic acid molecule ("single-stranded sample label"). In another embodiment, the sample label is a double-stranded nucleic acid molecule ("double-stranded sample label"). For a double stranded sample label, the disclosure further provides that the sample label can have no overhang (e.g. two blunt end), one overhang (e.g. one blunt end), or two overhang (no blunt end) for sample in various embodiments provided herein including in this Section 5.2.6 and Sections 3, 5.2.1 to 5.2.5 and 6. In one embodiment, the sample label is a double-stranded nucleic acid molecule comprising two 5' overhangs. In one embodiment, the sample label is a double-stranded nucleic acid molecule comprising two 3' overhangs. In one embodiment, the sample label is a double-stranded nucleic acid molecule comprising a 5' overhang and a 3' overhang. In one embodiment, the sample label is a double-stranded nucleic acid molecule comprising a 5' overhang and a blunt end. In one embodiment, the sample label is a double-stranded nucleic acid molecule comprising a 3' overhang and a blunt end.

When the sample label is a double-stranded nucleic acid molecules and has one or two overhangs, the sample label can hybridize via its overhangs with any nucleic acid component of the binding moiety, the immunocomplex formed by the two binding moieties, the receiving group, or a nucleic acid component coupled to the solid surface, in various embodiments of the methods provided herein. When the sample label is a single-stranded nucleic acid molecules, the sample label can hybridize with any nucleic acid component of the binding moiety, the immunocomplex formed by the two binding moieties, the receiving group, or a nucleic acid component coupled to the solid surface, in various embodiments of the methods provided herein.

As is clear from the disclosure, each of the target label, the presenting group, the binder, and/or the receiving group can be nucleic acid molecule. Accordingly, the sample label can hybridize via its overhangs with the target label, the presenting group, the binder, and/or the receiving group, when they are nucleic acid molecules or have a component that is a nucleic molecule. In one embodiment, the sample label hybridizes with a target label. In another embodiment, the sample label hybridizes with the presenting group (e.g. presenting group that is a nucleic acid molecule). In a further embodiment, the sample label hybridizes with a binder. In yet another embodiment, the sample label hybridizes with a receiving group. In one embodiment, the sample label hybridizes with the first target label. In another embodiment, the sample label hybridizes with the first presenting group (e.g. presenting group that is a nucleic acid molecule). In still another embodiment, the sample label hybridizes with the first tag. In a further embodiment, the sample label hybridizes with the first binder. In yet another embodiment, the sample label hybridizes with the first receiving group. In one embodiment, the sample label hybridizes with the second target label. In another embodiment, the sample label hybridizes with the second presenting group (e.g. presenting group that is a nucleic acid molecule). In still another embodiment, the sample label hybridizes with the second tag. In a further embodiment, the sample label hybridizes with the second binder. In yet another embodiment, the sample label hybridizes with the second receiving group.

Furthermore, any embodiment of the hybridization between the sample label and the component of the first binding moiety or the first receiving group can be combined with any embodiment of the hybridization between the sample label and the component of the second binding moiety or the second receiving group. Accordingly, in one embodiment, the sample label hybridizes with the first target label and the second target label. In another embodiment, the sample label hybridizes with the first target label and the second presenting group (e.g. presenting group that is a nucleic acid molecule). In still another embodiment, the sample label hybridizes with the first target label and the second tag. In a further embodiment, the sample label hybridizes with the first target label and the second binder. In yet another embodiment, the sample label hybridizes with the first target label and the second receiving group.

In one embodiment, the sample label hybridizes with the first presenting group (e.g. presenting group that is a nucleic acid molecule) and the second target label. In another embodiment, the sample label hybridizes with the first presenting group (e.g. presenting group that is a nucleic acid molecule) and the second presenting group (e.g. presenting group that is a nucleic acid molecule). In still another embodiment, the sample label hybridizes with the first presenting group (e.g. presenting group that is a nucleic acid molecule) and the second tag. In a further embodiment, the sample label hybridizes with the first presenting group (e.g. presenting group that is a nucleic acid molecule) and the second binder. In yet another embodiment, the sample label hybridizes with the first presenting group (e.g. presenting group that is a nucleic acid molecule) and the second receiving group.

In one embodiment, the sample label hybridizes with the first tag and the second target label. In another embodiment, the sample label hybridizes with the first tag and the second presenting group (e.g. presenting group that is a nucleic acid molecule). In still another embodiment, the sample label hybridizes with the first tag and the second tag. In a further embodiment, the sample label hybridizes with the first tag and the second binder. In yet another embodiment, the sample label hybridizes with the first tag and the second receiving group.

In one embodiment, the sample label hybridizes with the first binder and the second target label. In another embodiment, the sample label hybridizes with the first binder and the second presenting group (e.g. presenting group that is a nucleic acid molecule). In still another embodiment, the sample label hybridizes with the first binder and the second tag. In a further embodiment, the sample label hybridizes with the first binder and the second binder. In yet another embodiment, the sample label hybridizes with the first binder and the second receiving group.

In one embodiment, the sample label hybridizes with the first receiving group and the second target label. In another embodiment, the sample label hybridizes with the first receiving group and the second presenting group (e.g. presenting group that is a nucleic acid molecule). In still another embodiment, the sample label hybridizes with the first receiving group and the second tag. In a further embodiment, the sample label hybridizes with the first receiving group and the second binder. In yet another embodiment, the sample label hybridizes with the first receiving group and the second receiving group.

A person of ordinary skill in the art would understand that when the a double-stranded sample label hybridizes with two items as described in this Section 5.2.6 including this and the preceding 6 paragraphs, in some embodiments, the double-stranded sample label hybridizes with the first item via its 5' overhang and the second item via its 3' overhang. In other embodiments, the double-stranded sample label hybridizes with the first item via its 3' overhang and the second item via its 5' overhang. In other embodiments, the double-stranded sample label hybridizes with the first item via its 5' overhang and the second item via its 5' overhang. In still further embodiments, the double-stranded sample label hybridizes with the first item via its 3' overhang and the second item via its 3' overhang. When the a double-stranded sample label hybridizes with one item as described in this Section 5.2.6 including this and the preceding 6 paragraphs, in some embodiments, the double-stranded sample label hybridizes with the item via its 5' overhang. In certain embodiments, the double-stranded sample label hybridizes with the item via its 3' overhang. When the sample label is a single-stranded sample label, such sample label can hybridizes with any one item or two item as described in this Section 5.2.6 including this and the preceding 6 paragraphs, via any parts or its nucleic acid sequence, including either end, both ends (5' end and 3' end), and any internal sequences.

In some specific embodiments, the sample label hybridizes with the first target label via an overhang (e.g. 5' overhang or 3' overhang) of the sample label. In another specific embodiment, the sample label hybridizes with the second target label via an overhang (e.g. 5' overhang or 3' overhang) of the sample label. In another embodiment, the sample label hybridizes with the first target label via an overhang (e.g. 5' overhang or 3' overhang) of the sample label and hybridizes with the second target label via an overhang (e.g. 5' overhang or 3' overhang) of the sample label. In another embodiment, the sample label hybridizes with the first target label via the 5' overhang of the sample label and hybridizes with the second target label via the 3' overhang of the sample label. In one embodiment, the sample label hybridizes with the first target label via the 5' overhang of the sample label and hybridizes with the second target label via the 5' overhang of the sample label. In a further embodiment, the sample label hybridizes with the first target label via the 3' overhang of the sample label and hybridizes with the second target label via the 5' overhang of the sample label. In yet another embodiment, the sample label hybridizes with the first target label via the 3' overhang of the sample label and hybridizes with the second target label via the 3' overhang of the sample label.

As described in detail in Section Sections 3, 5.2.4.1, 5.2.5 and 6, in various embodiments of the methods provided herein, including the methods provided in this Section 5.2.6, the nucleic acid report can be generated by linking (i) either one of the first target label and the first presenting group (e.g. first tag), and (ii) either one of the second target label and the second presenting group (e.g. second tag). Accordingly, in one embodiment, the methods comprises generating the nucleic acid reporter by linking:

(a) the first tag and the second tag, and detecting the nucleic acid reporter composed of a fragment of the first tag and a fragment of the second tag;

(b) the first tag and a surrogate nucleic acid of the second tag (the "second surrogate"), and detecting the nucleic acid reporter composed of a fragment of the first tag and a fragment of the second surrogate;

(c) a surrogate nucleic acid of the first tag (the "first surrogate") and the second tag, and detecting the nucleic acid reporter composed of a fragment of the first surrogate and a fragment of the second tag; or (d) the first surrogate and the second surrogate, and detecting the nucleic acid reporter composed of a fragment of the first surrogate and a fragment of the second surrogate;

wherein the first tag or a fragment thereof is complementary to the first surrogate or a fragment thereof, and the second tag or a fragment thereof is complementary to the second surrogate or a fragment thereof.

Alternative, the methods provided herein comprises generating the nucleic acid reporter by linking:

(a) the first tag and the second target label, and detecting the nucleic acid reporter composed of a fragment of the first tag and a fragment of the second target label;

(b) the first tag and a surrogate nucleic acid of the second target label (the "second surrogate"), and detecting the nucleic acid reporter composed of a fragment of the first tag and a fragment of the second surrogate;

(c) a surrogate nucleic acid of the first tag (the "first surrogate") and the second target label, and detecting the nucleic acid reporter composed of a fragment of the first surrogate and a fragment of the second target label; or (d) the first surrogate and the second surrogate, and detecting the nucleic acid reporter composed of a fragment of the first surrogate and a fragment of the second surrogate; wherein the first tag or a fragment thereof is complementary to the first surrogate or a fragment thereof, and the second target label or a fragment thereof is complementary to the second surrogate or a fragment thereof.

Similarly, the methods provided herein comprises generating the nucleic acid reporter by linking:

(a) the first target label and the second tag, and detecting the nucleic acid reporter composed of a fragment of the first target label and a fragment of the second tag;

(b) the first target label and a surrogate nucleic acid of the second tag (the "second surrogate"), and detecting the nucleic acid reporter composed of a fragment of the first target label and a fragment of the second surrogate;

(c) a surrogate nucleic acid of the first target label (the "first surrogate") and the second tag, and detecting the nucleic acid reporter composed of a fragment of the first surrogate and a fragment of the second tag; or (d) the first surrogate and the second surrogate, and detecting the nucleic acid reporter composed of a fragment of the first surrogate and a fragment of the second surrogate; wherein the first target label or a fragment thereof is complementary to the first surrogate or a fragment thereof, and the second tag or a fragment thereof is complementary to the second surrogate or a fragment thereof.

Additionally, the methods provided herein comprises generating the nucleic acid reporter by linking:

(a) the first target label and the second target label, and detecting the nucleic acid reporter composed of a fragment of the first target label and a fragment of the second target label;

(b) the first target label and a surrogate nucleic acid of the second target label (the "second surrogate"), and detecting the nucleic acid reporter composed of a fragment of the first target label and a fragment of the second surrogate;

(c) a surrogate nucleic acid of the first target label (the "first surrogate") and the second target label, and detecting the nucleic acid reporter composed of a fragment of the first surrogate and a fragment of the second target label; or (d) the first surrogate and the second surrogate, and detecting the nucleic acid reporter composed of a fragment of the first surrogate and a fragment of the second surrogate;

wherein the first target label or a fragment thereof is complementary to the first surrogate or a fragment thereof, and the second target label or a fragment thereof is complementary to the second surrogate or a fragment thereof.

Furthermore, in various embodiments of the methods provided herein, including the methods provided in this Section 5.2.6, the nucleic acid report can be generated by linking (i) either one of the first target label and the first presenting group (e.g. first tag), (ii) either one of the second target label and the second presenting group (e.g. second tag), and (iii) the sample label. Accordingly, in some embodiments of the methods provided herein, including the methods provided in this Section 5.2.6 and the preceding 4 paragraphs, the linking for the methods comprises linking:

(i) (a) the first tag or the first surrogate thereof, (b) the second tag or the second surrogate thereof, and (c) a surrogate nucleic acid of the single-stranded sample label ("sample surrogate") or one strand of the double-stranded sample label;

(ii) (a) the first tag or the first surrogate thereof, (b) the second target label or the second surrogate thereof, and (c) a surrogate nucleic acid of the single-stranded sample label ("sample surrogate") or one strand of the double-stranded sample label;

(iii) (a) the first target label or the first surrogate thereof, (b) the second tag or the second surrogate thereof, and (c) a surrogate nucleic acid of the single-stranded sample label ("sample surrogate") or one strand of the double-stranded sample label; or (iv) (a) the first target label or the first surrogate thereof, (b) the second target label or the second surrogate thereof, and (c) a surrogate nucleic acid of the single-stranded sample label ("sample surrogate") or one strand of the double-stranded sample label;

wherein the sample label or a fragment thereof is complementary to the sample surrogate or a fragment thereof. In some specific embodiments, the linking in each of (i) to (iv) of this paragraph comprises linking (c) between (a) and (b). In other specific embodiments, the linking in each of (i) to (iv) of this paragraph comprises linking (a) to (c) in the direction of (a), then (c), and then (b). In one embodiment, the linking in each of (i) to (iv) of this paragraph comprises linking (a) to (c) in the direction of (b), then (c), and then (a). In another embodiment, the linking in each of (i) to (iv) of this paragraph comprises linking (a) to (c) in the direction of (c), then (a), and then (b). In a further embodiment, the linking in each of (i) to (iv) of this paragraph comprises linking (a) to (c) in the direction of (c), then (b), and then (a). In another embodiment, the linking in each of (i) to (iv) of this paragraph comprises linking (a) to (c) in the direction of (a), then (b), and then (c). In yet another embodiment, the linking in each of (i) to (iv) of this paragraph comprises linking (a) to (c) in the direction of (b), then (a), and then (c).

Accordingly, as is clear from the above description including in this Section 5.2.6, the disclosure provides that the nucleic acid reporter can be generated in some embodiments of the methods provided herein by linking (i) either one of the first target label and the first presenting group (e.g. first tag), (ii) either one of the second target label and the second presenting group (e.g. second tag), and/or (iii) a sample label. The disclosure further provides that such linking can be a ligation, for example blunt end ligation or a sticky end ligation, or any combination thereof. In one embodiment, the nucleic acid reporter is formed by sticky end ligation. In a further embodiment, the nucleic acid reporter is formed by blunt end ligation. In yet another embodiment, the nucleic acid reporter is formed by blunt end ligation at one end of the sample label and sticky end ligation at the other end of the sample label. In one embodiment, the nucleic acid reporter is formed by blunt end ligation at one end of the sample label and blunt end ligation at the other end of the sample label. In another embodiment, the nucleic acid reporter is formed by sticky end ligation at one end of the sample label and sticky end ligation at the other end of the sample label.

Additionally, in another embodiment, the nucleic acid reporter can be formed by other means of generating nucleic acid reporter known and practiced in the field. In one embodiment of the methods provided herein, including the methods provided in this Section 5.2.6, the nucleic acid reporter is formed by proximity ligation. In another embodiment, the nucleic acid reporter is formed by proximity extension. In yet another embodiment, the nucleic acid reporter is formed by PCR. In a specific embodiment, the nucleic acid reporter is formed by PCR with the template formed by linking (e.g. ligation of) (i) either one of the first target label and the first presenting group (e.g. first tag), (ii) either one of the second target label and the second presenting group (e.g. second tag), and/or (iii) a sample label, as described in this Section 5.2.6 including the preceding 7 paragraphs.

As is clear from the disclosure, the nucleic acid reporter generated in the methods provided herein, including in the methods in this Section 5.2.6, can comprise (i) either one of the first target label and the first presenting group (e.g. first tag), (ii) either one of the second target label and the second presenting group (e.g. second tag), and/or (iii) a sample label. Accordingly, the nucleic acid reporter generated in the methods provided herein, including in the methods in this Section 5.2.6, can comprise the first target ID, the second target ID, and/or the sample ID in all possible combinations and configurations provided herein including in this Section 5.2.6 and Sections 3, 5.2.1 to 5.2.5 and 6. In one embodiment, the nucleic acid reporter comprises the first target ID or a surrogate nucleic acid of the first target ID (the "first target ID surrogate"). In another embodiment, the nucleic acid reporter comprises the second target ID or a surrogate nucleic acid of the second target ID (the "second target ID surrogate"). In yet another embodiment, the nucleic acid reporter comprises the sample ID. In a further embodiment, the nucleic acid reporter comprises (a) the first target ID or the first target ID surrogate, and (b) the second target ID or the second target ID surrogate. In one embodiment, the nucleic acid reporter comprises (a) the first target ID or the first target ID surrogate, and (b) the sample ID. In another embodiment, the nucleic acid reporter comprises (a) the second target ID or the second target ID surrogate, and (b) the sample ID. In a further embodiment, the nucleic acid reporter comprises (a) the first target ID or the first target ID surrogate, (b) the second target ID or the second target ID surrogate, and (c) the sample ID. In some embodiments, the nucleic acid reporter comprises (a) the first target ID or the first target ID surrogate, (b) the second target ID or the second target ID surrogate, and (c) the sample ID, wherein the sample ID is in between (a) the first target ID or the first target ID surrogate and (b) the second target ID or the second target ID surrogate. In certain embodiments, the nucleic acid reporter comprises (a) the first target ID or the first target ID surrogate, (b) the second target ID or the second target ID surrogate, and (c) the sample ID, wherein (a), (b) and (c) are arranged sequentially as (a) then (c) and then (b). In other embodiments, the nucleic acid reporter comprises (a) the first target ID or the first target ID surrogate, (b) the second target ID or the second target ID surrogate, and (c) the sample ID, wherein (a), (b) and (c) are arranged sequentially as (b) then (c) and then (a). In one embodiment, the nucleic acid reporter comprises (a) the first target ID or the first target ID surrogate, (b) the second target ID or the second target ID surrogate, and (c) the sample ID, wherein (a), (b) and (c) are arranged sequentially as (a) then (b) and then (c). In another embodiment, the nucleic acid reporter comprises (a) the first target ID or the first target ID surrogate, (b) the second target ID or the second target ID surrogate, and (c) the sample ID, wherein (a), (b) and (c) are arranged sequentially as (b) then (a) and then (c). In yet another embodiment, the nucleic acid reporter comprises (a) the first target ID or the first target ID surrogate, (b) the second target ID or the second target ID surrogate, and (c) the sample ID, wherein (a), (b) and (c) are arranged sequentially as (c) then (a) and then (b). In a further embodiment, the nucleic acid reporter comprises (a) the first target ID or the first target ID surrogate, (b) the second target ID or the second target ID surrogate, and (c) the sample ID, wherein (a), (b) and (c) are arranged sequentially as (c) then (b) and then (a).

Additionally, in some embodiments of the methods provided herein, the nucleic acid reporter can contain a sample ID in the first surrogate, the second surrogate, the first target ID surrogate, or the second target ID surrogate, in each case as such first surrogate, second surrogate, first target ID surrogate, or second target ID surrogate is provided herein, including in this Section 5.2.6.

As the methods provided herein including in this Section 5.2.6 can correlate each analyte with the one or more target IDs provided herein, the assay methods can simultaneously detect at least two analytes in the sample by simultaneously detecting the target IDs associated with each analyte and correlating target IDs with analytes. Accordingly, in some embodiments, the assay methods provided herein simultaneously detect at least three, at least four, at least five, at least six, at least seven, at least eight, at least nine, at least ten, at least twelve, at least fifteen, at least twenty, at least thirty, at least forty, at least fifty, at least sixty, at least seventy, at least eighty, at least ninety, or at least one hundred analytes in the sample by simultaneously detecting the unique target IDs associated with each analyte. In further embodiments, the assay methods provided herein simultaneously detect about three, about four, about five, about six, about seven, about eight, about nine, about ten, about twelve, about fifteen, about twenty, about thirty, about forty, about fifty, about sixty, about seventy, about eighty, about ninety, or about one hundred analytes in the sample by simultaneously detecting the unique target IDs associated with each analyte. In certain embodiments, the assay methods provided herein simultaneously detect at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, at least 1000, at least 1100, at least 1200, at least 1300, at least 1400, at least 1500, at least 1600, at least 1700, at least 1800, at least 1900, or at least 2000 analytes in the sample by simultaneously detecting the unique target IDs associated with each analyte. In further embodiments, the assay methods provided herein simultaneously detect about 100, about 150, about 200, about 250, about 300, about 350, about 400, about 450, about 500, about 550, about 600, about 650, about 700, about 750, about 800, about 850, about 900, about 950, about 1000, about 1100, about 1200, about 1300, about 1400, about 1500, about 1600, about 1700, about 1800, about 1900, or about 2000 analytes in the sample by simultaneously detecting the unique target IDs associated with each analyte.

To ensure that the signal generated from the analyte falls in the detection range, the signal from the analyte can be amplified or enhanced or can be tuned down. Approaches provided herein for reducing the number of reporter molecules generated from a high-concentration target analyte include reducing a precise and known proportion of capturing so that the limited bandwidth of detection can be efficiently assigned to different target analytes. Accordingly, in some embodiments, the methods provided herein including in this Section 5.2.6 comprises the means for partial capturing as provided in Section 3 and 5.2.5. In one specific embodiment, the method provided herein comprises proportionally reducing the signal from at least one of the analytes, by adding a non-functional binder to the solution in step (1), wherein the non-functional binder competes with the first binder for binding to the analyte but is either unconjugated or conjugated to a presenting group that does not bind the first receiving group.

The disclosure provides that the true signals can be precisely determined and parsed out from various categories of noises, as the methods provides the correlation between the target IDs and the particular target. In some embodiments, only the nucleic acid reporter comprising the target IDs all correctly correlating with the target is determined as signal for that particular target. In one specific embodiment, In some embodiments, only the nucleic acid reporter comprising the two target IDs both correctly correlating with the target is determined as signal for that particular target. In another specific embodiment of the methods provided herein, including in this Section 5.2.6, detecting the analyte comprises the co-detection of the first and the second target IDs. In a further specific embodiment, of the methods provided herein, including in this Section 5.2.6, detecting the analyte in the step (4) of the methods comprises the co-detection of the first and the second target IDs.

As is clear from FIGS. 23A-23B, nucleic acid reporters comprising the first and the second target IDs can be sequenced and quantified. As such, to maintain the sensitivity and specificity of each assay for each analyte in a multiplex assay at the same level as a singleplex assay, reporters generated from the intended binding pair of the first binder and second binder for an analyte can be identified, parsed out from other reporters, and determined. In some embodiments of the methods provided herein including those in this Section 5.2.6, the reporters comprising target IDs (e.g. the first target ID and the second target ID) correlated with the intended binding pair of the first binder and the second binder for a target analyte can be determined and parsed out from the reporters comprising target IDs correlated with the first binder and the second binder not intended to pair up in binding a target analyte. In certain embodiments, the reporters generated from target labels (e.g. the first target label and the second target label) correlated with the intended binding pair of the first binder and the second binder for a target analyte can be determined and parsed out from the reporters generated from target labels correlated with the first binder and the second binder not intended to pair up in binding a target analyte. In other embodiments, the reporters generated from presenting groups (e.g. the first presenting group and the second presenting group) correlated with the intended binding pair of the first binder and the second binder for a target analyte can be determined and parsed out from the reporters generated from presenting groups correlated with the first binder and the second binder not intended to pair up in binding a target analyte.

The disclosure further provides and a person of ordinary skill in the art reading the application would understand that, in some embodiments of the methods provided herein including in this Section 5.2.6, the methods further comprising mixing a reference analyte so that the sample-to-sample variations can be normalized according to the reporters generated from the reference analyte. In one embodiment of the methods provided herein including in this Section 5.2.6, the method further comprises mixing a reference analyte. In another embodiment, the step (1) of the method further comprises mixing a reference analyte. In yet another embodiment, the reference analyte is an analyte that is absent in the sample. In a further embodiment, the reference analyte is a protein, a nucleic acid, or a chemical compound that is absent in the sample. In one embodiment, the reference analyte is a viral protein, a bacterial protein, or an insect protein. In another embodiment, the reference analyte is a viral nucleic acid molecule, a bacterial nucleic acid molecule, or an insect nucleic acid molecule.

As is clear from the disclosure, the various embodiments of the methods provide nucleic acid reporters comprising sample IDs and/or target IDs. As such, in some embodiments, the methods provided herein comprises simultaneously detecting the analyte in at least two samples, by simultaneously detecting the unique sample IDs in the nucleic acid reporters associated with each sample. In other embodiments, the methods provided herein comprises simultaneously detecting at least two analytes in at least two samples, by simultaneously detecting the unique sample IDs and unique target IDs associated with each analyte and the unique sample IDs associated with each sample. In some further embodiments, the methods provided herein further comprise simultaneously detecting any number of samples as provided in Sections 3, 5.2.5 and 6. In other embodiments, the methods provided herein further comprise simultaneously detecting any number of samples as provided in Sections 3, 5.2.5 and 6 in any combination of any number of targets as provided in Sections 3, 5.2.5 and 6. In some further embodiments, the methods provided herein further comprise pooling the nucleic acid reporters from the at least two samples before or simultaneously of the detection step in the method. In some additional embodiments, the methods provided herein further comprise pooling the nucleic acid reporters for the at least two analytes from the at least two samples before or simultaneously of the detection step in the method. In certain embodiments, the methods provided herein further comprise pooling any number of samples as provided in Sections 3, 5.2.5 and 6 before or simultaneously of the detection step in the method. In other embodiments, the methods provided herein further comprise pooling any number of samples as provided in Sections 3, 5.2.5 and 6 in any combination of any number of targets as provided in Sections 3, 5.2.5 and 6 before or simultaneously of the detection step in the method.

Additionally, in some embodiments of the methods provided herein including in this Section 5.2.6, the nucleic acid reporters in the multiplexing assay methods disclosed herein can be detected by multiplexed qPCR, multiplexed digital PCR, or NGS, as such multiplexed qPCR, multiplexed digital PCR, or NGS is provided in Sections 3, 5.2.5 and 6. In a specific embodiment, the nucleic acid reporters are detected by NGS. Such NGS is further provided in Sections 3, 5.2.5 and 6.

As described further above, the sample-to-sample variation of the reporters generated in the methods provided herein can be normalized according to the levels of reporters generated from the reference analyte. Accordingly, in one embodiment of the methods provided herein including in this Section 5.2.6, the method further comprises normalizing the reporters generated from the analytes of the samples against the reporter generated from the reference analyte. In another embodiment, the detecting step of the method further comprises normalizing the reporters generated from the analytes of the samples against the reporter generated from the reference analyte.

In some embodiments of the methods provided herein, the solid surface can be any suitable solid surface known and used in the field. In certain embodiments of the methods provided herein including in this Section 5.2.6, the solid surface can be any solid surface provided in Sections 3, 5.2.2 to 5.3.3 and 6. In some further embodiments of the methods provided herein including in this Section 5.2.6, the first solid surface can be any solid surface provided in Sections 3, 5.2.2 to 5.3.3 and 6 and the second solid surface can be any solid surface provided in Sections 3, 5.2.2 to 5.3.3 and 6. In one embodiment, the first solid surface is a magnetic particle surface. In another embodiment, the first solid surface is a well of a microtiter plate. In a further embodiment, the second solid surface is a magnetic particle surface. In yet another embodiment, the second solid surface is a well of a microtiter plate. In one embodiment, the first solid surface is a magnetic particle surface and the second solid surface is a magnetic particle surface. In another embodiment, the first solid surface is a magnetic particle surface and the second solid surface is a well of a microtiter plate. In a further embodiment, the first solid surface is a well of a microtiter plate and the second solid surface is a magnetic particle surface. In a further embodiment, the first solid surface is a well of a microtiter plate and the second solid surface is a well of a microtiter plate.

Additionally, the disclosure provides and a person of ordinary skill in the art reading the disclosure would understand that any embodiments of the methods provided in this Section 5.2.6 can be combined with any other embodiments provided in this Section 5.2.6 and other sections of the disclosure, including Sections 3, 4, 5.1, 5.2.1 to 5.2.5, 5.3, 5.4 and 6.

In one specific aspect, provided herein is an assay method for detecting an analyte in a sample, comprising:
(1) mixing a first binding moiety comprising a first binder and a first presenting group, a second binding moiety comprising a second binder and a second presenting group, and the sample in a solution, wherein:
  (i) the first and second binders bind to the analyte and form an immunocomplex,
  (ii) the immunocomplex is captured on a first solid surface in contact with the solution via binding between the first presenting group and a first receiving group coupled to the first solid surface, and
  (iii) the first binding moiety further comprises a first target label comprising a first identity barcode ("ID") that is analyte-specific ("target ID") and the second binding moiety further comprises a second target label comprising a second target ID;
(2) washing the first solid surface to remove unbound molecules;
(3) releasing the immunocomplex from the first solid surface by disrupting the binding between the first presenting group and the first receiving group;
(4) introducing a second solid surface and recapturing the immunocomplex on the second solid surface via binding between the second presenting group and the second receiving group coupled to the second solid surface;
(5) washing the second solid surface to remove unbound molecules;
(6) binding a sample label comprising an ID that is sample-specific ("sample ID") (i) to the first target label, (ii) to the second target label, or (iii) to both the first target label and the second target label;
(7) generating a nucleic acid reporter from the immunocomplex based on proximity between the first target label and the second target label, wherein the nucleic acid reporter comprises the first target ID, the second target ID, and the sample ID;
(8) releasing the immunocomplex from the second solid surface by disrupting the binding between the second presenting group and the second receiving group; and
(9) detecting the nucleic acid reporter by qPCR, thereby detecting the analyte.

In another specific aspect, provided herein is an assay method for detecting an analyte in at least two samples, comprising:
(1) mixing a first binding moiety comprising a first binder and a first presenting group, a second binding moiety comprising a second binder and a second presenting group, and the samples in a solution, wherein:
  (i) the first and second binders bind to the analyte and form an immunocomplex,
  (ii) the immunocomplex is captured on a first solid surface in contact with the solution via binding between the first presenting group and a first receiving group coupled to the first solid surface, and
  (iii) the first binding moiety further comprises a first target label comprising a first identity barcode ("ID") that is analyte-specific ("target ID") and the second binding moiety further comprises a second target label comprising a second target ID;
(2) washing the first solid surface to remove unbound molecules;
(3) releasing the immunocomplex from the first solid surface by disrupting the binding between the first presenting group and the first receiving group;
(4) introducing a second solid surface and recapturing the immunocomplex on the second solid surface via binding between the second presenting group and the second receiving group coupled to the second solid surface;
(5) washing the second solid surface to remove unbound molecules;
(6) binding a sample label comprising an ID that is sample-specific ("sample ID") (i) to the first target label, (ii) to the second target label, or (iii) to both the first target label and the second target label;
(7) generating a nucleic acid reporter from the immunocomplex based on proximity between the first target label and the second target label, wherein the nucleic acid reporter comprises the first target ID, the second target ID, and the sample ID;
(8) pooling the nucleic acid reporters from the at least two samples;
(9) releasing the immunocomplex from the second solid surface by disrupting the binding between the second presenting group and the second receiving group;
(9) amplifying the nucleic acid reporters;
(10) purifying the nucleic acid reporters; and
(11) detecting the nucleic acid reporters by next generation sequencing (NGS), thereby detecting the analyte.

5.3 Systems

Provided herein are also systems for carrying out the assay methods disclosed herein. The systems disclosed herein can be used for detecting an analyte in a sample. The systems disclosed herein can also be used for detecting multiple analytes in a sample, an analyte in multiple samples, or multiple analytes in multiple samples. In some embodiments, the systems provided herein are for carrying out the assay methods for qualitatively detecting an analyte in a sample. In some embodiments, the systems provided herein are for carrying out the assay methods for quantitatively detecting an analyte in a sample. In some embodiments, the system provided herein is contained in a kit.

5.3.1 Systems with Two Capture Binders

In some embodiments, provided herein are systems for detecting an analyte in a sample comprising a first binder, a second binder, a first presenting group, a second presenting group, a first receiving group, and a second receiving group; wherein (i) the first and second binders bind non-interfering epitopes on the analyte; and (ii) the first and second presenting groups can bind the first and second receiving groups, respectively.

In some embodiments, the systems further comprise a first solid surface and a second solid surface. The first and second receiving groups can be coupled to the first and second solid surfaces, respectively. In some embodiments, the systems further comprise a detectable marker. The detectable marker can be conjugated to the first binder in the systems provided herein. The detectable marker can be conjugated to the second binder in the systems provided herein.

The first and the second binders can be conjugated to the first and second presenting groups, respectively. In some embodiments, the first binder is conjugated to the first presenting group in the systems provided herein. In some embodiments, the second binder is conjugated to the second presenting group in the systems provided herein. In some embodiments, both the first and the second binders are conjugated to the first and second presenting groups, respectively, in the systems provided herein.

In some embodiments, the first solid surface is coupled with the first receiving group in the systems provided herein. In some embodiments, the second first solid surface is coupled with the second receiving group in the systems provided herein. In some embodiments, both the first and second solid surfaces are coupled with the first and second receiving groups, respectively, in the systems provided herein.

The presenting groups and receiving groups can be any binding pairs disclosed herein, including, for example, antibody and antigen, ligand and receptor, complementary nucleic acids, biotin and avidin (or streptavidin or neutravidin), lectin and carbohydrates, and vice versa. In some embodiments, the first presenting group binds the first receiving group via a thioester group. The first presenting group can also bind the first receiving group via a disulfide linkage. The first presenting group can also bind the first receiving group via a cleavable linkage. In some embodiments, the second presenting group binds the second receiving group via a thioester group. The second presenting group can also bind the second receiving group via a disulfide linkage. The second presenting group can also bind the second receiving group via a cleavable linkage. In some embodiments, both the first and the second presenting groups bind the first and second receiving groups via a thioester group, a disulfide linkage, or a cleavable linkage, respectively.

In some embodiments, the first presenting group binds the first receiving group via a photocleavable linkage. The first presenting group can also bind the first receiving group via a chemically cleavable linkage. The first presenting group can also bind the first receiving group via an enzymatically cleavable linkage. In some embodiments, the second presenting group binds the second receiving group via a photocleavable linkage. The second presenting group can also bind the second receiving group a chemically cleavable linkage. The second presenting group can also bind the second receiving group via an enzymatically cleavable linkage. In some embodiments, both the first and second presenting groups bind the first and the second receiving groups via a photocleavable linkage, a chemically cleavable linkage, or an enzymatically cleavable linkage, respectively.

In some embodiments, provided herein are systems for detecting an analyte in a sample comprising a first binder, a second binder, a first nucleic acid tag (the "first tag"), a second nucleic acid tag (the "second tag"), a first nucleic acid capture probe (the "first probe"), and a second nucleic acid capture probe (the "second probe"); wherein (i) the first and second binders bind non-interfering epitopes on the analyte; (iii) the first probe or a fragment thereof is complementary to the first tag or a fragment thereof; and (iii) the second probe or a fragment thereof is complementary to the second tag or a fragment thereof.

In some embodiments, the systems provided herein further include a first solid surface and a second solid surface. The first and second solid surfaces can be coupled with the first and second probes, respectively. In some embodiments, the first solid surface is coupled with the first probe. In some embodiments, the second first solid surface is coupled with the second probe. In some embodiments, the first and second solid surfaces are coupled with the first and second probes, respectively.

The first and second binders can be conjugated to the first and second tags, respectively. In some embodiments, the first binder is conjugated to the first tag. In some embodiments, the second binder is conjugated to the second tag. In some embodiments, both the first and the second binder are conjugated to the first and second tags, respectively.

In some embodiments, systems provided herein further include a universal probe. The universal probe can be, for example, poly A or poly T. In some embodiments, the first solid surface is coupled with the universal probe in the systems provided herein.

In some embodiments, provided herein are systems for carrying out the NULISA assay disclosed herein for detecting an analyte, comprising: (1) a first antibody and a second antibody that binding non-interfering epitopes of the analyte; (2) a first nucleic acid tag (the "first tag"), a second nucleic acid tag (the "second tag"), a first nucleic acid capture probe (the "first probe"), and a second nucleic acid capture probe (the "second probe"); wherein the first probe or a fragment thereof is complementary to the first tag or a fragment thereof; and the second probe or a fragment thereof is complementary to the second tag or a fragment thereof. In some embodiments, complementary fragments of the first tag and the first probe consist of 10-25 A/T pairs, and complementary fragments of the second tag and the second probe consist of 10-25 A/T pairs.

5.3.2 Systems with One Capture Binder

In some embodiments, provided herein are systems for detecting an analyte in a sample comprising a first binder, a second binder, a first presenting group, a first receiving group, and a second receiving group; wherein (i) the first and second binders bind non-interfering epitopes on the analyte; (ii) the first presenting group can bind the first receiving group, and (iii) the second receiving group binds the first presenting group. In some embodiments, the second receiving group is the same as the first receiving group.

In some embodiments, systems provided herein further include a first solid surface and a second solid surface. The first solid surface and second solid surfaces can be coupled with the first and second receiving groups, respectively. In some embodiments, the first solid surface is coupled with the first receiving group in the systems provided herein. In some embodiments, the second first solid surface is coupled with the second receiving group in the systems provided herein. In some embodiments, both the first and second solid surfaces are coupled with the first and second receiving groups, respectively, in the systems provided herein.

In some embodiments, the first binder is conjugated with the first presenting group.

In some embodiments, the systems provided herein further include a detectable marker. In some embodiments, the detectable marker is conjugated to the second binder in the systems provided herein. In some embodiments, the first binder is conjugated to the first binder in the systems provided herein.

The presenting groups and receiving groups can be any releasable and renewable binding pairs disclosed herein, including, for example, antibody and antigen, ligand and receptor, complementary nucleic acids, biotin and avidin (or streptavidin or neutravidin), lectin and carbohydrates, and vice versa. In some embodiments, the first presenting group binds the first receiving group via a thioester group. The first presenting group can also bind the first receiving group via a disulfide linkage. The first presenting group can also bind the first receiving group via a cleavable linkage. In some embodiments, the first presenting group binds the second receiving group via a thioester group. The first presenting group can also bind the second receiving group via a disulfide linkage. The first presenting group can also bind the second receiving group via a cleavable linkage. In some embodiments, the first presenting group binds both the first and second receiving groups via a thioester group, a disulfide linkage, or a cleavable linkage, respectively.

In some embodiments, the first presenting group binds the first receiving group via a photocleavable linkage. The first presenting group can also bind the first receiving group via a chemically cleavable linkage. The first presenting group can also bind the first receiving group via an enzymatically cleavable linkage. In some embodiments, the first presenting group binds the second receiving group via a photocleavable linkage. The first presenting group can also bind the second receiving group a chemically cleavable linkage. The first presenting group can also bind the second receiving group via an enzymatically cleavable linkage. In some embodiments, the first presenting group binds the first and the second receiving groups via a photocleavable linkage, a chemically cleavable linkage, or an enzymatically cleavable linkage, respectively.

In some embodiments, provided herein are systems for detecting an analyte in a sample comprising a first binder, a second binder, a first nucleic acid tag (the "first tag"), a first nucleic acid capture probe (the "first probe"), a second nucleic acid capture probe (the "second probe"); wherein (i) the first and second binders bind non-interfering epitopes on the analyte; (ii) the first probe or a fragment thereof is complementary to the first tag or a fragment thereof; and (iii) the second probe or a fragment thereof is complementary to the first tag or a fragment thereof. In some embodiments, the second probe is the same as the first probe.

In some embodiments, systems provided herein further include a first solid surface and a second solid surface. The first solid surface can be coupled with the first probe. The second solid surface can be couple with the second probe. In some embodiments, in the systems provided herein, the first solid surface is coupled with the first probe. In some embodiments, in the systems provided herein, the second first solid surface is coupled with the second probe.

In the systems provide herein, the first binder can be conjugated to the first tag. Either the first binder or the second binder can be conjugated to the detectable marker. In some embodiments, in the systems provided herein, the first binder is conjugated to the first tag. In some embodiments, the first binder is conjugated to the detectable marker. In some embodiments, the second binder is conjugated to the detectable marker in the systems provided herein.

In some embodiments, provided herein are systems for carrying out the NULISA assay disclosed herein for detecting an analyte, comprising: (1) a first antibody and a second antibody that binding non-interfering epitopes of the analyte, and (2) a nucleic acid tag ("the tag") and a nucleic acid capture probe ("the probe"), wherein the probe or a fragment thereof is complementary to the tag or a fragment thereof. In some embodiments, the tag is conjugated to the first antibody. In some embodiments, complementary fragments of the tag and the probe consist of 10-25 A/T pairs, and complementary fragments of the second tag and the second probe consist of 10-25 A/T pairs. In some embodiments, the systems provided herein further include a solid surface. In some embodiments, the probe is coupled to the solid surface.

In some embodiments, the systems provided herein further include a second nucleic acid tag (the "second tag"). In some embodiments, the second tag is conjugated to the second antibody.

In some embodiments, the systems provided herein further include a second nucleic acid capture probe (the "second probe"). In some embodiments, the systems provided herein further include a second solid surface. In some embodiments, the second probe is coupled to the second solid surface.

In some embodiments, the second tag or a fragment thereof is complementary to the probe or a fragment thereof.

In some embodiments, the tag or a fragment thereof is complementary to the second probe or a fragment thereof.

5.3.3 Components of the Systems

The systems provided herein for detecting an analyte contain a first binder and a second binder that bind non-interfering epitopes of the analyte. The binders in the systems can be any binder disclosed herein, which can be a molecule or a portion of a molecule that binds a specific target analyte. A binder can comprise a protein, peptide, nucleic acid, carbohydrate, lipid, or small molecule. In some embodiments, a binder comprises an antibody. In some embodiments, a binder comprises an antigen-binding fragment of an antibody. In some embodiments, a binder comprises an antibody mimetic. In some embodiments, a binder comprises a small molecule.

The binders used in systems disclosed herein can be conjugated to presenting groups (e.g. nucleic acid tags). The binder and presenting group can be joined together either directly through a bond or indirectly through a linking group. The systems provided herein can further include a linking group. The linking group can be any linking group disclosed herein or otherwise known in the art.

The presenting groups and receiving groups used in the systems disclosed herein can be any binding pairs disclosed herein or otherwise known in the art, which include, but are not limited to, an antigen and an antibody against the antigen (including its fragments, derivatives or mimetics), a ligand and its receptor, complementary strands of nucleic acids, biotin and avidin (or streptavidin or neutravidin), lectin and carbohydrates, and vice versa. Additional binding pairs of "presenting groups" and "receiving groups" include fluorescein and anti-fluorescein, digioxigenin/anti-digioxigenin, and DNP (dinitrophenol)/anti-DNP, and vice versa. In some embodiments, binding pairs of "presenting groups" and "receiving groups" are complementary strands of nucleic acids, and are referred to as "tags" and "probes." In some embodiments, binding pairs of "presenting groups" and "receiving groups" are antigens and antibodies, or antigens and antibody fragments, and vice versa.

In some embodiments, the systems provided herein include a nucleic acid tag and a nucleic acid capture probe, wherein the tag or a fragment thereof is complementary to the probe or a fragment thereof. As a person of ordinary skill in the art would understand, any sequence with appropriate hybridization strength can be utilized.

In some embodiments, more than 80%, more than 85%, more than 90%, more than 95%, or more than 98% of the complementary fragments of the tag and the probe used in the systems provided herein are adenine ("A") and thymine ("T") pairs. In some embodiments, more than 80%, more than 85%, more than 90%, more than 95%, or more than 98% of the complementary fragments of the first tag and the first probe are A and T pairs. In some embodiments, more than 80%, more than 85%, more than 90%, more than 95%, or more than 98% of the complementary fragments of the second tag and the second probe are A and T pairs. In some embodiments, more than 80% of the complementary fragments of the first tag and the first probe are A and T pairs, and more than 80% of the complementary fragments of the second tag and the second probe are A and T pairs. In some embodiments, complementary fragments of the first tag and the first probe comprise A and T pairs, and complementary fragments of the second tag and the second probe comprise A and T pairs.

In some embodiments, the complementary fragments of a nucleic acid tag and a nucleic acid capture probe used in the systems provided herein consist of 10 to 30 base pairs, 10 to 25 base pairs, 12 to 20 base pairs, or 10 to 16 base pairs. In some embodiments, the complementary fragments of a nucleic acid tag and a nucleic acid capture probe used in the systems provided herein consist of 10 to 25 base pairs. In some embodiments, the complementary fragments of a nucleic acid tag and a nucleic acid capture probe used in the systems provided herein consist of 12 to 20 base pairs. In some embodiments, the complementary fragments of a nucleic acid tag and a nucleic acid capture probe used in the systems provided herein consist of 12 to 16 base pairs. In some embodiments, the complementary fragments of a nucleic acid tag and a nucleic acid capture probe used in the systems provided herein consist of 12 to 14 base pairs. In some embodiments, the complementary fragments of the first tag and the first probe consist of 10 to 25 base pairs. In some embodiments, the complementary fragments of the second tag and the second probe consist of 10 to 25 base pairs. In some embodiments, the complementary fragments of the first tag and the first probe consist of 12 to 20 base pairs. In some embodiments, the complementary fragments of the second tag and the second probe consist of 12 to 20 base pairs. In some embodiments, the complementary fragments of the first tag and the first probe consist of 12 to 16 base pairs. In some embodiments, the complementary fragments of the second tag and the second probe consist of 12 to 16 base pairs.

The solid surface used in the systems disclosed herein can also include any support known in the art on which can be used for immobilization of molecules. In some embodiments, the solid surface can be any surfaces suitable of attaching nucleic acid and facilitates the assay step. Examples of solid surfaces include beads (e.g., magnetic beads, xMAP® beads), particles, colloids, single surfaces, tubes, chips, multiwell plates, microtiter plates, slides, membranes, cuvettes, gels, and resins. Exemplary solid surfaces can include surfaces of magnetic particles, and wells of microtiter plates. When the solid phase is a particulate material (e.g., beads), it can be distributed in the wells of multi-well plates to allow for parallel processing. In some embodiments, the solid surface is the surface of a magnetic bead. The magnetic beads can be coupled with a presenting group. In some embodiments, the magnet beads can be carboxylate-modified magnetic beads, amine-blocked magnetic beads, Oligo(dT)-coated magnetic beads, streptavidin-coated magnetic beads, Protein A/G coated magnetic beads, or silica-coated magnetic beads. In some embodiments, the solid surface is a well of a microtiter plate. In some embodiments, the first and second solid surfaces are the same. In some embodiments, the first and second solid surfaces are different. In some embodiments, both the first and second solid surfaces used in the assay methods disclosed herein are surfaces of magnetic particles. In some embodiments, both the first and second surfaces used in the assay methods disclosed herein are surfaces of microtiter plates.

Any detection marker known in the art can be included in a system of this disclosure. In some embodiments, the detection marker is a colorimetric detection reagent, a fluorescent detection reagent, or a chemiluminescent detection reagent. In some embodiments, the colorimetric detection reagent includes PNPP (p-nitrophenyl phosphate), ABTS (2,2'-azino-bis(3-ethylbenzothiazoline-6-sulphonic acid)) or OPD (o-phenylenediamine). In some embodiments, the fluorescent detection reagent includes QuantaBlu™ or QuantaRed™ (Thermo Scientific, Waltham, MA). In some embodiments, the luminescent detection reagent includes luminol or luciferin. In some embodiments, the detection reagent includes a trigger (e.g., H2O2) and a tracer (e.g., isoluminol-conjugate).

In some embodiments, the systems provided herein further include a secondary antibody. Secondary antibodies can be monoclonal or polyclonal antibodies. Secondary antibodies can be derived from any mammalian organism, including bovine, mice, rats, hamsters, goats, camels, chicken, rabbit, and others. Secondary antibodies can include, for example, an anti-human IgA antibody, an anti-human IgD antibody, an anti-human IgE antibody, an anti-human IgG antibody, or an anti-human IgM antibody. Secondary antibodies can be conjugated to enzymes (e.g., horseradish peroxidase (HRP), alkaline phosphatase (AP), luciferase, and the like) or dyes (e.g., colorimetric dyes, fluorescent dyes, fluorescence resonance energy transfer (FRET)-dyes, time-resolved (TR)-FRET dyes, and the like). In some embodiments, the secondary antibody is a polyclonal rabbit-anti-human IgG antibody, which is HRP-conjugated.

In some embodiments, the system provided herein for detecting an analyte is contained in a kit. In some embodiments, the kits of this disclosure can include an ancillary reagent. In some embodiments, the kits provided herein further comprise an immobilization buffer, a washing buffer, a release buffer, or any combination thereof.

In some embodiments, the ancillary reagent is an immobilization buffer, which can be any immobilization reagent known in the art, including covalent and non-covalent immobilization reagents. Covalent immobilization reagents can include any chemical or biological reagent that can be used to covalently immobilize a peptide or a nucleic acid on a surface. Covalent immobilization reagents can include, for example, a carboxyl-to-amine reactive group (e.g., carbodiimides such as EDC or DCC), an amine reactive group (e.g., N-hydroxysuccinimide (NHS) esters, imidoesters), a sulfhydryl-reactive crosslinker (e.g., maleimides, haloacetyls, pyridyl disulfides), a carbonyl-reactive crosslinker groups (e.g., hydrazides, alkoxyamines), a photoreactive crosslinker (e.g., aryl azides, dizirines), or a chemoselective ligation group (e.g., a Staudinger reaction pair). Non-covalent immobiliazation reagents include any chemical or biological reagent that can be used to immobilize a peptide or a nucleic acid non-covalently on a surface, such as affinity tags (e.g., biotin) or capture regents (e.g., streptavidin or anti-tag antibodies, such as anti-His6 or anti-Myc antibodies).

The kits of this disclosure can include combinations of immobilization reagents. Such combinations include, for example, EDC and NHS, which can be used, for example, to immobilize a protein of this disclosure on a surface, such as a carboxylated dextrane matrix (e.g., on a BIAcore™ CM5 chip or a dextrane-based bead). Combinations of immobilization reagents can be stored as premixed reagent combinations or with one or more immobilization reagents of the combination being stored separately from other immobilization reagents.

A large selection of washing buffers are known in the art, such as tris(hydroxymethyl)aminomethane (Tris)-based buffers (e.g., Tris-buffered saline, TBS) or phosphate buffers (e.g., phosphate-buffered saline, PBS). Washing buffers can include detergents, such as ionic or non-ionic detergents. In some embodiments, the washing buffer is a PBS buffer (e.g., about pH 7.4) including Tween®20 (e.g., about 0.05% Tween®20).

In some embodiments, the kits provided herein further include a stock 20×SSC buffer.

In some embodiments, the kits provided herein further include instructions for carrying out the assay methods provided herein.

5.3.4 Systems with Target IDs and/or Sample IDs

In one aspect, provided herein is a system for detecting an analyte in a sample comprising (i) a first binding moiety comprising a first binder, a first presenting group, and a first target label; (ii) a second binding moiety comprising a second binder and a second target label; and (iii) a first receiving group; and wherein (i) the first and second binders bind epitopes on the analyte; and (ii) the first presenting group binds the first receiving groups.

As described in Section 5.1, target label can provide identifiers that can be correlated with the particular target to facilitate the detection and identification of a target molecule. As such, in some embodiments of the systems provided herein including those in this section (Section 5.3.4) and in the preceding paragraph, each target label can comprises one or more target IDs. In one specific embodiment, the first target label comprises a first target ID. In another embodiment, the second target label comprises a second target ID. In yet another embodiment, the first target label comprises a first target ID and the second target label comprises a second target ID.

In one aspect, provided herein is a system for detecting an analyte in a sample comprising (i) a first binding moiety comprising a first binder, a first presenting group, and a first target label comprising a first identity barcode ("ID") that is analyte-specific ("target ID"); (ii) a second binding moiety comprising a second binder and a second target label comprising a second target ID; and (iii) a first receiving group; and wherein (i) the first and second binders bind epitopes on the analyte; and (ii) the first presenting group binds the first receiving groups.

In one aspect, provided herein is a system for detecting an analyte in a sample comprising a first binding moiety comprising a first binder and a first presenting group, a second binding moiety comprising a second binder, and a first receiving group; wherein
  (i) the first and second binders bind non-interfering epitopes on the analyte;
  (ii) the first presenting group binds the first receiving groups;
  (iii) the first binding moiety comprises a first target label comprising a first identity barcode ("ID") that is analyte-specific ("target ID"); and
  (iv) the second binding moiety comprises a second target label comprising a second target ID.

As described above in Section 5.2.1.1, the first and second binders and the analyte can be released from the binding stemmed from the first binder (i.e., between the first presenting group and the first receiving group), and be recaptured via the second binder to further increase the signal-to-noise ratio. FIGS. 21A-21F depict exemplary schematic representations of a system including such two captures. Accordingly, in one embodiment of the system provided herein, the second binding moiety further comprises a second presenting group, a second receiving group, and wherein the second presenting group binds the second receiving groups. As such, in one embodiment, the system provided herein comprises a first binding moiety comprising a first binder and a first presenting group, a second binding moiety comprising a second binder, a second presenting group, a first receiving group, and a second receiving group; wherein
  (i) the first and second binders bind non-interfering epitopes on the analyte;
  (ii) the first presenting group binds the first receiving groups;
  (iii) the second presenting group binds the second receiving groups;
  (iv) the first binding moiety comprises a first target label comprising a first identity barcode ("ID") that is analyte-specific ("target ID"); and
  (v) the second binding moiety comprises a second target label comprising a second target ID.

Each binding moiety can comprise one or more target labels. In one embodiment, the first binding moiety comprises one target label. In another embodiment, the first binding moiety comprises two target labels. In a further embodiment, the first binding moiety comprises three target labels. In yet another embodiment, the first binding moiety comprises four target labels. In yet another embodiment, the first binding moiety comprises five or more target labels. In one embodiment, the second binding moiety comprises one target label. In another embodiment, the second binding moiety comprises two target labels. In a further embodiment, the second binding moiety comprises three target labels. In yet another embodiment, the second binding moiety comprises four target labels. In yet another embodiment, the second binding moiety comprises five or more target labels. In some embodiments, the target labels between the first binding moiety and the second binding moiety are different. In certain embodiments, the target labels between the first binding moiety and the second binding moiety are identical. In some further embodiments, the target labels within the first binding moiety are different. In other embodiments, the target labels within the first binding moiety are identical. In some further embodiments, the target labels within the second binding moiety are different. In other embodiments, the target labels within the second binding moiety are identical. In some embodiments, the first binding moiety have any target labels as provided in this paragraph and the second binding moiety have any target labels as provided in this paragraph in any combination. In one specific embodiment, the first binding moiety comprises a first target label and the second binding moiety comprises a second target label, wherein the first target label and the second target label are different. In another specific embodiment, the first binding moiety comprises a first target label and the second binding moiety comprises a second target label, wherein the first target label and the second target label are identical.

Additionally, in some embodiments of the systems provided herein including those in this section (Section 5.3.4) and in the preceding paragraph, each target label can comprises one or more target IDs. In one embodiment, the first target label comprises a first target ID. In another embodiment, the second target label comprises a second target ID. In some embodiments, the target IDs between the first target label and the second target label are different. In certain embodiments, the target IDs between the first target label and the second target label are identical. In one specific embodiment, the first target label comprises a first target ID and the second target label comprises a second target ID, wherein the first target ID and the second target ID are different. In another specific embodiment, the first target label comprises a first target ID and the second target label comprises a second target ID, wherein the first target ID and the second target ID are identical.

As described further above in Section 5.2.5, in addition to analyte-specific "target IDs," the nucleic acid reporters generated in the systems provided herein can also include sample-specific "sample IDs." FIGS. 22 and FIGS. 23A-23B provide exemplary schematic representations for generating a nucleic acid reporter with sample IDs and FIGS. 24A-24B and 25A-25C provide confirmatory data showing such multiplexing assays, wherein the analyte is detected by signals determined via the target ID in the target label and the sample ID as generated in the nucleic acid reporter, thereby parsing out the samples via the sample IDs and analyte via the target IDs. Accordingly, in one embodiment, the system provided herein further comprises a sample label comprising sample ID," wherein the sample label binds (i) to the first target label, (ii) to the second target label, or (iii) to both the first target label and the second target label. In one specific embodiment, the system provided herein comprises: a first binding moiety comprising a first binder and a first presenting group, a second binding moiety comprising a second binder, a second presenting group, a first receiving group, a second receiving group, and a sample label; wherein
  (i) the first and second binders bind non-interfering epitopes on the analyte;
  (ii) the first presenting group binds the first receiving groups;
  (iii) the second presenting group binds the second receiving groups;
  (iv) the first binding moiety comprises a first target label comprising a first identity barcode ("ID") that is analyte-specific ("target ID");
  (v) the second binding moiety comprises a second target label comprising a second target ID; and
  (vi) the sample label comprising an ID that is sample-specific ("sample ID"), where in the sample label binds (i) to the first target label, (ii) to the second target label, or (iii) to both the first target label and the second target label.

Similarly as described further above in Section 5.2.5, in some embodiments of the systems provided herein, including those of this section (Section 5.3.4), each nucleic acid reporter can comprise one or more target IDs and/a sample ID. In one embodiment, the nucleic acid reporter formed in each sample contains a sample ID. In another embodiment, the nucleic acid reporter formed in each sample contains a target ID. In a further embodiment, the nucleic acid reporter formed in each sample contains the first target ID. In still another embodiment, the nucleic acid reporter formed in each sample contains the second target ID. In yet another embodiment, the nucleic acid reporter formed in each sample contains a sample ID and the first target ID. In one embodiment, the nucleic acid reporter formed in each sample contains a sample ID and the second target ID. In another embodiment, the nucleic acid reporter formed in each sample contains the first target ID and the second target ID. In a further embodiment, the nucleic acid reporter formed in each sample contains the first target ID and the second target ID, wherein the nucleic acid reporter lacks a sample ID. In yet another embodiment, the nucleic acid reporter formed in each sample contains the first target ID, the second target ID, and a sample ID.

As the nucleic acid reporter is generated from an immunocomplex that is formed from the first binding moiety comprising the first target label, the second binding moiety comprising the second target label, the analyte, and/or the sample label, such immunocomplex formed in the systems provided herein (including in this section (Section 5.3.4)) can similarly comprise one or more target IDs and/a sample ID. In one embodiment, the immunocomplex formed in each sample contains a sample ID. In another embodiment, the immunocomplex formed in each sample contains a target ID. In a further embodiment, the immunocomplex formed in each sample contains the first target ID. In still another embodiment, the immunocomplex formed in each sample contains the second target ID. In yet another embodiment, the immunocomplex formed in each sample contains a sample ID and the first target ID. In one embodiment, the immunocomplex formed in each sample contains a sample ID and the second target ID. In another embodiment, the immunocomplex formed in each sample contains the first target ID and the second target ID. In a further embodiment, the immunocomplex formed in each sample contains the first target ID and the second target ID, wherein the immunocomplex lacks a sample ID. In yet another embodiment, the immunocomplex formed in each sample contains the first target ID, the second target ID, and a sample ID.

Furthermore, as the sample ID is contained in the sample label and the target ID is contained in the target label, the immunocomplex formed in the systems provided herein (including in this section (Section 5.3.4)) can comprise one or more target labels and/a sample label. In one embodiment, the immunocomplex formed in each sample contains a sample label. In another embodiment, the immunocomplex formed in each sample contains a target label. In a further embodiment, the immunocomplex formed in each sample contains the first target label. In still another embodiment, the immunocomplex formed in each sample contains the second target label. In yet another embodiment, the immunocomplex formed in each sample contains a sample label and the first target label. In one embodiment, the immunocomplex formed in each sample contains a sample label and the second target label. In another embodiment, the immunocomplex formed in each sample contains the first target label and the second target label. In a further embodiment, the immunocomplex formed in each sample contains the first target label and the second target label, wherein the immunocomplex lacks a sample label. In yet another embodiment, the immunocomplex formed in each sample contains the first target label, the second target label, and a sample label.

As is clear from the disclosure, in the systems provided herein including those provided in this section (Section 5.3.4), the presenting group in the first binding moiety and the presenting group in the second binding moiety each can be any embodiments of presenting group provided in the disclosure including those provided in Sections 3, 5.1, 5.2.1 to 5.2.6, 5.3.1 to 5.3.3, and 6. The combination of the presenting group in the first binding moiety and the presenting group in the second binding moiety can be any combination of any embodiments of presenting group provided in the disclosure including those provided in Sections 3, 5.1, 5.2.1 to 5.2.6, 5.3.1 to 5.3.3, and 6. In one embodiment of the systems provided herein, the first presenting group is a polypeptide fused to the first binder. In another embodiment of the systems provided herein, the first presenting group is a polynucleotide conjugated to the first binder. In yet another embodiment of the systems provided herein, the first presenting group is a chemical compound conjugated to the first binder. In one embodiment of the systems provided herein, the second presenting group is a polypeptide fused to the second binder. In another embodiment of the systems provided herein, the second presenting group is a polynucleotide conjugated to the second binder. In yet another embodiment of the systems provided herein, the second presenting group is or a chemical compound conjugated to the second binder.

In some embodiments of the systems provided herein, the first presenting group is selected from the group consisting of a polypeptide fused to the first binder, a polynucleotide conjugated to the first binder, or a chemical compound conjugated to the first binder; and the second presenting group is selected from the group consisting of a polypeptide fused to the second binder, a polynucleotide conjugated to the second binder, or a chemical compound conjugated to the second binder. In one embodiment, the first presenting group is a polypeptide fused to the first binder and the second presenting group is a polypeptide fused to the second binder. In one embodiment, the first presenting group is a polypeptide fused to the first binder and the second presenting group is a polynucleotide conjugated to the second binder. In one embodiment, the first presenting group is a polypeptide fused to the first binder and the second presenting group is a chemical compound conjugated to the second binder. In one embodiment, the first presenting group is a polynucleotide conjugated to the first binder and the second presenting group is a polypeptide fused to the second binder. In one embodiment, the first presenting group is a polynucleotide conjugated to the first binder and the second presenting group is a polynucleotide conjugated to the second binder. In one embodiment, the first presenting group is a polynucleotide conjugated to the first binder and the second presenting group is a chemical compound conjugated to the second binder. In one embodiment, the first presenting group is a chemical compound conjugated to the first binder and the second presenting group is a polypeptide fused to the second binder. In one embodiment, the first presenting group is a chemical compound conjugated to the first binder and the second presenting group is a polynucleotide conjugated to the second binder. In one embodiment, the first presenting group is a chemical compound conjugated to the first binder and the second presenting group is a chemical compound conjugated to the second binder.

The disclosure further provides that the system further comprises reagents for PCR amplification of the nucleic acid reporter. As is clear from the disclosure, such PCR can be any PCR as provided in this and other sections, such as Sections 5.2.4 (including 5.2.4.1 and 5.2.4.2), 5.2.5 and 6, as well as any suitable PCR known and practiced in the field.

The disclosure further provides that the systems provided in this Section 5.3.4 further comprises reagents for DNA purification. In some embodiments, the systems provided herein further comprise reagents for DNA purification by selecting fragments of a given size of nucleic acids that is known and practiced in the field. In one embodiment, the systems provided herein further comprise reagents for DNA purification by affinity purification. In one embodiment, the systems provided herein further comprise reagents for DNA purification by affinity purification with a nucleic acid affinity tag that is complementary to the nucleic acid reporter or a fragment thereof. In one embodiment, the systems provided herein further comprise reagents for DNA purification by affinity purification with a nucleic acid affinity tag that hybridizes to the nucleic acid reporter or a fragment thereof. In other embodiment, the systems provided herein further comprise reagents for DNA purification by binding to an affinity tag and eluting in low-salt buffer or water after proper wash, which results in the nucleic acid reporter free of contaminating nucleotides, primers, adapters, adapter dimers, enzymes, buffer additives, or salts.

As illustrated in FIGS. 8A-8G, the binders provided herein for the systems can bind directly or indirectly to analyte. As such, in some embodiments of the systems provided herein, including the systems of this Section (Section 5.3.4), the binder binds to the analyte directly. In other embodiments of the systems provided herein, the binder binds to the analyte indirectly. Accordingly, in some embodiments, the first binder binds to the analyte directly. In other embodiments, the second binder binds to the analyte directly. In yet other embodiments, the first binder binds to the analyte indirectly. In still yet other embodiments, the second binder binds to the analyte indirectly. Furthermore, any embodiments of binding relationship between the first binder and the analyte can be combined with any embodiments of binding relationship between the second binder and the analyte. In one specific embodiment, the first binder binds to the analyte directly and the second binder binds to the analyte directly. In another embodiment, the first binder binds to the analyte directly and the second binder binds to the analyte indirectly. In yet another embodiment, the first binder binds to the analyte indirectly and the second binder binds to the analyte directly. In still yet another embodiment, the first binder binds to the analyte indirectly and the second binder binds to the analyte indirectly.

As illustrated in FIG. 8G, the binders can bind to an analyte indirectly through an intermediary, e.g. a primary antibody against the analyte. As such, in some embodiments of the system provided herein, including the systems of this Section (Section 5.3.4), the binder binds to a primary antibody or a fragment thereof that binds directly to the analyte. Therefore, in some embodiments, the first binder binds to a first primary antibody or a fragment thereof that binds directly to the analyte. In other embodiments, the second binder binds to a second primary antibody or a fragment thereof that binds directly to the analyte. In yet other embodiment, the first binder binds to a first primary antibody or a fragment thereof that binds directly to the analyte, and the second binder binds to a second primary antibody or a fragment thereof that binds directly to the analyte. In a further embodiment, the first binder binds directly to the analyte, and the second binder binds to a second primary antibody or a fragment thereof that binds directly to the analyte. In some other embodiments, the first binder binds to a first primary antibody or a fragment thereof that binds directly to the analyte, and the second binder binds directly to the analyte.

As is clear from the disclosure that the two binders can simultaneously bind to an analyte, in some embodiments of the systems provided herein, including the systems of Sections 5.1 and 5.2, the first and second binders can bind epitopes on the analyte that permit simultaneous binding, thereby increasing the specificity of the detection. In some embodiments, the first and second binders bind to non-interfering epitopes on the analyte. In other embodiments, the first and second binders bind to non-overlapping epitopes on the analyte. In other embodiments, the first and second binders bind to different epitopes on the analyte. In yet other embodiments, the first and second binders bind to separate epitopes on the analyte. In still yet other embodiments, the first and second binders bind to two epitopes on the analyte to which the two binders can simultaneously and separately bind without having any steric hindrance.

As provided in the disclosure, including the disclosure of Sections 3, 5.1, 5.2.1 to 5.2.6, 5.3.1 to 5.3.3, and 6, in some embodiments of the systems provided herein, including those provided in this Section 5.3.4, the presenting group can be nucleic acid. Similarly, in some embodiments of the systems provided herein, including those provided in this Section 5.3.4, the receiving group can be nucleic acid. In one embodiment, the presenting group that is nucleic acid binds the receiving group. In another embodiment, the first presenting group is a first nucleic acid tag (the "first tag") and the first receiving group is a first nucleic acid capture probe (the "first probe"). In a further embodiment, the second presenting group is a second nucleic acid tag (the "second tag") and the second receiving group is a second nucleic acid capture probe (the "second probe"). In yet another embodiment, (i) the first presenting group is a first nucleic acid tag (the "first tag") and the first receiving group is a first nucleic acid capture probe (the "first probe"); and (ii) the second presenting group is a second nucleic acid tag (the "second tag") and the second receiving group is a second nucleic acid capture probe (the "second probe"). In one embodiment, the first probe is a protein that specifically binds to the first tag. In another embodiment, the first probe is a protein and nucleic acid complex that specifically binds to the first tag. In yet another embodiment, the first probe is a nucleic acid molecule, wherein the first probe or a fragment thereof is complementary to the first tag or a fragment thereof. In a further embodiment, the first probe is a nucleic acid molecule, wherein the first probe or a fragment thereof hybridizes with the first tag or a fragment thereof. In one embodiment, the second probe is a protein that specifically binds to the second tag. In another embodiment, the second probe is a protein and nucleic acid complex that specifically binds to the second tag. In yet another embodiment, the second probe is a nucleic acid molecule, wherein the second probe or a fragment thereof is complementary to the second tag or a fragment thereof. In a further embodiment, the second probe is a nucleic acid molecule, wherein the second probe or a fragment thereof hybridizes with the second tag or a fragment thereof.

Additionally, such first tag, first probe, second tag, and second probe can be combined as provided in the preceding paragraph in various ways. Accordingly, in one embodiment, the first probe is a protein that specifically binds to the first tag and the second probe is a protein that specifically binds to the second tag. In another embodiment, the first probe is a protein that specifically binds to the first tag and the second probe is a protein and nucleic acid complex that specifically binds to the second tag. In yet another embodiment, the first probe is a protein that specifically binds to the first tag and the second probe is a nucleic acid molecule, wherein the second probe or a fragment thereof is complementary to the second tag or a fragment thereof. In a further embodiment, the first probe is a protein that specifically binds to the first tag and the second probe is a nucleic acid molecule, wherein the second probe or a fragment thereof hybridizes with the second tag or a fragment thereof.

Additionally, in one embodiment, the first probe is a protein and nucleic acid complex that specifically binds to the first tag and the second probe is a protein that specifically binds to the second tag. In another embodiment, the first probe is a protein and nucleic acid complex that specifically binds to the first tag and the second probe is a protein and nucleic acid complex that specifically binds to the second tag. In yet another embodiment, the first probe is a protein and nucleic acid complex that specifically binds to the first tag and the second probe is a nucleic acid molecule, wherein the second probe or a fragment thereof is complementary to the second tag or a fragment thereof. In a further embodiment, the first probe is a protein and nucleic acid complex that specifically binds to the first tag and the second probe is a nucleic acid molecule, wherein the second probe or a fragment thereof hybridizes with the second tag or a fragment thereof.

Alternatively, in one embodiment, the first probe is a nucleic acid molecule, wherein the first probe or a fragment thereof is complementary to the first tag or a fragment thereof, and the second probe is a protein that specifically binds to the second tag. In another embodiment, the first probe is a nucleic acid molecule, wherein the first probe or a fragment thereof is complementary to the first tag or a fragment thereof, and the second probe is a protein and nucleic acid complex that specifically binds to the second tag. In yet another embodiment, the first probe is a nucleic acid molecule, wherein the first probe or a fragment thereof is complementary to the first tag or a fragment thereof, and the second probe is a nucleic acid molecule, wherein the second probe or a fragment thereof is complementary to the second tag or a fragment thereof. In a further embodiment, the first probe is a nucleic acid molecule, wherein the first probe or a fragment thereof is complementary to the first tag or a fragment thereof, and the second probe is a nucleic acid molecule, wherein the second probe or a fragment thereof hybridizes with the second tag or a fragment thereof.

In addition, in one embodiment, the first probe is a nucleic acid molecule, wherein the first probe or a fragment thereof hybridizes with the first tag or a fragment thereof, and the second probe is a protein that specifically binds to the second tag. In another embodiment, the first probe is a nucleic acid molecule, wherein the first probe or a fragment thereof hybridizes with the first tag or a fragment thereof, and the second probe is a protein and nucleic acid complex that specifically binds to the second tag. In yet another embodiment, the first probe is a nucleic acid molecule, wherein the first probe or a fragment thereof hybridizes with the first tag or a fragment thereof, and the second probe is a nucleic acid molecule, wherein the second probe or a fragment thereof is complementary to the second tag or a fragment thereof. In a further embodiment, the first probe is a nucleic acid molecule, wherein the first probe or a fragment thereof hybridizes with the first tag or a fragment thereof, and the second probe is a nucleic acid molecule, wherein the second probe or a fragment thereof hybridizes with the second tag or a fragment thereof.

The complementarity provided in the preceding paragraphs can be complementarity of various levels so long as the binding of the complementary fragment provides sufficient binding for the capture, washing and/or release for the various systems provided herein. In one embodiment of the systems provided herein including in this Section 5.3.4, the complementarity is at least 80%, at least 81%, at least 82%, at least 83%, at least 84%, at least 85%, at least 86%, at least 87%, at least 88%, at least 89%, at least 90, at least 91%, at least 92%, at least 93%, at least 94%, at least 95%, at least 96%, at least 97%, at least 98%, or at least 99% complementation. In another embodiment, the complementarity is about 80%, about 81%, about 82%, about 83%, about 84%, about 85%, about 86%, about 87%, about 88%, about 89%, about 90, about 91%, about 92%, about 93%, about 94%, about 95%, about 96%, about 97%, about 98%, or about 99% complementation.

The presenting group and the receiving group can be bound, linked, coupled, or otherwise connected together for the systems provided herein, including systems provided in this Section (Section 5.3.4), via various embodiments of binding, linking, coupling or otherwise connecting the presenting group and the receiving group provided anywhere in the disclosure, including in Sections 3, 5.3.1, 5.3.2, and 6. In one embodiment of the system provided herein, the first presenting group binds the first receiving group via a thioester group, a disulfide linkage, or a cleavable linkage. In another embodiment of the system provided herein, the second presenting group binds the second receiving group via a thioester group, a disulfide linkage, or a cleavable linkage. In yet another embodiment of the system provided herein, the first presenting group binds the first receiving group via a thioester group, a disulfide linkage, or a cleavable linkage; and the second presenting group binds the second receiving group via a thioester group, a disulfide linkage, or a cleavable linkage. In one embodiment of the system provided herein, the first presenting group binds the first receiving group via a photocleavable linkage, a chemically cleavable linkage, or an enzymatically cleavable linkage. In another embodiment of the system provided herein, the second presenting group binds the second receiving group via a photocleavable linkage, a chemically cleavable linkage, or an enzymatically cleavable linkage. In yet another embodiment of the system provided herein, the first presenting group binds the first receiving group via a photocleavable linkage, a chemically cleavable linkage, or an enzymatically cleavable linkage; and the second presenting group binds the second receiving group via a photocleavable linkage, a chemically cleavable linkage, or an enzymatically cleavable linkage. In one embodiment of the system provided herein, the first presenting group binds the first receiving group via a protein-protein interaction. In another embodiment of the system provided herein, the second presenting group binds the second receiving group via a protein-protein interaction. In yet another embodiment of the system provided herein, the first presenting group binds the first receiving group via a protein-protein interaction; and the second presenting group binds the second receiving group via a protein-protein interaction. In one embodiment of the system provided herein, the first presenting group binds the first receiving group via biotin to streptavidin or avidin. In another embodiment of the system provided herein, the second presenting group binds the second receiving group via biotin to streptavidin or avidin. In yet another embodiment of the system provided herein, the first presenting group binds the first receiving group via biotin to streptavidin or avidin; and the second presenting group binds the second receiving group via biotin to streptavidin or avidin. In some embodiments, the first presenting group binds the first receiving group via any one of the embodiments provided in this paragraph and the second presenting group binds the second receiving group via any one of the embodiments provided in this paragraph. As such, the disclosure provides that any embodiment provided in this paragraph for the binding between the first presenting group and the first receiving group can be combined with any other embodiment provided in this paragraph for the binding between the second presenting group and the second receiving group.

As provided in the disclosure, including the disclosure of Sections 3, 5.1, 5.2.1 to 5.2.6, 5.3.1 to 5.3.3, and 6, in some embodiments of the systems provided herein, including those provided in this Section 5.3.4, the presenting group can be nucleic acid. Similarly, in some embodiments of the systems provided herein, including those provided in this Section 5.3.4, the receiving group can be nucleic acid. In certain embodiments, the presenting group that is nucleic acid binds or hybridizes to the receiving group that is nucleic acid. Accordingly, in some embodiments, the first presenting group is a first nucleic acid tag (the "first tag") and the first receiving group is a first nucleic acid capture probe (the "first probe"), wherein the first probe or a fragment thereof is complementary to the first tag or a fragment thereof. In certain embodiments, the second presenting group is a second nucleic acid tag (the "second tag") and the second receiving group is a second nucleic acid capture probe (the "second probe"), wherein the second probe or a fragment thereof is complementary to the second tag or a fragment thereof. In one embodiment, the first presenting group is a first nucleic acid tag (the "first tag") and the first receiving group is a first nucleic acid capture probe (the "first probe"), wherein the first probe or a fragment thereof is complementary to the first tag or a fragment thereof; and the second presenting group is a second nucleic acid tag (the "second tag") and the second receiving group is a second nucleic acid capture probe (the "second probe"), wherein the second probe or a fragment thereof is complementary to the second tag or a fragment thereof.

Accordingly, in some specific embodiment of the systems provided herein comprises: a first binding moiety comprising a first binder and a first tag, a second binding moiety comprising a second binder, a second tag, a first probe, a second probe, and a sample label; wherein
  (i) the first and second binders bind non-interfering epitopes on the analyte;
  (ii) the first tag binds the first probes;
  (iii) the second tag binds the second probes;
  (iv) the first binding moiety comprises a first target label comprising a first identity barcode ("ID") that is analyte-specific ("target ID");
  (v) the second binding moiety comprises a second target label comprising a second target ID; and
  (vi) the sample label comprising an ID that is sample-specific ("sample ID"), where in the sample label binds (i) to the first target label, (ii) to the second target label, or (iii) to both the first target label and the second target label.

The disclosure further provides and a person of ordinary skill in the art reading the disclosure would understand that the receiving group can be bound, linked, coupled, or otherwise connected to the solid surface for the systems provided herein, including systems provided in this Section (Section 5.3.4), via various embodiments of binding, linking, coupling or otherwise connecting the receiving group and the solid surface provided anywhere in the disclosure, including in Sections 3, 5.2.3, and 6. As the receiving group could be nucleic acid capture probes, the disclosure thus provides that the nucleic acid capture probe (e.g. first probe and/or second probe) can be bound, linked, coupled, or otherwise connected to the solid surface for the systems provided herein, including systems provided in this Section (Section 5.3.4), via various embodiments of binding, linking, coupling or otherwise connecting the nucleic acid capture probe (e.g. first probe and/or second probe) and the solid surface provided anywhere in the disclosure, including in Sections 3, 5.2.3, and 6. In one embodiment of the systems provided herein, including systems provided in this Section (Section 5.3.4), the first probe is directly coupled to the first solid surface. In another embodiment, the first probe hybridizes with a universal probe that is directly coupled to the first solid surface. In a further embodiment, the first probe is conjugated with biotin, which binds the streptavidin or avidin that is directly coupled to the first solid surface. In yet another embodiment, the first probe is conjugated with a chemical compound (e.g. FITC), which binds an antibody that specifically binds such compound (e.g. FITC) and is directly coupled to the first solid surface. In one embodiment of the systems provided herein, including systems provided in this Section (Section 5.3.4), the second probe is directly coupled to the second solid surface. In another embodiment, the second probe hybridizes with a universal probe that is directly coupled to the second solid surface. In a further embodiment, the second probe is conjugated with biotin, which binds the streptavidin or avidin that is directly coupled to the second solid surface. In yet another embodiment, the second probe is conjugated with a chemical compound (e.g. FITC), which binds an antibody that specifically binds such compound (e.g. FITC) and is directly coupled to the second solid surface.

In certain embodiments, any embodiment provided in the preceding paragraph for the binding, linking, coupling, or otherwise connection between the first probe and the first solid surface can be combined with any other embodiment provided in the preceding paragraph for the binding, linking, coupling, or otherwise connection between the second probe and the second solid surface. Accordingly, in one embodiment of the systems provided herein, including systems provided in this Section (Section 5.3.4), the first probe is directly coupled to the first solid surface and the second probe is directly coupled to the second solid surface. In another embodiment, the first probe is directly coupled to the first solid surface and the second probe hybridizes with a universal probe that is directly coupled to the second solid surface. In a further embodiment, the first probe is directly coupled to the first solid surface and the second probe is conjugated with biotin, which binds the streptavidin or avidin that is directly coupled to the second solid surface. In yet another embodiment, the first probe is directly coupled to the first solid surface and the second probe is conjugated with a chemical compound (e.g. FITC), which binds an antibody that specifically binds such compound (e.g. FITC) and is directly coupled to the second solid surface. In one embodiment, the first probe hybridizes with a universal probe that is directly coupled to the first solid surface and the second probe is directly coupled to the second solid surface. In another embodiment, the first probe hybridizes with a universal probe that is directly coupled to the first solid surface and the second probe hybridizes with a universal probe that is directly coupled to the second solid surface. In a further embodiment, the first probe hybridizes with a universal probe that is directly coupled to the first solid surface and the second probe is conjugated with biotin, which binds the streptavidin or avidin that is directly coupled to the second solid surface. In yet another embodiment, the first probe hybridizes with a universal probe that is directly coupled to the first solid surface and the second probe is conjugated with a chemical compound (e.g. FITC), which binds an antibody that specifically binds such compound (e.g. FITC) and is directly coupled to the second solid surface. In one embodiment, the first probe is conjugated with biotin, which binds the streptavidin or avidin that is directly coupled to the first solid surface and the second probe is directly coupled to the second solid surface. In another embodiment, the first probe is conjugated with biotin, which binds the streptavidin or avidin that is directly coupled to the first solid surface and the second probe hybridizes with a universal probe that is directly coupled to the second solid surface. In a further embodiment, the first probe is conjugated with biotin, which binds the streptavidin or avidin that is directly coupled to the first solid surface and the second probe is conjugated with biotin, which binds the streptavidin or avidin that is directly coupled to the second solid surface. In yet another embodiment, the first probe is conjugated with biotin, which binds the streptavidin or avidin that is directly coupled to the first solid surface and the second probe is conjugated with a chemical compound (e.g. FITC), which binds an antibody that specifically binds such compound (e.g. FITC) and is directly coupled to the second solid surface. In one embodiment, the first probe is conjugated with a chemical compound (e.g. FITC), which binds an antibody that specifically binds such compound (e.g. FITC) and is directly coupled to the first solid surface and the second probe is directly coupled to the second solid surface. In another embodiment, the first probe is conjugated with a chemical compound (e.g. FITC), which binds an antibody that specifically binds such compound (e.g. FITC) and is directly coupled to the first solid surface and the second probe hybridizes with a universal probe that is directly coupled to the second solid surface. In a further embodiment, the first probe is conjugated with a chemical compound (e.g. FITC), which binds an antibody that specifically binds such compound (e.g. FITC) and is directly coupled to the first solid surface and the second probe is conjugated with biotin, which binds the streptavidin or avidin that is directly coupled to the second solid surface. In yet another embodiment, the first probe is conjugated with a chemical compound (e.g. FITC), which binds an antibody that specifically binds such compound (e.g. FITC) and is directly coupled to the first solid surface and the second probe is conjugated with a chemical compound (e.g. FITC), which binds an antibody that specifically binds such compound (e.g. FITC) and is directly coupled to the second solid surface.

As described above in Sections 3, 5.2.3, 5.2.4, and 5.2.5, the nucleic acid capture probes can be collaboratively captured on the solid surface. In one embodiment of the systems provided herein, including in this Section (Section 5.3.4), the first tag and second tag are collaboratively captured on the first solid surface. In another embodiment of the systems provided herein, the first tag and second tag are collaboratively captured on the second solid surface. In a further embodiment of the systems provided herein, the first tag and second tag are collaboratively captured on the first solid surface. In yet another embodiment of the systems provided herein, the first tag and second tag are collaboratively captured on the second solid surface. In some embodiments, the collaborative capture of this Section (Section 5.3.4) including this paragraph for the systems provided herein can take different formats, including any embodiments described in Sections 3, 5.2.3, 5.2.4, and 5.2.5. In one specific embodiment, the first tag and second tag are collaboratively captured on the first solid surface in any format embodied in Sections 3, 5.2.3, 5.2.4, and 5.2.5. In a further embodiment, the first tag and second tag are collaboratively captured on the second solid surface in any format embodied in Sections 3, 5.2.3, 5.2.4, and 5.2.5. In yet another embodiment, the first tag and second tag are collaboratively captured on the second solid surface in step (2b) in any format embodied in Sections 3, 5.2.3, 5.2.4, and 5.2.5. In some embodiments, the first tag and second tag are collaboratively captured on the first solid surface in any format embodied in Sections 3, 5.2.3, 5.2.4, and 5.2.5 and the first tag and second tag are collaboratively captured on the second solid surface in any format embodied in Sections 3, 5.2.3, 5.2.4, and 5.2.5. In certain embodiments, the first tag and second tag are collaboratively captured on the first solid surface in step (1) in any format embodied in Sections 3, 5.2.3, 5.2.4, and 5.2.5 and the first tag and second tag are collaboratively captured on the second solid surface in step (2b) in any format embodied in Sections 3, 5.2.3, 5.2.4, and 5.2.5. In some embodiments, the first solid surface is coupled with both the first probe and an additional nucleic acid probe, and wherein the additional probe or a fragment thereof is complementary to the first tag or a fragment thereof. In certain embodiments, the second solid surface is coupled with both the second probe and an additional nucleic acid probe, and wherein the additional probe or a fragment thereof is complementary to the second tag or a fragment thereof. In other embodiments, the first solid surface is coupled with both the first probe and an additional nucleic acid probe, and wherein the additional probe or a fragment thereof is complementary to the first tag or a fragment thereof, and the second solid surface is coupled with both the second probe and an additional nucleic acid probe, and wherein the additional probe or a fragment thereof is complementary to the second tag or a fragment thereof.

In any of the embodiments of the systems provided herein that involves nucleic acid binding or hybridization, the complementary fragments of two nucleic acids can be of any length that provides sufficient interaction for the purpose of binding the presenting group (e.g. the first tag and/or the second tag) and the receiving group (e.g. the first probe and/or the second probe) or binding the receiving group (e.g. the first probe and/or the second probe) and the solid surface (e.g. the first solid surface and/or the second solid surface). In some embodiments of the systems provided herein, such complementary fragments can be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, or more base pairs. In one embodiment of the systems provided herein, the complementary fragments of the first tag and the first probe consist of 10 to 30 base pairs. In another embodiment of the systems provided herein, the complementary fragments of the first tag and the first probe consist of 20 to 30 base pairs. In yet another embodiment of the systems provided herein, the complementary fragments of the first tag and the first probe consist of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs. In one embodiment of the systems provided herein, the complementary fragments of the second tag and the second probe consist of 10 to 30 base pairs. In another embodiment of the systems provided herein, the complementary fragments of the second tag and the second probe consist of 20 to 30 base pairs. In yet another embodiment of the systems provided herein, the complementary fragments of the second tag and the second probe consist of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs. In one embodiment of the systems provided herein, the complementary fragments of the first tag and the first probe consist of 10 to 30 base pairs and the complementary fragments of the second tag and the second probe consist of 10 to 30 base pairs. In another embodiment of the systems provided herein, the complementary fragments of the first tag and the first probe consist of 20 to 30 base pairs and the complementary fragments of the second tag and the second probe consist of 20 to 30 base pairs. In yet another embodiment of the systems provided herein, the complementary fragments of the first tag and the first probe consist of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs and the complementary fragments of the second tag and the second probe consist of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs.

For any of the embodiments of the systems provided herein that involves nucleic acid binding or hybridization, the complementary fragments of two nucleic acid can be a pair of complementary A and/or T rich sequences or a pair of complementary G and/or C rich sequences for the purpose of binding the presenting group (e.g. the first tag and/or the second tag) and the receiving group (e.g. the first probe and/or the second probe) or binding the receiving group (e.g. the first probe and/or the second probe) and the solid surface (e.g. the first solid surface and/or the second solid surface). In one embodiment of the systems provided herein, the first tag comprises an A and/or T rich sequence and the first probe comprises a complementary T and/or A rich sequence. In another embodiment, the first tag comprises a poly-A and/or poly-T sequence and the first probe comprises a complementary poly-T and/or poly-A sequence. In a further embodiment, the first tag comprises an G and/or C rich sequence and the first probe comprises a complementary C and/or G rich sequence. In yet another embodiment, the first tag comprises a poly-G and/or poly-C sequence and the first probe comprises a complementary poly-C and/or poly-G sequence. In one embodiment of the systems provided herein, the second tag comprises an A and/or T rich sequence and the second probe comprises a complementary T and/or A rich sequence. In another embodiment, the second tag comprises a poly-A and/or poly-T sequence and the second probe comprises a complementary poly-T and/or poly-A sequence. In a further embodiment, the second tag comprises an G and/or C rich sequence and the second probe comprises a complementary C and/or G rich sequence. In yet another embodiment, the second tag comprises a poly-G and/or poly-C sequence and the second probe comprises a complementary poly-C and/or poly-G sequence.

In one embodiment of the systems provided herein, the first tag comprises an A and/or T rich sequence and the first probe comprises a complementary T and/or A rich sequence, and the second tag comprises an A and/or T rich sequence and the second probe comprises a complementary T and/or A rich sequence. In another embodiment, the first tag comprises an A and/or T rich sequence and the first probe comprises a complementary T and/or A rich sequence, and the second tag comprises a poly-A and/or poly-T sequence and the second probe comprises a complementary poly-T and/or poly-A sequence. In a further embodiment, the first tag comprises an A and/or T rich sequence and the first probe comprises a complementary T and/or A rich sequence, and the second tag comprises an G and/or C rich sequence and the second probe comprises a complementary C and/or G rich sequence. In yet another embodiment, the first tag comprises an A and/or T rich sequence and the first probe comprises a complementary T and/or A rich sequence, and the second tag comprises a poly-G and/or poly-C sequence and the second probe comprises a complementary poly-C and/or poly-G sequence.

In one embodiment of the systems provided herein, the first tag comprises a poly-A and/or poly-T sequence and the first probe comprises a complementary poly-T and/or poly-A sequence, and the second tag comprises an A and/or T rich sequence and the second probe comprises a complementary T and/or A rich sequence. In another embodiment, the first tag comprises a poly-A and/or poly-T sequence and the first probe comprises a complementary poly-T and/or poly-A sequence, and the second tag comprises a poly-A and/or poly-T sequence and the second probe comprises a complementary poly-T and/or poly-A sequence. In a further embodiment, the first tag comprises a poly-A and/or poly-T sequence and the first probe comprises a complementary poly-T and/or poly-A sequence, and the second tag comprises an G and/or C rich sequence and the second probe comprises a complementary C and/or G rich sequence. In yet another embodiment, the first tag comprises a poly-A and/or poly-T sequence and the first probe comprises a complementary poly-T and/or poly-A sequence, and the second tag comprises a poly-G and/or poly-C sequence and the second probe comprises a complementary poly-C and/or poly-G sequence.

In one embodiment of the systems provided herein, the first tag comprises an G and/or C rich sequence and the first probe comprises a complementary C and/or G rich sequence, and the second tag comprises an A and/or T rich sequence and the second probe comprises a complementary T and/or A rich sequence. In another embodiment, the first tag comprises an G and/or C rich sequence and the first probe comprises a complementary C and/or G rich sequence, and the second tag comprises a poly-A and/or poly-T sequence and the second probe comprises a complementary poly-T and/or poly-A sequence. In a further embodiment, the first tag comprises an G and/or C rich sequence and the first probe comprises a complementary C and/or G rich sequence, and the second tag comprises an G and/or C rich sequence and the second probe comprises a complementary C and/or G rich sequence. In yet another embodiment, the first tag comprises an G and/or C rich sequence and the first probe comprises a complementary C and/or G rich sequence, and the second tag comprises a poly-G and/or poly-C sequence and the second probe comprises a complementary poly-C and/or poly-G sequence.

In one embodiment of the systems provided herein, the first tag comprises a poly-G and/or poly-C sequence and the first probe comprises a complementary poly-C and/or poly-G sequence, and the second tag comprises an A and/or T rich sequence and the second probe comprises a complementary T and/or A rich sequence. In another embodiment, the first tag comprises a poly-G and/or poly-C sequence and the first probe comprises a complementary poly-C and/or poly-G sequence, and the second tag comprises a poly-A and/or poly-T sequence and the second probe comprises a complementary poly-T and/or poly-A sequence. In a further embodiment, the first tag comprises a poly-G and/or poly-C sequence and the first probe comprises a complementary poly-C and/or poly-G sequence, and the second tag comprises an G and/or C rich sequence and the second probe comprises a complementary C and/or G rich sequence. In yet another embodiment, the first tag comprises a poly-G and/or poly-C sequence and the first probe comprises a complementary poly-C and/or poly-G sequence, and the second tag comprises a poly-G and/or poly-C sequence and the second probe comprises a complementary poly-C and/or poly-G sequence.

In certain embodiments of the systems provided herein, including those provided in the preceding 5 paragraphs, the complementary sequences have a short length such that the binding from complementary sequences is weaker than both the binding between first binder and the analyte and the binding between the second binder and the analyte, thereby keeping immunocomplex stable in any releasing from solid surface. In some specific embodiments, the A and/or T rich sequence has a short length such that the binding from complementary A and/or T rich sequence is weaker than both the binding between first binder and the analyte and the binding between the second binder and the analyte, thereby keeping immunocomplex stable in any releasing from solid surface. In other specific embodiments, the poly-A and/or poly-T sequence has a short length such that the binding from complementary poly-A and/or poly-T sequence is weaker than both the binding between first binder and the analyte and the binding between the second binder and the analyte, thereby keeping immunocomplex stable in any releasing from solid surface. In yet other specific embodiments, the G and/or C rich sequence has a short length such that the binding from complementary G and/or C rich sequence is weaker than both the binding between first binder and the analyte and the binding between the second binder and the analyte, thereby keeping immunocomplex stable in any releasing from solid surface. In some further specific embodiments, the poly-G and/or poly-C sequence has a short length such that the binding from complementary poly-G and/or poly-C sequence is weaker than both the binding between first binder and the analyte and the binding between the second binder and the analyte, thereby keeping immunocomplex stable in any releasing from solid surface.

The analyte detected in the systems provided herein, including the systems provided in this Section 5.3.4, can be various molecules as described in Sections 3, 5.2.2, and 6. In one specific embodiment, the analyte is a binding pair of two molecules; wherein the first binder binds one molecule of the binding pair, and the second binder binds the other molecule of the binding pair. In another embodiment, the analyte is a nucleic acid, and the first and second binders for the nucleic acid analyte comprise nucleic acids that are complementary to different fragments of the nucleic acid analyte. In yet another embodiment, the analyte is a peptide or a protein, and (i) the first binder is an antibody or an antibody fragment that specifically binds the analyte; (ii) the second binder is an antibody or an antibody fragment that specifically binds the analyte; or both (i) and (ii).

The analyte detected in the systems provided herein, including the systems provided in this Section 5.3.4, can be from various samples as described in Sections 3 and 6. In some specific embodiment of the systems provided herein, the sample is a bodily fluid sample. In one embodiment, the sample is a tissue sample. In one embodiment, the sample is a cell sample. In one embodiment, the sample is a blood sample. In one embodiment, the sample is a bone marrow sample. In one embodiment, the sample is a plasma sample. In one embodiment, the sample is a serum sample. In one embodiment, the sample is a urine sample. In one embodiment, the sample is a cerebrospinal fluid sample.

The disclosure provides that the target label, the binder, and the presenting group can have various configurations in each binding moiety for various embodiments of the systems provided herein, including those of this Section 5.3.4 and Sections 3, 5.2.1 to 5.2.5 and 6. In one embodiment of the systems provided herein, including those of this Section 5.3.4, the target label is directly bound to the binder. In another embodiment, the target label is indirectly bound to the binder. In yet another embodiment, the first target label is directly bound to the first binder. In a further embodiment, the first target label is indirectly bound to the first binder. In some embodiments, the second target label is directly bound to the second binder. In certain embodiments, the second target label is indirectly bound to the second binder. In one embodiment, the first target label is directly bound to the first binder and the second target label is directly bound to the second binder. In another embodiment, the first target label is directly bound to the first binder and the second target label is indirectly bound to the second binder. In yet another embodiment, the first target label is indirectly bound to the first binder and the second target label is directly bound to the second binder. In a further embodiment, the first target label is indirectly bound to the first binder and the second target label is indirectly bound to the second binder. In one embodiment of the systems provided herein, including those of this Section 5.3.4, the target label is conjugated to the binder. In another embodiment, the target label is non-covalently bound to the binder. In a further embodiment, the target label is conjugated to the presenting group. In another embodiment, the target label is non-covalently bound to the presenting group. In yet another embodiment, the target label is part of the presenting group, for example, the target label and the presenting group are both nucleic acid and the target label is a nucleic acid fragment within the sequence of the presenting group. In one embodiment of the systems provided herein, including those of this Section 5.3.4, the first target label is conjugated to the first binder. In another embodiment, the first target label is non-covalently bound to the first binder. In a further embodiment, the first target label is conjugated to the first presenting group. In another embodiment, the first target label is non-covalently bound to the first presenting group. In yet another embodiment, the first target label is part of the first presenting group, for example, the first target label and the first presenting group are both nucleic acid molecules and the first target label is a nucleic acid fragment within the sequence of the first presenting group. In one embodiment of the systems provided herein, including those of this Section 5.3.4, the second target label is conjugated to the second binder. In another embodiment, the second target label is non-covalently bound to the second binder. In a further embodiment, the second target label is conjugated to the second presenting group. In another embodiment, the second target label is non-covalently bound to the second presenting group. In yet another embodiment, the second target label is part of the second presenting group, for example, the second target label and the second presenting group are both nucleic acid molecules and the second target label is a nucleic acid fragment within the sequence of the second presenting group.

The disclosure provides that the target label, the binder, and the presenting group can have various configurations in each binding moiety for various embodiments of the systems provided herein, including those of this Section 5.3.4 and Sections 3, 5.2.1 to 5.2.5 and 6. In one embodiment of the systems provided herein, including those of this Section 5.3.4, the target label is conjugated to the binder. In another embodiment, the target label is non-covalently bound to the binder. In a further embodiment, the target label is conjugated to the presenting group. In another embodiment, the target label is non-covalently bound to the presenting group. In yet another embodiment, the target label is part of the presenting group, for example, the target label and the presenting group are both nucleic acid and the target label is a nucleic acid fragment within the sequence of the presenting group. In one embodiment of the systems provided herein, including those of this Section 5.3.4, the first target label is conjugated to the first binder. In another embodiment, the first target label is non-covalently bound to the first binder. In a further embodiment, the first target label is conjugated to the first presenting group. In another embodiment, the first target label is non-covalently bound to the first presenting group. In yet another embodiment, the first target label is part of the first presenting group, for example, the first target label and the first presenting group are both nucleic acid molecules and the first target label is a nucleic acid fragment within the sequence of the first presenting group. In one embodiment of the systems provided herein, including those of this Section 5.3.4, the second target label is conjugated to the second binder. In another embodiment, the second target label is non-covalently bound to the second binder. In a further embodiment, the second target label is conjugated to the second presenting group. In another embodiment, the second target label is non-covalently bound to the second presenting group. In yet another embodiment, the second target label is part of the second presenting group, for example, the second target label and the second presenting group are both nucleic acid molecules and the second target label is a nucleic acid fragment within the sequence of the second presenting group.

The configuration among the first target label, the first binder, and the first presenting group in the first binding moiety can be any embodiment provided herein including in this Section 5.3.4 and in the preceding paragraph and such embodiment can be combined with any embodiment of configuration among the second target label, the second binder, and the second presenting group in the second binding moiety provided herein including in this Section 5.3.4 and in the preceding paragraph. In one specific embodiment of the systems provided herein, including those of this Section 5.3.4, the first target label is conjugated to the first binder and the second target label is conjugated to the second binder. In another embodiment, the first target label is conjugated to the first binder and the second target label is non-covalently bound to the second binder. In a further embodiment, the first target label is conjugated to the first binder and the second target label is conjugated to the second presenting group. In another embodiment, the first target label is conjugated to the first binder and the second target label is non-covalently bound to the second presenting group. In yet another embodiment, the first target label is conjugated to the first binder and the second target label is part of the second presenting group, for example, the second target label and the second presenting group are both nucleic acid molecules and the second target label is a nucleic acid fragment within the sequence of the second presenting group.

In some specific embodiments of the systems provided herein, including those of this Section 5.3.4, the first target label is non-covalently bound to the first binder and the second target label is conjugated to the second binder. In another embodiment, the first target label is non-covalently bound to the first binder and the second target label is non-covalently bound to the second binder. In a further embodiment, the first target label is non-covalently bound to the first binder and the second target label is conjugated to the second presenting group. In another embodiment, the first target label is non-covalently bound to the first binder and the second target label is non-covalently bound to the second presenting group. In yet another embodiment, the first target label is non-covalently bound to the first binder and the second target label is part of the second presenting group, for example, the second target label and the second presenting group are both nucleic acid molecules and the second target label is a nucleic acid fragment within the sequence of the second presenting group.

In some specific embodiments of the systems provided herein, including those of this Section 5.3.4, the first target label is conjugated to the first presenting group and the second target label is conjugated to the second binder. In another embodiment, the first target label is conjugated to the first presenting group and the second target label is non-covalently bound to the second binder. In a further embodiment, the first target label is conjugated to the first presenting group and the second target label is conjugated to the second presenting group. In another embodiment, the first target label is conjugated to the first presenting group and the second target label is non-covalently bound to the second presenting group. In yet another embodiment, the first target label is conjugated to the first presenting group and the second target label is part of the second presenting group, for example, the second target label and the second presenting group are both nucleic acid molecules and the second target label is a nucleic acid fragment within the sequence of the second presenting group.

In some specific embodiments of the systems provided herein, including those of this Section 5.3.4, the first target label is non-covalently bound to the first presenting group and the second target label is conjugated to the second binder. In another embodiment, the first target label is non-covalently bound to the first presenting group and the second target label is non-covalently bound to the second binder. In a further embodiment, the first target label is non-covalently bound to the first presenting group and the second target label is conjugated to the second presenting group. In another embodiment, the first target label is non-covalently bound to the first presenting group and the second target label is non-covalently bound to the second presenting group. In yet another embodiment, the first target label is non-covalently bound to the first presenting group and the second target label is part of the second presenting group, for example, the second target label and the second presenting group are both nucleic acid molecules and the second target label is a nucleic acid fragment within the sequence of the second presenting group.

In some specific embodiments of the systems provided herein, including those of this Section 5.3.4, the first target label is part of the first presenting group, for example, the first target label and the first presenting group are both nucleic acid molecules and the first target label is a nucleic acid fragment within the sequence of the first presenting group, and the second target label is conjugated to the second binder. In another embodiment, the first target label is part of the first presenting group, for example, the first target label and the first presenting group are both nucleic acid molecules and the first target label is a nucleic acid fragment within the sequence of the first presenting group, and the second target label is non-covalently bound to the second binder. In a further embodiment, the first target label is part of the first presenting group, for example, the first target label and the first presenting group are both nucleic acid molecules and the first target label is a nucleic acid fragment within the sequence of the first presenting group, and the second target label is conjugated to the second presenting group. In another embodiment, the first target label is part of the first presenting group, for example, the first target label and the first presenting group are both nucleic acid molecules and the first target label is a nucleic acid fragment within the sequence of the first presenting group, and the second target label is non-covalently bound to the second presenting group. In yet another embodiment, the first target label is part of the first presenting group, for example, the first target label and the first presenting group are both nucleic acid molecules and the first target label is a nucleic acid fragment within the sequence of the first presenting group, and the second target label is part of the second presenting group, for example, the second target label and the second presenting group are both nucleic acid molecules and the second target label is a nucleic acid fragment within the sequence of the second presenting group.

Similarly, the binder and the presenting group can have various configurations in each binding moiety for various embodiments of the systems provided herein, including those of this Section 5.3.4 and Sections 3, 5.2.1 to 5.2.5 and 6. In one embodiment of the systems provided herein, including those of this Section 5.3.4, the presenting group is directly bound to the binder. In another embodiment, the presenting group is indirectly bound to the binder. In yet another embodiment, the first presenting group is directly bound to the first binder. In a further embodiment, the first presenting group is indirectly bound to the first binder. In some embodiments, the second presenting group is directly bound to the second binder. In certain embodiments, the second presenting group is indirectly bound to the second binder. In one embodiment, the first presenting group is directly bound to the first binder and the second presenting group is directly bound to the second binder. In another embodiment, the first presenting group is directly bound to the first binder and the second presenting group is indirectly bound to the second binder. In yet another embodiment, the first presenting group is indirectly bound to the first binder and the second presenting group is directly bound to the second binder. In a further embodiment, the first presenting group is indirectly bound to the first binder and the second presenting group is indirectly bound to the second binder. In one embodiment of the systems provided herein, including those of this Section 5.3.4, the presenting group is conjugated to the binder. In another embodiment, the presenting group is non-covalently bound to the binder. In a further embodiment, the presenting group is conjugated to the presenting group. In another embodiment, the presenting group is non-covalently bound to the presenting group. In yet another embodiment, the presenting group is part of the presenting group, for example, the presenting group and the presenting group are both nucleic acid and the presenting group is a nucleic acid fragment within the sequence of the presenting group. In one embodiment of the systems provided herein, including those of this Section 5.3.4, the first presenting group is conjugated to the first binder. In another embodiment, the first presenting group is non-covalently bound to the first binder. In a further embodiment, the first presenting group is conjugated to the first presenting group. In another embodiment, the first presenting group is non-covalently bound to the first presenting group. In yet another embodiment, the first presenting group is part of the first target label, for example, the first presenting group and the first target label are both nucleic acid molecules and the first presenting group is a nucleic acid fragment within the sequence of the first target label. In one embodiment of the systems provided herein, including those of this Section 5.3.4, the second presenting group is conjugated to the second binder. In another embodiment, the second presenting group is non-covalently bound to the second binder. In a further embodiment, the second presenting group is conjugated to the second presenting group. In another embodiment, the second presenting group is non-covalently bound to the second presenting group. In yet another embodiment, the second presenting group is part of the second target label, for example, the second presenting group and the second target label are both nucleic acid molecules and the second presenting group is a nucleic acid fragment within the sequence of the second target label.

The configuration among the first presenting group, the first binder, and the first presenting group in the first binding moiety can be any embodiment provided herein including in this Section 5.3.4 and in the preceding paragraph and such embodiment can be combined with any embodiment of configuration among the second presenting group, the second binder, and the second presenting group in the second binding moiety provided herein including in this Section 5.3.4 and in the preceding paragraph. In one specific embodiment of the systems provided herein, including those of this Section 5.3.4, the first presenting group is conjugated to the first binder and the second presenting group is conjugated to the second binder. In another embodiment, the first presenting group is conjugated to the first binder and the second presenting group is non-covalently bound to the second binder. In a further embodiment, the first presenting group is conjugated to the first binder and the second presenting group is conjugated to the second presenting group. In another embodiment, the first presenting group is conjugated to the first binder and the second presenting group is non-covalently bound to the second presenting group. In yet another embodiment, the first presenting group is conjugated to the first binder and the second presenting group is part of the second target label, for example, the second presenting group and the second target label are both nucleic acid molecules and the second presenting group is a nucleic acid fragment within the sequence of the second target label.

In some specific embodiments of the systems provided herein, including those of this Section 5.3.4, the first presenting group is non-covalently bound to the first binder and the second presenting group is conjugated to the second binder. In another embodiment, the first presenting group is non-covalently bound to the first binder and the second presenting group is non-covalently bound to the second binder. In a further embodiment, the first presenting group is non-covalently bound to the first binder and the second presenting group is conjugated to the second presenting group. In another embodiment, the first presenting group is non-covalently bound to the first binder and the second presenting group is non-covalently bound to the second presenting group. In yet another embodiment, the first presenting group is non-covalently bound to the first binder and the second presenting group is part of the second target label, for example, the second presenting group and the second target label are both nucleic acid molecules and the second presenting group is a nucleic acid fragment within the sequence of the second target label.

In some specific embodiments of the systems provided herein, including those of this Section 5.3.4, the first presenting group is conjugated to the first presenting group and the second presenting group is conjugated to the second binder. In another embodiment, the first presenting group is conjugated to the first presenting group and the second presenting group is non-covalently bound to the second binder. In a further embodiment, the first presenting group is conjugated to the first presenting group and the second presenting group is conjugated to the second presenting group. In another embodiment, the first presenting group is conjugated to the first presenting group and the second presenting group is non-covalently bound to the second presenting group. In yet another embodiment, the first presenting group is conjugated to the first presenting group and the second presenting group is part of the second target label, for example, the second presenting group and the second target label are both nucleic acid molecules and the second presenting group is a nucleic acid fragment within the sequence of the second target label.

In some specific embodiments of the systems provided herein, including those of this Section 5.3.4, the first presenting group is non-covalently bound to the first presenting group and the second presenting group is conjugated to the second binder. In another embodiment, the first presenting group is non-covalently bound to the first presenting group and the second presenting group is non-covalently bound to the second binder. In a further embodiment, the first presenting group is non-covalently bound to the first presenting group and the second presenting group is conjugated to the second presenting group. In another embodiment, the first presenting group is non-covalently bound to the first presenting group and the second presenting group is non-covalently bound to the second presenting group. In yet another embodiment, the first presenting group is non-covalently bound to the first presenting group and the second presenting group is part of the second target label, for example, the second presenting group and the second target label are both nucleic acid molecules and the second presenting group is a nucleic acid fragment within the sequence of the second target label.

In some specific embodiments of the systems provided herein, including those of this Section 5.3.4, the first presenting group is part of the first target label, for example, the first presenting group and the first target label are both nucleic acid molecules and the first presenting group is a nucleic acid fragment within the sequence of the first target label, and the second presenting group is conjugated to the second binder. In another embodiment, the first presenting group is part of the first target label, for example, the first presenting group and the first target label are both nucleic acid molecules and the first presenting group is a nucleic acid fragment within the sequence of the first target label, and the second presenting group is non-covalently bound to the second binder. In a further embodiment, the first presenting group is part of the first target label, for example, the first presenting group and the first target label are both nucleic acid molecules and the first presenting group is a nucleic acid fragment within the sequence of the first target label, and the second presenting group is conjugated to the second presenting group. In another embodiment, the first presenting group is part of the first target label, for example, the first presenting group and the first target label are both nucleic acid molecules and the first presenting group is a nucleic acid fragment within the sequence of the first target label, and the second presenting group is non-covalently bound to the second presenting group. In yet another embodiment, the first presenting group is part of the first target label, for example, the first presenting group and the first target label are both nucleic acid molecules and the first presenting group is a nucleic acid fragment within the sequence of the first target label, and the second presenting group is part of the second target label, for example, the second presenting group and the second target label are both nucleic acid molecules and the second presenting group is a nucleic acid fragment within the sequence of the second target label.

As is clear from the disclosure, in some embodiments of the systems provided herein, including the systems of this Section 5.3.4 and Sections 3, 5.2.1 to 5.2.5 and 6, the target label (e.g. the first target label and/or the second target label) can be a nucleic acid molecule. In one embodiment, the first target label is a nucleic acid molecule. In another embodiment, the second target label is a nucleic acid molecule. In a further embodiment, the first target label is a nucleic acid molecule and the second target label is a nucleic acid molecule. The disclosure further provides that in some embodiments of the systems provided herein, including the systems of this Section 5.3.4 and Sections 3, 5.2.1 to 5.2.5 and 6, when the target label is a nucleic acid molecule, the target label hybridizes with the receiving group that is also a nucleic acid molecule. In one embodiment, the first target label hybridizes with the first tag. In another embodiment, the second target label hybridizes with the second tag. In a further embodiment, the first target label hybridizes with the first tag and the second target label hybridizes with the second tag.

Additionally, the disclosure provides sample label comprising sample ID, wherein the sample label binds to the immunocomplex for various embodiments of the systems provided herein, including the systems of this Section 5.3.4 and Sections 3, 5.2.1 to 5.2.5 and 6. The sample label can bind to any component of the binding moiety, the immunocomplex formed by the two binding moieties (e.g. the first binding moiety and the second binding moiety), the receiving group, or a component coupled to the solid surface. In one embodiment, the sample label binds to a target label. In another embodiment, the sample label binds to the presenting group (e.g. presenting group that is a nucleic acid molecule). In a further embodiment, the sample label binds to a binder. In yet another embodiment, the sample label binds to a receiving group. In one embodiment, the sample label binds to the first target label. In another embodiment, the sample label binds to the first presenting group (e.g. presenting group that is a nucleic acid molecule). In still another embodiment, the sample label binds to the first tag. In a further embodiment, the sample label binds to the first binder. In yet another embodiment, the sample label binds to the first receiving group. In one embodiment, the sample label binds to the second target label. In another embodiment, the sample label binds to the second presenting group (e.g. presenting group that is a nucleic acid molecule). In still another embodiment, the sample label binds to the second tag. In a further embodiment, the sample label binds to the second binder. In yet another embodiment, the sample label binds to the second receiving group.

Furthermore, any embodiment of the binding between the sample label and the component of the first binding moiety or the first receiving group can be combined with any embodiment of the binding between the sample label and the component of the second binding moiety or the second receiving group. Accordingly, in one embodiment, the sample label binds to the first target label and the second target label. In another embodiment, the sample label binds to the first target label and the second presenting group (e.g. presenting group that is a nucleic acid molecule). In still another embodiment, the sample label binds to the first target label and the second tag. In a further embodiment, the sample label binds to the first target label and the second binder. In yet another embodiment, the sample label binds to the first target label and the second receiving group.

In one embodiment, the sample label binds to the first presenting group (e.g. presenting group that is a nucleic acid molecule) and the second target label. In another embodiment, the sample label binds to the first presenting group (e.g. presenting group that is a nucleic acid molecule) and the second presenting group (e.g. presenting group that is a nucleic acid molecule). In still another embodiment, the sample label binds to the first presenting group (e.g. presenting group that is a nucleic acid molecule) and the second tag. In a further embodiment, the sample label binds to the first presenting group (e.g. presenting group that is a nucleic acid molecule) and the second binder. In yet another embodiment, the sample label binds to the first presenting group (e.g. presenting group that is a nucleic acid molecule) and the second receiving group.

In one embodiment, the sample label binds to the first tag and the second target label. In another embodiment, the sample label binds to the first tag and the second presenting group (e.g. presenting group that is a nucleic acid molecule). In still another embodiment, the sample label binds to the first tag and the second tag. In a further embodiment, the sample label binds to the first tag and the second binder. In yet another embodiment, the sample label binds to the first tag and the second receiving group.

In one embodiment, the sample label binds to the first binder and the second target label. In another embodiment, the sample label binds to the first binder and the second presenting group (e.g. presenting group that is a nucleic acid molecule). In still another embodiment, the sample label binds to the first binder and the second tag. In a further embodiment, the sample label binds to the first binder and the second binder. In yet another embodiment, the sample label binds to the first binder and the second receiving group.

In one embodiment, the sample label binds to the first receiving group and the second target label. In another embodiment, the sample label binds to the first receiving group and the second presenting group (e.g. presenting group that is a nucleic acid molecule). In still another embodiment, the sample label binds to the first receiving group and the second tag. In a further embodiment, the sample label binds to the first receiving group and the second binder. In yet another embodiment, the sample label binds to the first receiving group and the second receiving group.

The sample label can be a nucleic acid molecules and the sample ID in the sample label can be a nucleic acid sequence that identifies or correlates with a sample in various embodiments provided herein including in this Section 5.3.4 and Sections 3, 5.2.1 to 5.2.5 and 6. In one embodiment, the sample label is a single-stranded nucleic acid molecule ("single-stranded sample label"). In another embodiment, the sample label is a double-stranded nucleic acid molecule ("double-stranded sample label"). For a double stranded sample label, the disclosure further provides that the sample label can have no overhang (e.g. two blunt end), one overhang (e.g. one blunt end), or two overhang (no blunt end) for sample in various embodiments provided herein including in this Section 5.3.4 and Sections 3, 5.2.1 to 5.2.5 and 6. In one embodiment, the sample label is a double-stranded nucleic acid molecule comprising two 5' overhangs. In one embodiment, the sample label is a double-stranded nucleic acid molecule comprising two 3' overhangs. In one embodiment, the sample label is a double-stranded nucleic acid molecule comprising a 5' overhang and a 3' overhang. In one embodiment, the sample label is a double-stranded nucleic acid molecule comprising a 5' overhang and a blunt end. In one embodiment, the sample label is a double-stranded nucleic acid molecule comprising a 3' overhang and a blunt end.

When the sample label is a double-stranded nucleic acid molecules and has one or two overhangs, the sample label can hybridize via its overhangs with any nucleic acid component of the binding moiety, the immunocomplex formed by the two binding moieties, the receiving group, or a nucleic acid component coupled to the solid surface, in various embodiments of the systems provided herein. When the sample label is a single-stranded nucleic acid molecules, the sample label can hybridize with any nucleic acid component of the binding moiety, the immunocomplex formed by the two binding moieties, the receiving group, or a nucleic acid component coupled to the solid surface, in various embodiments of the systems provided herein.

As is clear from the disclosure, each of the target label, the presenting group, the binder, and/or the receiving group can be nucleic acid molecule. Accordingly, the sample label can hybridize via its overhangs with the target label, the presenting group, the binder, and/or the receiving group, when they are nucleic acid molecules or have a component that is a nucleic molecule. In one embodiment, the sample label hybridizes with a target label. In another embodiment, the sample label hybridizes with the presenting group (e.g. presenting group that is a nucleic acid molecule). In a further embodiment, the sample label hybridizes with a binder. In yet another embodiment, the sample label hybridizes with a receiving group. In one embodiment, the sample label hybridizes with the first target label. In another embodiment, the sample label hybridizes with the first presenting group (e.g. presenting group that is a nucleic acid molecule). In still another embodiment, the sample label hybridizes with the first tag. In a further embodiment, the sample label hybridizes with the first binder. In yet another embodiment, the sample label hybridizes with the first receiving group. In one embodiment, the sample label hybridizes with the second target label. In another embodiment, the sample label hybridizes with the second presenting group (e.g. presenting group that is a nucleic acid molecule). In still another embodiment, the sample label hybridizes with the second tag. In a further embodiment, the sample label hybridizes with the second binder. In yet another embodiment, the sample label hybridizes with the second receiving group.

Furthermore, any embodiment of the hybridization between the sample label and the component of the first binding moiety or the first receiving group can be combined with any embodiment of the hybridization between the sample label and the component of the second binding moiety or the second receiving group. Accordingly, in one embodiment, the sample label hybridizes with the first target label and the second target label. In another embodiment, the sample label hybridizes with the first target label and the second presenting group (e.g. presenting group that is a nucleic acid molecule). In still another embodiment, the sample label hybridizes with the first target label and the second tag. In a further embodiment, the sample label hybridizes with the first target label and the second binder. In yet another embodiment, the sample label hybridizes with the first target label and the second receiving group.

In one embodiment, the sample label hybridizes with the first presenting group (e.g. presenting group that is a nucleic acid molecule) and the second target label. In another embodiment, the sample label hybridizes with the first presenting group (e.g. presenting group that is a nucleic acid molecule) and the second presenting group (e.g. presenting group that is a nucleic acid molecule). In still another embodiment, the sample label hybridizes with the first presenting group (e.g. presenting group that is a nucleic acid molecule) and the second tag. In a further embodiment, the sample label hybridizes with the first presenting group (e.g. presenting group that is a nucleic acid molecule) and the second binder. In yet another embodiment, the sample label hybridizes with the first presenting group (e.g. presenting group that is a nucleic acid molecule) and the second receiving group.

In one embodiment, the sample label hybridizes with the first tag and the second target label. In another embodiment, the sample label hybridizes with the first tag and the second presenting group (e.g. presenting group that is a nucleic acid molecule). In still another embodiment, the sample label hybridizes with the first tag and the second tag. In a further embodiment, the sample label hybridizes with the first tag and the second binder. In yet another embodiment, the sample label hybridizes with the first tag and the second receiving group.

In one embodiment, the sample label hybridizes with the first binder and the second target label. In another embodiment, the sample label hybridizes with the first binder and the second presenting group (e.g. presenting group that is a nucleic acid molecule). In still another embodiment, the sample label hybridizes with the first binder and the second tag. In a further embodiment, the sample label hybridizes with the first binder and the second binder. In yet another embodiment, the sample label hybridizes with the first binder and the second receiving group.

In one embodiment, the sample label hybridizes with the first receiving group and the second target label. In another embodiment, the sample label hybridizes with the first receiving group and the second presenting group (e.g. presenting group that is a nucleic acid molecule). In still another embodiment, the sample label hybridizes with the first receiving group and the second tag. In a further embodiment, the sample label hybridizes with the first receiving group and the second binder. In yet another embodiment, the sample label hybridizes with the first receiving group and the second receiving group.

A person of ordinary skill in the art would understand that when the a double-stranded sample label hybridizes with two items as described in this Section 5.3.4 including this and the preceding 6 paragraphs, in some embodiments, the double-stranded sample label hybridizes with the first item via its 5' overhang and the second item via its 3' overhang. In other embodiments, the double-stranded sample label hybridizes with the first item via its 3' overhang and the second item via its 5' overhang. In other embodiments, the double-stranded sample label hybridizes with the first item via its 5' overhang and the second item via its 5' overhang. In still further embodiments, the double-stranded sample label hybridizes with the first item via its 3' overhang and the second item via its 3' overhang. When the a double-stranded sample label hybridizes with one item as described in this Section 5.3.4 including this and the preceding 6 paragraphs, in some embodiments, the double-stranded sample label hybridizes with the item via its 5' overhang. In certain embodiments, the double-stranded sample label hybridizes with the item via its 3' overhang. When the sample label is a single-stranded sample label, such sample label can hybridizes with any one item or two item as described in this Section 5.3.4 including this and the preceding 6 paragraphs, via any parts or its nucleic acid sequence, including either end, both ends (5' end and 3' end), and any internal sequences.

In some specific embodiments, the sample label hybridizes with the first target label via an overhang (e.g. 5' overhang or 3' overhang) of the sample label. In another specific embodiment, the sample label hybridizes with the second target label via an overhang (e.g. 5' overhang or 3' overhang) of the sample label. In another embodiment, the sample label hybridizes with the first target label via an overhang (e.g. 5' overhang or 3' overhang) of the sample label and hybridizes with the second target label via an overhang (e.g. 5' overhang or 3' overhang) of the sample label. In another embodiment, the sample label hybridizes with the first target label via the 5' overhang of the sample label and hybridizes with the second target label via the 3' overhang of the sample label. In one embodiment, the sample label hybridizes with the first target label via the 5' overhang of the sample label and hybridizes with the second target label via the 5' overhang of the sample label. In a further embodiment, the sample label hybridizes with the first target label via the 3' overhang of the sample label and hybridizes with the second target label via the 5' overhang of the sample label. In yet another embodiment, the sample label hybridizes with the first target label via the 3' overhang of the sample label and hybridizes with the second target label via the 3' overhang of the sample label.

As the systems provided herein including in this Section 5.3.4 can correlate each analyte with the one or more target IDs provided herein, the systems can simultaneously detect at least two analytes in the sample by simultaneously detecting the target IDs associated with each analyte and correlating target IDs with analytes. Accordingly, in some embodiments, the systems provided herein simultaneously detect at least three, at least four, at least five, at least six, at least seven, at least eight, at least nine, at least ten, at least twelve, at least fifteen, at least twenty, at least thirty, at least forty, at least fifty, at least sixty, at least seventy, at least eighty, at least ninety, or at least one hundred analytes in the sample by simultaneously detecting the unique target IDs associated with each analyte. In further embodiments, the systems provided herein simultaneously detect about three, about four, about five, about six, about seven, about eight, about nine, about ten, about twelve, about fifteen, about twenty, about thirty, about forty, about fifty, about sixty, about seventy, about eighty, about ninety, or about one hundred analytes in the sample by simultaneously detecting the unique target IDs associated with each analyte. In certain embodiments, the systems provided herein simultaneously detect at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, at least 1000, at least 1100, at least 1200, at least 1300, at least 1400, at least 1500, at least 1600, at least 1700, at least 1800, at least 1900, or at least 2000 analytes in the sample by simultaneously detecting the unique target IDs associated with each analyte. In further embodiments, the systems provided herein simultaneously detect about 100, about 150, about 200, about 250, about 300, about 350, about 400, about 450, about 500, about 550, about 600, about 650, about 700, about 750, about 800, about 850, about 900, about 950, about 1000, about 1100, about 1200, about 1300, about 1400, about 1500, about 1600, about 1700, about 1800, about 1900, or about 2000 analytes in the sample by simultaneously detecting the unique target IDs associated with each analyte.

The disclosure further provides and a person of ordinary skill in the art reading the application would understand that, in some embodiments of the systems provided herein including in this Section 5.3.4, the systems further comprising reference analyte so that the sample-to-sample variations can be normalized according to the reporters generated from the reference analyte. In one embodiment of the systems provided herein including in this Section 5.3.4, the system further comprises a reference analyte. In another embodiment, the step (1) of the system further comprises a reference analyte. In yet another embodiment, the reference analyte is an analyte that is absent in the sample. In a further embodiment, the reference analyte is a protein, a nucleic acid, or a chemical compound that is absent in the sample. In one embodiment, the reference analyte is a viral protein, a bacterial protein, or an insect protein. In another embodiment, the reference analyte is a viral nucleic acid molecule, a bacterial nucleic acid molecule, or an insect nucleic acid molecule.

As is clear from the disclosure, the various embodiments of the systems provide nucleic acid reporters comprising sample IDs and/or target IDs. As such, in some embodiments, the systems provided herein comprises simultaneously detecting the analyte in at least two samples, by simultaneously detecting the unique sample IDs in the nucleic acid reporters associated with each sample. In other embodiments, the systems provided herein comprises simultaneously detecting at least two analytes in at least two samples, by simultaneously detecting the unique sample IDs and unique target IDs associated with each analyte and the unique sample IDs associated with each sample. In some further embodiments, the systems provided herein further comprise simultaneously detecting any number of samples as provided in Sections 3, 5.2.5 and 6. In other embodiments, the systems provided herein further comprise simultaneously detecting any number of samples as provided in Sections 3, 5.2.5 and 6 in any combination of any number of targets as provided in Sections 3, 5.2.5 and 6.

Additionally, in some embodiments of the systems provided herein including in this Section 5.3.4, to detect the nucleic acid reporters, the multiplexing systems disclosed herein can further comprise reagents and/or machines for multiplexed qPCR, multiplexed digital PCR, or NGS, as such multiplexed qPCR, multiplexed digital PCR, or NGS is provided in Sections 3, 5.2.5 and 6. In a specific embodiment, the multiplexing system can further comprise reagents and/or machines for NGS. Such NGS is further provided in Sections 3, 5.2.5 and 6.

Additionally, the disclosure provides and a person of ordinary skill in the art reading the disclosure would understand that any embodiments of the systems provided in this Section 5.3.4 can be combined with any other embodiments provided in this Section 5.3.4 and other sections of the disclosure, including Sections 3, 4, 5.1, 5.2.1 to 5.2.5, 5.3, 5.4 and 6.

In some embodiments, the system provided herein for detecting an analyte is contained in a kit. In some embodiments, the kits of this disclosure can include an ancillary reagent. In some embodiments, the kits provided herein further comprise a binding buffer, an immobilization buffer, a washing buffer, a release buffer, or any combination thereof.

In one aspect, provided herein is a system for detecting an analyte in a sample comprising (1) a first binding moiety comprising a first binder, a first presenting group, and a first target label comprising a first identity barcode ("ID") that is analyte-specific ("target ID"); (2) a second binding moiety comprising a second binder, a second presenting group, and a second target label comprising a second target ID; (3) a first receiving group, a first solid surface, a second receiving group, and a second solid surface; (4) reagents for ligation and a sample label comprising an ID that is sample-specific ("sample ID"); and (5) reagents for quantitative PCR; wherein (i) the first and second binders bind to the analyte and form an immunocomplex; (ii) the first receiving group is coupled to the first solid surface and is configured to capture the first presenting group; (iii) the second receiving group is coupled to the second solid surface and is configured to capture the second presenting group; (iv) the first target label is directly or indirectly bound to the first binder and the second target label is directly or indirectly bound to the second binder; (v) the first presenting group is directly or indirectly bound to the first binder and the second presenting group is directly or indirectly bound to the second binder; and (vi) the sample label binds to both the first target label and the second target label.

In some embodiments, the system provided herein for detecting an analyte is contained in a kit. In some embodiments, the kits of this disclosure can include an ancillary reagent. In some embodiments, the kits provided herein further comprise a binding buffer, an immobilization buffer, a washing buffer, a release buffer, or any combination thereof.

In one aspect, provided herein is a system for detecting an analyte in a sample comprising (1) a first binding moiety comprising a first binder, a first presenting group, and a first target label comprising a first identity barcode ("ID") that is analyte-specific ("target ID"); (2) a second binding moiety comprising a second binder, a second presenting group, and a second target label comprising a second target ID; (3) a first receiving group, a first solid surface, a second receiving group, and a second solid surface; and (4) reagents for ligation and a sample label comprising an ID that is sample-specific ("sample ID"); wherein (i) the first and second binders bind to the analyte and form an immunocomplex; (ii) the first receiving group is coupled to the first solid surface and is configured to capture the first presenting group; (iii) the second receiving group is coupled to the second solid surface and is configured to capture the second presenting group; (iv) the first target label is directly or indirectly bound to the first binder, and the second target label is directly or indirectly bound to the second binder; (v) the first presenting group is directly or indirectly bound to the first binder, and the second presenting group is directly or indirectly bound to the second binder; and (vi) the sample label binds to both the first target label and the second target label.

In some embodiments, the system provided herein for detecting an analyte is contained in a kit. In some embodiments, the kits of this disclosure can include an ancillary reagent. In some embodiments, the kits provided herein further comprise a binding buffer, an immobilization buffer, a washing buffer, a release buffer, or any combination thereof.

5.4 Nucleic Acid Linked Immunocomplexes

Figure 18A:
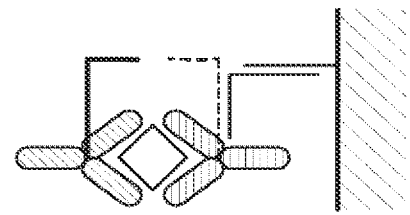
FIGS. 18A-18C depicts the basic configurations of the nucleic acid linked immunocomplex provided herein.
Figure 18B:
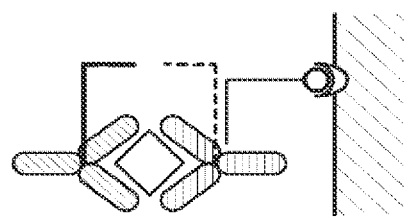
Figure 18C:
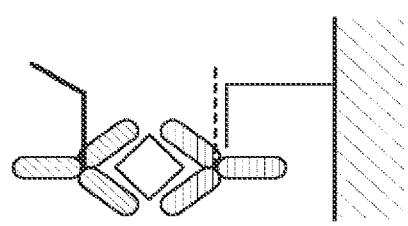

As described above, provided herein are also NUcleic acid Linker Immunocomplexes (NULI) formed when the assay methods are carried out in vitro. In some embodiments, provided herein are NULIs comprising an analyte, two binders that bind non-interfering epitopes on the analyte, wherein at least one binder is conjugated with a nucleic acid tag, a capture probe that hybridizes to the tag and a solid surface. In some embodiments, the capture probe is directly coupled to the solid surface (FIG. 18A). In some embodiments, the capture probe is indirectly coupled to the solid surface via a streptavidin/biotin binding pair (FIG. 18B). In some embodiments, the capture probe is indirectly coupled to the solid surface via hybridization to a second capture probe that is directly coupled to the surface (FIG. 18C).

In some embodiments of the NULIs described above, the two binders are covalently linked by a continuous nucleic acid molecule (FIG. 19A). In some embodiments of the NULIs provided herein, the two nucleic acid tags are directly connected by hybridization (FIG. 19B). In some embodiments of the NULIs provided herein, the two nucleic acid tags are indirectly connected through an intermediary nucleic acid molecule (FIG. 19C). In some embodiments of the NULIs provided herein, the two nucleic acid tags are indirectly connected through more than one intermediary nucleic acid molecules (FIG. 19D).

It is noted that any combination of the above-listed embodiments, for example, with respect to one or more reagents, such as, without limitation, nucleic acid tags or probes, solid surfaces and the like, are also contemplated in relation to any of the various methods and/or kits provided herein.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed herein.

Particular embodiments of this invention are described herein, including the best mode known to the inventors for carrying out the invention. Upon reading the foregoing description, variations of the disclosed embodiments shall become apparent to individuals working in the art, and it is expected that those skilled artisans can employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference in its entirety as if each individual publication or patent application were specifically and individually indicated to be incorporated by reference. The publications discussed herein are provided solely for their disclosure prior to the filing date of the present application. Nothing herein is to be construed as an admission that the present invention is not entitled to antedate such publication by virtue of prior invention. Further, the dates of publication provided can be different from the actual publication dates which can need to be independently confirmed.

A number of embodiments of the invention have been described. Nevertheless, it will be understood that various modifications may be made without departing from the spirit and scope of the invention. Accordingly, the descriptions in the Experimental section are intended to illustrate but not limit the scope of invention described in the claims.

6. EXAMPLES 6.1 A NULISA Assay 6.1.1 Formation of Immunocomplex (FIG. 4B(a))

Two binders (Binder 1 and Binder 2), which can be antibodies or any other binding moieties capable of specifically binding to the target analyte, are added to the sample. Each binder is conjugated with a single-strand nucleic acid tag, Tag 1 and Tag 2, respectively. The two binders bind to the target analyte and form an immunocomplex.

In some embodiments, the concentration of each of Binder 1 and Binder 2 in the solution in which the immunocomplex is formed is within the range of 0.1 nM to 10 nM.

In some embodiments, the concentration of Binder 1 and Binder 2 each is within the range of 0.1 nM to 8 nM. In some embodiments, the concentration of Binder 1 and Binder 2 each is within the range of 0.1 nM to 6 nM. In some embodiments, the concentration of Binder 1 and Binder 2 each is within the range of 0.1 nM to 4 nM. In some embodiments, the concentration of Binder 1 and Binder 2 each is within the range of 0.1 nM to 2 nM. In another embodiment, the concentration of Binder 1 and Binder 2 each is within the range of 0.2 nM to 2 nM. In another embodiment, the concentration of Binder 1 and Binder 2 each is within the range of 0.2 nM to 1 nM.

In some embodiments, the concentration of Binder 1 is about 0.1 nM, about 0.2 nM, about 0.4 nM, about 0.6 nM, about 0.8 nM, about 1 nM, about 1.2 nM, about 1.4 nM, about 1.6 nM, about 1.8 nM, about 2.0 nM, about 2.5 nM, about 3.0 nM, about 4.0 nM, about 5.0 nM, about 6.0 nM, about 7.0 nM, about 8.0 nM, about 9.0 nM, or about 10.0 nM. In some embodiments, the concentration of Binder 2 is about 0.1 nM, about 0.2 nM, about 0.4 nM, about 0.6 nM, about 0.8 nM, about 1 nM, about 1.2 nM, about 1.4 nM, about 1.6 nM, about 1.8 nM, about 2.0 nM, about 2.5 nM, about 3.0 nM, about 4.0 nM, about 5.0 nM, about 6.0 nM, about 7.0 nM, about 8.0 nM, about 9.0 nM, or about 10.0 nM.

In some embodiments, the sample is a blood sample. In some embodiments, the sample is a serum sample. In some embodiments, the sample is a plasma sample. The sample can be in the range of 0 to 1 mL, 0.001 to 0.9 mL, 0.001 to 0.8 mL, 0.001 to 0.7 mL, 0.001 to 0.6 mL, 0.001 to 0.5 mL, 0.001 to 0.4 mL, 0.001 to 0.3 mL, 0.001 to 0.2 mL, 0.001 to 0.1 mL, 0.001 to 0.08 mL, 0.001 to 0.05 mL, 0.001 to 0.02 mL, 0.001 to 0.01 mL, 0.001 to 0.008 mL, 0.001 to 0.005 mL, or 0.001 to 0.002 mL. In some embodiments, the sample is in the range of 0.005 to 0.4 mL.

In some embodiments, the binding reaction is conducted at temperature between 20 to 37° C. In some embodiments, In some embodiments, the binding reaction is conducted at room temperature. In some embodiments, the binding reaction is conducted at about 25° C. In some embodiments, the binding reaction is conducted at about 22ºC.

In some embodiments, the salt concentration for the binding reaction is in the range of 0.5×SSC to 2×SSC. In some embodiments, the salt concentration for the binding reaction is in the range of 1×SSC to 1.5×SSC. In some embodiments, the salt concentration for the binding reaction is about 0.5×SSC, about 1.0×SSC, about 1.5×SSC, about 2.0×SSC, or about 2.5×SSC. As is known in the art, the saline-sodium citrate (SSC) buffer is used as a hybridization buffer, to control stringency for washing steps in protocols for hybridization of nucleic acid molecules. A 20× stock solution consists of 3 M sodium chloride and 300 mM trisodium citrate (adjusted to pH 7.0 with HCl).

6.1.2 Capture of the Immunocomplex onto the First Surface (FIG. 4B(b))

The sample containing the immunocomplex is brought into contact with the first solid surface which is coupled with the first nucleic acid capture probe molecules ("CP1" or the "first probe"). A segment of CP1 is complementary to the sequence of a portion of Tag 1, which enables the immunocomplex to be captured on the first surface. Washing is conducted to remove any excess unbound molecules in solution, which include free Binder 2 and any non-target proteins or other molecules.

The solid surface can be any surfaces suitable of attaching nucleic acid and facilitates the assay step, which include, but not limited to, surfaces of magnetic particles, wells of microtiter plates, etc. The complementary sequence between Tag 1 and CP1 are designed to facilitate the specific hybridization between Tag 1 to CP1 and, at the same time, later dissociation of the hybridized immunocomplex. In one embodiment, sequences without G/C can be used which, with appropriate length, can provide sufficient strength in hybridization, and can be dissolved under low salt condition during release without disruption to the immunocomplex. Specific examples of the useful sequence include poly T/A or poly "TA"/" "AT", etc. As a person of ordinary skill in the art would understand, any sequence with appropriate hybridization strength can be utilized.

The workflow of steps described above in the example can be altered. For example, Binder 1 can be pre-bound to the first surface, which, upon contacting the sample, captures the analyte. Binder 2 can be added subsequently or concurrently with sample to form the immunocomplex on the surface through multiple rounds of addition/incubation/washing steps.

In some embodiments, the complementary sequence between Tag 1 and CP1 does not have G/C, and have a length in the range of 8 to 30 base pairs. In some embodiments, the complementary sequence is in the range of 10 to 25 base pairs. In some embodiments, the complementary sequence is in the range of 12 to 20 base pairs. In some embodiments, the complementary sequence is in the range of 12 to 16 base pairs. In one embodiment, the complementary sequence between Tag 1 and CP1 does not have G/C, and have 8 base pairs, 9 base pairs, 10 base pairs, 12 base pairs, 14 base pairs, 16 base pairs, 18 base pairs, 20 base pairs, 22 base pairs, 25 base pairs, 28 base pairs, or 30 base pairs.

In some embodiments, the hybridization reaction is conducted at temperature between 20 to 37ºC. In some embodiments, the hybridization reaction is conducted at room temperature. In some embodiments, the hybridization reaction is conducted at 25° C. In some embodiments, the hybridization reaction is conducted at 22ºC.

In some embodiments, the salt concentration for the hybridization reaction is in the range of 0.5×SSC to 2×SSC. In some embodiments, the salt concentration for the binding reaction is in the range of 1×SSC to 1.5×SSC. In some embodiments, the salt concentration for the hybridization reaction is about 0.5×SSC, about 1.0×SSC, about 1.5×SSC, about 2.0×SSC, or about 2.5×SSC.

6.1.3 Release of the Immunocomplex from the First Surface. (FIG. 4B(c))

A release buffer is brought into contact with the first surface and the assay parameters are set to promote the dissolution of the hybridization, releasing the immunocomplex to the solution. The assay parameters can include appropriate salt concentration and/or temperature elevation, or any other conditions that facilitate the dissolution of hybridization bond without disturbing the antibody-protein binding in the immunocomplex. The proper condition for release can be determined by a person of ordinary skill in the art via routine experimentation.

The hybridization between Tag 1 and CP1 can be disrupted with low salt concentration. In some embodiments, a release buffer contains salt concentration in the range of 0.02×SSC to 0.30×SSC is used as the release buffer. In some embodiments, a release buffer contains salt concentration in the range of 0.05×SSC to 0.2×SSC. In some embodiments, a release buffer contains salt concentration at about 0.02× SSC, at about 0.03×SSC, at about 0.04×SSC, at about 0.05×SSC, at about 0.06×SSC, at about 0.08×SSC, at about 0.1×SSC, at about 0.12×SSC, at about 0.14×SSC, at about 0.16×SSC, at about 0.18×SSC, at about 0.20×SSC, at about 0.22×SSC, at about 0.24×SSC, at about 0.26×SSC, at about 0.28×SSC, or at about 0.30×SSC.

In some embodiments, the release of the immunocomplex from the first surface is conducted at temperature between 20 to 37°C. In some embodiments, the release of the immunocomplex from the first surface is conducted at room temperature. In some embodiments, the release of the immunocomplex from the first surface is conducted at 25°C. In some embodiments, the release of the immunocomplex from the first surface is conducted at 22°C.

In some embodiments, the incubation time with the release buffer is within 30 minutes before it brought back up to higher salt concentration, typically but not necessarily in the range of 1×SSC to 1.5×SSC. In some embodiments, the incubation time with the release buffer is within 25 minutes. In some embodiments, the incubation time with the release buffer is within 20 minutes. In some embodiments, the incubation time with the release buffer is within 15 minutes. In some embodiments, the incubation time with the release buffer is within 10 minutes. In some embodiments, the incubation time with the release buffer is within 8 minutes.

6.1.4 Recapture of the Immunocomplex onto the Second Surface (FIG. 4B(d))

The release buffer containing released immunocomplex is brought back into higher salt concentration, and then in contact with a clean second solid surface, which are pre-conjugated with a second nucleic acid capture probe ("CP2" of the "second probe"). Because CP2 contains a sequence complementary to that of Tag 2, the immunocomplex is recaptured on the second surface. Additional washing can be conducted to remove unbound molecules, which include free Binder 1 that are not part of the immunocomplex.

In some embodiments, CP1 and CP2 are different sequences that are complementary to fragments of Tag 1 and Tag 2, respectively. In some embodiments, CP1 and CP2 are the same sequence that are complementary to Tag 1 only thus recapturing the immunocomplex to Surface 2 through Binder 1. In some embodiments, the capture/release cycle can be conducted once or additional round(s) on either binder. In some embodiments, the capture/release cycle can be carried out solely on one binder alone.

Figure 16:
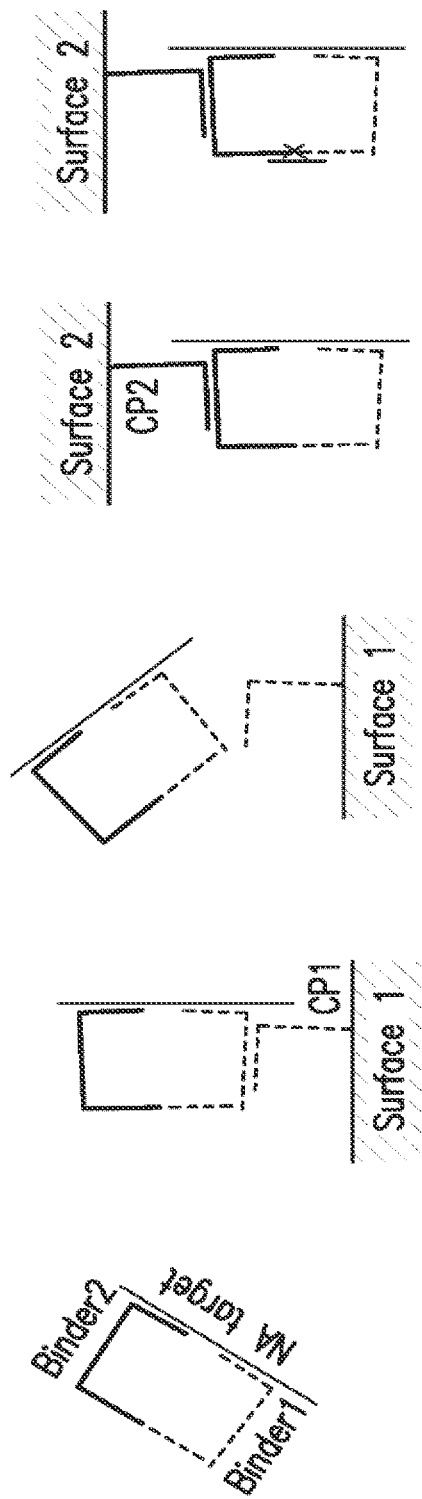

6.2 NULISA for EGFR Detection (FIG. 16)

6.2.1 Preparation of Binder 1 and Binder 2 Protein-Oligonucleotide Complexes Binder 1 and Binder 2 were selected from a library of EGFR binders to occupy non-interfering epitopes on the EGFR surface. Both binders were functionalized by oligonucleotide conjugation to the C-terminal cysteine.

Binder 1 was conjugated with complementary, pre-hybridized oligonucleotides CP(/5AmMC6/AATGA-TACGGCGAC-CACCGAAAAAAAAAAAAAAAAAAAAAAAAAAA) (SEQ ID NO: 53) and R(/5Phos/TCGAGTCT-TATCGGTGGTCGCCGTATCATT) (SEQ ID NO: 54)

Binder 2 was conjugated with complementary, pre-hybridized oligonucleotides L(/5AmMC6/CAAGCAGAA-GACGGCATACGAACACTCTTTCCCTA-CACGACGCTCTTCC GATCTTATATTAATCTGCAC) (SEQ ID NO: 55) and CP2(/5BiosG/GAGCGTCGTGTAGGGAAAGAGTGTTCGTATGCCG) (SEQ ID NO: 56)

Briefly, equimolar amounts of complementary oligonucleotides were mixed in CB buffer (100 mM sodium phosphate, 150 mM sodium chloride, 5 mM EDTA, pH7.2), heated to 94° C. and slowly cooled to 25° C. at a rate of 0.1°C/s. Subsequently, 10 times molar excess of PEGylated SMCC linker (Thermo Scientific, Catalog No. 22102) was added to oligonucleotide duplex and incubated in 25° C. for 30 minutes. Oligonucleotides were desalted to remove excess of the linker. The C-terminal cysteines of Binder 1 and 2 were reduced by 1-hour incubation at 25° C. with immobilized TCEP reducing gel (Thermo Scientific, Catalog No. 77712). Protein-oligonucleotide conjugation was carried out by incubating equimolar amounts of reduced protein with SMCC activated oligonucleotides for 1 hour at 25° C. Binder 1 and Binder 2 protein-oligonucleotide conjugate was separated from unreacted proteins and oligonucleotides by anion exchange chromatography.

6.2.2 NULISA Immunoassay

Binder 1 and Binder 2 protein-oligonucleotide conjugates were mixed and diluted to 1 nM and 0.2 nM respectively in blocking buffer (1×SSC, 0.2% BSA, 0.05% Tween 20). Different amounts of EGFR (100 pM-25 aM) were then added to 100 µl of the Binder 1 and 2 mix allowing the formation of the sandwich immunocomplex. After incubation at 25° C. for 1 h, 1 µl of pre-blocked Sera-Mag oligo(dT)-coated magnetic particles (GE Health, 38152103010150) was added to each sample to capture the immunocomplex. After another hour at 25° C., the magnetic particles were washed 4 times with 120 µl washing buffer (1×SSC, 0.05% Tween20) to remove unbound Binder 1.

50 µl of elution buffer (0.1×SSC) was added to each sample to release the immunocomplex for 10 minutes. The magnetic particles were collected by applying magnetic force, and the supernatant containing the freed immunocomplex was transfer to a new tube containing 2× volume of washing buffer (2×SSC, 0.1% Tween20) and 1 µl pre-blocked Sera-Mag streptavidin-blocked magnetic particles for 10 minutes. This step recaptured the immunocomplex to magnetic particles through biotin-streptavidin interaction. The magnetic particles were then washed twice with 120 µl washing buffer to remove unbound Binder 2.

Figure 17:
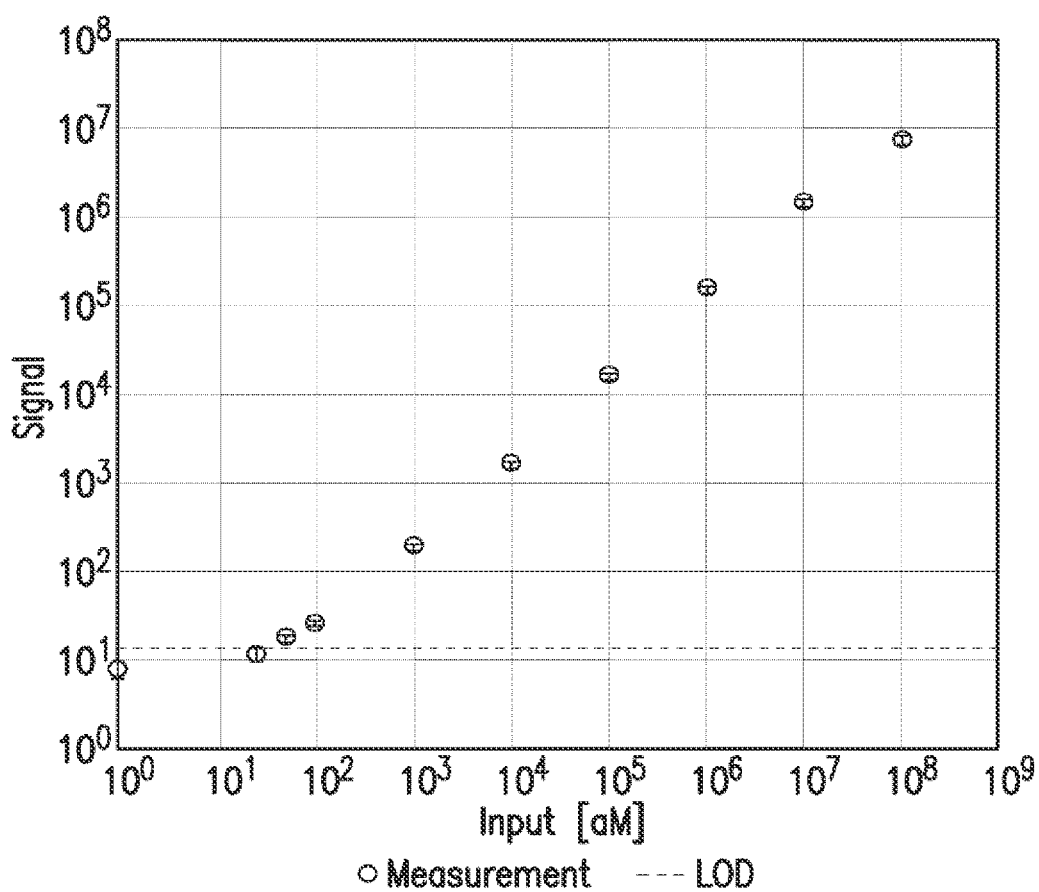
FIG. 17 is the titration curve for human EGFR-Fc protein detection using a NULISA immunoassay.

On-bead ligation was performed by adding 20 µl ligation buffer (1×NEB T4 ligation buffer, 1 µM CNT oligonucleotides (TTTGACTCGAGTGCAGAATT) (SEQ ID NO: 57), 0.05 µl NEB T7 ligase) and incubating at 25° C. for 5 minutes. This step resulted in the ligation of the conjugated DNA sequences on Binder 1 and Binder 2 that formed an immunocomplex together with EGFR. The samples were washed one more time with 120 µl washing buffer and the ligation products were eluted with 20 µl water at 70° ° C. for 10 minutes.

qPCR was performed to quantify the amount of ligation product in each sample using oligonucleotides P5(AATGA-TACGGCGACCACCGA) (SEQ ID NO: 58), P7(CAAGCAGAAGACGGCATACGA) (SEQ ID NO: 59) and SBS3(/56-FAM/CACTCTTTCCCTA-CACGACGCTCTT/3IABKFQ/) (SEQ ID NO: 60). The LOD was determined by calculating mean blank +3 standard deviations of the blank. The results of this experiment are presented in FIG. 17. As shown, sensitivity of protein detection at attomolar (aM) level was achieved.

6.3 Improvement in Sensitivity by Releasing of Immunocomplex

An alternative NULISA workflow was employed, as shown in FIGS. 20A-20D. In this experiment, immunocomplex was captured to a bead surface through a releasable bond. Signal generation was performed with or without releasing the immunocomplex back to solution. As shown in FIG. 20E, signal was masked by background around 1 fM of input when immunocomplex was not released. However, releasing the immunocomplex back to solution before signal generation significantly reduced background and improved assay sensitivity.

6.4 Multi-Plex NULISAseq

Five pairs of antibodies against five different analytes were conjugated with oligos that contains different Target ID, as shown as SEQ ID NOs: 1 to 20 in Sequence Table. They were mixed and diluted to 20-200 pM in diluent buffer (1×SSC, 0.2% BSA, 0.05% Tween 20). Different amounts of mixed analytes (1 pM to 39 aM for each) were then added to the mixture of antibody-oligo conjugates allowing the formation of the sandwich immunocomplex. After incubation at 25° C. for 1 h, the samples were transferred to a Kingfisher machine, where 1 µl of pre-blocked Sera-Mag oligo(dT)-coated magnetic particles (GE Healthcare) was added to each sample to capture the immunocomplex. After another hour at 25° C., the magnetic particles were washed 3 times with 100 µl washing buffer (1×SSC, 0.05% Tween20) and transferred to 100 µl of elution buffer (0.2× SSC, 0.05% Tween20) to release the immunocomplex for 10 minutes. The Sera-Mag oligo(dT)-coated magnetic particles were removed by applying magnetic force and 1 µl pre-blocked Sera-Mag streptavidin-blocked magnetic particles (GE Healthcare) was added to each sample to recapture the immunocomplex through biotin-streptavidin interaction for 10 minutes. The magnetic particles were then washed twice with 100 µl washing buffer and transferred to 100 µl ligation buffer (1×NEB T4 ligation buffer, 200 nM prehybridized CNT/SMI oligos, 0.25 µl NEB T4 ligase) and incubating at 25° C. for 10 minutes. Different CNT/SMI oligos containing unique Sample ID were used for each sample (see SEQ ID NOs: 21 to 52 in Sequence Table). This step resulted in the incorporation of Sample ID through ligation of the conjugated DNA sequences on a capture and detection antibody pair that formed an immunocomplex. The samples were washed one more time with 100 µl washing buffer and the ligation products were eluted with 25 µl of elution buffer at 70° C. for 10 minutes. The eluates containing ligation products were pooled together to be purified and concentrated using a NEB DNA purification kit. The ligation products were then amplified by 18 cycles of PCR using NEB Q5 high-fidelity PCR kit and primers P5(5'-AATGA-TACGGCGACCACCGA), P7(5'-CAAGCAGAAGACGG-CATACGA). The PCR product was purified using NEB DNA purification kit and diluted to 4 nM. It was then denatured in 0.1N NaOH and diluted to 20 pM with HT1 buffer (Illumina). The diluted denatured PCR product was mixed with equal amount of PhiX library and loaded to Illumina MiSeq Reagent Kit v3 and sequenced using MiSeq machine (70 cycles, single read). About 20M reads were recovered from the sequencing, in which about 10M reads were identified as ligation products from NULISA. The reads were counted based on their Target ID and Sample ID, representing signal for each assay in each sample. The results of this experiment are presented in FIG. 25C and Tables 1 and 2. As shown, the average coefficients of variation (CV) for all five analytes were all below 30%. Sensitivity of protein detection at attomolar (aM) level was achieved for all five assays, with three of them below 50 aM. The sequencing reads of reporters comprising target IDs from non-matching antibody pairs can be distinguished from the ones from matching pairs. As such, true signals can be parsed out from various kinds of noises.

TABLE 1

| Input | Average Reads | | | | | CV | | | | |
|---|---|---|---|---|---|---|---|---|---|---|
| | IL4 | IL6 | IL10 | TNFα | P24 | IL4 | IL6 | IL10 | TNFα | P24 |
| 1 pM | 960097 | 592003 | 421534 | 440328 | 255951 | 12% | 3% | 13% | 11% | 11% |
| 100 fM | 67014 | 49601 | 30877 | 33736 | 24398 | 21% | 13% | 26% | 9% | 18% |
| 10 fM | 7681 | 5617 | 4657 | 3956 | 3437 | 7% | 2% | 21% | 5% | 8% |
| 2.5 fM | 1612 | 1292 | 1313 | 1219 | 709 | 29% | 24% | 31% | 27% | 38% |
| 625 aM | 512 | 398 | 939 | 617 | 179 | 9% | 4% | 9% | 11% | 11% |
| 156 aM | 124 | 91 | 650 | 373 | 43 | 30% | 21% | 22% | 18% | 29% |
| 39 aM | 49 | 35 | 612 | 380 | 21 | 20% | 20% | 18% | 10% | 34% |
| No Ag | 10 | 4 | 429 | 255 | 6 | 64% | 68% | 21% | 15% | 48% |
| Ave | | | | | | 24% | 19% | 20% | 13% | 25% |

TABLE 2

| Assay | LOB (aM)* | LOD (aM)* |
|---|---|---|
| IL-4 | 6.6 | 20.3 |
| IL-6 | 4.0 | 16.7 |
| IL-10 | 64.8 | 299.7 |
| TNFα | 28.3 | 95.1 |
| P24 | 8.5 | 40.7 |

Curving fitting: 4P-Logistic model.

LoB = meanblank + 1.645(SDblank)

LoD = LoB + 1.645(SD low concentration sample)

From Clinical and Laboratory Standards Institute (CLSI)

Sequence Table

| SEQ ID NO: | Description | Sequence |
|---|---|---|
| 1 | Conjugate Oligo_1 for P24 capture Ab | /5Phos/TCGAGTCtccacaagaaATCTCGTATGCCGTCTTCTGCTTG |
| 2 | Conjugate Oligo_2 for P24 capture Ab | /5AmMC6/CCTTAGCACTGAACTTATCTAGACACAAGCAGAAGACGGCATACGAGATAAAAAAAAAAAAAAAAAAAAAA |
| 3 | Conjugate Oligo_1 for P24 detection Ab | /5AmMC6/AATGATACGGCGACCACCGAGATCTACACTCTTTCCCTACACGACGCTCTTCCGATCTtccacaagaaTCTGCAC |
| 4 | Conjugate Oligo_2 for P24 detection Ab | /5BiosG/AGATCGGAAGAGCGTCGTGTAGGGAAAGAGTGT |
| 5 | Conjugate Oligo_1 for IL-4 capture Ab | /5Phos/TCGAGTCtcacctcaggATCTCGTATGCCGTCTTCTGCTTG |
| 6 | Conjugate Oligo_2 for IL-4 capture Ab | /5AmMC6/CCTTAGCACTGAACTTATCTAGACACAAGCAGAAGACGGCATACGAGATAAAAAAAAAAAAAAAAAAAAAA |
| 7 | Conjugate Oligo_1 for IL-4 detection Ab | /5AmMC6/AATGATACGGCGACCACCGAGATCTACACTCTTTCCCTACACGACGCTCTTCCGATCTtcacctcaggTCTGCAC |
| 8 | Conjugate Oligo_2 for IL-4 detection Ab | /5BiosG/AGATCGGAAGAGCGTCGTGTAGGGAAAGAGTGT |
| 9 | Conjugate Oligo_1 for IL-6 capture Ab | /5Phos/TCGAGTCcagttaatccATCTCGTATGCCGTCTTCTGCTTG |
| 10 | Conjugate Oligo_2 for IL-6 capture Ab | /5AmMC6/CCTTAGCACTGAACTTATCTAGACACAAGCAGAAGACGGCATACGAGATAAAAAAAAAAAAAAAAAAAAAA |
| 11 | Conjugate Oligo_1 for IL-6 detection Ab | /5AmMC6/AATGATACGGCGACCACCGAGATCTACACTCTTTCCCTACACGACGCTCTTCCGATCTcagttaatccTCTGCAC |
| 12 | Conjugate Oligo_2 for IL-6 detection Ab | /5BiosG/AGATCGGAAGAGCGTCGTGTAGGGAAAGAGTGT |
| 13 | Conjugate Oligo_1 for IL-10 capture Ab | /5Phos/TCGAGTCgaacagctcaATCTCGTATGCCGTCTTCTGCTTG |
| 14 | Conjugate Oligo_2 for IL-10 capture Ab | /5AmMC6/CCTTAGCACTGAACTTATCTAGACACAAGCAGAAGACGGCATACGAGATAAAAAAAAAAAAAAAAAAAAAA |
| 15 | Conjugate Oligo_1 for IL-10 detection Ab | /5AmMC6/AATGATACGGCGACCACCGAGATCTACACTCTTTCCCTACACGACGCTCTTCCGATCTgaacagctcaTCTGCAC |
| 16 | Conjugate Oligo_2 for IL-10 detection Ab | /5BiosG/AGATCGGAAGAGCGTCGTGTAGGGAAAGAGTGT |
| 17 | Conjugate Oligo_1 for TNFα capture Ab | /5Phos/TCGAGTCcgctataatgATCTCGTATGCCGTCTTCTGCTTG |
| 18 | Conjugate Oligo 2 for TNFα capture Ab | /5AmMC6/CCTTAGCACTGAACTTATCTAGACACAAGCAGAAGACGGCATACGAGATAAAAAAAAAAAAAAAAAAAAAA |
| 19 | Conjugate Oligo_1 for TNFα detection Ab | /5AmMC6/AATGATACGGCGACCACCGAGATCTACACTCTTTCCCTACACGACGCTCTTCCGATCTcgctataatgTCTGCAC |
| 20 | Conjugate Oligo_2 for TNFα detection Ab | /5BiosG/AGATCGGAAGAGCGTCGTGTAGGGAAAGAGTGT |
| 21 | Sample Barcode 1 for 1 pM | cacctgtagt |
| 22 | Sample Barcode 2 for 1 pM | cttcggcgaa |

-continued

Sequence Table

| SEQ ID NO: | Description | Sequence |
|---|---|---|
| 23 | Sample Barcode 3 for 1 pM | acaacgacaa |
| 24 | Sample Barcode 4 for 1 pM | aagccaccaa |
| 25 | Sample Barcode 1 for 100 fM | tgtcgcggaa |
| 26 | Sample Barcode 2 for 100 fM | gtcaggtgaa |
| 27 | Sample Barcode 3 for 100 fM | gataaggcaa |
| 28 | Sample Barcode 4 for 100 fM | cacgactcaa |
| 29 | Sample Barcode 1 for 10 fM | agatgtagga |
| 30 | Sample Barcode 2 for 10 fM | gtgagattga |
| 31 | Sample Barcode 3 for 10 fM | tatccatcca |
| 32 | Sample Barcode 4 for 10 fM | acgagtcgta |
| 33 | Sample Barcode 1 for 2.5 fM | ttccttacga |
| 34 | Sample Barcode 2 for 2.5 fM | agctgttaca |
| 35 | Sample Barcode 3 for 2.5 fM | ccaaccgtca |
| 36 | Sample Barcode 4 for 2.5 fM | cctcaatcta |
| 37 | Sample Barcode 1 for 625 aM | cctcagatga |
| 38 | Sample Barcode 2 for 625 aM | ggtagctgca |
| 39 | Sample Barcode 3 for 625 aM | cagtcctata |
| 40 | Sample Barcode 4 for 625 aM | ggcgatctta |
| 41 | Sample Barcode 1 for 156 aM | tccgtgatag |
| 42 | Sample Barcode 2 for 156 aM | tagaacatgg |
| 43 | Sample Barcode 3 for 156 aM | tggcagatcg |
| 44 | Sample Barcode 4 for 156 aM | tcggctgttg |
| 45 | Sample Barcode 1 for 39 aM | ggcataacgg |
| 46 | Sample Barcode 2 for 39 aM | gttgacctgg |

-continued

Sequence Table

| SEQ ID NO: | Description | Sequence |
|---|---|---|
| 47 | Sample Barcode 3 for 39 aM | gtggtcgatg |
| 48 | Sample Barcode 4 for 39 aM | ccatataggc |
| 49 | Sample Barcode 1 for 0 aM | atacatccgg |
| 50 | Sample Barcode 2 for 0 aM | agagttggcg |
| 51 | Sample Barcode 3 for 0 aM | acagaggctg |
| 52 | Sample Barcode 4 for 0 aM | ttagttcacc |
| 53 | oligonucleotides CP of EGFR binder 1 | /5AmMC6/AATGATACGGCGACCACCGAAAAAAAAAAAAAAAAAAAAAAAA |
| 54 | oligonucleotides R of EGFR binder 1 | /5Phos/TCGAGTCTTATCGGTGGTCGCCGTATCATT |
| 55 | oligonucleotides L of EGFR binder 2 | /5AmMC6/CAAGCAGAAGACGGCATACGAACACTCTTTCCCTACACGACGCTCTTCCGATCTTATATTAATCTGCAC |
| 56 | oligonucleotides CP2 of EGFR binder 2 | /5BiosG/GAGCGTCGTGTAGGGAAAGAGTGTTCGTATGCCG |
| 57 | Connector (CNT) used in detection of EGFR | TTTGACTCGAGTGCAGAATT |
| 58 | primer P5 used in qPCR detection of EGFR | AATGATACGGCGACCACCGA |
| 59 | primer P7 used in qPCR detection of EGFR | CAAGCAGAAGACGGCATACGA |
| 60 | primer SBS3 used in qPCR detection of EGFR | /56-FAM/CACTCTTTCCCTACACGACGCTCTT/3IABKFQ/ |

7. REFERENCES

Boitieux, J. L., Groshemy, R., Thomas, D. & Ergan, F. Reversible immobilization of an antibody with a thiol-substituted sorbent: application to enzyme immunoassays. Anal. Chim. Acta 197, 229-237 (1987).

Brown 1981, U.S. Pat. No. 4,284,553

Bystrykh, L V (2012), Generalized DNA barcode design based on Hamming codes. PLOS ONE 7(5): e36852. Doi:10.1371/journal.pone.0036852

Buschmann, T (2013), Levenshtein error-correcting barcodes for multiplexed DNA sequencing. BMC Bioinformatics. 2013; 14: 272.

Chan 1976, Effects of subunit interactions on the activity of lactate dehydrogenase studied in immobilized enzyme systems, Biochemistry 1976, 15, 19, 4215-4222

Cheung 2012, Immobilized metal ion affinity chromatography: a review on its applications. Appl. Microbiol. Biotechnol. 96, 1411-1420 (2012).

Duerksen-Hughes 1989, Affinity chromatography using protein immobilized via arginine residues: purification of ubiquitin carboxyl-terminal hydrolases, Biochemistry, 1989 Oct. 17; 28 (21):8530-6

Engvall E (1971), Enzyme-linked immunosorbent assay (ELISA). Quantitative assay of immunoglobulin G. Immunochemistry. 1971 September; 8(9):871-4.

Engvall E (1972), Enzyme-linked immunosorbent assay, ELISA, J. Immu. 109 (1): 129-135. ISSN 0022-1767.

Greenwood C (2015), Proximity assays for sensitive quantification of proteins, Biomol. det. and quan. 4 (2015) 10-16, doi:10.1016/j.bdq.2015.04.002

Ham 2016, In situ regeneration of bioactive coatings enabled by an evolved Staphylococcus aureus sortase A, nat. comm, doi: 10.1038/ncomms11140

Haque 2017, Challenges in Using ctDNA to Achieve Early Detection of Cancer; bioRxiw preprint Hui 2013, Antimicrobial N-halamine polymers and coatings: a review of their synthesis, characterization, and applications. Biomacromolecules 14, 585-601 (2013).

IDT (2019), Photo-cleavable spacer,

Kosa, N. M., Haushalter, R. W., Smith, A. R. & Burkart, M. D. Reversible labeling of native and fusion-protein motifs. Nat. Methods 9, 981-984 (2012).

Leriche G (2012), Cleavable linkers in chemical biology, Bioorganic & Med. Chem., Vol. 20, No. 2, 571-581, doi:10.1016/j.bmc.2011.07.048

Lundberg, et al. (2011), Homogeneous antibody-based proximity extension assays provide sensitive and specific detection of low-abundant proteins in human blood, Nuc. Acid res. Vol 39, no. 15, e102, doi: 10.1093/nar/fke424

Margot N (2018), Measurement of plasma HIV-1 RNA below the limit of quantification (<20 copies/mL) of commercial assays with the integrase HIV RNA single-copy assay. J Clin Virol 2018 November; 108:50-52. Doi:10.1016/j.jcv.2018.09.003. Epub 2018 Sep. 10.

MilliporeSigma (2019), SMCxPRO™ Immunoassay system brochure,

Nguyen 2005, Mild conditions for releasing mono and bis-biotnylated macromolecules from immobilized streptavidin, Biomol. Eng. 22 (2005) 147-150

Nong R Y (2013), Solid-phase proximity ligation assays for individual or parallel protein analysis with readout via real-time PCR or sequencing, Nature protocols, vol. 8, no. 6, 1234-1249, 2013; doi:10.1038/nprot.2013.070

Notomi et al. (2000), Loop-mediated isothermal amplification of DNA, Nuc. Acid Res. Vol 28, No. 12, e63.

Potuckova L (2011), Rapid and sensitive detection of cytokines using functionalized nanoparticle-based immune-PCR, comparison with immune-PCR and ELISA, J. Immu. Meth. 371 (2011) 38-47

Rabuka, D. Chemoenzymatic methods for site-specific protein modification., Curr. Opin. Chem. Biol. 14, 790-796 (2010).

Rashidian, M., Song, J. M., Pricer, R. E. & Distefano, M. D. Chemoenzymatic reversible immobilization and labeling of proteins without prior purification. J. Am. Chem. Soc. 134, 8455-8467 (2012).

Rissin D M (2010), Single-molecule enzyme-linked immunosorbent assay detects serum proteins at subfemtomolar concentrations, Nat. Biotech. Vol. 28, No. 6, June 2010, doi: 10.1038/nbt. 1641

ThermoFisher (2019), QuantiGene assays application guide,

Wan et al. (2018), Photocleavage-based affinity purification of biomarkers from serum: Application to multiplex allergy testing. PLOS ONE 13(2): e0191987.

Watanabe T (2018), The immune complex transfer enzyme immunoassay: mechanism of improved sensitivity compared with conventional sandwich enzyme immunoassay. JIM (2018), doi:10.1016/j.jim.2018.05.010

Yamamoto M (2017), A study of high, middle and low molecular weight adimponectin in urine as a surrogate marker for early diabetic nephropathy using ultra-sensitive ICT-EIA. Annals of clin. Biochem., doi: 10.1177/0004563217748681

Yeung D (2016), Evaluation of highly sensitive immunoassay technologies for quantitative measurement of sub-pg/mL levels of cytokines in human serum. J. Imm. Meth. (2016), doi: 101016/j.jim.2016.08.003

---

What is claimed is:

1. An assay method for detecting a protein or polypeptide in at least a first biological sample and a second biological sample, comprising:
   (1) forming an immunocomplex in solution by adding, to each of a first assay reaction comprising the first biological sample and a second assay reaction comprising the second biological sample, a first binding moiety and a second binding moiety, wherein:
      (i) the first binding moiety comprises a first antibody or a first antibody fragment that binds the protein or polypeptide, a first presenting group comprising a nucleic acid tag that is conjugated to the first antibody or the first antibody fragment, and a first nucleic acid target label that is hybridized with the nucleic acid tag and is not covalently attached to the first antibody or the first antibody fragment, wherein:
         the nucleic acid tag comprises a poly A or poly T sequence,
         the first nucleic acid target label comprises a first identity barcode that is specific to the protein or polypeptide,
         the first nucleic acid target label is hybridized to the nucleic acid tag, and
         the first presenting group and the first nucleic acid target label comprise different polynucleotides:
      (ii) the second binding moiety comprises a second antibody or second antibody fragment that binds the protein or polypeptide, a second nucleic acid target label that is conjugated to the second antibody or the second antibody fragment, and a second presenting group comprising a biotinylated nucleic acid capture probe that is hybridized with the second nucleic acid target label and is not covalently attached to the second antibody or the second antibody fragment, wherein:
         the second nucleic acid target label comprises a second identity barcode that is specific to the protein or polypeptide, and
         the second presenting group and the second nucleic acid target label comprise different polynucleotides; and
      (iii) the immunocomplex comprises the first binding moiety, the second binding moiety, and the protein or polypeptide;
   (2) to each of the first assay reaction and the second assay reaction, introducing first paramagnetic beads coupled with a poly-T or poly-A sequence, and capturing the immunocomplex on the first paramagnetic beads by hybridization between the poly-A sequence from the first binding moiety and the poly-T sequence from the first paramagnetic beads, or between the poly-T sequence from the first binding moiety and the poly-A sequence from the first paramagnetic beads;
   (3) washing the first paramagnetic beads, in each of the first assay reaction and the second assay reaction, to remove unbound molecules;
   (4) releasing the immunocomplex from the first paramagnetic beads, in each of the first assay reaction and the second assay reaction, by disrupting the hybridization between the poly-A sequence from the first binding moiety and the poly-T sequence from the first paramagnetic beads, or between the poly-T sequence from the first binding moiety and the poly-A sequence from the first paramagnetic beads;
   (5) to each of the first assay reaction and the second assay reaction, introducing second paramagnetic beads coupled with streptavidin or avidin and recapturing the immunocomplex on the second paramagnetic beads via binding between the biotin from the second binding moiety and the streptavidin or avidin from the second paramagnetic beads;
   (6) washing the second paramagnetic beads, in each of the first assay reaction and the second assay reaction, to remove unbound molecules;
   (7) to each of the first assay reaction and the second assay reaction, introducing a double-stranded nucleic acid sample label that comprises a 5' overhang and a 3' overhang, wherein one of the overhangs hybridizes with the first nucleic acid target label and the other overhang hybridizes with the second nucleic acid target label and an identity barcode that is sample-specific, hybridizing the 5' overhang and the 3' overhang of the sample label to the first nucleic acid target label and the second nucleic acid target label, and completing proximity-based ligation between (i) the first nucleic acid target label and the nucleic acid sample label and (ii) the second nucleic acid target label and the nucleic acid sample label, to generate a nucleic acid reporter that is conjugated to the second antibody or second antibody fragment and is not covalently attached to the first antibody or first antibody fragment, wherein the nucleic acid reporter comprises the first nucleic acid target label comprising the first identity barcode that is specific to the protein or polypeptide, the second nucleic acid target label comprising the second identity barcode that is specific to the protein or polypeptide, and the identity barcode that is sample-specific, wherein the identity barcode that is sample-specific is positioned between the first identity barcode that is specific to the protein or polypeptide and the second identity barcode that is specific to the protein or polypeptide;
   (8) pooling the nucleic acid reporters from the first assay reaction with the nucleic acid reporters from the second assay reaction together to form a pooled sample; and
   (9) detecting the protein or polypeptide in the first biological sample and the second biological sample by detecting the nucleic acid reporters in the pooled sample.

2. The assay method of claim 1, wherein in step (9), detecting the protein or polypeptide comprises co-detection of the first identity barcode that is specific to the protein or polypeptide and the second identity barcode that is specific to the protein or polypeptide.

3. The assay method of claim 1, wherein the nucleic acid reporter is detected by next generation sequencing.

4. The assay method of claim 1, wherein the sample is a serum sample, a plasma sample, or a cerebrospinal fluid sample.

5. The assay method of claim 1, wherein the sample is derived from a cell sample or a tissue sample.

6. The assay method of claim 1, wherein in step (9), detecting the protein or polypeptide comprises PCR amplification of the nucleic acid reporters in the pooled sample.

7. The assay method of claim 1, wherein:
   the first antibody or first antibody fragment has a binding affinity to the protein or polypeptide of at least $10^{-4}$ M; and
   the second antibody or second antibody fragment has a binding affinity to the protein or polypeptide of at least $10^{-4}$ M.

* * * * *